(12) United States Patent
Plachter et al.

(10) Patent No.: US 11,591,373 B2
(45) Date of Patent: Feb. 28, 2023

(54) HCMV VACCINE STRAIN

(71) Applicant: Bodo Plachter, Ansbach (DE)

(72) Inventors: Bodo Plachter, Ansbach (DE); Christine Zimmermann, Wiesbaden (DE)

(73) Assignee: Universitätsmedizin der Johannes Gutenberg-Univsersität Mainz, Mainz (DE)

( * ) Notice: Subject to any disclaimer, the term of this patent is extended or adjusted under 35 U.S.C. 154(b) by 0 days.

(21) Appl. No.: 16/972,249

(22) PCT Filed: Jun. 28, 2019

(86) PCT No.: PCT/EP2019/067355
§ 371 (c)(1),
(2) Date: Dec. 4, 2020

(87) PCT Pub. No.: WO2020/002614
PCT Pub. Date: Jan. 2, 2020

(65) Prior Publication Data
US 2021/0230228 A1 Jul. 29, 2021

Related U.S. Application Data

(60) Provisional application No. 62/692,021, filed on Jun. 29, 2018.

(30) Foreign Application Priority Data

Jun. 29, 2018 (EP) .................... 18180863

(51) Int. Cl.
*C07K 14/005* (2006.01)
*A61K 39/245* (2006.01)
*C12N 7/00* (2006.01)
*A61K 39/00* (2006.01)

(52) U.S. Cl.
CPC .......... *C07K 14/005* (2013.01); *A61K 39/245* (2013.01); *C12N 7/00* (2013.01); *A61K 2039/5254* (2013.01); *C12N 2710/16121* (2013.01); *C12N 2710/16122* (2013.01); *C12N 2710/16134* (2013.01); *C12N 2710/16152* (2013.01)

(58) Field of Classification Search
CPC .............. C07K 14/005; A61K 39/245; A61K 2039/5254; A61K 39/12; C12N 7/00; C12N 2710/16121; C12N 2710/16122; C12N 2710/16134; C12N 2710/16152; C12N 7/045; A61P 31/12
See application file for complete search history.

(56) References Cited

U.S. PATENT DOCUMENTS 8,173,792 B2   5/2012  Wandless et al.
2015/0307850 A1* 10/2015 Fu .......................... A61P 37/04
                                                              424/230.1

FOREIGN PATENT DOCUMENTS

| EP | 18176735.1   |        | 6/2018  |
| WO |   0053729    | A2     | 9/2000  |
| WO | 2011124371   | A1     | 10/2011 |
| WO | 2014089158   | A1     | 6/2014  |
| WO | 2015061851   | A1     | 5/2015  |

OTHER PUBLICATIONS

Van Damme E, Van Loock M. Functional annotation of human cytomegalovirus gene products: an update. Front Microbiol. May 19, 2014;5:218 (Year: 2014).*

Yu D, Silva MC, Shenk T. Functional map of human cytomegalovirus AD169 defined by global mutational analysis. Proc Natl Acad Sci U S A. Oct. 14, 2003;100(21):12396-401. Epub Sep. 30, 2003. (Year: 2003).*

Stinski MF. Human cytomegalovirus: glycoproteins associated with virions and dense bodies. J Virol. Aug. 1976;19(2):594-609. (Year: 1976).*

Schneider-Ohrum K, Cayatte C, Liu Y, Wang Z, Irrinki A, Cataniag F, Nguyen N, Lambert S, Liu H, Aslam S, et. al. Production of Cytomegalovirus Dense Bodies by Scalable Bioprocess Methods Maintains Immunogenicity and Improves Neutralizing Antibody Titers. J Virol. Oct. 28, 2016;90(22):10133-10144. (Year: 2016).*

Pepperl S, Munster J, Mach M, Harris JR, Plachter B. Dense bodies of human cytomegalovirus induce both humoral and cellular immune responses in the absence of viral gene expression. J Virol. Jul. 2000;74(13):6132-46. (Year: 2000).*

Dunn et al., "Functional profiling of a human cytomegalovirus genome", Proc Natl Acad Sci, 2003, vol. 100, No. 24, pp. 14223-14228.

Kim et al., "Consecutive Inhibition of ISG15 Expression and ISGylation by cytomegalovirus regulators", PLOS Pathog, 2016, vol. 12, No. 8, pp. 1-28.

Bianco and Mohr, "Restriction of Human cytomegalovirus replication by ISG15, a host effector regulated by cGAS-STING double-stranded-DNA sensing", J. Virol., 2017, vol. 91, No. 9, 1-13.

Marchini et al.,"Human cytomegalovirus with IE-2 (UL122) deleted fails to express early lytic genes", J Virol., 2001, vol. 75, No. 4, pp. 1870-1878.

Sauer et al., "Subviral dense bodies of human cytomegalovirus stimulate maturation and activation of monocyte-derived immature dendritic cells", J. Virol., 2013, vol. 87, No. 20, pp. 11287-11291.

Vashee et al., "Cloning, Assembly, and Modification of the Primary Human Cytomegalovirus Isolate Toledo by Yeast-Based Transformation-Associated Recombination", msphere, 2017, vol. 2, No. 5, 1-17.

Andreoni et al., "A rapid microneutralization assay for the measurement of neutralizing antibody reactive with human cytomegalovirus", J Virol Methods, 1989, vol. 23, No. 2, pp. 157-168.

(Continued)

*Primary Examiner* — Rachel B Gill
(74) *Attorney, Agent, or Firm* — Rothwell, Figg, Ernst & Manbeck, P.C.

(57) ABSTRACT

The present invention relates to nucleic acid molecules encoding a recombinant human cytomegalovirus (HCMV) strain, dense bodies produced by said HCMV strain and preparations of said dense bodies for use in medicine, particularly as a vaccine against HCMV.

23 Claims, 9 Drawing Sheets

Figure 1:
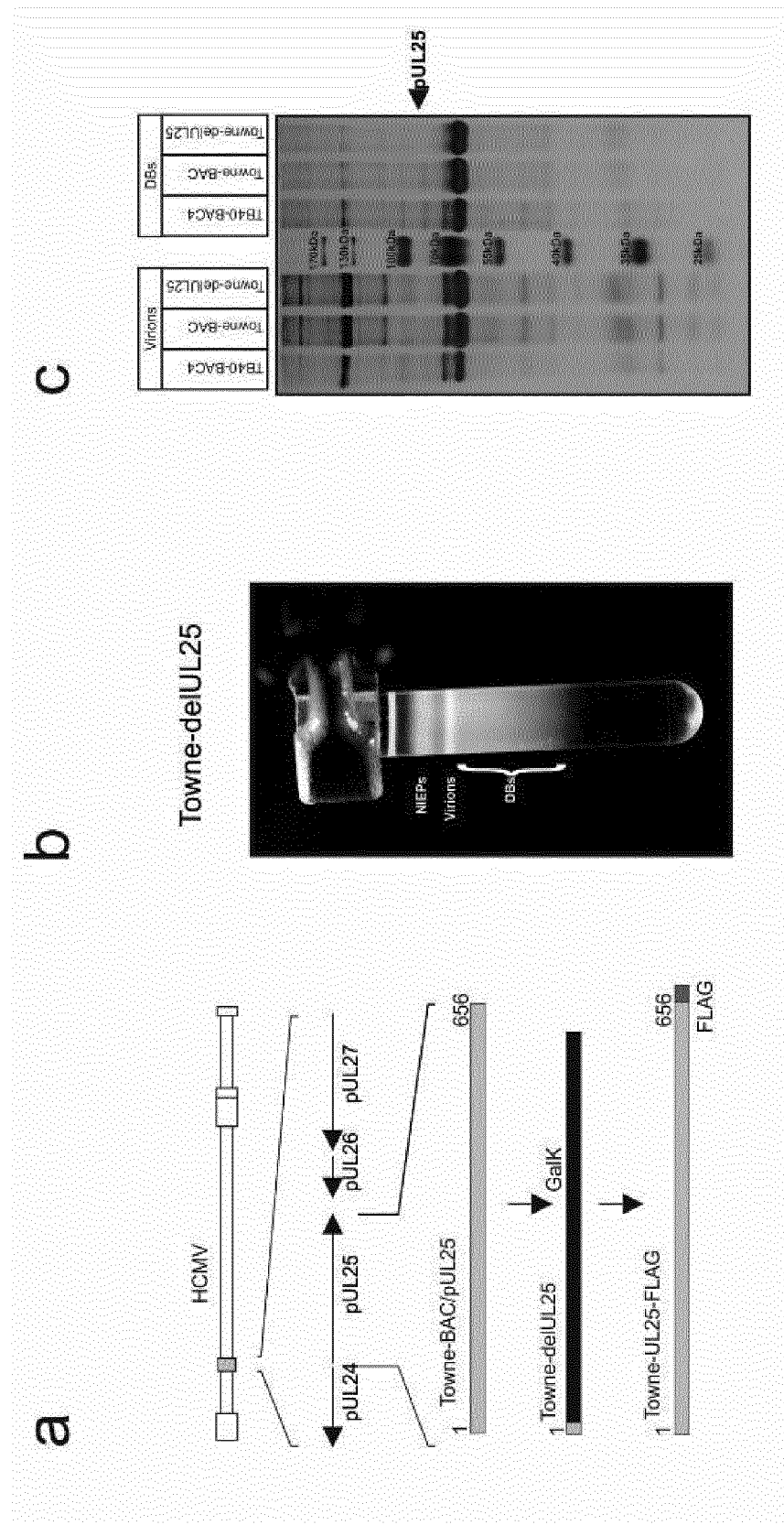
Figure 1:
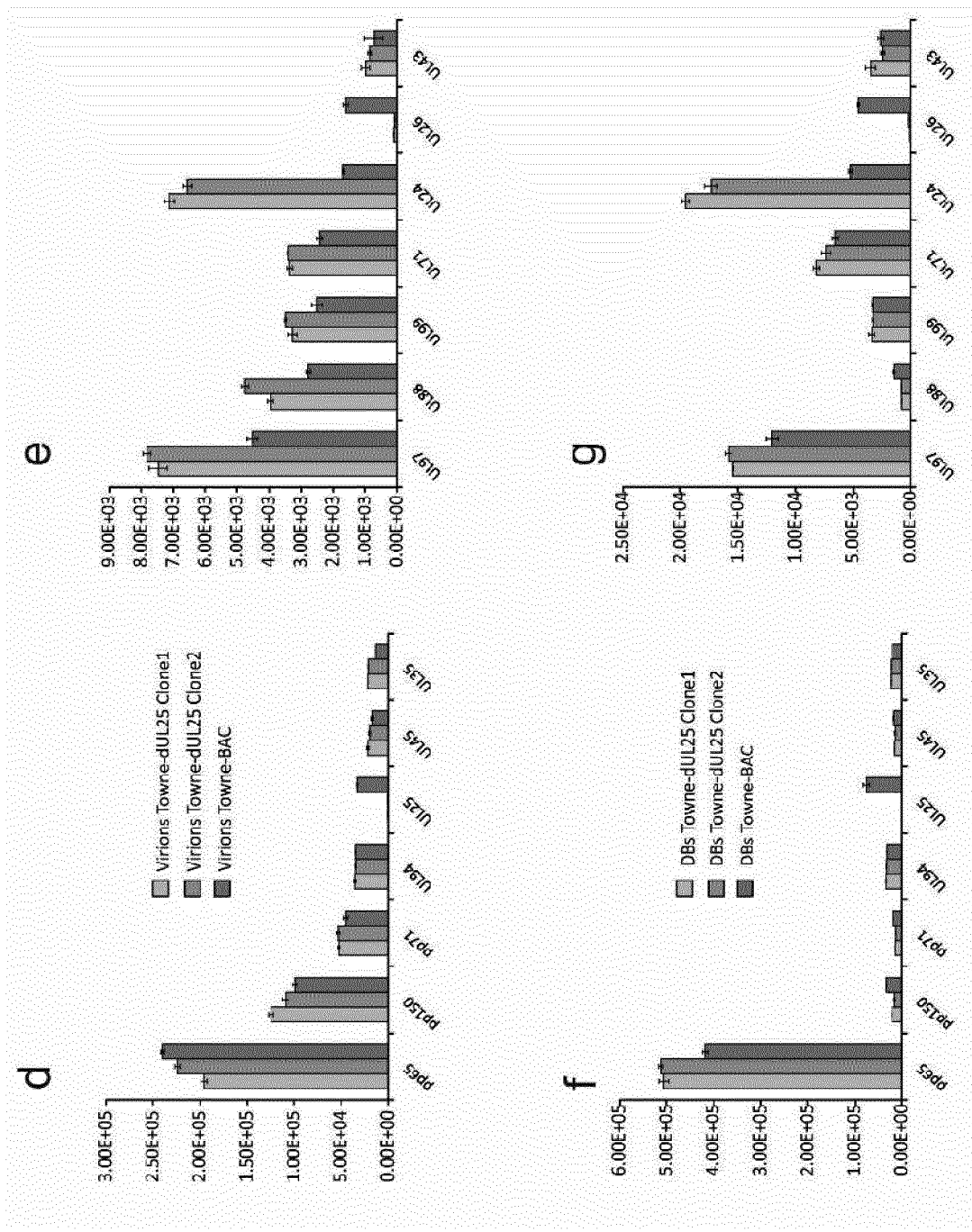

Specification includes a Sequence Listing.

(56) References Cited

OTHER PUBLICATIONS

Plachter et al., "Analysis of proteins encoded by IE regions 1 and 2 of human cytomegalovirus using monoclonal antibodies generated against recombinant antigens", Virology, 1993, vol. 193, No. 2, 642-652.

O'Connor et al., "Construction of large DNA segments in *Escherichia coli*", Science,1989, vol. 244, No. 4910, pp. 1307-1312.

Fleckenstein et al., "Cloning of the complete human cytomegalovirus genome in cosmids", Gene, 1982, vol. 18, No. 1, pp. 39-46.

Chee et al.,"Analysis of the protein-coding content of the sequence of human cytomegalovirus strain AD169", Curr Top Microbiol Immunol., 1990, vol. 154, pp. 126-169.

Tullis, et al., "Efficient replication of adeno-associated virus type 2 vectors: a cis-acting element outside of the terminal repeats and a minimal size", J Virol., 2000, vol. 74, No. 24, pp. 11511-11521.

Baldick et al., "Human cytomegalovirus tegument protein pp71 (ppUL82) enhances the infectivity of viral DNA and accelerates the infectious cycle", J Virol., 1997, vol. 71, No. 6, pp. 4400-4408.

Jones and Muzithras, "A cluster of dispensable genes within the human cytomegalovirus genome short component: IRS1, US1 through US5, and the US6 family" J Virol., 1992, vol. 66, No. 4, pp. 2541-2546.

Warming et al., "Simple and highly efficient BAC recombineering using galK selection", Nucleic Acids Res., 2005, vol. 33, No. 4, pp. 1-12.

Kroemmelbein et al., "Adenovirus E1A/E1B Transformed Amniotic Fluid Cells Support Human Cytomegalovirus Replication", Viruses, 2016, vol. 8, No. 37, pp. 1-20.

Reyda et al., "The tegument protein pp65 of human cytomegalovirus acts as an optional scaffold protein that optimizes protein uploading into viral particles", J Virol., 2014, vol. 88, No. 17, pp. 9633-9646.

Villarroya-Beltr et al., "ISGylation—a key to lock the cell gates for preventing the spread of threats", J Cell Sci., 2017, vol. 130, No. 18, pp. 2961-2969.

Rowe et al., "Cytopathogenic agent resembling human salivary gland virus recovered from tissue cultures of human adenoids", Proc Soc Exp Biol Med., 1956, vol. 92, No. 2, pp. 418-424.

Ostermann et al., "Complete Genome Sequence of a Human Cytomegalovirus Strain AD169 Bacterial Artificial Chromosome Clone" Genome Announc., 2016. vol. 4, No. 2, pp. 1-2.

Borst et al., "Cloning of human cytomegalovirus (HCMV) genome as an infectious bacterial artifical chromosome in *Escherichia coli*: a new approach for construction of HCMV mutants", J Virol., 1999, vol. 73, No. 10, pp. 8320-8329.

Cayette et al., "Cytomegalovirus vaccine strain towne-derived dense bodies induce broad cellular immune responses and neutralizing antibodies that prevent infection of fibroblasts and epithelial cells". J Virol., 2013, vol. 87, No. 20, pp. 11107-11120.

Schneider et al., "Production of cytomegalovirus dense bodies by scalable bioprocess methods maintains immunogenicity and improves neugtralizing antibody titers", J. Virol., 2016, vol. 90, No. 22, pp. 10133-10144.

Wang et al., "A replication-defective human cytomegalovirus vaccine for prevention of congenital infection", Sci Transl Med., 2016, vol. 8, No. 362, pp. 1-9.

Barrero et al., "An improved reversibly dimerizing mutant of the FK506-binding protein FKBP", Cell Logist., 2016,vol. 6, No. 3, pp. 1-8.

Banaszynski et al., "A rapid, reversible, and tunable method to regulate protein function in living cells using synthetic small molecules", Cell, 2006, vol. 126, No. 5, pp. 995-1004.

Das et al., "Identification of human cytomegalovirus genes important for biogenesis of the cytoplasmic virion assembly complex", J Virol., 2014, vol. 88, No. 16, pp. 9086-9099.

Glass et al., "Conditional and reversible disruption of essential herpesvirus proteins" Nat Methods, 2009, vol. 6, No. 8, pp. 577-580 + supplemental material.

Omoto and Mocarski, "Cytomegalovirus UL91 is essential for transcription of viral true late (gamma2) genes", J Virol, 2013, vol. 87, No. 15, pp. 8651-8664.

Perng et al., "The human cytomegalovirus gene UL79 is required for the accumulation of late viral transcripts", J Virol., 2011, vol. 85, No. 10, pp. 4841-4852.

Tandon and Mocarski, "Cytomegalovirus pUL96 is critical for the stability of pp150-associated nucleocapsids", J Virol., 2011, vol. 85, No. 14, pp. 7129-7141.

Imiere and Gibson, "Isolation of human cytomegalovirus intranuclear capsids, characterization of their protein constituents, and demonstration that the B-capsid assembly protein is also abundant in noninfectious enveloped particles", J Virol., 1985, vol. 56, No. 1, pp. 277-283.

Irmiere and Gibson, "Isolation and characterization of a noninfectious virion-like particle released from cells infected with human strains of cytomegalovirus", Virology, 1983, vol. 130, No. 1, pp. 118-133.

Borst et al., "The human cytomegalovirus UL51 protein is essential for viral genome cleavage-packaging and interacts with the terminase subunits pUL56 and pUL89", J Virol., 2013, vol. 87, No. 3, pp. 1720-1732.

Mersseman et al., "Exogenous introduction of an immunodominant peptide from the non-structural IE1 protein of human cytomegalovirus into the MHC class I presentation pathway by recombinant dense bodies". J Gen Virol., 2008, vol. 89, No. 2, pp. 369-379.

Varnum et al., "Identification of proteins in human cytomegalovirus (HCMV) particles: the HCMV proteome", J Virol., 2004, vol. 78, No. 20, pp. 10960-10966.

Buescher et al., "The proteome of human cytomegalovirus virions and dense bodies is conserved across different strains", Med Microbiol Immunol, 2015, vol. 204, No. 3, pp. 285-293.

Schmolke et al., "The dominant phosphoprotein pp65 (UL83) of human cytomegalovirus is dispensable for growth in cell culture", J Virol, 1995, vol. 69, No. 10, pp. 5959-5968.

European Patent Office, issued in patent appl. No. PCT/EP2019/067355, International Search Report and Written Opinion dated Oct. 2, 2019, 16 pgs.

European Patent Office, issued in patent appl. No. 18180863.5, Extended European Search Report dated Dec. 10, 2018, 8 pgs.

Plotkin SA et al., "Candidate cytomegalovirus strain for human vaccination" Infect Immun., 1975, vol. 12, No. 3, pp. 521-527.

* cited by examiner

HCMV VACCINE STRAIN

CROSS REFERENCE TO RELATED APPLICATION

This application is a 35 U.S.C. 371 National Phase Entry Application from PCT/EP2019/067355, filed Jun. 28, 2019, which claims the benefit of European Patent Application No. 18180863.5 filed on Jun. 29, 2018 and U.S. Ser. No. 62/692,021, filed on Jun. 29, 2018, the disclosures of which are incorporated herein in their entirety by reference.

The instant application contains a Sequence Listing which has been submitted via EFS-Web and is hereby incorporated by reference in its entirety. Said Sequence Listing, created on Jun. 19, 2019, is named D00-19-06-2019-Sequence_Listing and is 1 kilobytes in size.

The present invention relates to nucleic acid molecules encoding a recombinant human cytomegalovirus (HCMV) strain, dense bodies (DBs) produced by said HCMV strain and preparations of said dense bodies for use in medicine, particularly as a vaccine against HCMV.

Infection with the human cytomegalovirus (HCMV) is a major cause of disease in patients with a compromised immune status, e.g. following solid organ or hematopoietic stem cell transplantation. Furthermore, transmission of the virus during pregnancy may result in congenital infection. Such infection may occur at a frequency of up to two percent of all life births in Western countries. Thus congenital HCMV infection is a major public health concern. The development of an HCMV vaccine consequently is a top-priority health-care goal.

Several vaccine candidates have been established. These include recombinant protein vaccines based on the immunodominant envelope glycoprotein B (gB), vaccines expressing immunogenic viral gene products including gB plus the T cell targets ppUL83 [pp65] and/or the major immediate early protein 1 (IE1) using DNA plasmid or peptide-based technologies; vector-based vaccine approaches including the expression of gB and other HCMV antigens using life virus or virus-like particle (VLP) systems; and replication-impaired or replication-effective HCMV (attenuated vaccines or disabled single-cycle vaccines).

Dense bodies (DBs), i.e. viral particles released after infection of mammalian cells by HCMV which are surrounded by a lipid membrane in which viral glycoproteins are embedded but which do not contain viral DNA nor capsids, were found to be highly immunogenic as described in WO 2000/053729 the content of which is herein incorporated by reference. DBs containing fusion proteins are described in WO 2011/124371 the content of which is herein incorporated by reference.

Infection with HCMV leads to the release of type I interferons (IFNs) from infected cells. The release of IFNs leads, via their engagement with interferon receptors on the cell surface, to the downstream induction of interferon-stimulated genes (ISGs). Many of the gene products of ISGs have antiviral functions. HCMV has evolved a number of strategies to subvert this IFN response in order to support its own replication.

The present inventors have generated viral mutants with deletions in abundant tegument protein genes. Rationale of these experiments was the definition of proteins that were essential for the production of DBs. It was found that deletion of the gene encoding the viral protein pUL25, an abundant constituent of DBs did not alter DB-production.

The pUL25 protein (e.g. Accession no. UniProtKB - B8YE61 from strain AD169) is known to be dispensable for HCMV replication (1). Surprisingly, the present inventors could show that pUL25 deletion decreases the metabolic stability of another viral protein pUL26 and its packaging into virions and DBs. The protein pUL26 has been found by others to counteract conjugation of proteins with interferon-stimulated-gene-15 (ISG15) (2,3).

ISG15 is known to be induced by infection with different viruses. Current thinking is that ISG15 is covalently attached to all de novo synthesized proteins, thereby tagging them for degradation. Consequently, viral multiplication is restricted on the level of availability of viral proteins for morphogenesis. The pUL26 protein has been identified as one gene to interfere with this process. ISGylation restricts HCMV replication in human foreskin fibroblast (HFF) cells (3). A pUL26-deletion mutant showed enhanced susceptibility to the antiviral effect of interferon-ß (2).

The present inventors could now show that cells infected with a pUL25-deletion mutant HCMV strain display enhanced overall protein ISGylation. In addition, increased steady-state levels of free ISG15 were found. Consequently, it is assumed that pUL25 interferes with antiviral defense against HCMV, mediated by ISGylation.

The molecular background of that finding may be that pUL25 forms a complex with pUL26 in both extracellular particles and infected cells. Deletion of pUL25 leads to reduced protein stability of pUL26. As a functional consequence, the replication of an UL25-deletion mutant strain proved to be more sensitive to IFN-ß, compared to a UL25-positive strain. Taken together, these results indicate that a pUL25 deletion mutant HCMV strain is attenuated for replication in the presence of an innate immune response in a human host. On the other hand, infection of HFF cells with a pUL25 deletion mutant results in an efficient release of DBs, thus providing an HCMV strain suitable for the production of an HCMV vaccine, in particular of a DB-based HCMV vaccine.

The finding that an HCMV strain deficient in UL25 expression still produces large amounts of DBs is highly surprising. According to the inventor's previous results, pUL25 is the second-most abundant protein constituent of DBs produced from HCMV wild-type strains. Thus, formation of DBs without pUL25 is a surprising result also in respect to the inventors' previous finding that deletion of the UL83 gene, i.e. the gene encoding the most abundant constituent of DBs pp65, completely abrogates DB formation (36).

WO 2014/089158 relates to a cytomegalovirus which has been recombinantly altered to express a heterologous polypeptide and to allow for external control of viral replication. The heterologous polypeptide may be an antigen, antibody or immune modulator. Gene cassettes comprising the nucleic acids encoding the heterologous polypeptides may be inserted into the CMV genome in regions encoding non-essential genes reciting a list of about 90 non-essential genes. The cassettes can be inserted in the ORF of a non-essential gene, replace the ORF of a non-essential gene or be inserted between two ORFs encoding non-essential genes. Examples of UL25-deficient strains and dense bodies from such strains, particularly the use of such dense bodies in medicine are not provided.

WO 2015/061851 relates to a CMV strain comprising interferon-ß useful in immuno-stimulatory compositions and vaccines. The CMV strain may have a loss of function mutation in, or deletion of, a gene encoding a non-essential protein providing about 90 examples of such genes.

Examples of UL25-deficient strains and dense bodies from such strains, particularly the use of such dense bodies in medicine are not provided.

A first aspect of the present invention refers to a nucleic acid molecule encoding the genome of a recombinant HCMV strain, wherein the recombinant HCMV strain does not encode a functional pUL25 protein.

The recombinant HCMV strain may be any strain, in particular an HCMV strain which is capable of producing DBs after infection of a mammalian, particularly human target cell. For example, the recombinant HCMV strain may be a genetically modified variant of any suitable HCMV strain, e.g. a genetically modified variant of the HCMV strain Towne or a genetically modified variant of the HCMV strain AD169, wherein the genetic modification includes the absence of a functional gene encoding the viral pUL25 protein.

The recombinant HCMV strain of the invention is attenuated compared to a reference HCMV strain which differs from the strain of the invention in that it encodes a functional pUL25 protein. This attenuation results in an increased sensitivity to an innate immune response, e.g. increased sensitivity to an innate interferon response, and/or to in an increased sensitivity to the presence of exogenously added interferons such as IFN-ß. The increased sensitivity can be determined as an increased ISGylation of proteins in HCMV-infected cells and/or as a reduced replication in HCMV-infected cells in the presence of exogenously added IFN-ß. Thus, the UL25-negative HCMV strain of the invention is suitable for the use as a vaccine strain, in particular for the use as production strain for a vaccine, e.g. a DB-based vaccine.

Compared to a non-attenuated reference strain, the use of an attenuated HCMV strain without functional UL25 gene in medical applications allows safer handling and treatment protocols, in particular for the production and administration of a DB-based vaccine, without concomitant loss in efficacy.

In certain embodiments, the recombinant HCMV strain is a genetically modified variant of the HCMV strain Towne isolated by Plotkin et al. (19) and present in a Towne-BAC clone (1,4), e.g. as deposited at GenBank under Accession no. AY315197.

In certain embodiments, the recombinant HCMV strain is a genetically modified variant of the HCMV strain AD169 isolated by Rowe et al. (20) and present in an AD169-BAC clone (21,22), e.g. as deposited at GenBank under Accession no. KU317610.

In certain embodiments, the UL25 negative HCMV strain of the invention comprises a functional UL24 gene and expresses a functional pUL24 protein (e.g. Accession no. UniProtKB P16760-1 from strain AD169).

In certain embodiments of the invention, the recombinant HCMV strain encodes functional viral gH (UL 75), gL (UL 115), UL 128, UL 130 and UL 131A proteins which are capable of forming a functional pentameric complex. The presence of a pentameric complex in a DB-based vaccine was found to generate a strong neutralizing antibody response against HCMV infection (5).

In a particular embodiment, the recombinant HCMV strain is a genetically modified UL25-negative variant of the HCMV strain Towne which encodes a functional UL130 gene and thus encodes a functional pentameric complex, and further does not encode a functional Green Fluorescent Protein (GFP) in contrast to the previously available Towne genome present in Towne-BAC (1,4).

In a specific embodiment, the nucleic acid molecule encodes a UL25-negative variant of the recombinant HCMV strain Towne-UL130repΔGFP, the manufacture and characterization of which is described in co-pending application EP 18 176 735.1, the content of which is herein incorporated by reference.

In other embodiments, the nucleic acid molecule encodes a UL25-negative variant of a recombinant HCMV strain which does not encode all functional viral proteins of the pentameric complex, e.g. a UL25-negative variant of the HCMV strain Towne which does not encode a functional UL130 gene.

In certain embodiments, the nucleic acid molecule may additionally encode a fusion protein, e.g. a fusion protein as disclosed in WO 2011/124371. In certain embodiments, the nucleic acid molecule does not encode any functional heterologous, i.e. non-HCMV protein. For example, the nucleic acid molecule does not encode a functional interferon-ß gene.

In certain embodiments, the genome of the recombinant HCMV strain is characterized by the absence of a nucleic acid sequence encoding a selectable marker in a form which can be expressed in a mammalian cell, e.g. a human cell. For example, the genome of the recombinant HCMV strain may include selection marker genes such as galK or a chloramphenicol resistance gene which however are in operative linkage with prokaryotic expression control sequences so that they cannot be expressed in a mammalian cell.

The nucleic acid molecule of the present invention may be any single-stranded or double-stranded nucleic acid molecule, e.g. an RNA or a DNA molecule. In certain embodiments, the nucleic acid molecule is a double-stranded DNA molecule.

The nucleic acid molecule may be present as such or being located on a vector, e.g. a BAC vector or a yeast vector. Suitable yeast vectors are described in (6).

Transfection or infection of mammalian target cells with the nucleic acid molecule of the invention results in the production of viral particles and DBs, i.e. viral particles without capsid or viral DNA. In certain embodiments, the target cell is a human cell, e.g. a human fibroblast cell, such as a human foreskin fibroblast cell (HFF) or a human lung fibroblast cell, such as MRC-5 (ATCC CCL-171).

A further aspect of the present invention is a DB produced by transfection or infection of a mammalian target cell, particularly a human target cell, e.g. a human fibroblast cell, with a HCMV strain, particularly by infection with a HCMV strain as described above, wherein the DB is free from the viral protein pUL25.

A DB according to the present invention may be a subviral particle released after transfection or infection of a mammalian target cell, e.g. a human fibroblast cell, by HCMV, in particular after infection by a recombinant HCMV strain as described above, wherein:
the particle is surrounded by lipid membrane in which viral glycoproteins are embedded, and
the particle does not contain substantial amounts of viral DNA or capsids.

Further, according to the above mentioned aspect, the DB particle is free from the viral protein pUL25.

Preferably, the particle comprises a pentameric complex consisting of viral proteins gH, gL, UL128, UL130 and UL131, in particular as described above and is free from GFP. Further, the particle may comprise the viral protein UL24.

The DB may be isolated from the cell culture supernatant of virus-infected or nucleic acid-transfected cells as described above by conventional methods, e.g. gradient centrifugation. By this means, a preparation of DBs is obtained.

A further aspect of the present invention relates to a preparation of DBs as described above in a pharmaceutically acceptable carrier, e.g. a liquid carrier including an aqueous carrier, a non-aqueous carrier or any combination thereof.

In certain embodiments, the preparation comprises DBs which have been subjected to an inactivation treatment, e.g. UV irradiation. Inactivation may be determined by the absence of detectable virus contamination. This may be achieved, e.g. by the absence of de novo HCMV IE1 protein expression in indicator cell cultures (7), by the quantification of the DNA content of DB-preparations, by the quantification of viral genomic DNA in cell culture supernatants of indicator cell cultures, exposed to the DB-preparations or by electron microscopic analysis of DB-preparations.

In certain embodiments, preparation comprises DBs which have not been subjected to an inactivation treatment.

The DB preparation according to the present invention is characterized by an increased sensitivity against an interferon response in a human host, and is capable of eliciting an immediate antiviral immune response in a human host.

Thus, the use of an attenuated UL25 deletion strain will increase the safety of handling of the HCMV vaccine strain as well as the production, handling and formulation of DBs obtained from said strain. Further, the use of an attenuated UL25 deletion strain will also increase the safety of the application of the strain or DBs obtained from said strain as a vaccine, particularly the safety of the application as a DB-based vaccine. Even in case the DB preparation would contain minor amounts of viral DNA and/or infectious viral particles, the risk for the patient is reduced to the attenuation resulting from the absence of pUL25 and the resulting increase of the sensitivity of the virus to the host's innate immunity, in particular on the host's interferon response.

A further aspect of the present invention refers to a preparation of DBs as described above for use in medicine, particularly in human medicine, more particularly for use as a vaccine against HCMV. The preparation of the present invention is suitable for use in preventing and/or ameliorating the occurrence of an HCMV associated disorder in a vaccinated subject, e.g. a human subject, and/or for inhibiting transmission of an HCMV infection from a vaccinated subject e.g. a human subject, to a further subject.

For example, the preparation may be used for the treatment and/or prevention of HCMV-related complications of transplantation, e.g. the transplantation of solid organs such as hearts, kidneys, livers, or lungs or of hematopoietic stem cells. Further the composition is suitable for preventing the pre- or perinatal transmission of HCMV.

The composition of the present invention is suitable for administration by the parenteral route, e.g. by subcutaneous or intramuscular administration. In certain embodiments, the preparation is administered together with an adjuvant. In other embodiments, the preparation is administered without additional adjuvant.

The vaccine of the invention may be used to prevent prenatal infection or HCMV related disorders following prenatal infection. A desired target population for the vaccine would consequently be children or adolescent female subjects. A second desired target population would be patients receiving allogeneic or autologous transplants, e.g. solid organs or hematopoietic stem cells. On a further perspective, a vaccination of the general population would be conceivable.

In a further particular embodiment, the preparation of the invention is for use in maintaining the innate immunity, e.g. by not negatively affecting the interferon response to HCMV infection in a vaccinated human subject.

Furthermore, the present invention relates to a method of preparing a dense body preparation as described above by infection or transfection of target cells, e.g. human fibroblast cells as described above, and isolating DBs from the supernatant of the cell culture medium.

Furthermore, the invention relates to a method for vaccinating a subject, particularly a human subject, against HCMV, comprising administering an immunogenetically effective dose of a DB preparation as described above to a human subject in need thereof.

In addition to the above aspects, the present inventors infected mammalian target cells with a conditionally replication-defective HCMV strain under replication-permissive conditions and produced DBs from the infected cells under non-replication permissive conditions. Surprisingly, a preparation of DBs could be obtained under non-replication permissive conditions providing decreased amounts of infectious contaminants which increases the safety of a vaccine.

This aspect of the present invention can be implemented in combination with the above mentioned aspects, e.g. by using a conditional replication-defective HCMV strain which is deficient in pUL25 protein production as described above. It should be noted, however, that any other type of conditional replication-defective HCMV strain may be used. Further, all other embodiments which have been described for the above aspects also find application in the aspects as described in the following.

Conditional replication-defective HCMV strains comprising a gene encoding a replication-essential HCMV protein fused to a destabilizing protein domain are e.g. known from WO 2014/089158, herein incorporated by reference. The production of DBs from such HCMV strains, however, has not been disclosed.

The use of such HCMV strains and infectious HCMV particles from such strains under replication-permissive as well as non-replication permissive conditions for the production of DBs is contemplated within the present invention.

Thus, a further aspect of the present invention relates to the production of HMCV-derived DBs comprising the steps:

(a) infecting a mammalian target cell with an HCMV strain comprising at least one gene encoding a replication-essential HCMV protein fused to a destabilizing protein domain under conditions where a stabilizing ligand of said destabilizing protein domain is present, and
(b) culturing the cell under conditions wherein the stabilizing ligand is absent, and HCMV DBs are produced.

In certain embodiments, the stabilizing ligand is removed from the cell culture in step (b) after a predetermined period of time, for example, after about 1 day to about 7 days, or after about 3 to about 4 days.

In certain embodiments the method may comprise the step of isolating the DB from the mammalian target cell. The mammalian target cell is a cell as described for the above embodiments. The DB may be purified from the culture medium according to known methods, e.g. by glycerol-tartrate density gradient ultra-centrifugation.

In this aspect of the present invention, a replication-essential HCMV protein fused to a destabilizing protein domain is provided. In a specific embodiment, the replication-essential protein is the pUL51 protein. Further examples of suitable replication-essential proteins to be used in this aspect of the present invention are as follows:

| ORFs | Function |
|---|---|
| UL37.1 | Anti-apoptotic |
| UL44 | DNA replication |
| UL50 | Egress |
| UL52 | DNA packaging/cleavage |
| UL53 | Egress |
| UL54 | DNA polymerase |
| UL56 | DNA packaging/cleavage |
| UL57 | ssDNA binding protein |
| UL70 | Helicase/primase |
| UL77 | DNA packaging/cleavage |
| UL80 | Capsid assembly |
| UL84 | DNA replication |
| UL89.1 | DNA packaging/cleavage |
| UL98 | Alkaline nuclease |
| UL102 | Helicase/primase |
| UL104 | DNA packaging/cleavage |
| UL105 | Helicase/primase |
| UL122 | IE2 (transcription) |

The destabilizing protein domain may be an FKBP protein, e.g. an FKBP12 protein or a mutant thereof, particularly the F36V mutant of FKBP12. A stabilizing ligand for a destabilizing FKBP protein domain is, for example, the compound Shield-1 as described in (23), herein incorporated by reference. The use of the FKBP-Shield-1 system in association with HCMV genes has inter alia been described in several papers (24-29). None of these papers, however, disclose production of DBs from conditional replication-competent HCMV strains.

A further example of a destabilizing protein domain is dihydrofolate reductase (dHFR) which may be stabilized by the compound trimethoprim as ligand (cf. U.S. Pat. No. 8,173,792 B2, herein incorporated by reference).

In this aspect of the present invention, the HCMV strain may be a strain which does not encode a functional pUL25 protein as described above, or any other suitable HCMV strain.

A further aspect of the invention relates to HCMV DBs produced by infection of a mammalian target cell with a recombinant HCMV strain encoded by nucleic acid molecule comprising at least one replication-essential HCMV gene fused to a gene encoding a destabilizing protein domain. This DB comprises the HCMV protein pp65 as the main constituent and optionally further HCMV proteins pp150, pp71 and pp28. In certain embodiments, the dense body is free from the protein pUL25.

In certain embodiments, a DB preparation produced as described above is characterized by a reduced contamination with infectious virus particles, e.g. by a contamination reduced by a factor of at least 2, 5, 10, 100 or more compared to a DB preparation produced from a replication-competent HCMV reference strain, i.e. an HCMV strain which is genetically identical except that it does not encode a fusion protein of a replication-essential HCMV protein and a destabilizing protein domain. The contamination of infectious particles may be determined by quantification of the DNA content of a DB-preparation, e.g. by quantitative polymerase chain reaction (PCR). Such contamination may also be determined by applying the material to indicator fibroblast cell cultures in serial dilutions and staining these cells after 1 or 2 days of incubation with an antibody against the viral immediate-early 1 (IE1) protein. The numbers of positive cells may be determined in a light microscope and may be used as a measure for the numbers of contaminating infectious virions in the material.

Thus, the DB-preparation as described above is suitable for use in medicine, particularly for use as a vaccine against HCMV, more particularly in human medicine.

Further, the invention relates to the use of a recombinant HCMV strain encoded by a nucleic acid molecule comprising at least one replication-essential HCMV gene fused to a gene encoding a destabilizing protein domain for the production of a HCMV DB preparation.

Still a further aspect relates to the use of an HCMV particle produced by infection of a mammalian target cell with a recombinant HCMV strain encoded by a nucleic acid molecule comprising at least one replication-essential HCMV gene fused to a gene encoding a destabilizing protein domain for the production of an HCMV DB-preparation.

According to these aspects, a DB-preparation substantially without concomitant production of infectious HCMV particles can be achieved under non-replication permissive cell culture conditions.

Thus, the invention also relates to the use of a recombinant HCMV strain encoded by a nucleic acid molecule comprising at least one replication-essential HCMV gene fused to a gene encoding a destabilizing protein domain for increasing the safety of a DB-based HCMV vaccine. The recombinant HCMV strain may be used for the infection of a mammalian target cell, allowing the production of a DB in said target cell under non-replication permissive conditions, wherein a DB preparation without contamination by infectious particles may be obtained.

Finally, the invention relates to the use of an HCMV particle produced by infection of a mammalian target cell with a recombinant HCMV strain encoded by a nucleic acid molecule comprising at least one replication-essential HCMV gene fused to a gene encoding a destabilizing protein domain for increasing the safety of a DB-based HCMV vaccine. The recombinant HCMV particle may be used for the infection of a mammalian target cell allowing the production of a DB in said target cell under non-replication permissive conditions wherein a DB preparation without contamination by infectious particles may be obtained.

As outlined above, a conditional replication-competent HCMV strain as described above may be combined with other embodiments as described herein.

In certain embodiments, the conditional replication-competent HCMV strain encodes functional viral gH (UL75), gL (UL115), UL 128, UL130 and UL131a proteins which are capable of forming a functional pentameric complex.

In a particular embodiment, the conditional replication-competent HCMV strain is a genetically modified UL25-negative variant of the HCMV strain Towne which encodes a functional UL130 gene, and thus a functional pentameric complex, and further does not encode a functional Green Fluorescent Protein (GFP).

Further, the present invention shall be explained in more detail by the following Figures and Examples.

FIGURE LEGENDS

FIG. 1: Deletion of the UL25 gene has no apparent impact on HCMV virion- or DB-morphogenesis.

a, schematic representation of the mutant viruses Towne-delUL25 and Towne-UL25-FLAG. The location of the UL25 gene with respect to neighboring genes is shown by arrows. Towne-delUL25 was generated by inserting a galK expression cassette into the UL25 open reading frame. The 5'-287 nucleotides of the UL25 open reading frame were retained to prevent impairment of the promoter of the adjacent UL24 gene. The strain Towne-UL25-FLAG was generated by replacing the galK expression cassette by wt-UL25, C-terminally fused to an antibody tag (FLAG). b, purification of DBs, virions and non-infectious enveloped particles (NIEPs) by glycerol-tartrate ultracentrifugation. The different fractions are indicated. c, separation of purified virion and DB fractions from the indicated strains by PAGE. Proteins were visualized by silver staining. Molecular weight markers and the putative position of pUL25 are indicated. d-g, mass spectrometry of the outer tegument protein composition of virions and DBs of two different clones of Towne-delUL25 and of Towne-BAC. The mean of three technical replicates of each sample was measured in parts-per-million (ppm). Bars represent the standard error. (d) and (e), proteome of virions. (f) and (g), proteome of DBs. Note the different scales in (d) and (f) versus (e) and (g), respectively.

Figure 2:
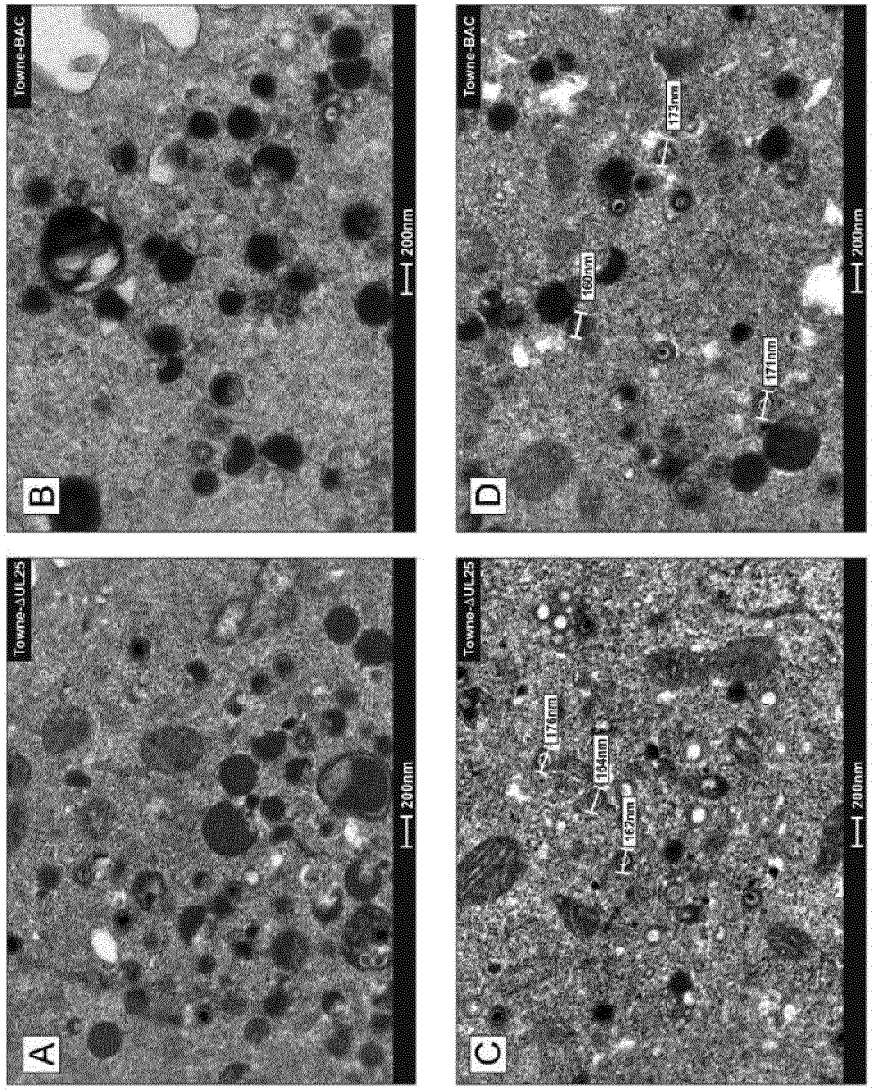

FIG. 2: DB and virion morphogenesis is indistinguishable in cells infected with the parental strain or mutant Towne-delUL25.

Transmission electron micrographs of cells infected with either Towne-delUL25 or Towne-BAC. A and C, images of cytoplasmic virion and DB formation of human foreskin fibroblast (HFF) cells) infected with Towne-delUL25. B and D, images of cytoplasmic virion and DB formation of HFF cells infected with Towne-BAC. Bars indicate diameters of particles from both strains.

Figure 3:
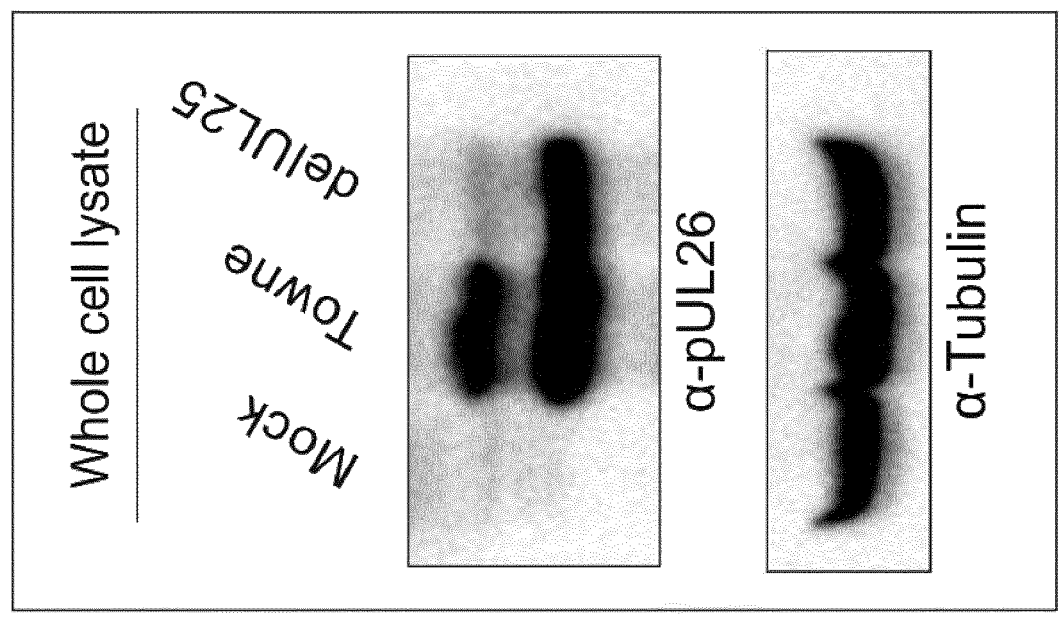

FIG. 3: Immunoblot analysis of steady-state levels of pUL26 in infected cells.

HFF cells were infected with Towne-delUL25, or Towne-BAC, respectively. After 6 days, whole cell lysates were collected and run out on an SDS-PAGE. After transfer to PVDF membranes, a Western blot was performed using antibodies against pUL26 and alpha-tubulin.

Figure 4:
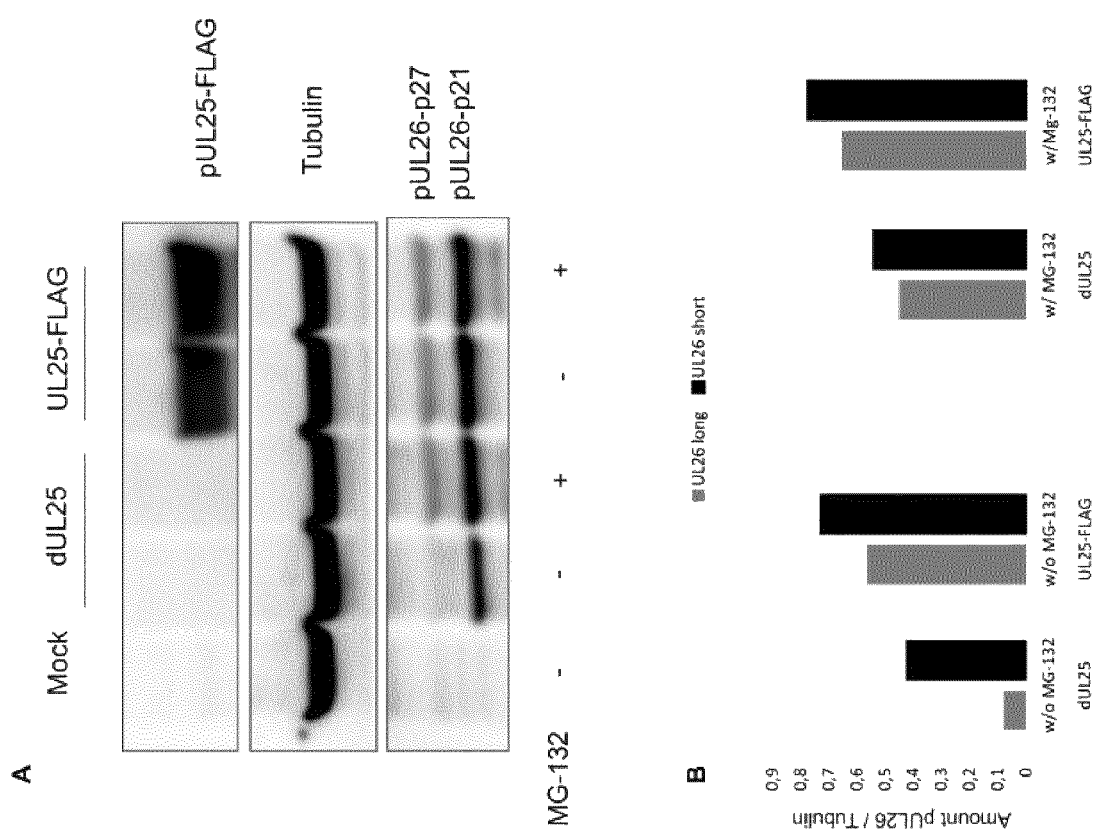

FIG. 4: Immunoblot analysis of pUL26 degradation in the absence of pUL25.

HFF cells were infected with Towne-delUL25, or Towne-UL25-FLAG, respectively. After 6 days, some samples were treated with MG132 for 16 hours and whole cell lysates were subsequently collected. SDS-PAGE and a Western blot probed against pUL26 were performed (A) and protein levels of pUL26 were quantified (B).

Figure 5:
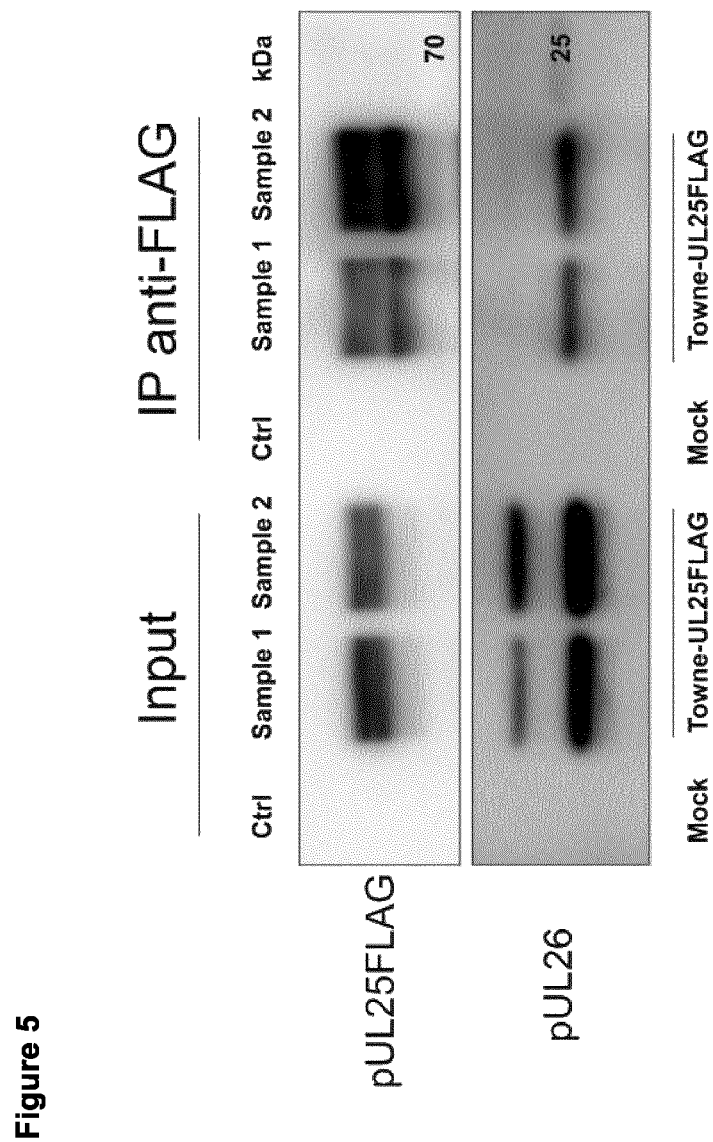

FIG. 5: Immunoprecipitation of FLAG-tagged pUL25 of two independent biological replicates.

HFF cells were infected with Towne-UL25FLAG at an multiplicity of infection (m.o.i.) of 1, and harvested 6 d.p.i. Cell lysates were precipitated using anti-FLAG conjugated magnetic beads and precipitates were analyzed in a Western blot, probed against anti-FLAG and anti-UL26 antibody. Uninfected HFF served as a negative control. MW-markers in kDa are depicted.

Figure 6:
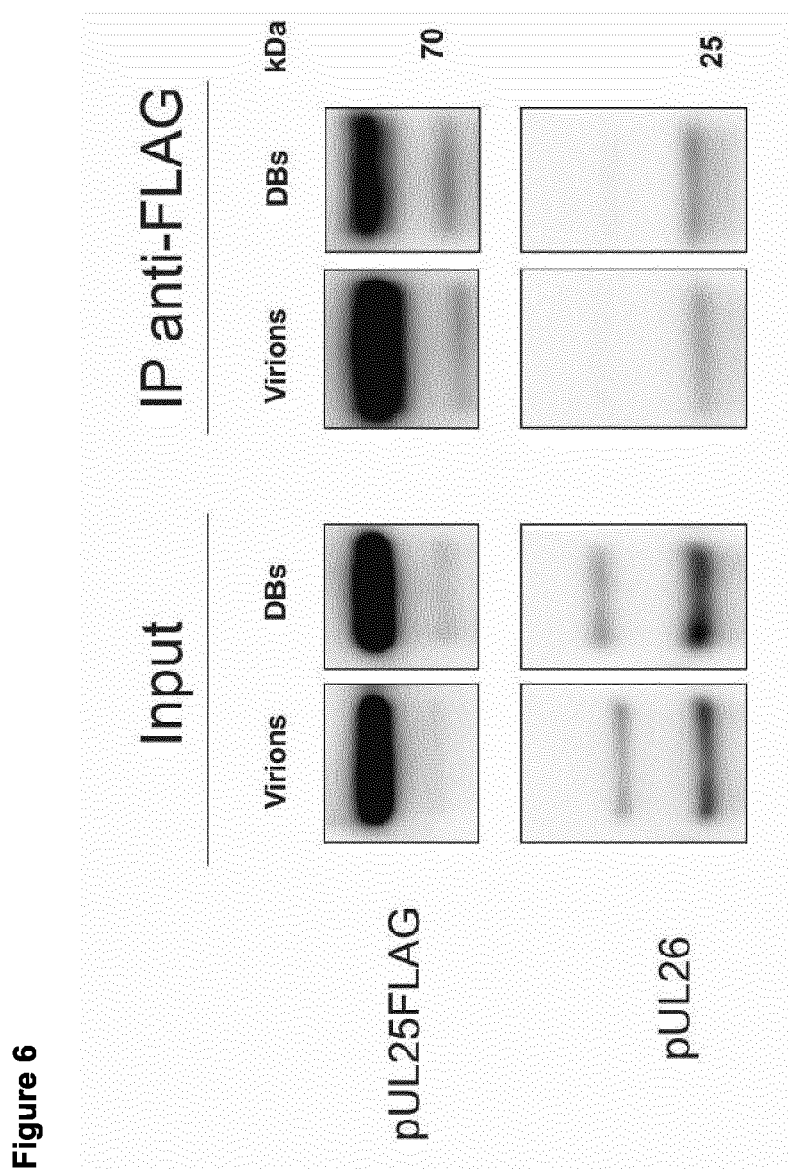

FIG. 6: Immunoprecipitation of FLAG-tagged pUL25 of cell-free viral particles.

Cell-free virions and DBs were lysed and precipitated using anti-FLAG conjugated magnetic beads and precipitates were analysed in a Western blot, probed against anti-FLAG and anti-UL26 antibody.

Figure 7:
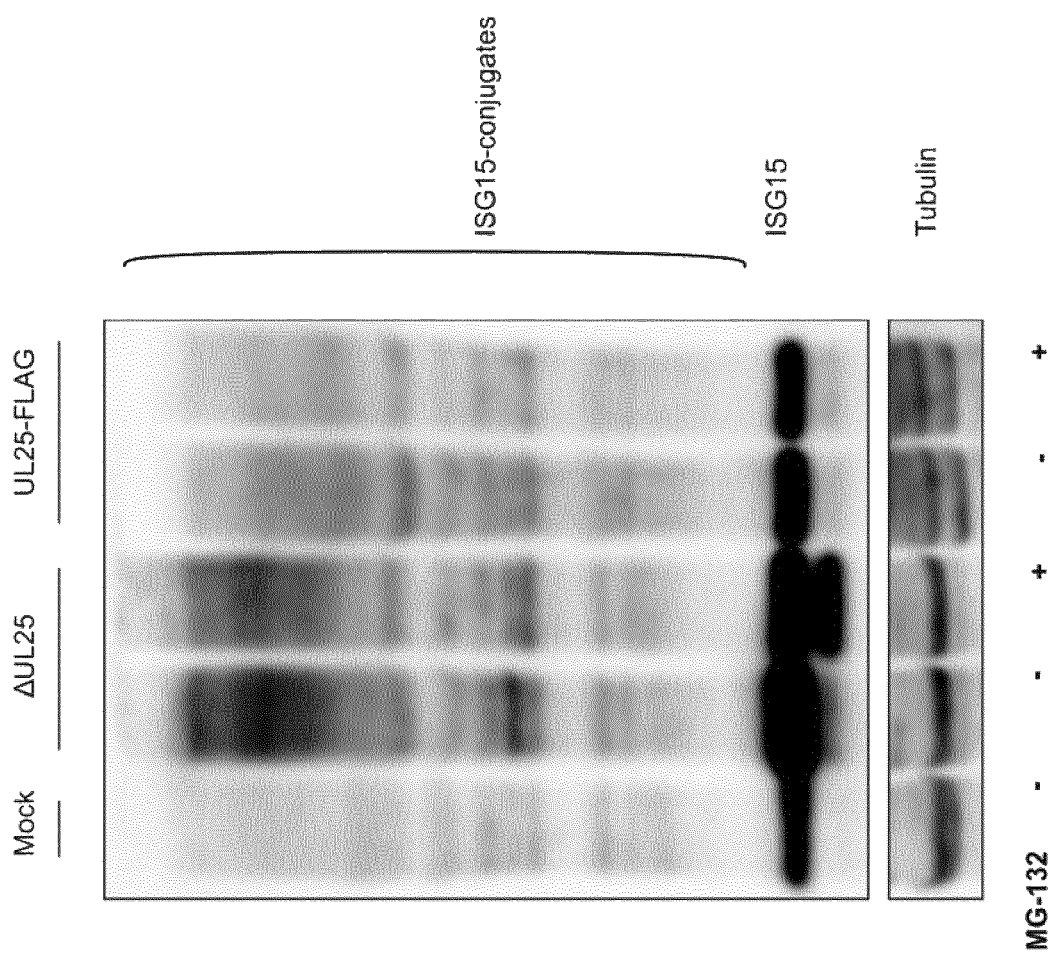

FIG. 7: Interferon stimulated gene 15 (ISG15) expression and ISGylation in infected cells.

HFF cells were infected with Towne-dUL25 or Towne-UL25-FLAG. After 6 days, some samples were treated with MG132 for 16 hours and whole cell lysates subsequently collected. SDS-PAGE was performed and a Western blot was probed against an ISG15 antibody.

Figure 8:
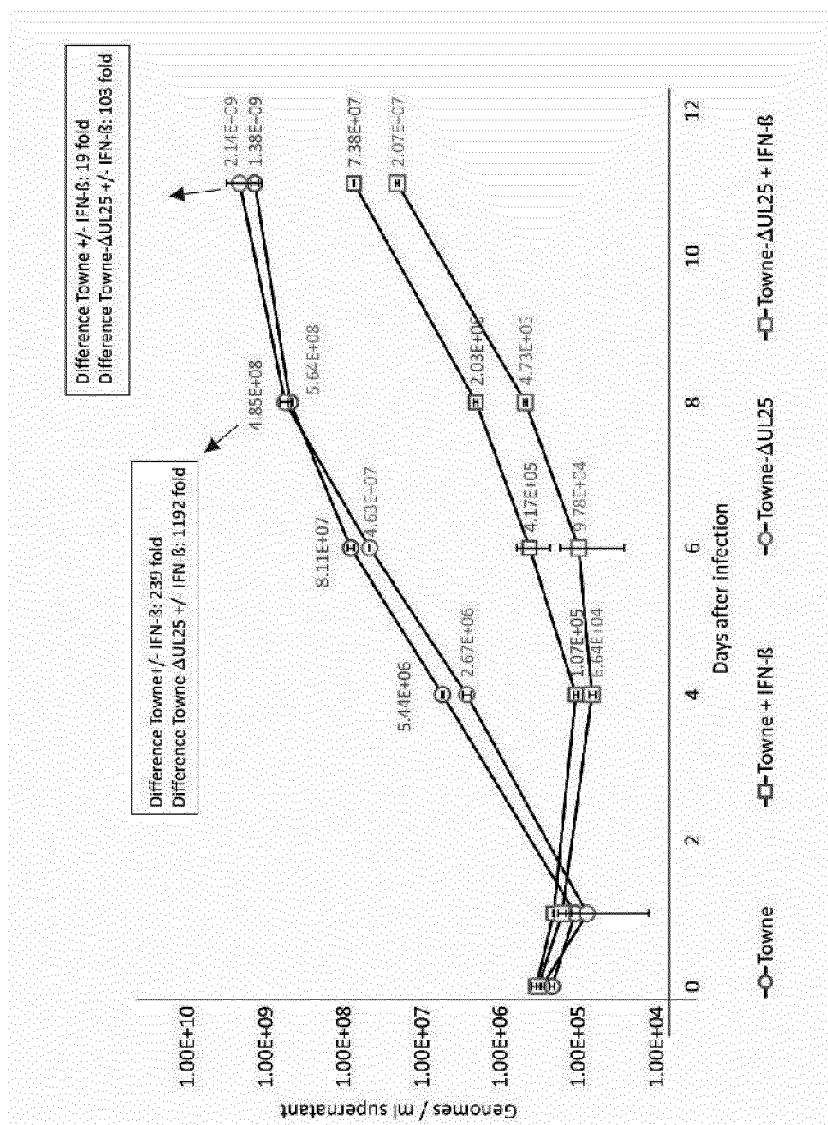

FIG. 8: Release of viral genomes from HFF, infected with Towne-BAC or Towne-delUL25, respectively in the presence or absence of IFN-ß.

100 U/ml IFN-ß was applied to HFF cultures 12 hours before infection. Cells were subsequently infected at an m.o.i. of 0.05. Cell culture supernatants were collected at the indicated time points. Viral DNA concentration in samples of cell culture supernatants was tested by qPCR. The values in each sample are indicated in the figure together with relative reduction values (+IFN-ß/−IFN-ß). All values are means of three technical replicates.

FIG. 9: Harvest of HCMV-DB in a Shield-dependent production system. HFF cells were infected with the conditional replication-defective strain HCMV-UL51-FKBP in initial presence of Shield-1 (1 µM). After 3.5 days, the Shield-1 containing medium was replaced with Shield-1-free medium. Supernatants of the cells were harvested 1 week upon initial infection and DBs were purified via glycerol-tartrate density gradient ultracentrifugation (left picture). The indicated DB fraction was isolated and analyzed via SDS-PAGE and instant-blue staining (right picture). The main constituent of the DB fraction is represented by the phosphoprotein 65 (pp65) as indicated by the arrow.

EXAMPLES

Example 1: Production of Dense Bodies from an UL25-Deficient HCMV Strain

1. Materials and Methods
1.1 Cells and Viruses.

Human foreskin fibroblast (HFF) cells were cultivated in MEM media containing 5% fetal calf serum (FCS).

Virus reconstitution was achieved by transfecting of BAC DNA into HFF cells. BACmid DNA for transfection was obtained from *E. coli* using the Plasmid Purification Kit (Macherey & Nagel, Duren, Germany) according to the manufacturer's instructions. Transfections into HFF were performed using the Superfect transfection reagent (Qiagen, Hilden, Germany). For this, HFF cells were seeded on 6-well plates at a density of $1 \times 10^5$ cells/well using different BAC-DNA concentrations for transfection. Cells were subsequently passaged until plaques became visible. The infectious supernatant was then transferred to uninfected cells for passaging of the virus. All HCMV strains were propagated on HFF. Viral stocks were obtained by collecting the culture supernatants from infected HFF cells, followed by low speed centrifugation to remove cell debris. Supernatants were frozen at −80° C. until further use.

Virus titers were determined by staining for the expression of the immediate-early 1 protein ppUL123 (IE1), using monoclonal antibody p63-27 (8), kindly provided by William Britt. For this, $5 \times 10^3$ HFF cells were seeded in each well of a 96-well plate. The following day, virus stocks were diluted to $10^{-3}$ and $10^{-4}$ in culture medium and were added to the cells in octuplet replicates. Cells were fixed after 48 h for 20 min using 96% ethanol. The primary antibody p63-27 (8) was added for 1 h in a humidified chamber at 37° C. Detection was performed by adding an anti-mouse IgG, coupled to horseradish-peroxidase (Rabbit-anti-Mouse Immunoglobulin HRP; Dako, Hamburg, Germany) at a dilution of 1:500 for 1 h and by subsequent staining with 3-amino-9-ethyl-carbazole (AEC)/$H_2O_2$ for another hour. IE1-positive cells were counted and titers were determined as means of octuplet values.

1.2 Generation of HCMV Strains Towne-delUL25 and Towne-UL25FLAG

The HCMV Towne-BAC represented the basis on which the Towne-delUL25 and Towne-UL25FLAG were generated. The former, Towne-delUL25, or a UL130-positive variant thereof, will serve as the parental genome for the establishment of a new-generation DB vaccine. The HCMV Towne-BAC was constructed by homologous recombination of a modified version of the vector pMBO1374, named pUSF-3, and the wild-type Towne viral DNA (4). pMBO1374 is a derivative of the F-plasmid vector pMBO131, in which a 645 bp HaeII fragment containing the multiple cloning site-embedded lacZ gene of pBluescript II KS (+) was subcloned into the unique SalI site of pMBO131, resulting in the insertion of several unique cloning sites (9). pUSF-3 additionally contains prokaryotic genetic elements for maintenance as BAC in E. coli, HCMV DNA sequences for direct homologous recombination to the unique short region of the viral genome, and a GFP marker for identification and purification of recombinant HCMV in eukaryotic cells (4).

In order to construct pUSF-3, the unique BamHI site and one of the two ClaI sites in pMBO1374 were removed. The two HCMV DNA fragments in pUSF-3 that were used as flanking HCMV DNA for homologous recombination were derived from the cosmid clone pCM1052 that contains a fragment of the genome of HCMV strain AD169 (10) by PCR. The primers used for amplification of the DNA fragments were derived from the published sequence of AD169 HCMV (11), and extended with BamHI and HindIII overhangs. The HCMV DNA fragments were digested with BamHI and ligated to yield a 5.2 kb fragment, which in turn was digested by HindII and cloned into the HindIII site. Finally, a PCR amplicon with the SV40 early promoter, GFP gene and polyA derived from pGET-07 (12) was cloned into the remaining ClaI site. For homologous recombination, HFF cells were electroporated with wild-type Towne viral DNA purified from total virus particles isolated from HFF cells infected with the Towne strain of HCMV, with linearized (BamHI digested) pUSF-3, and with an expression plasmid for HCMV tegument protein pp71 (13). Upon homologous recombination, the flanking DNA deletes 8.9 kb of DNA within the US region of HCMV (IRS1 after aa719, reading frames US1 to US11 plus the C-terminal third of US12) that are dispensable for HCMV replication in cell culture (14). Sequences of the Towne-BAC isolate have been deposited in the GenBank database (Accession no. AY315197) (1).

Strain Towne-delUL25 (Towne-dUL25) was generated by inserting the gene encoding the bacterial galK into the UL25 open reading frame of Towne-BAC, using the procedure by Warming et al. (15). By this, the UL25 open reading frame was replaced by the galK cassette starting with base pair 288, thereby disrupting pUL25 expression. A DNA region, encoding amino acids 1-287 remained in the BAC construct (Towne-delUL25-BAC). After transfection of Towne-delUL25-BAC into fibroblasts, the virus Towne-delUL25 was reconstituted.

To generate the revertant virus Towne-UL25FLAG, a gene fragment encoding the FLAG-Tag epitope (DYKDDDDK) was inserted at the 3'-end of the UL25 open reading frame, using Towne-delUL25-BAC as a template and the galK procedure for selection (15). The resulting BAC-clone Towne-UL25FLAG-BAC was reconstituted by transfecting it's DNA into fibroblasts. Generation of a viral master stock was performed as detailed in the previous section. The recombinant virus expressed pUL25 with a FLAG-Tag, attached to the C-terminus of the protein.

1.3 Virus and Dense Body (DB) Purification

DBs were produced in human fibroblast cells upon infection with a recombinant HCMV seed virus. This seed virus was obtained upon transfection of cells with a BAC-plasmid encoding a genetically modified version of the genome of the HCMV Towne strain.

For particle purification $1.8 \times 10^6$ primary HFF cells were grown in 20 175-$cm^2$ tissue culture flasks in minimal essential medium (MEM; Gibco-BRL, Glasgow, Scotland) supplemented with 5% FCS, L-glutamine (100 mg/liter), and gentamicin (50 mg/liter) for 1 day. The cells were infected with 0.5 ml of a frozen stock of the strain Towne-UL130rep$\Delta$GFP of HCMV as described in EP 18 176 735.1. The virus inoculum was allowed to adsorb for 1.5 h at 37° C. The cells were incubated for at least 7 days.

When the cells showed a CPE (cytopathic effect) of late HCMV infection (usually at day 7 post-infection [p.i.]), the supernatant was harvested and centrifuged for 10 min at 2,800 rpm to remove cellular debris. After that, the supernatant was collected and centrifuged at 30,000 rpm (70 min; 10° C.) in a SW32Ti rotor in a Beckman Optima L-90K ultracentrifuge. The pellets were resuspended in 2 ml of 1× phosphate-buffered saline (PBS). Glycerol tartrate gradients were prepared immediately before use. For this, 4 ml of a 35% Na-tartrate solution in 0.04 M Na-phosphate buffer, pH 7.4, was applied to one column, and 5 ml of a 15% Na-tartrate-30% glycerol solution in 0.04 M Na-phosphate buffer, pH 7.4, was applied to the second column of a gradient mixer. The gradients were prepared by slowly dropping the solutions into Beckman Ultra-clear centrifuge tubes (14 by 89 mm), positioned at an angle of 45°. 1 ml of the viral particles was then carefully layered on top of the gradients. Ultracentrifugation was performed without braking in a Beckman SW41 swing-out rotor for 60 min at 23,000 rpm and 10° C. The particles were illuminated by light scattering (FIG. 1) and collected from the gradient by penetrating the centrifuge tube with a hollow needle below the band. Samples were carefully drawn from the tube with a syringe.

The particles were washed with 1×PBS and pelleted in an SW41 swing-out rotor for 90 min at 24,000 rpm and 10° C. After the last centrifugation step, the DBs and virions were resuspended in 250 µl to 350 µl 1×PBS and stored at −80° C. The protein concentration of the purified DBs and virions was determined with the Pierce BCA Protein Assay Kit (Thermo Scientific, Bonn, Germany).

1.4 Preparation of Samples for Transmission Electron Microscopy

Two flasks HFF cells (1.74 million cells per flask) were infected at an m.o.i. of 0.8. Cells were incubated for 6 days and were subsequently detached from the support using trypsin. The cells from the two flasks were pooled and centrifuged at 1,200 rpm. Cells were then fixed by adding 1 ml fixative and resuspending the cells carefully. Following a centrifugation step for 5 min at 1,200 rpm, the cell pellet was again resuspended in 1 ml fixative. The cells were subsequently incubated for 1 h at room temperature and then again centrifuged for 5 min at 1,200 rpm. The cells were then resuspended in washing buffer and centrifuged. The procedure was repeated twice. After the final washing step, the cells were not centrifuged but incubated for 10 min at room temperature. Cells were then transferred in Eppendorf tubes. Samples were then further processed for transmission electron microscopy as previously described (16).

Fixative 5 ml 2× stock cacodylate/sucrose (0.2 M cacodylate; 0.2 M sucrose)

1 ml 10× glutaraldehyde (25% GA)

ad 10 ml $H_2O_{dd}$

Washing Buffer:

6.5 ml 2× stock cacodylate/sucrose (0.2 M cacodylate; 0.2 M sucrose)

6.5 ml $H_2O_{dd}$ 1.5 Replication Kinetics and Interferon-β Treatment

Subconfluent HFF cells were treated with IFN-β (100 U/ml). After 12 hours incubation, the cells were infected with Towne-BAC or Towne-delUL25, respectively, at an m.o.i. of 0.05. Infected cells in absence of IFN-β served as control. Culture supernatant samples were collected at time points 4 hours, and 1,4,6,8, and 11 days post infection, (2×1 ml cell culture supernatant and 1×10$^6$ cells, respectively). Viral DNA was purified from the supernatant and infected cells using the High Pure Viral Nucleic Acid Kit by Roche, according to the Roche standard protocol. Quantitative PCR was performed using forward (fwd) and reverse (rev) primers.

Interferon ß (IFN-ß)

PeproTech; Nr. 300-02BC

Specific activity (according to the manufacturer's information): 5×10$^8$ U/mg diluted in 0.1% BSA/$H_2O_{dd}$ TaqMan-PCR Analysis of Viral DNA—Concentrations in Cell Culture Supernatants.

DNA out of 200 μl cell culture supernatant was isolated using the High Pure Viral Nucleic Acid Kit from Roche according to the manufacturer's instructions. The DNA was finally eluted in 100 μl elution buffer.

TaqMan-Batch:

45 μl mastermix (including probe, primers dNTPs, buffer, and Taq-polymerase)+5 μl DNA per sample Analyses were performed in triplicate technical replicates

```
Probe:      5' CCACTTTTGCCGATGTAACGTTTCTTGCAT-TMR    (SEQ ID NO. 1)

fwd-Primer: 5' TCATCTACGGGGACACGGAC 3'                (SEQ ID NO. 2)

rev-Primer: 5' TGCGCACCAGATCCACG 3'                   (SEQ ID NO. 3)
```

Taq-Polymerase: HotStar Taq Plus from Qiagen

Standard: Dilution of Cosmid pCM1049 (10)

TaqMan-program:

95° C. 5 min

42×95° C. 15 sec+60° C. 1 min

TaqMan-apparatus: 7500 Real Time PCR System, Applied Biosystems

TaqMan-Software: 7500 System Software 1.6 Immunoprecipitation and Western Blot

HFF cells were infected with the respective HCMV strains. Infected HFF cells were harvested, washed and resuspended in lysis buffer (0.5 M NaCl, 0.05 M Tris-HCl, 0.5% NP-40, 10 mM DTT). Cell lysates were sonicated (1×10 sec, 30% output) and proteins were subsequently bound to specific antibodies (anti-FLAG M2, Sigma, or anti tubulin antibody) over night at 4° C. in a rotator. Antibody-protein complexes were then collected by IgG magnetic beads for 2 hours at room temperature (RT). Magnetic beads were washed 3 times with lysis buffer and subsequently resuspended with Laemmli sample buffer. Protein samples were loaded and run on 10% SDS-PAGE and transferred to PVDF membranes. The filters were probed against specific primary antibodies. Quantitative analyses were performed by using tubulin as an internal standard. For this, the ECL-detection substrate Best Western Femto (Thermo Fisher) and a ChemiDoc Scanner (Biorad) Scanner were used.

1.7 Proteasome Inhibitor

To investigate, whether pUL26 is prone to proteasomal degradation in absence of UL25, HFF cells were infected with Towne-BAC or Towne-delUL25, respectively, at a m.o.i. of 1. At 6 d.p.i. cells were treated with 10 μM of MG-132 proteasome inhibitor (Sigma) for 16 hours. Cells then were harvested, lysed and levels of pUL26 were analysed via immunoblot.

1.8 Mass Spectrometry

The quantitative proteomics analyses of purified viral particles were performed using ion-mobility enhanced data-independent acquisition on a Synapt G2-S mass spectrometer as published (17). Statistical analysis of the data sets was performed using the ANOVA analysis tool provided by MS-Excel 2010.

2. Results 2.1 Deletion of UL25 does not Alter DB-Formation and Release and has Limited Impact on the Outer Tegument Protein Upload into Virions and DBs.

To be able to address the role of the viral protein pUL25, a mutant, devoid of UL25 was generated in the genetic background of HCMV strain Towne, using BAC mutagenesis.

The UL25 open reading frame was deleted by inserting a galK expression cassette (FIG. 1a). HFF cells were infected with this mutant, and virions and DBs were purified using glycerol tartrate gradient centrifugation (FIG. 1b). The material was loaded on an SDS-PAGE along with the corresponding specimens of the parental Towne strain and the TB40/e strain. The resulting protein patterns of virions and DBs of the three strains were compared by polyacrylamide-gel electrophoresis, followed by silver staining. Little differences could be seen, except for the lack of a protein band of roughly 80 kDa, corresponding to pUL25 in the DB-preparations of Towne-delUL25 (FIG. 1c). To be able to investigate wt-pUL25, a revertant virus of Towne-delUL25, termed Towne-UL25-FLAG was constructed as depicted in FIG. 1a, using again the galK technology.

To investigate the protein pattern of virions and DBs more accurately, label-free mass spectrometry was used. The results confirmed the lack of pUL25 in virions and DBs of Towne-delUL25 (FIGS. 1d and f). Most of the other outer tegument proteins were unaffected in their upload by UL25 deletion. Only pUL24 was reproducibly enhanced in its upload (FIGS. 1e and g), as verified by a second, independent analysis (not shown). Most remarkable, however, was the finding that pUL26 was almost completely absent in pUL25-negative virions and DBs (FIGS. 1e and g), indicating that its presence in HCMV particles was dependent on the presence of pUL25 in infected cells. The latter result was also confirmed in an independent experiment (not shown).

To investigate if lack of pUL25 altered cytoplasmic particle morphogenesis, transmission electron microscopy was performed on HFF cells that had been infected with Towne-delUL25 or Towne-BAC (FIG. 2). No apparent differences were noted by inspecting multiple infected cells. In addition, the diameter of virions was conserved between the two strains.

2.2 Levels of pUL26 are Reduced in Towne-delUL25 Infected Fibroblasts

Results from quantitative mass spectrometry indicted that pUL26 was packaged in reduced amounts into virions and DBs of Towne-delUL25, compared with the respective particles from the parental Towne-BAC strain. To investigate, if that was due to reduced levels of pUL26 in Towne-delUL25 infected cells on immunoblot analysis was carried out. The levels of pUL26 appeared to be markedly reduced in Towne-delUL25 infected cells (FIG. 3). This indicated that either pUL26 synthesis or pUL26 stability was altered in the absence of pUL25.

2.3 pUL25 Promotes pUL26 Protein Stability.

To investigate, if pUL26 protein stability was influenced by the presence of pUL25, cells were infected with Towne-delUL25 or Towne-UL25-FLAG, respectively. The proteasomal inhibitor MG132 was added to some samples at 6 d.p.i. Cell lysates were collected and subjected to SDS-PAGE and Western blot analysis, using a pUL26-specific antibody (FIG. 4). The intensity of the bands was measured and normalized to the intensity of the internal tubulin control. The results showed that both known isoforms of pUL26 were reduced in Towne-delUL25 infected cells and that particularly, the long isoform was stabilized in cells, treated with MG132. This indicated that pUL26 was stabilized by the presence of pUL25.

2.4 pUL25 Interacts with pUL26 in HCMV Infected Cells.

To investigate, if the impact of pUL25 on pUL26 stability was related to an interaction of the two proteins, co-immunoprecipitation analyses (Co-IP) were performed. Cells were infected with Towne-UL25-FLAG. Cell lysates were collected at 6 d.p.i. and were subjected to Co-IP, using the FLAG-Tag specific antibody M2 (FIG. 5). Using two biological replicates (samples 1 and 2), the experiments showed that pUL26 co-immunoprecipitated with pUL25, indicating that both proteins formed a complex in infected cells.

2.5 pUL25 Interacts with pUL26 in Purified HCMV Virions and DBs.

To investigate, if pUL25 was also interacting with pUL26 in extracellular virions and DBs, Co-IP experiments were repeated on purified viral particles. Again, pUL26 could be precipitated, using the pUL25-FLAG specific antibody M2 (FIG. 6).

Taken together, the results indicate that pUL25 forms a complex with pUL26, thereby stabilizing the latter protein and that this complex is subsequently packaged into the tegument of HCMV virions as well as into DBs.

2.6 ISGylation of Proteins and Levels of Free ISG15 Increase in the Absence of pUL25.

Interferons are essential for the innate immune response to virus infections. They trigger the transcription of hundreds of interferon-stimulated genes (ISGs), whose protein products exhibit antiviral activity. The interferon-stimulated gene 15 encodes an ubiquitin-like protein (ISG15) which is induced by type I IFNs. Protein modification by ISG15 (ISGylation) is known to inhibit the replication of many viruses (18). HCMV induced ISG15 accumulation is triggered by the hosts' detection of cytoplasmic double-stranded DNA (dsDNA). A recent report showed that pUL26 interfered with the ISGylation of proteins in HCMV infected cells (2).

To investigate, if deletion of UL25 had an impact on HCMV induced repression of ISGylation, cells were infected with Towne-delUL25 and Towne-UL25-FLAG, respectively. Cells were infected for 6 days. In some instances, MG132 was added 16 h prior to sampling. Cell lysates were subsequently subjected to Western blot analysis. Tubulin served as an internal control. ISGylation was indeed repressed following Towne-UL25-FLAG infection (control). This repression was alleviated following infection with Towne-delUL25. These results show that pUL25 was involved in suppression of ISGylation in HCMV infected cells (FIG. 7). In addition, the levels of free ISG15 were enhanced in Towne-delUL25 infected cells. Consequently, lack of pUL25 increases the interferon-stimulated gene response in HCMV infected cells.

2.7 Deletion of UL25 Renders HCMV Replication More Sensitive to IFN-ß.

HCMV infection leads to the induction of ISG15 expression and enhances overall protein ISGylation in cell culture (2,3). pUL26 has been reported to be involved in suppressing ISGylation, leading to enhanced viral replication. This effect can be alleviated by the addition of IFN-ß to infected cultures. Others could show that the level of alleviation was increased, when cells were infected with a UL26-null virus (2).

To test, if a virus strain deficient in the expression of pUL25 was also more susceptible to the interferon response, cells were infected with Towne-delUL25 and Towne-BAC, respectively and were kept in the presence of absence of IFN-ß. Samples of culture supernatants were collected at different time points after infection. The levels of viral genomes in these samples, representing release of progeny virus, were determined by quantitative PCR (FIG. 8). The experiments showed that Towne-delUL25 was clearly more susceptible to IFN-ß-treatment, compared to the wt-strain Towne-BAC. These results support the notion that infection of a human host with an HCMV strain, deficient in pUL25-expression would be efficiently controlled by the innate immune system.

Example 2: Use of Shield-1 for the Production of HCMV-Derived Dense-Bodies

We tested whether a conditional replication-defective HCMV strain, e.g. HCMV strain which is only replication-competent in the presence of the stabilizing ligand Shield-1 can be used for the production of a HCMV-vaccine based on HCMV-derived DBs.

General Concept

A replication-essential HCMV protein, e.g. the protein UL51, is tagged with a destabilizing protein domain, e.g. an FKBP protein, particularly the F36V mutant of the 107 residue protein FKBP12 (ddFKBP). In the absence of a stabilizing ligand, e.g. the cell-permeable small-molecule ligand Shield-1, the ddFKBP-tagged protein is unstable and thus degraded. Binding of Shield-1 to the destabilizing domain stabilizes the fusion protein and shields it from degradation, thus restoring function of the fusion protein (23).

A BAC-derived "seed-virus", a safety-vector encoding a FKBP-tagged replication-essential protein, is used for the production of the DBs. For example, the gene product of UL51 of this strain is tagged with DD-FKBP. Since UL51 is essential for genome packaging and thereby also for progeny production, infectious HCMV-particles can only be produced in the presence of Shield-1. In the absence of Shield-1 the strain can infect cells but is not able to replicate while the production of DB is not impaired.

For the generation of seed-virus-stocks, mammalian target cells, e.g. human fibroblast cells such as MRC-5 or HFF cells are infected with the seed-virus in the presence of Shield-1 (e.g. 1 µM) for e.g. about 1 week. Shield-1 may be additionally supplemented with e.g. 1 µM every 48 h to ensure viral replication. Supernatants may be harvested and viral particles isolated according to known methods (30).

For the generation of DBs as vaccine, human fibroblast cells such as MRC-5 cells are infected with the particles of the seed virus in the presence of Shield-1 for a sufficient time period to ensure viral propagation through the cell culture. After a suitable time period, e.g. after about 3.5 days, Shield-1 containing cell culture medium is replaced with Shield-1-free cell culture medium to provide the production of DB without concomitant production of infectious particles. After a suitable time period, e.g. about 1 week after initial infection, supernatants are harvested and DB isolated according to known methods (31).

Experimental Proof

To show that DBs can be produced in a Shield-1-dependent system the HCMV strain HCMV-UL51-FKBP (32) was used to infect HFF cells, which are permissive to HCMV-laboratory strains. The test virus HCMV-UL51-FKBP expresses a DD-FKBP-tagged UL51 gene product and the production of infectious virus particles is dependent on Shield-1.

To prove the production of DB in the absence of Shield-1, which would be the major feature of the potential vaccine seed-virus, HFF cells were infected with HCMV-UL51-FKBP in initial presence of 1 µM Shield-1 to ensure viral propagation through the cell culture. After 3.5 days Shield-1 containing medium was replaced with Shield-1-free cell culture medium to prevent viral replication and provide the exclusive production of non-infectious DBs.

1 week post infection, supernatants were harvested and the particles were fractionated by glycerol-tartrate density gradient ultracentrifugation. After centrifugation the gradient contains a clearly visible fraction of DBs: a broad area of particles with various densities, visible by light scattering, as it has been reported before (33). These DBs were isolated and analyzed by SDS-PAGE and instant-blue staining to visualize the proteinaceous composition of the DB fraction.

It has been shown, that the phosphoprotein (pp)65 (ppUL83) is the most abundant protein found in HCMV DB (6, 7). In accordance to this data, also in the DB fraction isolated from HCMV-UL51-FKBP-infected HFFs with the described Shield-1-treatment, pp65 is the main constituent. Additionally, pp150, pp71 and pp28 can be found in this DB-preparation, which is in line with previous data (34,35). Thus, this proof-of-concept study shows that HCMV-UL51-FKBP-derived DB can be produced under these conditions in the absence of Shield-1.

LIST OF REFERENCES

1. Dunn W, Chou C, Li H, Hai R, Patterson D, Stoic V, Zhu H, Liu F. 2003. Functional profiling of a human cytomegalovirus genome. Proc Natl Acad Sci USA 100: 14223-14228.
2. Kim Y J, Kim E T, Kim Y E, Lee M K, Kwon K M, Kim K I, Stamminger T, Ahn J H. 2016. Consecutive Inhibition of ISG15 Expression and ISGylation by Cytomegalovirus Regulators. PLoS Pathog 12:e1005850.
3. Bianco C, Mohr I. 2017. Restriction of Human Cytomegalovirus Replication by ISG15, a Host Effector Regulated by cGAS-STING Double-Stranded-DNA Sensing. J Virol 91.
4. Marchini A, Liu H, Zhu H. 2001. Human cytomegalovirus with IE-2 (UL122) deleted fails to express early lytic genes. J Virol 75:1870-1878.
5. Sauer C, Klobuch S, Herr W, Thomas S, Plachter B. 2013. Subviral dense bodies of human cytomegalovirus stimulate maturation and activation of monocyte-derived immature dendritic cells. J Virol 87:11287-11291.
6. Vashee S, Stockwell T B, Alperovich N, Denisova E A, Gibson D G, Cady K C, Miller K, Kannan K, Malouli D, Crawford L B, Voorhies A A, Bruening E, Caposio P, Fruh K. 2017. Cloning, Assembly, and Modification of the Primary Human Cytomegalovirus Isolate Toledo by Yeast-Based Transformation-Associated Recombination. mSphere 2.
7. Andreoni M, Faircloth M, Vugler L, Britt W J. 1989. A rapid microneutralization assay for the measurement of neutralizing antibody reactive with human cytomegalovirus. J Virol Methods 23:157-167.
8. Plachter B, Britt W J, Vornhagen R, Stamminger T, Jahn G. 1993. Analysis of proteins encoded by IE-regions 1 and 2 of human cytomegalovirus using monoclonal antibodies generated against recombinant antigens. Virology 193:642-652.
9. O'Connor M, Peifer M, Bender W. 1989. Construction of large DNA segments in *Escherichia coli*. Science 244: 1307-1312.
10. Fleckenstein B, Müller I, Collins J. 1982. Cloning of the complete human cytomegalovirus genome in cosmids. Gene 18:39-46.
11. Chee M S, Bankier A T, Beck S, Bohni R, Brown C M, Cerny R, Horsnell T, Hutchison C A, Kouzarides T, Martignetti J A, Preddie E, Satchwell S C, Tomlinson P, Weston K M, Barrell B G. 1990. Analysis of the protein-coding content of the sequence of human cytomegalovirus strain AD169. Curr Top Microbiol Immunol 154:125-169.
12. Tullis G E, Shenk T. 2000. Efficient replication of adeno-associated virus type 2 vectors: a cis-acting element outside of the terminal repeats and a minimal size. J Virol 74:11511-11521.
13. Baldick C J, Jr., Marchini A, Patterson C E, Shenk T. 1997. Human cytomegalovirus tegument protein pp71 (ppUL82) enhances the infectivity of viral DNA and accelerates the infectious cycle. J Virol 71:4400-4408.
14. Jones T R, Muzithras V P. 1992. A cluster of dispensable genes within the human cytomegalovirus genome short component: IRS1, US1 through US5, and the US6 family. J Virol 66:2541-2546.
15. Warming S, Costantino N, D L C, Jenkins N A, Copeland N G. 2005. Simple and highly efficient BAC recombineering using galK selection. Nucleic Acids Res 33:e36.
16. Krömmelbein N, Wiebusch L, Schiedner G, Büscher N, Sauer C, Florin L, Sehn E, Wolfrum U, Plachter B. 2016. Adenovirus E1A/E1B Transformed Amniotic Fluid Cells Support Human Cytomegalovirus Replication. Viruses 8.
17. Reyda S, Tenzer S, Navarro P, Gebauer W, Saur M, Krauter S, Buscher N, Plachter B. 2014. The tegument protein pp65 of human cytomegalovirus acts as an optional scaffold protein that optimizes protein uploading into viral particles. J Virol 88:9633-9646.
18. Villarroya-Beltri C, Guerra S, Sanchez-Madrid F. 2017. ISGylation—a key to lock the cell gates for preventing the spread of threats. J Cell Sci 130:2961-2969.
19. Plotkin S A, Furukawa T, Zygraich N, Huygelen C. 1975. Candidate cytomegalovirus strain for human vaccination. Infect Immun 12:521-527.
20. Rowe W P, Hartley J W, Waterman S, Turner H C, Huebner R J. 1956. Cytopathogenic agent resembling human salivary gland virus recovered from tissue cultures of human adenoids. Proc Soc Exp Biol Med 92:418-424.

21. Borst E M, Hahn G, Koszinowski U H, Messerle M. 1999. Cloning of the human cytomegalovirus (HCMV) genome as an infectious bacterial artificial chromosome in *Escherichia coli*: a new approach for construction of HCMV mutants. J Virol 73:8320-8329.
22. Ostermann E, Spohn M, Indenbirken D, Brune W. 2016. Complete genome sequence of a human cytomegalovirus strain AD169 bacterial artificial chromosome clone. Genome Announc. 4(2): e 00091-16.
23. Banaszynski L A, Chen L C, Maynard-Smith L A, Ooi A G, Wandless T J. 2006. A rapid, reversible, and tunable method to regulate protein function in living cells using synthetic small molecules. Cell 126:995-1004.
24. Das, S., Ortiz, D. A., Gurczynski, S. J., Khan, F., Pellett, P. E. 2014. Identification of human cytomegalovirus genes important for biogenesis of the cytoplasmic virion assembly complex. J. Virol 88:9086-9099.
25. Glass, M., Busche, A., Wagner, K., Messerle, M., Borst, E. M. 2009. Conditional and reversible disruption of essential herpesvirus proteins. Nat Methods 6:577-579.
26. Omoto, S., Mocarski, E. S. 2013. Cytomegalovirus UL91 is essential for transcription of viral true late (gamma2) genes. J Virol 87:8651-8664.
27. Perng, Y. C., Qian, Z., Fehr, A. R., Xuan, B., Yu, D. 2011. The human cytomegalovirus gene UL79 is required for the accumulation of late viral transcripts. J Virol 85:4841-4852.
28. Tandon, R., Mocarski, E. S. 2011. Cytomegalovirus pUL96 is critical for the stability of pp150-associated nucleocapsids. J Virol 85:7129-7141.
29. Wang, D., Freed, D. C., He, X., Li, F., Tang, A., Cox, K. S., Dubey, S. A., Cole, S., Medi, M. B., Liu, Y., Xu, J., Zhang, Z. Q., Finnefrock, A. C., Song, L., Espeseth, A. S., Shiver, J. W., Casimiro, D. R., Fu, T. M. 2016. A replication-defective human cytomegalovirus vaccine for prevention of congenital infection. Sci Transl Med 8:362ra145.
30. Irmiere A, Gibson W. 1985. Isolation of human cytomegalovirus intranuclear capsids, characterization of their protein constituents, and demonstration that the B-capsid assembly protein is also abundant in noninfectious enveloped particles. J Virol 56:277-283.
31. Irmiere A, Gibson W. 1983. Isolation and characterization of a noninfectious virion-like particle released from cells infected with human strains of cytomegalovirus. Virology 130:118-133.
32. Borst E M, Kleine-Albers J, Gabaev I, Babic M, Wagner K, Binz A, Degenhardt I, Kalesse M, Jonjic S, Bauerfeind R, Messerle M. 2013. The human cytomegalovirus UL51 protein is essential for viral genome cleavage-packaging and interacts with the terminase subunits pUL56 and pUL89. J Virol 87:1720-1732.
33. Mersseman V, Besold K, Reddehase M J, Wolfrum U, Strand D, Plachter B, Reyda S. 2008. Exogenous introduction of an immunodominant peptide from the nonstructural IE1 protein of human cytomegalovirus into the MHC class I presentation pathway by recombinant dense bodies. J Gen Virol 89:369-379.
34. Varnum S M, Streblow D N, Monroe M E, Smith P, Auberry K J, Pasa-Tolic L, Wang D, Camp D G, Rodland K, Wiley S, Britt W, Shenk T, Smith R D, Nelson J A. 2004. Identification of proteins in human cytomegalovirus (HCMV) particles: the HCMV proteome. J Virol 78:10960-10966.
35. Büscher N, Paulus C, Nevels M, Tenzer S, Plachter B. 2015. The proteome of human cytomegalovirus virions and dense bodies is conserved across different strains. Med Microbiol Immunol 204: 285-293.
36. Schmolke S., Kern H. F., Drescher P., Jahn G., Plachter B. 1995. The Dominant Phosphoprotein pp65 (UL83) of Human Cytomegalovirus Is Dispensable for Growth in Cell Culture. J. Virol. 69(10):5959-5968.

The invention claimed is:

1. A nucleic acid molecule encoding the genome of a recombinant human cytomegalovirus (HCMV) strain, wherein the recombinant HCMV strain does not encode a functional pUL25 protein, and wherein the recombinant HCMV strain does not encode a functional heterologous protein.

2. The nucleic acid molecule of claim 1, wherein the recombinant HCMV strain encodes functional viral gH (pUL75), gL (pUL115), pUL128, pUL130 and pUL131A proteins suitable to form a pentameric complex.

3. The nucleic acid molecule of claim 1, wherein the recombinant HCMV strain is derived from the HCMV strain Towne as present in Towne-BAC deposited under GenBank Accession no. AY315197 (SEQ ID NO:4).

4. A dense body produced by infection of a mammalian target cell with an HCMV strain, wherein said HCMV strain comprises a nucleic acid molecule according to claim 1, wherein the dense body does not comprise a pUL25 protein, and the dense body is isolated from the culture supernatant of said virus-infected cell.

5. The dense body of claim 4, which comprises a pentameric complex consisting of viral proteins gH, gL, pUL128, pUL130 and pUL131A.

6. A preparation of dense bodies according to claim 4 in a pharmaceutically acceptable carrier.

7. The preparation of claim 6, wherein said pharmaceutically acceptable carrier is suitable for administration to a human subject in need thereof.

8. The preparation of claim 6, wherein said pharmaceutically acceptable carrier is suitable for administration in a vaccine against HCMV.

9. The preparation of claim 6, wherein said pharmaceutically acceptable carrier is suitable for administration in a method for preventing and/or ameliorating an occurrence of an HCMV-associated disorder in a vaccinated human subject and/or for inhibiting transmission of an HCMV infection to a further human subject.

10. The preparation of claim 6, wherein said pharmaceutically acceptable carrier is suitable for administration in a vaccine against HCMV which provides an increased interferon response in a vaccinated human subject compared to a reference HCMV strain which encodes a functional UL25 protein.

11. A method for the manufacture of a dense body-based vaccine against HCMV comprising the step of formulating a nucleic acid molecule of claim 1 with a pharmaceutically acceptable carrier and adjuvant.

12. A method for vaccinating a human subject against HCMV, comprising administering an immunogenically effective dose of the dense body preparation of claim 6 to a human subject in need thereof.

13. A method of producing an HCMV dense body, comprising the steps:
(a) infecting a mammalian target cell with an HCMV strain comprising at least one gene encoding a replication-essential HCMV protein, wherein the replication-essential HCMV protein is selected from the group consisting of pUL51 pUL37.1, pUL44, pUL50, pUL52, pUL53, pUL54, pUL56, pUL57, pUL70, pUL77, pUL80, pUL84, pUL89.1, pUL98, pUL102, pUL104, pUL105, and pUL122 fused to a gene encoding a destabilizing protein domain under conditions wherein a stabilizing ligand of said destabilizing protein domain is present, wherein the destabilizing protein domain is an FKBP protein and the stabilizing ligand is Shield-1, wherein the HCMV strain does not encode a functional heterologous protein other than FKBP protein, wherein the HCMV strain does not encode a functional heterologous protein, and
(b) culturing the cell under conditions wherein the stabilizing ligand is absent, and an HCMV dense body is produced.

14. The method of claim 13 wherein in step (b) the stabilizing ligand is removed from the cell culture after a predetermined period of time.

15. The method of claim 13 further comprising the step:
(c) isolating the dense body from the cell.

16. The method of claim 13 wherein the replication essential protein is pUL51.

17. The method of claim 13 wherein the destabilizing protein domain is a mutant of FKBP12.

18. A HCMV dense body produced by infection of a mammalian target cell with a recombinant HCMV strain encoded by a nucleic acid molecule comprising at least one replication-essential HCMV gene, wherein the replication-essential HCMV protein is selected from the group consisting of pUL51 pUL37.1, pUL44, pUL50, pUL52, pUL53, pUL54, pUL56, pUL57, pUL70, pUL77, pUL80, pUL84, pUL89.1, pUL98, pUL102, pUL104, pUL105, and pUL122 fused to a gene encoding a destabilizing protein domain, wherein the destabilizing protein domain is an FKBP protein and wherein the recombinant HCMV strain does not encode a functional heterologous protein other than FKBP protein, and wherein the recombinant HCMV strain does not encode a functional heterologous protein.

19. The dense body of claim 18 comprising HCMV protein pp65 as the main constituent and further comprising HCMV proteins pp150, pp71 and pp28.

20. A preparation of HCMV dense bodies according to claim 18 in combination with a pharmaceutically acceptable carrier suitable for administration to a human subject.

21. The method of claim 13, wherein the production of the dense body is substantially without concomitant production of infectious HCMV particles.

22. A method for increasing the safety of a HCMV vaccine comprising:
(a) providing a recombinant HCMV strain encoded by a nucleic acid molecule comprising at least one replication-essential HCMV gene, wherein the replication-essential HCMV protein is selected from the group consisting of pUL51 pUL37.1, pUL44, pUL50, pUL52, pUL53, pUL54, pUL56, pUL57, pUL70, pUL77, pUL80, pUL84, pUL89.1, pUL98, pUL102, pUL104, pUL105, and pUL122, which is fused to a gene encoding a destabilizing protein domain, wherein the destabilizing protein domain is a FKBP protein, wherein the recombinant HCMV strain does not encode a functional heterologous protein other than FKBP protein, wherein the recombinant HCMV strain does not encode a functional heterologous protein, and
(b) infecting a mammalian target cell with the recombinant HCMV strain to produce a HCMV dense body particle.

23. The method of claim 14 wherein the destabilizing protein domain is the F36V mutant of the FKBP12 protein.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Probe

<400> SEQUENCE: 1
ccacttttgc cgatgtaacg tttcttgcat                                      30

<210> SEQ ID NO 2
<211> LENGTH: 20
<212> TYPE: DNA
<213> ORGANISM: Artificial Sequence
<220> FEATURE:
<223> OTHER INFORMATION: fwd-primer

<400> SEQUENCE: 2
tcatctacgg ggacacggac                                                 20

<210> SEQ ID NO 3
<211> LENGTH: 17
<212> TYPE: DNA
<213> ORGANISM: Artificial Sequence
<220> FEATURE:
<223> OTHER INFORMATION: rev-Primer
```

-continued

<400> SEQUENCE: 3
tgcgcaccag atccacg                                                  17

<210> SEQ ID NO 4
<211> LENGTH: 222047
<212> TYPE: DNA
<213> ORGANISM: Human herpesvirus 5 strain Towne
<220> FEATURE:
<221> NAME/KEY: misc_feature
<222> LOCATION: (29535)..(29535)
<223> OTHER INFORMATION: n is a, c, g, or t

<400> SEQUENCE: 4

| | | | | | |
|---|---|---|---|---|---|
| cratdrdays | tmbramcctc | gcctatttaa | cctccaccca | cttcaacaca | cacctgccgc       60 |
| acaatcatgc | cagccacagc | cacaaacagc | acccacacca | cgccgcttca | cccacagtac      120 |
| caacacacgc | taccccttaca | ccacagcaac | acacaaccgc | ctatccaaac | ctcggacaaa      180 |
| cacgccaacg | aagaacaccg | cacgcagatg | gagctcgacg | ccgcggatta | cgccgcttgc      240 |
| gcgcaggccc | gccaacacct | ctacgctcca | acacaacccc | aactacacgc | ataccccgac      300 |
| gccaaccctc | aggaaagcgc | tcatttttcc | acagaacatc | accatcaact | gacgcatcta      360 |
| cttcacaaca | ttggcgaagg | cgcagcgctc | ggctaccccg | tccccgcgc  | ggaaatccgc      420 |
| cgcggcggtg | gcgaccgggc | cgacagcgca | agcgacttcg | acgccgactg | ctggtgcatg      480 |
| tggggacgct | tcggaaccat | gggccgccaa | cctatcgtga | ccttactgtt | ggcgcgccaa      540 |
| cgcgacggcc | tcgctgactg | gaacgtcgta | cgctgccgcg | gcacaggctt | tcgcgcacac      600 |
| gattccgagg | acggcgtctg | tgtctggcgt | cagcacctgg | ttttttact  | cggaggccac      660 |
| ggccgccgtg | tacagttaga | acgtccatcc | gcgggagaag | cccaagctcg | aggcctattg      720 |
| ccacgcatcc | ggatcacccc | catctccaca | tctccacgcc | caaaaccacc | ccagcccacc      780 |
| atatccaccg | catcgcaccc | acatgctacg | actcgcccac | atgacacgct | ctttcctatc      840 |
| ccttctacac | cctcagccac | ggttcacaat | ccccgaaacc | acgccgtcca | acttcacgcc      900 |
| gaaacgaccc | gcacatggcg | ctgggcacga | cgccggtgaac | gtggcgcgtg | gatgccggcc      960 |
| gaaacattta | catgtcccaa | ggataaacgt | ccccggtaga | cggggtaggg | ggatctacca     1020 |
| gcccagggat | cgcgtatttc | gccgccacgc | tgcttcaccg | atatccaata | aacccatccc     1080 |
| ctcgccacga | cgtctccgcg | tatctttgta | gcctcaggaa | tccgtcccca | cgtccatcca     1140 |
| tcccgagcac | tccacacgct | ataacagacc | acggacacgg | caaatgcatg | caaacttctc     1200 |
| atttattgtg | tctactactc | tgtgttgcta | cagggagtga | aggggggtgaa | ggcaaacaaa     1260 |
| aaaaaaagga | acaaaataat | agattagcag | aaggaataat | ccgtgcgacc | gagcttgtgc     1320 |
| ttcttttgtt | ataaggaggc | aaatatacta | gggaaaactt | aagaatagga | agaaaccgag     1380 |
| gtttgggaga | aaagctgaga | taaaatagcg | cattttccat | acagaggttg | ttgttttttgt     1440 |
| ggatcctaag | aggtttcaag | tgcgaatctc | aaagttctca | cgagaatatt | gtcttcaaga     1500 |
| atcgacaact | gtggtccaag | attttttttt | ggtcttttta | ggttctgcga | gggacatcac     1560 |
| gatggatcgt | tgcgatgaag | tcacgcgtac | gcctctggtg | tggcgcggtg | tcgtgacagg     1620 |
| agagtgtgtt | ttcagtgcag | agctgtcttg | attcctatat | ccgagtatct | gttttctcgt     1680 |
| aaggacggta | atcttctttg | gtgtaagtac | atctaaaagc | tgcaaactat | attttaaggg     1740 |
| ctgtctctag | gtgtactttg | atgctggagt | ttttcgctgt | gttgatgtga | ataaatctac     1800 |
| tactactatt | atatgcagaa | agagtgatta | tgccgagaca | agattgcatt | ggctgaactg     1860 |

```
tttcaaaaac gcctacactc tacttatccg taaacctaag gtaatactat gtgtaagttg    1920
ttttttttc ttttttgtagt aaaatggtga tacgtgcaat taaaactgta ttccatgttt    1980
ccatcctttc atttcaactt taaaggcggc tttgagagcg aagaagtgcg aggataaaaa    2040
tggatgactc cttcgtgtcc agggagtcga ctactgcaac gctgattgat taaaagatgg    2100
tctccgatga tgatgttgtt attgatcgaa tcatggtgca gaacggcgac ggagaggagc    2160
gtgtccgccg ccgggaaggt ggtctctttc tcttttcttt tttcaagaaa tcttccatgt    2220
gtttatcgta gtgatcgaaa tcgactgatc tcggttctt tttgttggtt tcttttcggt     2280
taatcatgta ttgttttctt ttttacaga aagatacttt tttcatgagc aattcctcgc      2340
ccggcgccgg catgccgagg tggggccact gcgatcagcg catgccgac gccgacccgg      2400
ggatcttgga ttcaccgttt tctctcttct ctctctacat acagaccggg tggcaggagc    2460
ggtaaggaat catcgtcgtc tttcattctt cgatgattat ggtaatacta aatcttatct    2520
aggagcatat acatctaaga ttggagtact agtagtcgtt tgtggtttct attttttttt    2580
atatttatct atgacagttt ttctgttttt cgttttgata ataatataat aaaaactcat    2640
ggacgtgaaa tctggcttgg ttgtggtgat ttcattctca ttattgttgt tttcttccg      2700
tcttgcggat gaagatgttg cgatgcggtt gttgttggtg ttgctataca ccagagagag    2760
tgatcttttt gttcttctgg ttcatttcct atgattgttt ggctgctgac cgacgcgtca    2820
ggatgtgcag gcatgcggg gaatcaggac cggacacggg ataatttcat ctacctatac     2880
ggagatcgcg gtcctcgcca tgaggatcgc gacaggcgcg tcgagggggc aggaacaccc    2940
ttgcggattg acattcttgg tggtgtttcg ttgttgtcgg tagttgttgt tgacgatgag    3000
gataaataaa aatgaccttg ttttttgttct gttttctctc gttgggaatc gtcgactttg   3060
aattcttcga gttatcggaa agctgaggta cccaaatgtc tgtagctttt ttctttttac    3120
cctcttgttt atcatctgcg attcgtggta ggtaggagag ggaaatgata atccgagatt    3180
aaggaaagga gaagataaaa aataaaaaaa aataataaaa cagaagccga ccggccgccg    3240
acccgttccc caggaccagc ctacgaggaa cggataacgc ggtggcgacg gcagcggtgg    3300
tggcgctggg ggtggcggta gtggtgctgc tgatggtagt cgggacggag gagagacgat    3360
gcatacatac acgcgtgcat gctgcatggg tggatggtac ggccgggaga cgcggaagag    3420
aaactcacat aaaaaggtga taaaaagagc ggttgaaaaa agaaaacgag attcgaccag    3480
acagaagaga aggaccgggg cttggcgacc cttccacgac tgccgttgtc atctcggctc    3540
ctccatcttc tcccggccac gggcggctaa gtcaccgccg ttctccccat ccgtccgagc    3600
gccgaccgac cagccggccg attcgcccgc cggggcttct ggagaacgcc ggggcagcag    3660
cgatctgggg aagccgctaa acccctgcgt ttttatatgg tagctctgcc gagcgcgggc    3720
tgacgcgttg agtaagcgga aagacgtgtg tgacgaaaag gggtcccatg gtatttcacg    3780
tgacgatgag gagatgcggt ttggagcaca tacggtttag aaaaagggag ttgtcgtgac    3840
aagggctgag ggacctctgt ctccatgtgt gtataaaaag caaggcacgt tcataatgta    3900
aaaaagaaca cgttgtaaac aagctattgc tgtatcattc ggctgactat gcttcattcg    3960
gactgatttt cttttcctaa cggcgtaact taaagtgatt aacgtatgat atttgttccc    4020
cagagttata ctatagtcat catcctaaaa ttcagatata aatgaacaca tgtcgtatgg    4080
gattattaag aaaccgaaac tctccacagt tcaccatctt cttcgtcatt caaccgatga    4140
cccactccgt acaacgaatc agtctgctgc gtcatattgc aaagcacaag cgacgtatgc    4200
gaacaacttg aaacacaggc tgttgtattg atgaccgttg taccattatt agtcacatcg    4260
```

```
tatagagact ctccaccgtc atcccatgtt tcccacccga tggaaaaccg tcttctatca   4320
tcaactgtgg taagatttcg accctgcgag gtattcagtt tcctcatatc cataacctgg   4380
attttatcat taaaccccaa tattaaacac ttttttagta ccccccaccc accaaaaaat   4440
gtgactggac cggttcctag cagctctggg agccatgttc aggttgaacc acagctacag   4500
cgaaaccgag tccagtgacc ggtaaccacg tccagcccct gcgtatgtac cagtccaagc   4560
acgtccggtc attgttctac acaggaaatc taactaggtc aacgtaacct aacactctct   4620
aaacctaatt tttagtagtc aaataccata attcaccgct gtactcgtct ttattctctc   4680
cgaaccaacg accaaggtcg acaacgccat cgttacccct cgtgatattg cacagatcta   4740
aagatgtatg agtacaattc gttacacaaa cgcttgatcc attattcact agaggtgcat   4800
gtctccctgt tacattacat aaccatcctt gattcagatg gctccatttc gtagtcatcg   4860
ggtcgttttt gtgttcaatg gttacattgt caccacttttt aacctctact ttattgaaac   4920
ccgcaccttc atgtataaac accgtcatga aacacgctat aagtaccccc cccccacaa   4980 tggaatgctg ccaaaccggt tatttcccgt tatagccatg gcgttcctaa gcaagagcta   5040
acgccgaacc taatgcagta aaaagcgctt gcagccagaa ccagcttatg taccagccac   5100
gataacatcc ggtgattgtt tccacaggaa atcctaccag gcaaagcccc gcttgttgtg   5160
ttcctgacca ccttgtttag caattcgtaa actgtcagcc tagcgacgtc cgtttagatc   5220
aaaagtcacg tatatagcga cgctgtttcc accgtttcc ccgtcccgcc gtttccgaac   5280
aacccacccg ggttcagaca accgaccacc aacagaaata tacacacaga ccaccgggag   5340
ttcagttaaa gatttcatca ggtttatttt ggctgctgct agtcttttgc ttcttagaaa   5400 aaaaatacccc atatagagaa ataatgatag tttgacaaca catatggcag ggatttcttc   5460
ttcatcaata agatatgcaa ttcccccagg gagagacttt caacaattga atttacaaaa   5520
acaaaattac atcaggagaa agagaggata cattaataaa tatattatat ctggtgtata   5580
tactgaatgc tgctggttca taaggtaacg atgctacttt ttttaattcc aagatggttt   5640
ttctttgtta gtcttttgtt gacttgctgg ttcctaaaag ttcgcaaaaa cgattgtgtg   5700 aagatttat gacgttggtt gactagttca tgagattctg ctgtacgtgt gatggttatt   5760
cgctggttcg ttctaagatg agtatcgtac tgtgtctgcg atggtcgtct cttactggca   5820
ttctctcggc tgcctcttgc tttcatgatt gaaaaggaaa aaaggactcc gagggcgcgg   5880
tcatctttta cttttcggtt ttctcattgg cgggtcagag gtagtcagat catgagactg   5940
tcgtggtcga tgaaactgtg tctgctcaag tgacgtccat ttcttgtacg gagaaaaaag   6000
tcatcgggat aaataaggct atacaaggcg ttgtcaagcg tgcggctcta aacaaattaa   6060
gcgatacaaa attacagtaa tacgaataat aaattacccc cctcccccctg tggtcccccg   6120 agacgagagc cacccatcgt gtactctcgc accacccacg accacagagg gaggcgggac   6180
gaagagacga cgcagagcgc catctcctcc tgaaggccgg cgacgttaac tgctacagct   6240
gcggcggcga cgacgacagc tgcgatttgt cggccgacat gccgatggta tgggcggcgg   6300
cggcagtggc cgcggcagcg gggaggagag gagagagaag aggagcgggg cgtccgaagg   6360
cgaggatggc atggtctcgc cggagcgccc ggcttttatg ggacactcgc gtccggttgg   6420
gcattgccca caggaagatg agtcacaact tccaaaccat cttgagaccc gagtaacggt   6480
ttacaggtcg cacgccagtc tcagctaaaa acagcggaca gtcccacgct gtttctgttg   6540
tggctctctc cagtttcctc atcgccatcc cggtctccgt cgtcatcgga agaataccat   6600
```

-continued

```
ccgctctcat gcggcagtcg atcgacctcg acgaacgaga cgcggcgacg cctctctacg    6660
gccgactggt tgtggtggtg aaagaagagc accagcaatc ccaggaggag caacaagccc    6720
tcacatgtcc aggaggtcgg ggagagggcc tgtcggagat ggccgtgagg catcacgtac    6780
ggcagctgag gagaaacgga gaagaaagga aaattaccgt caggggccgg ggttcttatt    6840
agaaaaacag cacgtaggtc aggatccaga tgctaatggc gatcatgatg acgatgatca    6900
tgcaggccaa gacgcggcgc accaatgccg aatccaagag ccgccgtgcc gccggttggt    6960
ggctggcggc atctagagac atggtttggg ggggaccggc ggcgcgaaaa gacagggaga    7020
tggacagtga cacggtgttt tgttatgatt aggacatggg gaccggaagc cgagacagag    7080
tactacagag tgttgaaggg taacgtgagg gagatcatgt catgggcggg ctgaagaccg    7140
tgcggggagg atcgacgtgt gcggtgcttg tggaacacgg tgttttaata tgtatccgcg    7200
tgtaatgcac gcggtgtgct ttttagcact cggtttgata agctacgtgg ccgtttgcgc    7260
cgaaaacacg gttaccacca attgtctcgt gaaacagaa aatacccacc taacatgtaa     7320
gtgcaatccg aatagcacat ctaccaatgg cagcaggtgc cacgcgatgt gcaaatgccg    7380
ggtcacagaa cccattacaa tgctaggcgc atactcggcc tggggcgcgg gctcgttcgt    7440
ggccacgctg atagtcctgc tggtggtctt cttcgtaatt tacgcgcgcg aggaggagaa    7500
aaacaacacg ggcaccgagg tagatcaatg tctggcctat cggagcctga cacgcaaaaa    7560
gctggaacaa cacgcggcta aaagcagaa catctacgaa cggattccat accgaccctc     7620
cagacagaaa gataactccc cgttgatcga accgacgggc acagacgacg aagaggacga    7680
ggacgacgac gtctgacaag gaaggcgaga acgtgttttg caccatgcag acctacagca    7740 ccccctcac gcttgtcata gtcacgtcgc tgttttttgtt cacaactcag ggaagttcat     7800
cgaacgccgt cgaaccaacc aaaaaacccc taaagctcgc caattaccgc gccacctgcg    7860
aggaccgtac acgtactctg gttaccaggc ttaacactag ccatcacagc gtagtctggc    7920
aacgttatga tatctacagc agatacatgc gtcgtatgcc gccactttgc atcattacag    7980
acgcctataa agaaaccacg catcagggtg gcgcaacttt cacgtgcacg cgccaaaatc    8040
tcacgctgta caatcttacg gttaaagata cgggagtcta cctcctgcag gatcagtata    8100
ccggtgatgt cgaggctttt tacctcatca tccacccacg tagcttctgc cgagctttgg    8160
aaacgcgtcg atgcttttat ccgggaccag ggagagttgt ggttacggat tcccaagagg    8220
cagaccgagc aattatctcg gatttaaaac gccagtggtc cggcctctca ctccattgcg    8280
cctgggtttc gggactgatg atctttgttg gcgcactggt catctgcttt ctgcggtcgc    8340
aacgaatcgg ggaacaggac gctgaacggt tgcggacgga cctagatacg gaacctctgt    8400
tgttgacggt ggacgggat ttggagtaaa agatgcgcac acaacatcga cggtggaaca     8460
agtcatcata tacgcaaata atatgcatgt ttattatttt ttggattctg cagaaaagca    8520
agtgtaacaa caccactatc gccaatactt ccacgtcgat tacacccaca agcttaatat    8580
ctactacaca actgacatct acgttacaaa ccaccgaaat gtctaccact atgttcacat    8640
cctccaatgg caacgtcaac acatccacag gattcactgc aagctctgta aaaggcacag    8700
acgtgacctc aactatttcc accatatcta cccaaacatc tacaactaac gtaactgtaa    8760
taacaacttc accaaacggc gacacgaatt catcgacaca gcatgtaacc gatagtactg    8820
tgactttgca aactatatca ttatcaacca acactactac tatgataaat gcaaatgaaa    8880
acgtcactac accgcttcca acttgctcat cgcctaacag tacaaataat acgatatcaa    8940
aagaatctga aacattattg gaggcggcac aaggagacaa tattactata acacacaacc    9000
```

```
taaccatcac atcgtgctac aaaacagcct ggcttagaca ttttaatata tccacacacg   9060
gaaaatacac ccatcccaac ataagaaatg gaaaatatca taaccattca ttgaaaatcc   9120
tccattcgcg tatactatgt gagtggcaca caaattatct aaaacatcac tatgatttat   9180
gttttacatg cgatcgtaat ttatctttat ctctgtacgg tcttaatttt actcattctg   9240
gtaaatatag ctttcgatgt tataaaactg ggcatccctc cgaacaaaat caaaacttta   9300
atctgcaaat acatcctaga aacaacacaa acgggacaca cgtgaatccc tgggtatgtg   9360
aagaaccaaa gcacgaatgg gacacttctc ataaaccgac caattatgaa gacaatacag   9420
ccacatcatc tatagatcat ttataccgct ataacaatca ttctaacaca tcacacggca   9480
gacgcactac gtggacgtta gcattaattt gtgtagcctg cattctccta tttttcgtcc   9540
gacgagctct aaataaaaaa tatcatccat taagtgacga tataagtgaa tcagaattca   9600
tagttcgata caatcctgag cacgaggact aagcaacgtt tccggataaa tgtcttatga   9660
gaccatatca gaaataaaac gggcaagaaa gatcaacaac gtccgaagaa acatcaatgc   9720
ccgttaaccg aaatttaata acgttatgga ctggagattt acggttaagt ggacgttact   9780
gatgattacg atatctgaag gttgcaatga cacgtgctcc tgtccgtgca attgcccttta  9840 cctccaccgc ctccactatc acaaattctt ctaactctgt caccgatgct aacagcactt   9900
cagctatcgc aaatggaacc acgcacaaac cctctaccgc ttcttcagtc gcatcagcaa   9960
ccacttcaac gctttcaaaa tcatcgtcaa gcgctacgcc aacattaacg ttttctacca  10020
ttcatagtac tactccctgg ttgaatacca gcaacataac ttgcaatggc agtttgtaca  10080
ccgtttataa acactctaat ttaaattacg aagtaattaa tgtaacagga tatgtcggtg  10140
gatacgtcac tttgaaaaac tgcagtagaa cggatgtatg gcacgatata gaatggataa  10200
aatatggacc tcgcgcacac caactgtgca gcattggaca ttattattca acttccccac  10260
tgaacggcat gtgtttagac tgcaataaga ccctctctcac tatatacaac gtaactaccg  10320
aacacgctgg aaaatacgtt ttgcaacgtt acagtgacgg taaaaaggaa aactactatt  10380
taaccgtgtt atcaggaact gcaacatcgt ctcctatacc tgataaatgt aaaacaaaag  10440
aggaatcaga ccagcataat agcagaacgt gggacaatgt aataaaaact gtaaaaaaca  10500
ctaacattcc cctgggaatt catgctgtat gggcgggtat agtggtatct gtggcactta  10560
tagccttata catgggtagc cgtcgcgtcc ccagaagacc gcgttataca aaacttccca  10620
aatacgaccc agatgaattt tagactaaaa cctaacatgc acatcaataa acttttgttt  10680 ttattttag ccaataatgt ctccgtgtgg tttttgtggg ttaagcactt atggtgtgaa  10740
gcagaatatt catagttatt aaaaacatgg gtatacaatg taacactaaa ctactgttac  10800
tagccgcgct aatagcaact gcaaccattc taactagcat tttagttccg gtacttttac  10860
atgaacaaga aaaacatttt taccggcgat tttttacgca aagtcaacat gtagaaagac  10920
ccatcacggt aactcaggga gatacagttt acctgaacgg tagtaataat ccctgcaact  10980
attccagttt ctggaactac ggcagttgcg aactttgtgg atggaacgga tacatacata  11040
aacagtacca cgaaaacaaa tcatgctctc cgcgatttac atgttttaac gacacaaaag  11100
gtctcagact taataacgtt acatctagcg attcaggaac atacacggaa tacgtgtatg  11160
aatgcgattt gccatgtaat acaagtgact atgatgaata tgacatacta aactatcttg  11220
acaattgtac tactaccata aacagcacca attatattat taccgtattg tctccacgtc  11280
attctaaaca caccaattcc cacatatcca cgctggttgg acagctgccg tggtgacggt  11340
```

```
aattataatc tgcgttttga cttactttaa cgttccggca accctgaaac gcaaactacg    11400
aactagaaac aacgctaccc acataccgtg attacaaagt acccacacta gttcattcag    11460
gataaatttg tgctttgtgt agctctcaga aattgtacaa ccccgctttt ccactccgtc    11520
atgaaagatc gtaataaact acttatatgt attatcttta ttttcaccat gtgcctcatc    11580
tgtctttact ttaaacgccg ttgtattcct accccatctc cagacaaggc agatctgcga    11640
gtggaatttc cttcgttatc tccgtgtgtc ggcatacagt gcgctccatg aaaagacgcg    11700
tgatacatag cgtactccag gacggtacag tttatgagaa cataattcaa ggaaagtgca    11760
ggttcctgtt gctatgttac cacaggagat cacggaacat aaatgttttc tgcgtatgtt    11820
tttataaaag agcgtctcga agcagtttga gccacactac ggtccagatg acgagcgtaa    11880
tcaaaaatat gccgcgtagt agtcgaaagc cgtactgagc gtgcgaagcg ggtagggtgc    11940
cgaacgacgg gtatgcgtcg tcgtcatctt tgactataag gatcgcgacc gagttttctg    12000
gcatggtaaa agctgcccac tgtggcaggt atgtagcgta tccggtttgg aatcgttcgg    12060
ctctggtccg ggggatagtg aggaattctc agggatgat atgggaccca atcactggat    12120
aagacaaggg ttttccccg taagatgatc ctcgtatcac atgaggtctg gatatgtata    12180
aatgaggagt gaaataggca cagggaatca gatgccggcc ttgtgatgca gccgctggtt    12240
ctctcggcga aaaactgtc gtctttgctg acttgcaaat acatcccgcc ttaagtgatg    12300
agtctataaa gcaccgttgt ctgggtacgg taaaagtgac tcggattgta gcacgtcatt    12360
tttttttgtt tttgcatcgt ttatcgtcac cactagtgca atattttgat cgtaaggctg    12420
aaagagtatc gttatgatgc ttagagcgtg gagattgatg gtactacttg ccgcgtactg    12480
ttattatgtt tttgcgaatt gttcaatcag cacgacgact gctcctgtgg aatggaagtc    12540
tcccaaccgt cagattccca agaatattac ttgcgctaat tactcaggga ccgtcggcgg    12600
taacgttact tttcagggtc tcaagaataa aacggaagat ttttatctt ggctactcgg    12660 gtctggttat aagtccattt gctcgttctt cccgcaactc cctggtgatt ctaatgagca    12720
gcattacaga tatgaagtaa ccaacctcac gtacaattgc acctatgacc gcctgacgtt    12780
actgaatctg acaacggaaa acagcaggaa ttactatttc agaagagaag atgcgaattc    12840
caccttctat tactcttgtt acaatctgac cgtgtcctaa agatcgcacg tgaagttcca    12900
cagaaccgcg cagctgtagc tattgtgttt acgttgcttt tgaaatgtta agcgtccta    12960 cggcgctaac atgtttctag gctactctga ctgtgtagat cccggccttg ctgcgtatcg    13020
tgtatctaga tcacgcttaa agctcgtgtt gtcttttgtg tggttgatcg gtttgcgtct    13080
ccatgattgt gccacgttcg agtcctgctg ttacgacatc accgaggcgg agagtaacaa    13140
ggctatatca agggacgaag cagcattcac ctccagcgtg agcactcgta caccatccct    13200
ggcgatcgcg cctcctcctg accgatcgat gctgttgtcg cgggaggaag aactcgttcc    13260
gtggagtcgt ctcatcatca ctaagcagtt ctacggaggc ctgattttcc acaccacctg    13320
ggtcaccggc ttcgtcttgc taggacttt gacgctttc gccagcctgt ttcgcgtacc    13380
acaatccatc tgtcgtttct gcatagaccg tctccgggac atcgcccgtc ctctgaaata    13440
ccgctatcaa cgtctcgtcg ctaccgtgta gctagttagc cagctgtgta tagtttgttg    13500
tgttttgctt ttgcatattt gttttcagtc agagagtctg aaacggggtg ggagggactt    13560
ttgcgggtag tgcacgctaa gatgaacggg tgggctgggg tgtgcttgat aactcactgt    13620
ttgaatacgc gctcacgcac atatgtagca ctcaacatgt tagcttttgc ccgcacgccc    13680
cggggcatgc cgagctgcct ttttaataaa gtctgggttt ccagatacgc gctggttctg    13740
```

```
attttgatgg tttgtgcctc tgaaggctca acgaattggg tcgtggtttc tcataggctg   13800
cctaactgta gcgcggtatc tacaacagtg ggacaaaacg ttgagttatg cggctcggcg   13860
tcatcaggtt gtaacataac ccaatgggga cgttaccaga atggaagtac gctgggccca   13920
tggtgtaccc tgtggggacc atatacccaa gtctcattag gacatcgtgt agcgttcggc   13980
tgttcttgga caacgttttt tatgtacaac ctttctcaaa atcatagtgg cacttattat   14040
cgaaaaggtg acaactgtac cgacaaacat ataacactat cttgtttcaa cttgacggtg   14100
catcccaagg cggctcagag cacaaccacc gtagtgacac ccacggtagt tacaaacgcc   14160
acggcgaatg tgtcacccat tacgtcgact ctagcgtaa attccagcgc gtttaaacac    14220
gttagttatc aacggcaaca gcgtgtcgaa acaggacgt catccaagaa cataactaac    14280
ttggcattca cctatggcag ctggggcgtt gcgatgctgc tgttcgccgc cgtgatggtg   14340
ctcattgatt tgggtttgcc tcaatcggct tggcggcgct ggcgaatcca cgtggacgat   14400
gaagaacgtg gtctgttaac gtaggaaata aaaagtactg tttgagcgtg actgtttcca   14460
aatcgtaccg tggtaaataa atcatggttt ccggcgtggg ttctcatctt atgacggttc   14520
cacgattccg ttggacagtg catcatgtgt acaataaact attgattttg gcgttgtttg   14580
cccccgtgat tttggaatcc gtcatctacg tgtatgcgcc agagggaggg aacgttaccc   14640
tggtatctaa cttcacttca aacatcagcg tacggtggtt tcgctgggac ggcaaccaca   14700
gtgatctcat ctgtttctac aagaccaaag aaggattttc aacgccttat gtgggtttaa   14760
gtctaagttg tgcggctagc cagatcacca tcttcaacct gacgttgaac aactcgggtc   14820
gttacggagc agaaggtttc atgaaaagcg gcgaaaatga acgttcctg tggtacaact    14880 taaccgtgac actgaaatct ctgaaaacta cctcagctaa taacgtaaca accatcgtta   14940
caacgacgcc gacggtgact ggcgcggaga gtaacgggac tagaaatgcc attttaacac   15000
cacaactacg tgctgttgct ggattctcca atcaaacgcc ctcggaaaac aacacacacc   15060
tggccttggt aggtgttgtc gtgttttttga ttctgatagt tgtttgtatt atgggtggt    15120 ggaaattgtt gtgtagtaaa tcagaattat agtaatgtgc ttttatcag ggagaaggtt    15180 ttgtgcccac aatgactagc ccgggactat ctacgtcgga aaattacaac ggaaattatg   15240
gactcacgaa gaccgccaat acaacgcgta caaataacag tgaccggaca acgttaggag   15300
ccagtgcgtc gttgttggga agcacggaga ctgcggtaaa ctttgacaac gcgactacga   15360
ttatcccaca acgtgtggaa cacccggttg gggaaataca atatcagaga acgacaacac   15420
attattcttg gatgctaatt attgtcatca ttctcattat ttttattatc atctgtctgc   15480
gagcacctcg aaaagtttac gatcgctgga aagacagtaa acagtatgga caagtgttca   15540
tgacggacac agaactatga tgttccggta cgcgttatta cttcgatgga taacaatcat   15600
tctttgtaca cgaaaatcca attattggaa ctacatatca acgccatgta cttctatagt   15660
tggctacagt ggccagaata tcagcttatc tcccgttaac aaattgtcag tcaaagacga   15720
tgcttttcaa tggtatatag acaaaccgag agttactaac gcactatgta tttatcaaaa   15780
taacgagtgc agtgtacaac ccaatgagaa cgctccgaac attaagtggc aatgtgtaca   15840
gaatcataca cttattctta ttaatttaac aactacatat agtagaaatt actattttaa   15900
ttcttttgaa acccttggag taacaatagc aaaatacaat accctgtgtt acaatgtcag   15960
tgtacattct gcctaccaaa cacactgttg tacaaccacg ttatccatgt attcacccac   16020
acccgtacac aggtcataca cattaacttc aaccaacttc acacatgtcg cggtccatta   16080
```

```
taccgccggt aacgttgaag cacaacacga tactgccacc ccacatacaa tgtggatcat    16140
accccctagtt atcgttataa caattatcgt tttaatttgt ttcaaatttc cccagaaagc   16200
ttggaataaa ttcacacaat accgatacaa cagtatgctc gccgccactt aaagaatcac   16260
cgtcgaggaa actaaaagct atgtacgttt attttttcagc tcactgtttg aataccgtaa  16320
acataatgac gtacatatac gtggttatac aacaggtgtt tgtgctatgc ggagactgat   16380
taaccatatc gtgaaccatg atcttttccg atggtctgtc gtgaccgcaa tgatatttta   16440
caggtattcc gaaacctgta tggaggtcac tgtcagagta ggtgatccag ttaccctcgg   16500
tagtggacat ggttatcatc caggacaaaa agtacactgg tataaccagt catgcgtcgg   16560
catcagcaac ggcgaaaata cgcatcctat ctgcacctac gaccctccta aacctggtag   16620
acaaaagaca atgaaaacca ctccgttgcc atcaccactg ttgtatgaat gtcacaattc   16680
cacattaagc attcttcatg taaacgtctc agatcccaga aactattgca ggcgaaaatg   16740
tccaccaaag ggtaactgtg agtttcccac atgttttaca ttatcgctga tttctagaac   16800
gacaaccacc agaagacccg acaaaaaaac tacgttgtcg cgattaaaaa ccacgccaaa   16860
taaacatacg cagcacaaaa gatccacgcg aggaacgtca cctaaagatt acaatgtaac   16920
gggtctgccg aaaggctttg cggactcgtt taccggtaac gtagaggcac atagagccaa   16980
agatgccgca cacagcgcat ggattctcat tgtcatcatc attatcatag tcgtcattct    17040
gttttttcttc aagattcctc aaagactccg agagaaatgg gacaccaagg gataccttta   17100
caaagggacc gatggcctgc ccactacgga ctaattatcg tgagcggacg gatatgtccg   17160
gtttcaaact cactgtttga atataggac agtccctacg gaacctgaga acatgtggaa    17220
atcacctgtg gtagaatgct gctcaggtac attaccttc atcgcgaaaa ggtactttac    17280
ctaacggctg catgcatctt tggtgtctac atcagcctcc atgatgcctg cataccggtg   17340
gttggcaaga taggtaccaa cgttacgttg aacgcggtag atgttctccc ccctcgcgat   17400
caagttcgtt ggtcatacgg tccaggcggg caaggctaca tgttatgcat tttcactggc   17460
acatcaacaa caacgtttaa cagcacgcgc tttaattttt catgtctgag taattacagc   17520
ctcctcctca ttaacgttac cgcgcagtat agtactacct atcgtactat gacatcgcta   17580
gacgattggc gtcaccaaca acataaccat ggttttcgat ggactttaga cacatgttac   17640
aatctgacag tgaacgaaaa cggtacattc cccactacca ccaccaaaaa gcccactacg   17700
actacgagaa cgacaactac cacaacacaa aaaacaacca ccacgagaac aaccaccacc   17760
gccaagaaga cgacgataag cactacccat cataaacact ccagtcccaa aaaatccacc   17820
accccctaaca gtcacgtaga acatcacgtt ggttttgaag ccacagcagc ggaaacaccg   17880
ttacaaccaa gcccacagca ccaacacgtg gctacacacg ccctctgggt tttagcggtc   17940
gtaatcgtta ttatcatcat tatcattttc tactttcgaa taccgcaaaa gctgtggctg   18000
ctctggcagc atgacaagca cggcatcgtg ctcatccccc aaaccgatct gtaagcaagt   18060
cgcgtaggaa atgattgcat gaaatcactg tgaaacgcca actccgtgcc agctggcgcg   18120
gcggacaggc ctttgacgta tttgaagcca ggcgcgctct cgataccgaa aggatccaag   18180
ggggctttcc aaagccgacg tccctgattc ccttcataaa gctgttgacc ggccctagaa   18240
agaccaagag catgctgtgg gcccactgcg gtcgcttctt gcgttatcat ctgctcccgc   18300
tgctactgtg tagactgcca ttcttactct tttttcagcg gccgcagtgg gcccacggct   18360
tggacattgt cgaggaggac gagtggctac gggaaataca aggagcgacg taccagctgt   18420
ccatagtgcg ccaagctatg cagcacgccg gattccaagt cagagcggcg tcggtcatga   18480
```

```
tacggcgaaa cgccgttgac ctggaccgac cgccgctttg gtcgggatcg ctcccgcatt   18540
tgcccgtcta cgatgtgcgt tccccgcggc cgttgagacc gccgtcatca cagcatcacg   18600
ccgtatcacc cgaactgccg tcgcgaaacg ggatacgttg gcagtaccaa gagctgcagt   18660
atctggtgga agaacaacgg cggcgaaatc agtcgcgtaa tgcgattccg agaccctcgt   18720
tcccccctcc ggatccacca tcgcagccgg cagaggatgc acgagacgcg gacgcagaac   18780
gtgccgaatc accacacagt gcagaaagca ccgtcagcca cggcgcgagt gacaacgcag   18840
tgcggcgacg gcacgaaaga cggcgctata acgctctgac ggtccgcagc agggactcgc   18900
tgctcctgac gcgaatacgc ttctccaacc aacggtgttt cggacgcggg cgtctgagac   18960
atcccgcggg aagcggtccc aacaccggcg gaccgcgacc cggcggtgcg ggactccgtc   19020
aactacgcca acaactgacg gtccgctggc agctgttccg cctacggtgc cacgtgttgga  19080 cacagcaagt ctctagccag atcagaaccc gctgggagga aagcaacgtc gtgagccaga   19140
cggccacgcg agtacgtacg tggttttgtgc aaagaaccac gttgtggcgt cgcacgtggg   19200
ttccgggaca gaacccggcg gccgaagcgc aagaactggc cgtcataccg ccggcaccca   19260
cggtgctccg gcagaacgag gaaccacgtc aacagcttac gggagaggag acaagaaatt   19320
caacgcacac tcaacgtgaa gaagtggagg acgtttcgag agagggcgcg agagaaggga   19380
atgatgggag ccgagcaagt ggaaacgacg agagaaggaa taatgcggga agatatgatg   19440
atgatcatga ggttcaagag ccgcaggtca cttatccagc gggacaagga gaactgaata   19500
ggaggtcaca ggaggagaac gaggaaggtg gaccgtgtga atcgccgcca atgacgacaa   19560
atacgctgac cgtggcctgt ccgccccgag aaccccgca tcgtgccctg tttcgtctat    19620
gcttaggact gtgggtctcg agctacctgg ttcgacggcc catgacgatt tagaatacac   19680
cgagccattc ctttatttcc ccccatcccc ggtcgcttat gcgtgtcaaa cactaccaat   19740
aaagataatc tgccaatcgc acctatata taatatgtgg tcgcgtgtgg tcttttttaag   19800 gagctctgaa acacagacag gtatgggcgg tggccggctg ccgccgctgt ggctgccgct   19860
gctgatcgcc tggagcgagt ggggcaactg ctgcctcgat gcgcctccgg tggtgcgttc   19920
gccctgtctg cagccggtgc gcgaccgcaa ccgcgagcgg aacccgggct caccgcagtt   19980
gctgccttac ggcgaccgtc tggaggtggc ctgcatcttc cccgcgcacg actggccaga   20040
ggtctctatc cgagtccacc tctgctactg gcccgagatc gtgcgttcgc tggtggtgga   20100
cgcacgcagc ggtcaggtgt tacacaacga cgccagctgt tacatcgccg gcgggcgctg   20160
gcgcttcgag gacggcggcg cggcgcagcg gctgagcctc tcgtttcggc ttatcaccga   20220
gaccgcgggc acctacacct gcgtgctggg caacgagacc cacagcctgg cgaccgagac   20280
cacggcgctg tgccgacg tgcacgacct gcgccactcg gaccgctcct gcgacctagc   20340
tttcggatct cgctcacaga cgcggtacct gtggacgccc gatccctcca ggttgcgcag   20400
tataaactgt ggttgggagg gtgaacggca ccgcgtggtc cactacatcc ccggcacctc   20460
gggtctgctg ccctcgtgcg aggaggacga gcgcgaactg tgcgtgccct tcatcagcca   20520
gagcatcgcg gacaacaact gcagccaccg gcatcgggta gacggcgcta ggcggcgcta   20580
tcatctgcgg agggattact ggctgacgga tccgaagatc gggctgctgg ccgcgggatc   20640
ggtggccctg acctccctct gccacctgct gtgctactgg tgttccgaat cgtaccggcg   20700
tctgaacacc gaagaggaaa acgaggcggc agaggaaact gccgcgggag aagcctctgc   20760
ggtagcggcg gcggccgtct ctgaggaaga gcagcagcgg gagtaaacga ggagagccat   20820
```

```
gaagcggatg attcgcagtc acggcaggaa aacggaatgt cagatgacgg gcgccggcga   20880
gcgacgcggc tctgccgtcg gtgcgctcat ctgcggcagc ggtacccgac gcggcagcgg   20940
cgccaacgaa cgccgcgact ccgacgtcgg tcccatcgcc cacagtagcg gtaccagacg   21000
cggttcggcg aatgaaacgt ccgcctgtac gcggaccgat caccagaagg cggacattgg   21060
gctgtggttc atgtttctgg tttttggact gtgttcgtgg ttggcgatgc ggtatcgcgc   21120
acaataaatt ttgaatcgat gtcaaggaac gcgtgttttg tattttattg gaatattgg    21180 cggggataaa ccgtttcgg atgtttaccc ttaatcttac cggggacctc gttgtcctct     21240
cctccttctt cctcggacac ggggctccat gctgacgtag gtaccgactg gggtcaaaag   21300
cctgggtact tatggggagc gcgcacaaag gaccgtcagg cgccggcatg gagcgtcgcc   21360
gaggtacggt accgctggga tgggtgtttt ttgttctttg cttatctgcc tcttccccgt    21420
gtgctgttga cctgggtagc aagtcctcca actcgacctg ccgcttgaat gtgactgagt   21480
tggcctcgat ccatcctggg gaaacgtgga cgttacacgg gatgtgtatt tctatctgct    21540
actacgagaa tgtgaccgaa gacgagatca tcggcgtggc ttttacttgg cagcataacg   21600
agtctgtggt tgacctgtgg ttgtaccaga cgacacggt gatccgcaat ttcagcgaca     21660
tcaccactaa catcttgcaa gacggactga aaatgcgaac cgtccctgtg actaaactgt   21720
acaccagccg catggtcact aatcttaccg tgggccgcta tgactgttta cgctgcgaga   21780
acggtacgat gaaaataatc gagcgcctct acgtccgatt gggctcacta tatccgagac   21840
cgcccggatc cgggctcgcc aaacacccct ccgtaagcgc cgacgaggaa ctgtccgcga   21900
ccttggcgag agacatcgtg ttggtctcgg ccatcactct gttcttcttc ttgttggccc   21960
tacggatccc ccagcgattg tgtcagcggc tgcgcattcg cctgccgcat cgataccagc    22020
ggttacgcac cgaggactga acggataacc gcaaaggcca cgtgcaacgt tcacgctgct   22080
ataagaaggc catgtccccc gtggacgggt ctctttgaca cgagcgcggc acgccgttgc   22140
cacgagcatg gatcacgcgc tcttcacaca cttcgtcggc cggccccgtc actgtcggtt   22200
ggaaatgttg attctggacg aacaggtgtc taagagatcc tgggacacca cggtttacca   22260
caggcgccgc agacatctac ctcgacgccg cgctccgtgc ggcccccaga ggcccgccga   22320
gattcccaaa agaagaaaaa aggcggccgt ccttctattt tggcacgatt tgtgctggct    22380
gtttcgacga ctttctttc tcgggagga ctcggagcca ctgatgtcgg atccggcacg     22440
gtctcccgaa gaggaggagt aaacaacaca cggctaagag gatacatcat caaagaagat   22500
aggaggggtc aaaacgcgga ctgaaagtat taacgccga tcatgtccga ggaactgtta    22560
ataaaacgcc atgatgacaa cgtggtgtct gacgttgttt gtgctgtgga tgttgagagt   22620
ggtgggaatg cacgtgttgc gttacgggta cacgggatt ttcgatgata catcgcatat     22680
gacgttgacc gtcgtgggga ttttgacgg gcaacacttt tttacctatc acgttaattc    22740
cagcgataga acgtcaagtc gggccaacgg taccatttct tggatggcca acgtctcggc   22800
ggcctacccc acctacctag acggggaaag agccaaaggt gaccttattt ttaaccaaac   22860
cgagcaaaac ctgttagagc tggaaattgc gttgggttac cggtcacaga gcgtgctgac   22920
gtggacgcac gagtgtaata ccacggaaaa cggtagtttt gtagccggtt acgagggatt   22980
tgggtgggac ggggaaactt taatggagct caaggataac ctgacactat ggacgggccc   23040
caattacgaa attagttggt tgaagcaaaa caaaacgtac atcgacggta aaattaaaaa   23100
catcagcgag ggggatacta caatacaaag gaactatctc aagggtaatt gcactcaatg   23160
gtccgtcatt tatagcgggt ttcaaacccc cgtcacccac ccagtggtaa agggcggtgt   23220
```

```
ccgaaaccag aatgacaaca gagctgaagc attctgtaca tcttacgggt tctttccagg   23280
ggaaattaat attacttta ttcattacgg tgataaggtg cccgaggata gcgagcctca    23340
atgcaatccg ctacttccca ccttggatgg gactttccat cagggatgtt acgtagccat   23400
cttttgcaat caaaactaca cctgccgcgt tacacacggt aattggacgg tggaaatccc   23460
catcagcgtt acctcacctg acgacagttc ctcggggag gtccccgatc acccgacagc    23520
taacaaacgc tataacacca tgaccatcag cagtgtcctc ctagccctgc ttttatgcgc   23580
tttgctattc gcgttcctgc actactttac caccttgaaa caatacctac gtaacctggc   23640
ctttgcgtgg cgctatcgca aggtccggtc gtcatgacca tcaacgccct gtatgagctg   23700
tttcgacgtc ggttaccgcg tgccccgtc aacacggtca tgtttctcac gcgacgcact    23760
cgtgatgggt tctgcggtcg gttgacgtcc atcgccacga attcccacta cactatgttc   23820
gtgttggatc acgggtccgt gcgcatcgag cgaccgagtc agtcagaagt ggattgcgcc   23880
agtttaatgg aaacgctgaa gcggattcgg ttacgaaatt cgtgggtagc gtcagaagac   23940
gagctagatg tgagtcgcag ggacgcgtga cacgaaacgc gttcaggatt aacgtaggtt   24000
ttcaaaataa cctacgtccg tgagtgacgc ggtttcgtgt tgaaacccgc gcccggttcc   24060
cacggtggtt tatgatgaaa ccggcgttgg ggatctacgc gggttcctca ttcaacctgc   24120
gaaaagagga agttgcggta aaaccacgtc aataaagacg tcaatgacac ctcaatgttg   24180
cgttggaacg gtctttatat atacaaacgc cgttatgctc agtgtccggc aagatgctcg   24240
ggatacgggc tatgctggtg atgctggatt actactggat acagttgaca acgctcaatg   24300
gcacccgaac caacaatacc gataccatct ttgtgtctct ccttaccggt cccaacggag   24360
ttacccgcac ggccatcggg ggtttgtatt caaactacac taatttaact ggaccatttg   24420
gcttcacttc aacaaacgca tcaataacca actcttccac tgagggtaat tggagcgtgg   24480
ctaatctgac agagagctgc atcaaccgcg tgagtccta tctgactacc ctctggcttc    24540
tgaactgcac tcaaaacaat acttattggt attctggaaa tgcttacaac cataccaata   24600
gcacctgtga aaatcaagtt tcgaaatatc tcttttccgg catgtgccag ctatggaaaa   24660
attggatcaa tattactttt aataacacta tcaaagtcga gttgctggga atgaaacac    24720 gctgcatgct gcttcctaaa cagtatactc tgaacgctac ggtagaatgg tacaacaaat   24780
ctgaaggtaa cgtaccaaaa gaatttatgg actatgttat cctgaccccc ttggcagtgc   24840
ttacatgtgg acttcaggaa gcttatatag tcgacaaggg tcgtagatac atgtatctgt   24900
tctccgtgtc ctgcgcggga atcacaggta ccgtatctat tatactcgtc tcccatcgc    24960 tgctcatcct catctgttac tatcgctgtg gccggcttct gatatgccca cgcggctttg   25020
aactcttgcc agaattcact gaggaagagg aggaaaaaga aaaattgtta acgcacaagg   25080
acattgaagt ccaggtgcct atccgcacgc ggcgactgct cgtcccttgg atccgggaga   25140
gcaaaatgtg ggtactacca cccccgctgc ctccacgacc tccccactta atagaattcc   25200
cgccgtctcc tccgccatcg cctggaccca tgcacatggt ggtctgcatg ccagcatgac   25260
ggactttgga ctctgagccc caagcggtac ggactacata ttttccataa atctacactg   25320
aacttgagca caaaaatact gacaatggac tggatataca gacttttata tgatccctgt   25380
acagatgtaa ataaaatgct tttatttaaa actggtccca atgttcttcg ggaatcatgg   25440 gatgggacg aggtacgcgg tagggagcaa aaccggcac atgggggga acatcgtcca     25500 gcagtagcac cagcggattg ggcaggggct gttgcggagg tcggtcgatg acgatgtcga   25560
```

```
tctccatcgg cagatccggt aacatctctt cgtctccctc accgaccagc actcggcgct   25620
gttctggatg tatatgattc tggaaaagcc tccgacgagc tcgcggcgcg tagaaagcca   25680
agcggcgcaa gggccggcga gcccgaaagt ccatgcgcac agatggcatg agtccttgag   25740
tgacggtggt gagctgggga cagggctac ctcccatcgc gacggtgaca gtggatccat    25800
gagagaggcg ccgcacgctg catggctaaa taccgtgaat cccctgacgt cgtctttcgt   25860
cccgaacgcg tcatgttggg ggcgaggcgt aaaccgtcga ggttgaaaaa ccgcgtatct   25920
gcggttcgtc cggactacgt tgtttttcag aagcggccac atgacctcga gatgtcgtca   25980
cccaaggtat ttaacggcac acagccagac gcgttcgtca gcagcgacgc cgacaagacc   26040
tcagcatggc tcggaggcta tggatactga gcttagccgt gaccttgacg gtggctttgg   26100
cggcaccttc tcagaaatcg aagcgcaggt aaacaggtaa gaaatacaaa aaataacgtg   26160
attgtgaacg cggttatcgt gttttttgcag cgtgacggtg gaacaaccca gtaccagcac   26220
taactccgat ggtaatacca cccccagcaa gaacgtaact ctcagtcagg ggggatccac   26280
caccgacgga aacgaagatt actccgggga agagtatgac gttttgatta cagacggaga   26340
tggcagcgaa catcagcaac cacaagagaa gaccgacgaa cacaagggag aacacaccaa   26400
agaaaatgaa aagaccccagt agcagcagat cccaagggtt aaagaccatg ttgactatct   26460 tgtttttat taaaaagctg taaggttctg ctctaaaaac accccgcctc cggtcttttt    26520
tcttttgtat tcggcacgcg aaacatggtt tcttcccata gcctgtctaa ctagccttcc   26580
cgtgagagtt tatgaacatg tatctcacca gaatgctagt ttgtagaggc tatgcgggat   26640
gctgcggcgg cgcgaccttc cctctccacc cagccccgtc aaaacacacg cgactcgagc   26700
ggttcgtatg aaaaataaaa aacagctttt tatttacagg aacgggaaa aaaaaggcac    26760 acggtccgtg ggagacgcgg gttcacgcgt cgtcaaaaag ttggtggtcc actccgtaag   26820
gacaggtagg cttatttagc ttccgcatgc tcctggttcc gtaataaatg ccgttttcgt   26880
ggcagcgtgt catgccgcga gtcacaaact ccatcaaact gtcggccacg atgcaaacgt   26940
gctgattgtt ggcagcaaag acgcgcatac agtcgtccac gaagaggttg atcacgtcgt   27000 agggcttac caaccagcct aaaggttcca cgtggttact gccgaccatg accctccagt    27060
cgttaatctc gctccagtcg tacagccgaa tcgtggagac gcgaatgacg ctgtaatcac   27120
ccatgaccat gagtcggccg cgatacgtag cacgccactg cgcgaacgcg tggatgtgca   27180
tgcagccggc cagcgctcta agcgaggcgg tgtgcggcag ctcctctggg acggtgatga   27240
agttgcagcg tcgcaaaccg atgttgagaa attcagtgat gctctcggcc acaaaggtca   27300
acgagtcaga gtagatgtgg tcggtccaca ggtacatggc gcccgaggcg cccaggtaca   27360
gttcagacgg cacgttgtga tcgcccttgt gtttaagaaa gttgtaggtg cagatgctgc   27420
cgacgaaacg cagcggctcg gggcagcaga ggtagctggc cagacgctgt gcatcccgtc   27480
cttcgtcgcg caccaagcgc cagcgacgcc ggataacgag gcagcggtct ttgggccaga   27540
ccagggccac gcgttgcccg ggtttccacg gtcgcgacgt cttaggaggc ctccagcggt   27600
cgagcagatt gagaaaacag tccttgatta ccgacatcgc ggtcgcgcgt cggtggacaa   27660
aaagaaatcg ggccgatccg gaaaaaaaaa aaaacgacgg caaacaccg ccgtgctcga    27720 gcgaagggtg gcggagggcc agaagatgcg gccttgacgg cgttggcagc gaaaaaattg   27780
gcacgcgagt caaacgggaa gtagcgtcgg tgttttatgc cccaagcagc gtcgtcgtca   27840
ctcgtggcgt cacagtcaac ggtgctgacg tcctttgggg cagtcgggca cgcgatcgta   27900
gatgccgttg tggccgctga aacgtcggtt ttcaaacagc aggttaagtc ccagacacat   27960
```

```
gaacgtgttg agattatctc ccacccggat gtagcggtcg tcgcgcacgt cgcaggcgta    28020
gacggccccg gtataggcga cgacgatggg gataaggtcg acgggccagc gcaagtgagg    28080
aaagggcgcg ttctcgccct tgaggctgac ggttcccagg ccgagaacgc gcattccgaa    28140
agcggttttg atgttgcgca gcaagtgacc gccttccacg ctgttttcga aacacctgag    28200
gttgcataga cgcagttccg ttcccggcgg gtacgtcaac ggcatgaact gcccgtggtg    28260
gcggatgatg aatcgcgcca tggtatccaa accgaggctc caggcgcgca acagcgggcg    28320
aaagtagcgc ttaaccaacg acgaggtcag gtagcgcatg cagtgcaggg tctcgacggc    28380
gcgcagcccg acgcgcgcaa actccatgag gttgcgggcc aggtagtaga cggcggtgtc    28440
ctcgcgtaca tagcaaaaaa catagccctc gtccgagatg aggcacacag cggtcttctt    28500
ctgctgatcc ggcgacaaca cgccctcgtt cacgaagcga cccacgaagg ccaggcgcgt    28560
ctggcaacac aggtagtgac tccaagcctt cacgtcctcc ggtttgaagt cctcgtccgt    28620
ctcgatctcc tgcagcacta ggttccagcc cggcggccag accacgggca cacctggcc    28680 tgcgttgatg cgcacgtaag cttccagaca gcccaggccg aactcggccg tgagcgccag    28740
gctagccaga tcgctcatgt gacgcgccga gtcagtgggc gagcccgggg gcccgtcgca    28800
caccacgctc cgtcttcttg tcctcaccgc ggccagcgtg gcgaggacac tttccgcgcc    28860
cgaggctgta tcttcggttt gcccgccgga gccggccctc actatataac gtcccgcccg    28920
ggtctcctcc atgtatgcag gtaagcaact gagccgaacg cacctcagca gacgagagga    28980
tgtcgtcgcg gcgtcgcagc tcgtcacgtc gctctggcga accctcgacg gtgatttata    29040 tccctcgag caacgaggac acgccggcgg atgaggaggc ggaggacagc gttttcacga     29100
gcacgcgggc gcgcagcgcc acggaagatc tggatcgcat ggaggccggt ttgtcgccct    29160
acagcgtctc ctcggacgct ccgtcgtcct tcgagctcgt gcgcgagacc ggcggcaccg    29220
gcgccgccaa gaaaccgagc gaaaagaaac gatcgtcgtc gcgtcggcaa ccgcagatcg    29280
cagcgggcgc gcctcggggc tcgccggcga cacccaaggc cggcaagtcg cctaaagtct    29340
cgcgaccgcc tagtgtgccc tcgctgcccg agaacggcgc cggcggcggt ggcgacgaat    29400
acagcagcag cggcggtagc agcagtcgca ccaccagtaa cagtagcaga agtaccagtc    29460
ccgtggcgcc aggtgagccg tccgctgccg agggcgatga gttttccttc tgcgacagcg    29520
acatcgaaga cttgnagcgc gaatgttacc gggtcagcgt ggccgacaat ctgggcttcg    29580
agcccagcgt ggtcgcgccg cagcacgtcg agtatctcaa attcgtgctg caagactttg    29640
acgtgcagca cctccgccgc ctcaacgaat gcatacccat gccggccttc gcgctcacca    29700
gcctcgtcga ccccgtctta aacaacgtag cgcctggcga gcgcgatctc acgcgtcgga    29760
taatcacgca cgcggtgatc atcaactatt actacgtggc gcaaaagaaa gcgcgccaca    29820
tggtggaggc catacggacc accgtgcggg gcgacacggt acgccaggta gccgcgcagg    29880
tcaacaacca gagccgttcg gggcgtgcgg ccgcgctagc gcttcacttt ctcacgtcac    29940
gaaaaggagt gacggacggc cagtacgcca cgtctctgcg gcggctggac gaagagctgc    30000
ggcatcgcgg cacgcccgaa tcgccgcggc tcaccgaggt ctaccagacg ctacgcgatt    30060
acaacgtgct cttctatacc gcccactaca cctcgcgcgg cgcgctctac ctctatcgac    30120
aaaacctgca gcggctcaac gagaaccacc ggggcatgct ccggctgctt tcggtcgaag    30180
agatatgcga agagcacacg ctcaacgatc tggcgttcct agtaggcgtc gagcttatga    30240
tcacgcactt tcaacgcacc attcgcgtgc tgcgctgcta tctccagcac cagctgcaga    30300
```

```
gcatctcgga gctgtgttac ctcatctatg tacaactgcc gtcgctgcgc gaagactacg   30360
cgcagctcag tgacgtgctc tactgggccg tcagtcaaaa ctacgactac gcgctctacg   30420
cgagcacgcc ggcgttgttt gacttttac gcgtcgtgcg tcagcaggac gccttcattt    30480
gcaccgacta cgtgtattgc gccctgcgcc tgctggcctg tcccgaccga cctattatcg   30540
gtgacaccgg cggcagcagt agctcccaac gcctcgtagg tgagtttatg gtgcgcgatc   30600
cgctgttgcg cgacccgcgc gccacccacc tgcgccagaa actcatcacc cgagacatat   30660
gcgtggcgcg gttgcaagcg cagccctcga gtcgacacat tccggtcgaa cacacgggtg   30720
tctcctccgt caccctgctc aaaatcttta gccaggtccc ccccgacgaa cgcgaagaag   30780
acacgttacg cgagatggct cttaaagcgt ttatggaagc gaacggtaat caccccgaac   30840
aaatctgccg atccccacca ccccgctgc cgccgcgcga ctatcctcaa cgcgacgagc     30900
gggaccgtca ccgtcgcgac cgccgcgaca gcggggaata ctgttgctga tggtggaacg   30960
aagcagcagg gcggaacggt ttatgataaa aagtcacagg aaagtatgtg ttgtttttta   31020
atgtaccaag aataaaaaat gcgtctacga ccaaagcggt gtgtggacgc tcgtcctctc   31080
tgtcttctcc gggttttttt tttcatgttt ttttttcttc ctatttttgtt acggcaacag  31140 cgctgatggc acgttgccgg cttcgaacat cgcgtcggtg atttcttgct tgcccggcgt   31200
cacacggtga cgtagcagcg cgcggctcac gtagcaggct gactcgcgga tgacctggcc   31260
gtcggcgtcg cgtcgcaggc ccgagcgttt gccgtgacgc agtctgccct gcgcagcgcg   31320
ctccacgtct tcaaagtagc tgtgtagcag gccgcgctcc agcagctgcg gcagcgagtc   31380
ggcggcgcgc accacaaagt tctcacggct gatctcgtag cacagcacgc tgccgtcggc   31440
cgccacgccg gccacgctgc ggtcccaact gaaaaggttg gcgagtccga tggtgccgat   31500
gacgcgcaac tgaccctggg tcaccaccag cagcttccag tattctacgt cgcgcgggt    31560 gaggatggtc tcctccacgt cgcagacaaa cagcgtgtag ccgcgcggat agggcagatc   31620
caggtggcga ccgcgctggc ggcgcataaa atcgtctaaa ttcaaaccgc cgtcgggtgc   31680
gcgcctgctc gtcatcgccg cgcctcgtcg gtcgatgacc ccacggtgct tataacgcgc   31740
cgccacggct tcatgtggcg tgacctccga cctcgtgagg ccgaaaacgg cgtacatgaa   31800
gacgctcaaa cttttgaatg tgggcccggt agcgcaccga gggccccggg gcggcgacga   31860
cggcgggtcc gagttccagc ggggccttgc ggcggcagcg gttagcctgg ttgctcagct   31920
cggcgtccga gagcgccgag ctgaactgcg gcagccgcgt gcgatcctgc ggcgcgtccc   31980
cgtgtcgcag cgagtgccag agcaggcgct ggacgcgcgc cgtctcgggc gtcggcggcg   32040
cgcgacagcc ccggcgcagc gtgaaaacgt gcaggcacaa cagctcgcgc ttgatgcgca   32100
gcgacacgct gcggtagtcg ggaatccgct gcaccagctc gagaaagtcg cagaaggtct   32160
ccacgaacgt gtcctcggtg aagcgaatgc gcttcagatc gtggacgtgt ttgcgaaacc   32220
gcgacagttc tcgacgttgc acggggttct gagcgagtcc cttgcgcagc agcgcagcct   32280
cgcctttaaa cagcctgatg agccgctgca cgtccccgct caacatacgt atacacgccg   32340
tgtactcgtg acgtatactg gcgcgcagca gccgaatgat acgcagggcc agcacggcgt   32400
tggaggccag gtacatggcg tagccgcgac gcggggttggc acaggccag cccgcgggga    32460 gcagaaagta gtcgtcgacc agcgtctgcg accagtcggc gaagcccagg tcacgtgata   32520
cgctgtcctg gacgcgggcc acgtcgccgg ccgtgaggtg gcggatcgcc ggcaggtgaa   32580
acgcgcccag gtgtcggttg cgctccagtc tcagctcggc gtgctccaaa cgggaatggt   32640
gggacgccac cgcggagggc gacaaagagg agtggtcatt gccgccgtgg ttaccgttgt   32700
```

```
ggttaccgcc gttgtcgcgc ccgtcgccgc actcgcaaaa ggccgcgtag aggtccttca  32760
acgccgcttc ggctcgcgcc ataaacgtgg cgtggaaaaa aacggcggcg cggtgcgtcc  32820
ggtacttgac gggcaacccg cggcacaggg ccgccggcag gcagcggccg atgagttcgc  32880
gctcctcggg ctccagaaac aggcacaggg tgccgtccag gcgcaggtac agctcctcgg  32940
tcatcgagca tagctgccgc aaataatggg tgcgcgtccc aaaggtcttg taatcgagca  33000
acgtgcacac cacgtattgc cccgtggcca cggccagagc gatgcgtttg gcggcgcgac  33060
tgatctctgg caagtactgc gcctcgtgca ccagacggcg gaaagcgccg gcgttgagcc  33120
agcgaaaatg ctgcggatcg ggcggcaagg gcacgcctcg aagcgcggcc cagacggcga  33180
ggtccgactc gagcgtcaga ccgcggatgt cgtacttgcc gtgcgccgta gcgcaggccg  33240
aatggaccag acagctgcgg cgaatgtaca ccatggcgtg cttgggatgt ttgggcgccg  33300
gcgttttctt tttctgaccg ccggcggccg ccagatcctc gggcgtgcga cacaacaggc  33360
cggcgcgcac agcctcctgt cgattacgaa tcggcgtcag gtaggcgcgc aggaactggt  33420
gacaaaactc ctcatcatca cgacagtcgt cgagatactc gtacgtggtg agcggatcac  33480
gaaataggcg ctcgtcaccg tcgtcatggt cttctttagc ctgctcctcc ggctgctggg  33540
ttggcagtgg aggcggcggc tgatccacgg ggttcatgac tgagaggaag aagaaggtgg  33600
cggcgaagcg acgcggagcg acggcggtaa agccaaacac cggctatata gctagtcatc  33660
acagtctcct ccttcacgac gccccgtgc cgctcacgct atccagcacg ctacggcccg  33720
aaaacacgta ctcgctgacg tcgtacgcgg gcgatgtatg gctgctcacc ggtttcgcgg  33780
cgacggttgc gctcgagtcc aacggcgaga agcaaaaacg ccgtgggcaa cgaaaccaga  33840
aggagccctg acggataaaa ccgcgcagcg tctcggccaa cttaaccagc atcgtaccgt  33900
acagcagtac gtgaatgccg ccgtgcgcgt ccataaatac ggctttgttc acgggctcca  33960
tccatccgat gactacaaag tgggcctgtt ctagcacgcc gatcacaaaa ttgttggcct  34020
cgtcggcctc ggccacgttc cacgagccga aagtgaaagt acaagcgggc gagccgccca  34080
ggcggatctt gctaccggcg tggagctgac atacgcgcag cagattggtg cggtcgtgca  34140
gtatctggga gagttcgtac atgcccgcaa aggtgtgctt aaaccacgcg ccctctacga  34200
tttcatccac gtagtcgcgc tcaaagaagc tgtacacggc aaagaggccg ttctcaaaaa  34260
actcgccgaa cgagagcccc agtacgtaca ccttgtcctc gccgggcagg tacgcaaagg  34320
cgtgcccgtg cccggagacc cagatctcgg gcgccgtgtt tgcgtccggc acgcattcgt  34380
acacactgac gaggccgata aagtacaagc ggccagcctg gcgcaggcac gagaagcgcc  34440
ggtaggtctt gtgatcgcgc accaccccaa agtactgagt gtcgcccagc atgatgccgt  34500
gcagcggcgg ccagcacagc gggagccaac gacccgccgt ggcgcgcacg tagcgctgca  34560
ggtgaacccc gctcgcacgc tcgcgcggct tcgggcgctt gtgggtccag gcatcacgca  34620
gaccgcgcca gatgctgctg aacttgggct gcccgcgcag atagagcgac gagagcgagt  34680
caaagtagcc cacgacgagc ctgtcgggag acacaagagc gcgaaaatca aacctagagc  34740
gacgacggtg aaaaaaccga ccagaagcgc gtgtctcaaa cacgctactt tcggttataa  34800
aaacaccgtc gccctatttc tgggcgtgtg tacactgatg actcacctac gcttttttgaa  34860 cggcagtctc agctcgggat tggcctcgta cagcgagctg cggtccacgg ggccgatact  34920
ctcgtagcga aagtcgtcga tgagcagcgc cagcccacg cgcacgaagc ccctgaggtc  34980
gcgcgccagc cgcaccaact tatcctgccc caccagcgcc gcgtacacgg tgcccgtgtc  35040
```

```
gccgcagaga atccgcacgc ggtgaaagaa ggtcttgtcc tcggcgccct caatttcgcc    35100
cagcggcatg acgggctcgc gcgtgtacaa cgaacgttga aagcggcgca gcatcgaggc    35160
cgagagcccc agatcgcgcg ccgtgcgcag cactagggaa tgcttctcgg gccagatgag    35220
ggtcagttgc gcctcgcggt gcgcctctac gtaggcgcag cgagcggcgg tgtcctcgca    35280
ggccagcaac tcgcggaaag ccagcaacga acgtaggtag cgaccgcgag cggaggcgcg    35340
cgagcggcgg cacagctcgg cccgatggtc gggatgcacc aagggcacgt tgggttgcag    35400
acgcgcgcag atggattcgt gcaccgggtc gcagcggatc atgcccttgg caaaaaatcc    35460
ggccagatcc gaggccaact cgtacaggca gtcctcttgc gcgtcgtagg cgaacacggc    35520
gccgtacgcg tccacgaaca cctggtaccg gcaggtggcg tgcgagaccg tgccaatgag    35580
atgcagagct cggaattcgc cgaaaaagtc gttctggcag tgctccagat cgatctcggt    35640
cagcgagtgc ggcgaatgct cgcccccgac cacgtagatg cactgcgagg gccagcccag    35700
cgatacgcac gagccctcga agcgccgcaa ataacgccgc aggccctcat agtcgcgtcg    35760
cacgcacaga tcgccaagt cgcgcgtgca aaagacctcg ggtaccaagc agcgtttgcg    35820
acgcggccga cgcgcgtgcc cgggcagagg aggaaggcgc gacggcggcg acgacgagga    35880
ggaagacgcc gtggccgccg agcagccctt gcgacggccg gacatgccgg cagtccgcga    35940
cgatccacag gagacaaaaa agcagaagca gcagtagtct cggcgacccg ctccaccccg    36000
tcctccacac gctcagccgc gactgagcgc cggggcgcgc cgctacttgg gttttttatag    36060 ccatctgccc cccgtctcgg gcacccggga gcgatctacg gagacctgac agcagttggg    36120
caacacaaga cagggaaata caaagacact tttaataaaa aacgagacta ctttgtgtgt    36180
gtgctccgta aactgtttat tctcccccctc cgtctcgctc tggatgggct ccgggtccgt    36240
caacacgcga cccgcgcggc aaaaggcacg ctgttgacgg cgcgagagcc cgtcgtgata    36300
gtccatcatg ccccggagat cgtgcacaaa gcagctgtcg ccgcgcagaa accgacgcag    36360
cgtctccacg tgctgcagct gtcggcgcgt atcaggagcc gtcatcgccg atgtcgtcat    36420
ctccctgaca ggcgcgtaga tggctccgcg agatcatgcg cgttttcaac cgccgtgaca    36480
catcaggtcc atcttgagct ggcgccgggc ctcgcgcagg tctcgcacgc gttgtgagcg    36540
ggaggcgagt tcggcttctt gctcgaactc ctgctgctca ctgtccgaga gggtgcgata    36600
aaaggcggca aagtcctcca agtcggctac atgcgcccctg ggtctgacgc tccaaagcgt    36660
acgcagtctg atgaagcgga cccatcgagc gtcacggcac gccgtcttga acgcggggcc    36720
cgggaagagg ttcttctccc cggcgcgctc gggccggcga ggccgacgcg gtttatatac    36780
accgtctcgg acggcgggac gccgagcccg cgccgcggcc gctcatccgg agacggcgga    36840
aaccgcggcg ccggaggaaa cggggaccgg caacgacggc ggcggcgacc agattatggg    36900
ggacaagccc acgcttgtga ccctgttgac cgtcgccgtg tcgtcgccgc caccgtcgtc    36960
gccgctgccg ctcgtcagct tcacggagct gctgttaccg ccgccgtccg tcgccgccgc    37020
tgcggtggcg gcaacagcga cgagcgaggt gggcgagaaa accgcggagc aagaggtagc    37080
ggctgcgggt ccggagaccg ggaatgagag aagagaaaac agggaggacg aaggagggga    37140
gacgaggacg acgggcacca ccgcggtcaa aaggtcgcac gacggtatcc ctcgccaact    37200
ggcagagcgc ctgcggctgt gccgccacat ggaccccgag caggactatc gtctgccggc    37260
gcaggacgtg gtgacctcgt ggatcgaagc gctacgcgac gcggaccgcg acaactacgg    37320
tcgctgcgtc cgccacgcca agattcaccg ttcggcctcg cacctgacgg cctacgagtc    37380
gtacttggtg tccatcaccg agcagtacaa cacggcctcg aacgtgacgg agaaagcttc    37440
```

```
gtacgtgcag ggctgcatct ttctctcgtt tcccgtcatt tacaacaaca cgcagggctg   37500
cggctacaag tacgactggt ccaacgtggt gacgcccaag gcggcgtacg ccgagctctt   37560
ctttctgctc tgctccacca gcgagagttc cgtggtgctg caaccgctca tcaccaaggg   37620
cgggctctgc tcgtccatgg cggtttacga cgaggaaacc atgcggcagt cgcaggcggt   37680
gcagatcggt tttctgcaca cacaactggt catggtgccc ttcgtgccgc acgcctgccc   37740
gcattacgcc gtgcctttca cgacgccggg aaagccgggc tgcggcggtg ctccgagcgg   37800
cgttgcgggg ttggaggagg cggcgccctt tggacgggtc agcgtcacgc ggcatggcgc   37860
gacgctgctg tgtcgcgtgg accatctgac ctggatcagt aagcgcgtaa ccacgtacgg   37920
acacaaaaaa attacgcgct acctcgcgca gttccgcggc acgatggacg acgacgaggc   37980
ggcgctaccc ggcgaggacg aggcgtggat cgcgtccaaa aacgtgcagt acgaattcat   38040
gggtctcatt ttcaccgtca acgtggattc actatgcgtg gacgcggaac agcgccaact   38100
gctgggcacc gtgccacct cccttctgtca ccgcgtctcg gacaagatca cggcgcgcaa   38160
catgccgcgc gccttttcct tctacttgct aacgagcgcg cagcgcgggt acgacctgcg   38220
atttagccgc aacccgtcac tcttttttag cggcgacgcg ctcaactgtc cgcttctcaa   38280
cgagcccaac gtgttttcgc tcacggtgca cgcgccttac gatatccact cggggtgca   38340 accgcggcag acggtggagt tggacttgcg ctacgtgcag atcacagacc ggtgtttctt   38400
ggtggccaac ttgccacacg aggacgcctt ttacacaggg cttagcgtgt ggcgcggcgg   38460
cgagccgctc aaagtcacgc tgtggacgcg cacgcgttcc atcgtgatcc cgcagggcac   38520
tcccatcgcc acgttgtatc aaatcaccga gggcgacggt aacgtgtact cgtacaatca   38580
ccacacggtg tttcggcaga tgcacgccgc cggagcaacc acgttctttc tgggcgacat   38640
gcaattgccc gcggacaact ttctcacgtc tccccatccc tgaccctccg tccgtcctcc   38700
tttcccgaca cgtcactatc cgatggtttc attaaaaagt acgtctgcgt gtgtgtttat   38760
taactattcc tccgtgttct taatcttctc gatcttttgg aggatgttct gcacggcgtc   38820
cgacggcgtt ttggcgcccc ccatgccggc agaacccggt tgcggccccg taccgctctt   38880
ctggggcgac gataggtcga aagccaccgt tttcatgccc gtcgtgctct tgacggggga   38940
acctacggcg gcggtccccg tcgagcggcg tgattgcaaa gccgcgctcg ccccgggttt   39000
caggatggag ggggaggcca caggcggcgc attcgatacg ctgcttttgg ccgtagacga   39060
cggtgggtaa acgtggttta ccgcgggata cgtcggcgtg gtcgaggcgg cccggctggt   39120
gccggacagg cgacccggcg cgctaccgct cacggggacc gagggcggtc gacctaccac   39180
cgccttgccg cccaaagtag gtttcaaaga aggaacaccg acgcggctgc cccgaccttt   39240
caccggagac ggaggggcac tcttggccgg ggacggagag gctgacgaaa gcatggacag   39300
cggcgacgtg acggggaca cgacatcatc ctccgtgggc gacaaaacgg acgccgaggc   39360
tgacggctgt cgagccgaag cggaagaggt tctcgcgcca gaagtcacgt tccttgatga   39420
cgttgtttta gacgaagccg gttgaggttg caacagcgtg gcgggtaccg tcgacggcgt   39480
gcccgatacc tgtttctcta cccttccctg aaccggtgtc gacgtcaccg tctgcgctcg   39540
ggcggacgcg tgcggcgtcg cgactcgctt gcccagcacc ggtttctggc tcgtggatgt   39600
cgtcgtcatt ggagacgata acttagcttt acgtattctg gacggcgtcg actgctcggg   39660
cgtctgactg ggaggcgaaa tgacgtcgtt gtaatcggac gacggtgttg tgtgtcccag   39720
gctgacgacg gagccggtgt ccgaggagtc gtcgtcttcc tcctcgctgt cttcgaccgg   39780
```

```
tgactctgca gtttggtccc ttaaagccca aacctcatca gcggcgttct gagacgctgt    39840
ttgtgtcacc gcggcgcgtg gagtcgacgg cctccgaggg gtggtggaca cgttgttttg    39900
agaagtcgtg gaagtcgtag gcatcctgaa gggattgtaa gccaggtgag gattcttgag    39960
ggcccacgcg cgttcgcgcg gccagttggc ggggttcata tccccgggca acggcgccgt    40020
cggagcccag ggcgagttac cgttgaccgg ggtttgggta cccgcgaagg taggtgtcgg    40080
ggccggagcg ggggccgtgg aaggattgac aggcgtcggc gtgaggatgg cagcgccggc    40140
gccagcaggg acgttaactc cggcgccgaa cgtcaacgtc ggttgctcga acttgtacgc    40200
ggtggtgacg ggcggtttgg cgctcgtctc ggtatccgtg atgtccaccg gcgtgtcggt    40260
gaaacgcgga tcttgacggt tgggggggata gccatccgag ctgtcggaat cctcgtcgcc    40320
cgagaaaaga tcccctcttg tctccgtgag cggcctcacg tcccacgcgc tgtcccgacg    40380
gacccttccc gggctggcct tggttacctg cggggagacg agactgaaag ccgcgtgacg    40440
ctgttgttgc tgcgggatgt tcaagggacc gctggtcggt ttctgactgc ccgaggataa    40500
catgccgctg aaaatgctgg aaacaccgtt gccactagcg gcgcccttgc cgctagttcc    40560
cggtttcttg atgggcgtaa agatgttttt ctcgtcatca tcatcgtcgt cgtcctcatc    40620
ggcactggag ccaaagagcc tccgggaggc gcccggttta cgtgtcgggg gcggcggttg    40680
ctgctgacgt tgctgcaggt tctgctgcct ctcctcccaa gccttcagct gctgtttctc    40740
acgctgcacc acctcgtcgt ccacccgttt ctgccgctcg cgacgctttt cctcttcgtc    40800
gtaatagccg acggccgccg aacgggcggc gtgggcgtcg gcggccggtg ccagagaacc    40860
atgggcctcg aagcggaacg gtttgtgtcc cttccaggga ctgcgatcc agctccagcc    40920 gtccagcggc tgcgtgggga catgtttctt gggtaccgac gagaaggctg aaccgccgcc    40980
gagcgagagg agattggcgt catcgtcaaa ctccaacgac ggcgggcgcg cgcccaaaaa    41040
ggtgtgcgcc gactgcggga agctgtccac gtagatgtca aagtcctcga tgagcagctc    41100
cagcagcgtg tcgccgagt caccgttttc cacggcgtgt ttgaggatat tgcgacagta    41160
gttggaatca aggaaaggc acatgcgcag ctccttgacc agcagcttgc agcgctcctg    41220
aatgcgcgcc agacatttgc gctccagctc ctcccaagac ctgcgcacgt tcatgatgag    41280
acggcccgtg tacacgagct tgttgacggc gttgaccagc gccgtgttgg cgtgccggtc    41340
caggttaagg tcgagcggtt tcacgcagaa catgttacgg cgcacaccct ccaggttttc    41400
ttcaatgcgc tgcacctccg tatccttgag gtgcacaaaa gcgatgggtt ccgtctggcc    41460
gatggctgtg accagcgtct cgcgcaccga catcttggcc agaatgaccg cgcttacgag    41520
cgcgcgctcc acaatctcag catcgtggcg tacgtccgta tcgaattcgg tacggtctag    41580
cacagccagg tggtcacgcg ccttaccacg atcaccgaac gggtaagtgt agccgcgacg    41640
cgccacggcc gcgcaacgca cctcgaactc ctcgagaacc gaggagaggt cggggttgtg    41700
gaaacgcagc tcgcggtagt atcccaacca aagcatgagc tcgttgaaca gcaccgtacg    41760
ccggtgcagg cgttttttcgc cacatttttt caggatcttg ggtgtgcct cgagatccac    41820 gtcgggcttt tgcgtgagat ggcgcagaaa gttgaccagg gccaccacat cgcgccgctg    41880
tagaccgata aactgcaaac tcatgctggc ttttctccag aacccggaag cgtcgtcgcc    41940
ccggactgcg cccgcggtct gctattcgtc cacgatggac accatcatcc acaacaccac    42000
ggtgagcgcc ccacctagag ggagggggg tagtttaata gcggaggcgg atacgcggtt    42060
ttcactctgg caccgctgac ttgtttcttt tgttttttgc tccgtgtgct tgttccgcct    42120
agaaccgcag taccagtact ccgcatgtca acagtacctg taacatgacg gagacgctat    42180
```

```
ccgccatccg cactacagaa gccgtgatca acacgttcat cattttcgtg ggcggcccgc  42240
tcaatgccat agtgttggtc acgcagctgc tcacgaaccg tgtattgggc tattcgacac  42300
ccaccatcta catgaccaac ctctattcca ctaattttct cacgctcacc gtgctgccct  42360
tcatcgtgtt gagcaaccag tggctactac ccgctagcgt gacttcgtgc aaattcttgt  42420
cggtaattta ttactcaagc tgcacagtgg gctttgccac cgtagccctg atcgccgccg  42480
accgataccg tgttcttcat aagcgtacct acgcgcggca gtcgtatcgc tctacctata  42540
taattttgct attgacttgg tttgccgggc tgatctttc catgcccgcg ccgtttaca  42600 ctacagtagt gatacataat ggtacagatg agaataccaa tgggcacgct acctgcgtac  42660
tgtacttcat agccgacgag gtgtacacgg tactactctc gtggaaagtg ctgctgacgc  42720
tagtgtgggg cgccgcgccc gttatcatga tgacgtggtt ctacgccttc ttctattcaa  42780
ccgtacagcg cgcatctcag aaacaaagga gtcgcacttt aaccttcgtc agcgtgttac  42840
tcatctcctt cgtggcgcta cagacgcctt acgtgtccat catgattttc aacagttacg  42900
ccacggccgc atggcccatg gactgcgaac acctgacact gcgacgcacc attggcacgc  42960
tgtcacgtct ggtaccccac ctacactgcc tcatcaatcc cattctgtac gcgctgctgg  43020
gtcatgactt tttgcagcgc atgcggcagt gtttccgcgg ccagttgctg gaccgccgcg  43080
ctttcctgag atcgcagcag aatcagcgag ctacagcgga gacaaatcta gcggctggca  43140
acaattcaca atcagtggct acgtcattag acaccaatag caaaaactgc aatcagcacg  43200
ccaaacgaag cgtgtctttc aattttccca gcggtacgtg gaaggcggt cagaaaaccg  43260 cgtccaacga cacatccaca aaaatccccc atcgactctc acaatcgcat cataacctca  43320
gcggggtatg agctttcctg ttactttatt cagaaagcac cagaacccgt cgccatttcc  43380
cctcatatac ggtacacgtc cccctgatct gtcatcacgg tacacagatt tcgcccgact  43440
gcggacaccg acggccaatc gcgtggcgta ggagtggcgc cccggcttca ttataacgcc  43500
acgtcggagc ccctgcgcgc cacaacgccg tccggcgcaa cttctgtctc ggcacggtac  43560
gataaaaacg acgtcccccg tcgacgttgt tttctccgag cggtgatcgt tcccgtccct  43620
ctcctccctc cgcggccccc acggcggcgg cccgctcgca cggacctata ctattaccgc  43680
cccaccgccg tcgtcgtcat gaacttcatc atcaccaccc gagacttctc caacgacgat  43740
tcagtcctgc gagccgccga gatgcgtgac aacgtggcag gctcgatttc caaagcgtac  43800
aagggtacgg tacgcgccga aggcaagaag aagctgctgc tgaagcactt gcccgtgccg  43860
cccggcggct gctcgcgccg caacagcaac ctcttcgttt tctgcaccga gcgcgactac  43920
cgcaagttcc accagggcat cgcacagctc aagcgcgcgc cggccgaact ggacccccac  43980
gagatccagc aagtcacggc cagtatccgc tgccgcctgc agcccagtct ccgcgagccg  44040
cccacgccgg ccgacgagct gcagacggct gtgtcgcgcg tgtgcgcgct cttcaaccag  44100
ttggttttca cggcccagct gcgccactac tgcgagcacc aggacaaggt ggtgagctac  44160
gcgcgcgacg agctgactaa acgctgcggc gaaaaatcgg cgctgggcgt ggaggtgcat  44220
caactggtag ccctgctgcc acacgagcgc caccgcgaac tgtgccacgt cctcatcggc  44280
ttgttgcacc agacgccgca catgtgggcg cgctccatcc gtctcatcgg acacctgcgc  44340
cactacctgc agaacagctt cctacacctg ttgatgaact caggtttgga tatcgcgcaa  44400
gtcttcgacg gctgttacca cagcgaggcc taccgcatgc tcttccagat cggtcatacg  44460
gactcggtgt cggcggccct ggaactttca cacagcgcgg cggccgggcc gcccgaggcc  44520
```

```
gatgagaaca acgacgaagg agaggaggac gacgacgagc tccgtcacag cgacccggcg   44580
ccgcttcacg agtccaagaa gccccgcaac gcccgtcgtc cccgcacacg cgtgccgcct   44640
cacgagcaaa agcccgaaga aaacgaggag gaagaagagg agctgtttcc ctcctgcaag   44700
gcaaccgcag cattcctgcg ggcagaaccc tccgtctcca acgacgacgg caacggcggc   44760
gaacgctgcg acacgctagc gaccgccctg cggcattgcg ccgacgaaga agacggacct   44820
ctagccagcc agaccgctgt gcgggtcgcc gcgaccccct caccttcagt caccccagcc   44880
cttacccccg tcacgtcccc cataaccccg ttgtgtattt aacgtcactg gagaacaata   44940
aagcgttgat ttctcaagtt ccgctctggt tttggtttcg ttttcaaagg gagccccatc   45000
atggcccaag gatcgcgagc cccatcgggc ccgccactgc ccgttctccc cgtggacgac   45060
tggctcaact ttcgggttga cctgtttggg gacgagcacc ggcgcctgct gctcgaaatg   45120
ttgacccagg gctgctccaa cttgtgtggg ctgctcaact ttggcgtgcc cagccccgta   45180
tacgcgctgg aggccctggt ggacttccag gtgcgcaacg cttttatgaa ggtaaagccc   45240
gtggcccagg agattatccg tatctgcatc ctcgctaacc actaccgcaa cagccgcgat   45300
gtgttgcggg acctgcgcac gcagctcgac gtgctgtact cggagccgct taagacgcgg   45360
ctgcttagag ggctcatccg actctgccgc gctgcgcaaa ccggcgtcaa gcccgaggac   45420
atcagcgtgc acctgggcgc cgacgatgtg acattcggcg tgctaaaacg agcgctggtc   45480
cggttgcacc gggtacgcga cgcgctgggg ctgcgcgcgt ctcccgaggc cgaggcacgc   45540
tatccgcgcc tcaccaccta taacctgctg ttccacccac cgcccttcac cacggtcgag   45600
gcggtggatc tgtgcgccga gaacctgtcc gacgtaacac aacgtcgtaa ccgaccgttg   45660
cgctgcctca cctccatcaa acgcccgggc tcacgcaccc tggaggacgc gctaaacgac   45720
atgtatctgt tgttgacgct gcgacactta cagctgcgac acgcgctgga gctacaaatg   45780
atgcaggact gggtggtgga acgctgcaac cgtctttgcg acgcgcttta cttttgttac   45840
acgcaagccc ccgaaacgcg gcagactttc gtcacgctgg tgcgtgggct ggaacttgcg   45900
cggcaacaca gcagtccggc cttccagccg atgctgtaca atctgttgca actactgacg   45960
cagctgcacg aggccaacgt gtacctctgc ccgggatatt tacatttcag cgcgtacaag   46020
ctgctaaaaa agatccaatc ggtctcggac gcccgcgagc gcggcgagtt cggggacgag   46080
gacgaagagc aggagaacga cggcgagccg cgtgaggccc agctcgatct cgaagccgat   46140
cccacagcgc gcgagggcga gctcttttc ttctccaaga acctgtacgg caacggcgag   46200
gttttccgcg tgcccgagca acccagccgc tacctgcgtc gacgtatgtt cgtggaacgg   46260
cctgaaaccc tgcagatctt ctataacttc cacgaaggca agatcaccac cgagacgtat   46320
cacctccagc gcatctatag catgatgatc gagggcgcct ctcggcagac gggcctgaca   46380
cccaagcgct tcatggaact cattgacaga gcacctctgg gccaggagtc ggaacccgag   46440
atcacagaac atcgcgattt atttgccgat gttttcgcc gtcctgtgac cgacgcagct   46500
tcttcgtcgt ccgcgtcttc gtcgtcgtcc tcagcatctc cgaattctgt ttcgctgccg   46560
tccgccaggt cgtcatccac acgaaccacc acgcccgcgt ccacgtacac ctcggccggg   46620
acttctacca cggggcctctt gctctcctct tcttccttgt cggggtcgca cggcattagc   46680
tccgcggacc tggagcagcc gccccggcaa cgacgccgca tggtcagcgt aaccctcttt   46740
tcgccctact cggtagccta cagccaccac cgacgtcacc gaagacgacg cagcccgcca   46800
cccgcacccc gagggccggc ccacacacgt ttcagggac ccgacagcat gccgagcact   46860
agctacggca gcgacgtcga agacccgcgg gacgatttgg ccgaaaatct acggcatctc   46920
```

```
taaacgcggt tttcctcttt ttatacgtgt ctgtctcagg acgagacgtt gatatcaata    46980
aaaataccgt caacgtggtt ttctaacagt gtggttttct ttattgacca gcggagtaca    47040
cagtttacga gtaaaaaaga cagggaaagg ttatataaaa tgctgtgtta tatacaaaaa    47100
catgcacata aacaaacggg accaccgtgc tcgtcatcct ctcctcaatc agttgttcat    47160
gtaggcgtgt ggcggggtga ggggcggcat gccgttggcg gcgccgggaa taatgtgtcg    47220
tcgaccggcg tcgcacacct tgaaacgccg tcggcgcacg cagcggtcgc aggacgggat    47280
atcccagagg aagcccatat aggtctcggg gtcctcgtcg tgaaagcggt aagagagttc    47340
aaggtggtgc aatgagcccg tccgagctcg cagcttctgg cgaacaccct ccacgtcatc    47400
ggtgcacagc gacagtgctg ggctgtcaca cagggcctga agctcctgcg gccacaggtg    47460
cgtggccagg ggcgagtccg tcgtcaccag tttgacgcag tgcatcaggt tctcggtgat    47520
ggcgtcgtac aggcgactct cagcctcctc gtgcgtcatc acgttccgag gcagcgacag    47580
ctcgtcgtcg tcatcctcgt caaacatgat catgggtca ggggtttttt tgggatgttg    47640
acaggtgggt gtcttttcca gacgcacgat ggcctcacgc cggctgctga acggtggtt    47700
tcggtgtccc ttcttteeea tgacgcaggt gaacataacc acgtcctcgg ccagacggta    47760
gacggcgtcc atggcggggt cgtagccgta gacgacgccg aaagtgtcca ccaagacgta    47820
ctggcgtacg agaaactctt tgcgttctgg cacctcgtgg cccagcgcgc ccaacagctg    47880
gtgataacag gtgatgcgcg gcacggtacg gatcatgagc tccatggtct ggatgctgcc    47940
gcccgcgcgg acaacgctga aggatgtttc cttgaacttc ataacctctg tgttgtgggt    48000
ccagaaggcg aaatgggtgt cgggacactc atcgaaaggg tcgtcgatgc tgtaggaagc    48060
gtagccccgc ttggtcacct cggccgacag gctctccacg tcaccgcggt agagcatgac    48120
ggcgttccag tagtcgtcgt actgcaccat gggccgctgg tagtcgcgca tagtgtggaa    48180
gtggtcgcag tgacgaaagc catgccgcag aaagtccttc atggtggccg ccagctcgta    48240
gacgcagtca cgcagatcat cgtagcagta gatgccgccg cgctgcccga tgagcacgat    48300
gagttggtag cgcataaagc ccggacccct gacgaagcca aagggtgca ggtattcctg    48360
acagcagacg taagcacctg gtggagaaat aagaaaaatc cacacacgtt gaaaacacct    48420
ggaaagaacg tgcccgagcg aacgtcctct ttccaggtgt cttcaacgac gtggggctta    48480
ccttgcgaac agacggtgcc catcttgccc acgaagggcc ccaggcgct gcgcgaacgg    48540
agctggatga agcagcgttc gggccaggcc acgtgcagcc gggtgccgca ttcctgctcc    48600
agaaagtcgt tgagaccgtt aaagtccccg gctcggatgg cgatgcagcc gtaggccatc    48660
aacgtgtccc gtaggtcgtc catgacggac tcctctacct tcgctcgccg acgctgcgct    48720
tctccagcca ccgctgcggt cgacagactc ctccgtccgc cttcggagaa ctacggcgcg    48780
gcggcacggc ctttatagac actatcagcg ttgacgtcag acgatccgat gaacgtcgtt    48840
ttttgtgctg gaacttccct cgtcccgaca aatgtagcgg aaatcttcaa gcaaatcgcg    48900
acgaagtccg atgaggagga tgcaaaagag gctgagcaac gcgatgctgc ccgccgccac    48960
agtacatatg ctcaacaacg cccagtgtcc caacgcgcga cttttggctc ggaggagagc    49020
cgaacggcgt tttttccaca tgatggataa cgtagtccaa tacctccatc cttcgcattc    49080
cgatgtccac atgggaagcg atgtcatgtt agttcccgta acgttgtgt tttttttatt    49140
gtttttcgta agcttaacgc tcctcttgag aaatcgcgga cacatgtctt gtagaaaaat    49200
ataatcactt tccgcatata ccgttaagat tgacatcaca gtgatggtgt tgttttctga    49260
```

```
agaagtcacg ttatcggtga cgttggtttc ctcccaattt acggatgact caaacggact   49320
cgtgcgcgcc agtgctcgca atacgtaact gcggccggta aggttaagcg tcagctgtcc   49380
catggtaata ttagtgtcat ttgtaaaaca cgcaacctcc ccgtagacct cggtgacgtt   49440
gatatcgcgg ctctcgttca ggatgcgcag gggaaaccag ccttccaggt ggtactgaaa   49500
accaaacgtg agcatgacgc tgtgccactg ccgacgtgat tgccgaaacg ttacgtttaa   49560
aggcagtttt gattcggctc cggcgcaggg gccgttgtag atttgcgtat gattgcacgt   49620
gcagtttaac cggcagttca tactcgtggc gttggaagtg acgttaatgt ccgtaccgtg   49680
gtacgtacat cggacagaaa caccgtatcc cgtgctccaa aacagcgtca acaacagcca   49740
cacagacacc tacgtgggga cgacacggga cttttattg acggagactc atgtttacac   49800
cctccccttt cccataggta aaacccacg tttataacac acgttgtttt tacctgaaac   49860
ccgcgcggcc cgtggacgcg acaaaaaacc gcggcactag aaagaaaatg aaacaagtat   49920
gtttattaag cagcatgtgg ggctaatagg ggggataact gaggtatagc aactattaaa   49980
aaatactaca aaaaaaaaaa gctgaacatg gtcatctagc agcaaagttc tccttctaga   50040
ccacgaccac catctgtacc acgtcgccct ccccggccgt gtacatcaca tccttcacca   50100
cgaccggcgg caacggcggc gacgaggaca actcgctctc gacggaggcc gggacgacag   50160
aggacggggg ggtggtggcg gcggaggacg gagggtggt gacggcagcg gggtcttctt   50220
ccgacacggg cgacggcaga ctcggcggcg cggacagcac ccgttgcgcc ggagcgtgag   50280
aaggctgaac cccggtggcc tggatgtggg ccaacgaatt ggctcgcagc gaatcgcgat   50340
ccacgaaggt cataggaatc ttcccttcgc ggatccgccg ctcagattcc aggatggcgc   50400
gcacgtagct gttcaccgat ttggcaaaag tgcgcggccc ctccgtattc ttgtcgcgac   50460
gcgcttccaa cacctgcttt tcgtagtcca gctggtggaa gaccatcacc aggtcgtcca   50520
tggtgtgcgc gtgctgacgg acgtgggagc gcacctccac cgggaacaga gcgttccaat   50580
actccagcac tatggcaccg tgccagaact gcgccatgct gggagccagg aaaaacagga   50640
taccggagtc gtaggcgaac acgtcccact tgggcgtcat gaacaacacc agctgacgcg   50700
tgggccgcct cgaagcttcc tcccaggcct cgatgacccc gaacatgatg agctcctggt   50760
ccaacggggg gcagtgtcgc tccagccaac tgatcttgct caggttcatc tgcagaaact   50820
cgtaggaggg gtcgcagatg cacacgtaga gacccgagtc gtgccgcagc ctggctccgc   50880
gcttcatcag tttcctcacc gcgtagcgaa gcgccacctt gcccaacgcc gacgcctgga   50940
tcagtccccc cacgtccatc tgcgtctgtc gccactcggc ctcgtccagc aggctcatga   51000
tagcggcggt gctatgcgtg gtcgtagtca tcctttctat ccttctctat gaatagcagc   51060
aatagcggta aagtcccttc ttatactatc ccggagtctg tggttttttt gtttaccct   51120 gcttactggt gagactgctg ggggccgttg tgctgcagca gccgagcttg tcgccgccgt   51180
tgccacagga accggtgcct ccgcagggc ttttgaggg cctcgcaggc ttctcgcgca   51240
agtcctgaga ggccctcggc gtcgatgggg ttcacctcgg gcgtccgagc ctcgtttct   51300 tcttcttcat cctcccttc ctcctccgtg tcctcccgct ctgtgtcctc cgttacgctc   51360
tcctccccgg cctcggccaa gagcgcggcc accaagtcca cggaccgctc ggtctccgag   51420
ttctcaccgt caatgacgcc atgttggcgg cgtaaccggt gccgagaacg ccgggtgagc   51480
gcacatgctt ttttcttct taaccaaggc gggagaggat cttcaaggcg ttttcgctgg   51540
atccagcggt agctaaagta ccaaaaggcc agcaggccca cgctacctaa cagattcacg   51600
tagactggag acataattaa agaaagaagt gaaacccgcg tgtgggtctc acgtcgtctt   51660
```

```
gaaacaccgt cttatataca tgaagatgcc ggacatgacg cgcccaagac acgtggggtt   51720
ttccccttag gcgacccgat ttcttaagat gtttttcatc ttcgcacgcg atgtactaca   51780
tcaaagggtc ggctgaccga ccgcattgac gcacagtttc cgagtacgcg cgtctcggag   51840
cacctgacgg tgagccaccc agctcacgcg gataggaaac aacactgacg tgaggggcaa   51900
ttcacgtcac tgacggctga cgggaataag acgggtgagg gatttccacc ttttcttaa    51960
gtgtgactgt ccttacggta aatcgcacct gtgacctctt aaccctcct ccctggtacc    52020
cgataacagt gaaaaacaca caccacacgt cacgacaccg atcgattttc tttattctta   52080
gtgtgatgat aggtaagggc actcgtgagg atgtgcagtt atcattatca agccttcttc   52140
aaggcgtagt gatgatcgtt gggcagaacc cccaggctcc tagcgatctg gaatagaag    52200
gaggagaacg agcccagggc cagaatgccc acagtgtaca tggcccaggt ctccagaccg   52260
aacgtggcgg gtcgcagctt cagatggtag gccacccgct ccgagagttg tgaatgctcg   52320
ttcaggcaac aggactgcag atgggtgagc ccaaaagcgc tttcgtttac gccgcgcacg   52380
tgcaccgtct gggccggaca atcctggtgt tgcgcgcgaa agtggtccag gcaggagact   52440
ccgtctgcgc ggcgatgtgt gttgttaccc acttcaatca acagcgtgtt aacggcaaga   52500
tgacgcgaga acgcgacgac ggtgttgctg gaggtctggc ggcagcagta caaaggcgcc   52560
cgtcatgaag acgtaggcag gggaattccc atattttat ggcttctttt aaaagtctgt    52620
gtccgactcc attcggcgct tttcccaaac cgtggtctcc tcgtcgtccg actcggtacc   52680
caggagatgg taagtctttt gccgcacgta gaaagctttc aacgtggagc aaaagatgag   52740
aataaagacc ccgaaaacga aacaaaccac gccgatcatg ccgatgcaga cgttcatgtc   52800
gacgtagccg gcggtgctgt tggcggtgcg gcaaaagagt gtcatgtcgt acgtgcacaa   52860
aaaacaccac acaccacagg ccaggtcgta gcgtagttat tattccgtag cagcaatgat   52920
ggtacagtca agcacatgat ctatttcccg ttatcccgat gttgacaccg tccccgttgt   52980
attggaattg tcccggttaa tcaccacggt gaacaccacg gccaagaaaa tgatccctaa   53040
tatagcgacc actaagagag caaaagtcca tttccagccg ttgtcaaagt acgccccgt    53100
ggtgggatgc atggtggcgg gcatttccat catatccatg tcgaacgtgt gtcgcggcga   53160
cggcgaacta accaggcagt acggggtcg atagggcggt gggctgcagt caggtggtgg    53220
cggcggtggc gtggaaaccg tcgtcgggca cagacccatg gcctgctcgt aggtgggggg   53280
cgcgtcgtcg tgatcccggt cgcggagcat cggcgtgggc tccatgtcgg tggcagtgac   53340
ggcgacggtg gtaactgtgg tggagacggt accgacggcg tccgcggctc accttcgagc   53400
aaagagcccc ttcttttttgc gcaaacgacg gcaaaacagt tctctgggac agccggtggc   53460
gcggtaagcg ggtgccacgc tttcagggtg tgtaaaacag tcgcgggcga agcagtagtt   53520
gttgcagaac cgcaagaacc cgacgcgaaa gaagcccagg agtccgcgcg ccagaaagtg   53580
cgcctgccgc gtctcgggat gcacgccgaa gacgcgccg ctctcgttca ccagtatgga    53640
gatgtccagg cgctgctgtg actccaccgg cacggcccgc accacaaata cctgcagcac   53700
gttcagcgag cacgtctctt ttaaccagtt gccgtgggcc ggatcctcgt aagtctggct   53760
cccgttcaag acgaccgtcg tcagcgcctc attaccgtct cgccagctga agatggaacc   53820
ctcgcgcttc atgcacaggc gccacagggc cagcaggtcg cgcgccaaca tgaactcgcg   53880
acccacgtcg ccgccggtct cgaagcggac atagcccagt tcttcgcgca gcggcgcgta   53940
gttgcgcagg ccctcctgca cgaagccgcg gaaaccggac cgcgacacca ggtacagcga   54000
```

```
ttccaccacg ggcgagtaga cgtagacgcg gccgccctcg ccgatgagta tgggtagcgg    54060
tgggcggccg atggcttcgc aacgactcac agtgcccacc ggcagcagga acttgtcgca    54120
gcacaggaag gtcttctcca aacctttaat attgagatgt ccaaagtagc caacgcgtaa    54180
caggtcgcag taggtgaaga accaaccgtt cggccagttg agacgcagca ccgtgccact    54240
gacgcgacga accagcttct gcaggtcctt gcgggcgtcg gcggtgacag agcagcggaa    54300
ggtctcgttg accagctcga cagccagcgc gtcctccagc gtgcgttcct tcatctcgtc    54360
gttaatgctc tggcggcgcc gccggatttc gtcgaaacgg gccgcggagg cggcgaccga    54420
cgcggaggtc gtccgaacgc cctctgtgac gctgtcgtcc ggccagtcaa gaaagctaag    54480
gctggcgctg cgccgcctaa agtgtccgat ccgcgcggga cgtcgctgag gaacggtggc    54540
tggtctgctg gggcgggtac ggccgcgggt gtccgcggac acgttagtta tacacgggat    54600
tgagtcacgt ggcacgttgc cagctgaaac cgccgtcgtc tccgccggcg ttttctccat    54660
cgcgggaccg cgccgtgcgc gcaggccgcg tgcccgggca cgcgctctag ccgcactttt    54720
gcttcttggt gttagggacg aactcgaacg ttacagaatc ctcgctgtcg ctctcctctt    54780
tcgcgtcgtt gaagtaattg ccggagttgc gatccaaacc gccgcctcct cctcctccgc    54840
cgccgcccga tccacctttg gacgtcaggt aactggtgat cttgtgctgc tcgtattttt    54900
ccttggagga aagaccgtga tcgtgatcac cgccgccgcc accgctgctc attttccgcg    54960
taccggaacc accgccgcca ccgcggtcgt gcttcttgcc gccaccgccg ccacctcctc    55020
ccagaccgcc gagacccatg ggctcgttca tgagatcgtt atccagaccc gggccgtcgt    55080
cgtgcagacc gccggcattg gccagcgaag agaggctgcc gccaccaccg ccgccgccac    55140
gcgacttgcc gctgttcccg acgtaatttt tgtcgaaggg atcgccacgc tggaaaggtt    55200
cctcggtgag aaagttctcc acggcgaaca gaccgttgcg gctggccacg tacaacagcg    55260
tgtcgtgctc cgtaactata cgcagcgtgc acggtagttt ggtgacggcg caattgagca    55320
gcgtctggta gaagttcttc agctgcacgt tgatacgcat gttttttacg ccgtggaaac    55380
tgacgcggtt attggccgtg aattccagct cgctgccgtt ggtcaggatg aacttgatgg    55440
ccggcggacc ggcgtgcacc agaatctgca cggtgcccgt agggcagggc gcttttttaa    55500
cgttacgctt gacgcgggta tgcggcccga tccacttaag caggtcggcc accacgccga    55560
aatcgagatc cacgtgcacg gccgaattct cgctttcgcg cacaatgtct tgaccgtgca    55620
cgcaggccga gctgaactcc atattgaaat cgggcgcgca catggagatc ttggccgaca    55680
ggtccgagat gtcctgcacg tagaacttgg tcaggtcctt gctggaggtc aggtacataa    55740
aattgccgag cagcggcgtg gaattgttaa tggtcttggg ctgaaacgac ttgtcggtga    55800
tgtagaggca tgagctgtta aaagtgattt ttgacacgca atgactgcgt accgtttgca    55860
agataagcga cggcgtgggc aagaaggtaa ccgtggtgtt ctccttgagc gcacggatca    55920
cagatcgcag ctgctggata gccgtcttgt acggcttcag ccgcagcgcc agcgtcggtg    55980
gctccgagag gcgcgtcttg cgatccatcc cggacagcgt gcaagtctcg actaaggagc    56040
gggcgcgagc gagcgaaagt tttatagaga gcacacacga cgaccgggaa cgctgcgaag    56100
acgcccggcg tctaataata cagcgcgccc gagccagcgg gccccgact aagaggcaca    56160
gtacttatat actccgacct taaagcgcca gtggtaccac ttgagcatcc tggccagaag    56220
cacgtcgggc gtcatccccg agtcatagta gaaaaccagg gccacgcact ggtccacaaa    56280
cacgctcagt tcacggccg ccatttccac gtcgttttgg atcgccggcg ccgcctgaa    56340
cagacactgc gtcgccttgc cctcctcctg gtgctgctcc aaccacgcgt aattcaccac    56400
```

```
gggcacgcgc agcggcctcc gcaccacagt ggggaagtaa cactcacggt tgggcgggca    56460
caatgaccac accgtctcct cctcgaacac ggtgccgcgc gaagcccata ctgacggcgt    56520
cacgccccac agatgcgcca cctcgtcgtc gggacccacc gccagaaact gacagttgcg    56580
caatccgaac tcgagcatgt cggcgcgcag cgcttcccag cgcgcgctgg cgatggagag    56640
ccgcggcaac cgatacaatt cgaaaatgaa tttgccctct tgatagatgg tgcgttcgaa    56700
ccattcgcag cgtggcaaac ccgacttgca caaatcgacg ctagcgcgca ccgcggcaaa    56760
gtacatgtgc tcaaagatgc gctcgatcaa gtcccaagag gcaaagtacg taaaccctaa    56820
ccgcataagc gcagtgtgca ggccagccac gccgatgtgc agcggacgca gttttttccag   56880 cgcgctctct acccaccatt cggacgccga cattagcgcg tccaagcgcg cgttgcccca    56940
aaccaccgcc tcggtcacca actcgcgcag cacgctcaaa tcaaagtaac gtcgcgtgtt    57000
ccccaaaacc acgtcgggta gatgcagctt ctgctcgtcg ctacgcgcaa acacgcagcg    57060
agccacgttc accgtcagcc gctgcaccgg catgtcacac tcgccaaagt ggcacgacgc    57120
catatcggga ctcaagcacg gcggcaggca cacgctgtcg gccataatcg agtacttgac    57180
tacgtgatgg acaaagacca ccgaggcacg gcccttgagc gcgcacagca acatcttttt    57240
cagaaaatcg tccgtgttca cgaccacctt ggggcacgat tgctcgcagc gcgaatactc    57300
tttctcgaaa gccgactcct gacccagatc cgagagccgc cggggagacag gccgcccgaa    57360 cagcgagtag cgctgctcac gcgcacggta gcgcttcatt aacacgctag gcacgttgaa    57420
agcgtagcaa accccgtca actccgacgt gctttctttg agaataaagt taatcacgcg    57480
gatagcggcc acgtcccaca tgtccacaaa cacacgtacc acgggtcgat gcacctcctt    57540
ctcgcgtatc aaatcgcagt atcccccag gcaacgaatc acgctgttca catcggcgtt    57600
gagtcgcgtt acgttcaccg acacagaaac gccgcaactc aaggtactca tccacttgca    57660
catggccgcc caactggcgt cacgcgagaa agggtcggcc gagatcagaa agtcgtactg    57720
cggcacgcga tcgaaaccca cggtagacat ggtgaaggta gacagcgaca gctgcccatc    57780
gcgacagcgc ttcaacaccg agtccaacac ttcgccctcg aaacgcgcat ccagatggaa    57840
acgatagatg cgcgagtgcc tactgttctc gatagcggcc gtcaacgcca cggcgatgcg    57900
caaaaacacg ccgcccgggc tctcgtcctg tccatgcagt tggcgacaca ccttatccaa    57960
acacaaaata gccgcgtaca agcccagca accggccaat tccacaaaac gcgccgtctc    58020
ctcggccagc ttgggtagat cctccatgtg acgcagcaca aaacggcgca ccgactcatc    58080
gcacagctcc gaagcgtaac acagtggcgt gcggcttcg cgcgcccagt tggctttgaa    58140
ataaaagcga cccaacagca gatcgcaacg cggcgagtga cgaatcagac agggaccgtg    58200
gcgcatgatg agctgaaaca gcctgaaact gcccaaaccg gcactgtgtc gcgacacggt    58260
gtccatctcg cgccacagcg cgttcctgtc ggacggcagc tcccgcgccg gctcctgtac    58320
gccacaaaag cgaaacttgc cccagtagcc gtgacaatga cacttttgc ccatcaacat    58380 gcgcgtagcc tgtatcggcg gcgatacttt gcagagtgaa gccccgaaat cgtcctcctc    58440
ctcgacactg tccagctcca tcctggtcgc gccggccgga ttgaaggtgc tcagaccgct    58500
actcacacgt ccaccgcgac tgggcacggc gggaccgctg tcacgcgtca acgacagcac    58560
agacggcgtg ccgtcgggag acggcgactc gggacgccaa ctgacgacgc cgccaccact    58620
cgtaaaaccc gctacacacg ctacgccgct cgatacgttg gtatttccag cggacgcttc    58680
cttgtcaccc ccgggcagcg gccccctcctc gagctcgctg tcatctcccc cggtagtatc    58740
```

```
agcggcggcc tctgccgacg attcctccgt ctcggtttcc gagccgcggc ttggaatcct    58800
acctggccgg caccgatgtg cgggcaccga ggacacccgc tgttcctcgt ccgcgtcagc    58860
cggattcata agtttacgag gaaaataaca aagaaatcag gtagatttca ataaagtgag    58920
tctagatggc gccgataact acggtttata aagtctgtgt gcgatgtgtt tattttttc    58980
ttctgtgtct cctccccgta tgctgtcagc gccgctcaga cgaattctcg aaagtctccc    59040
aattcgacgc taaagttgtc caaacggacg acggacagtt tgagttcttt gtgtaccagg    59100
aacgaggtgt gaatgtcgtc agccaggcac cagcccagct tttgtatgac cccggtacac    59160
agagggatct ggcgcgggcg cgtgatgcga cggttgacaa agctacagcg ctcgcgggcg    59220
aactttccgc gtgcaacgtc gaccagggtc tgccagtgtg cgatgctgga ggtgagcacg    59280
tagatgccgg gacgtgtttc gggcccgtca tagtcataga cgatgattaa atacacgtat    59340
tgcagccgtc cccgggtctc ttcccacgtc aggtacatgt ctttcggtat catcaacgcg    59400
aacacctccg ttttgagcgt gttgtaaagg tagccgcgca tgacgcaggt gagcaacgag    59460
gtgatgccca gcgagacggt cttaacgcag cccagcgtct caaggcggcg gtgcagcaga    59520
tgcgggccca ggtccagcca ctgcagcgcg gcgcgcgcgg ccgaggccgt gtacacgctt    59580
tcgagcaggc agcgcgtgct ggccgagacg ttggaggcgc gaatgcctaa caggtagagg    59640
ctgatgtaga ggtgtcgcgg cgagtcgcaa cccgtctcca tgcggatgag cagcgcgccc    59700
ggctgcgcct cgaactctac caggccctcg ggcacgaaga aacgcgccgt gagcgcctgg    59760
tgatcggcgt ggtagaggta gcgcaccgat atagtattta cctcgcgttt ggctttgagc    59820
gccgtcacta gttcattgtc ctcgtcggcc gggtcgcgcg gccgtttggc caccgcgcgc    59880
gcgtccatga tggcgaggcg cacggtagat ttcaaaaagt tgatagagca gctgcgggca    59940
cgggccacgg acaaagcgga ggcgttaaat accgtgagcc aattggagat cggcgcggtg    60000
gatgcccagg acgtgaccgc gagcgccgtg cgcgccttcg tgggtgcgtt gccgagctcg    60060
ggctaccact ttggcttcgt gcgtcagaac gtggtctttt acctcctaag ccacgccacg    60120
gtacagacgg cgcgcgaccc gctgtacgcc gccgagcagt tgcacgaaca gctggaccgc    60180
ttcctgcgac accagcacga cggcggcggg gacgaggacc ggttgccgtt ctaccacaac    60240
ggggccacgc tgacggcttt ccagaagctg ttgcagaccc tgcgcgagat ccagaccgta    60300
atagccgaac agagcggcgg caccgcgcg cggcggact tgatcgccag taacaacgcg    60360
tcggccgagc gccgcggcaa gaagggcggt tcgagttccg ggggccagca gccgctggtc    60420
cgccgggtga tcacgcagct ggaaacggct gccacggagg cgcggcccta cgtcaattgt    60480
cgcgccgtgg ccgaactcct ggacctgacc taccagcggc tcatctactg ggcctgcacg    60540
ctcatgccct acgtgttgtt tcggcgcgac accgacaccg aactggacac ggtgcttctg    60600
atgcattttt tttacacacg ctaccgttcg gttaacggcg atttggccgt ggagtttcaa    60660
aactacgtca agaacagcgt gcggcacatg agctctttcg tcagttccga tatcgacggc    60720
gaccagaagc ccggtgccga acacatgcgt gacgtcagct acaagctgtt cgtgggtaat    60780
ctgcaggcgc gtgacgccag cggcctcatg tttcccatca ttagcacgcg catctccacc    60840
gtgaaccttt acctgtcgcc cgaacgtatg ttttccacc cgggtctgat ctcgcgtctg    60900
ttgagtgagg aagtttcgcc gcgcgccaac ctagacgctt acgcgcgcgt gtgcgatcgc    60960
gtgctggaag accacttgca tacgccgcga cgcgtgcagc ggctactgga tctgacgcag    61020
atggtaacgc gactggtgga actgggtttc aatcacgata cctgcgcggc ctacgcgcaa    61080
atggcgctga tccagccggc cagtcagaag agctcgctct ttgtcagcga gattcgcgag    61140
```

```
aaactcatac agatcatcta caattttttac acgtttttca tgtgcctcta tgtgtacagc   61200
cccacgttcc tgttcgacca ccggcggcgg ttgattttgg agcagcatcg atccacgttg   61260
atcggctcca aggaggaact acagcacgtc tggagcaacg tgacactgaa cgtcaatacg   61320
cactttgcgg ttcagtacac ggaagaagac tttgaggcac atacgaaggg tgccacggag   61380
gcagagcgcg agtacctgta tcgggacctg cacagcaagt ggggcgtgca cctgtttacc   61440
ttgcgtccgt ctcgcggcgc ggccggcgcg gcctcgcctt tgcctccgct tgacggcgtc   61500
acacgctccg acatcttacg cgaatgcgcg ctcgttaatc tgaacgaagg ccgcgtcaac   61560
tacgcctccc tgctagcctt cagccatcat cccgagttcc ccagcatctt cgcgcagttg   61620
gtggtggtaa ctgaattttc ggagatcttt ggtatcccgc agggcctgtt tcaagccgtg   61680
ggttcgccgc gtcttttcgc gctcattcag ctgtgtcgtg tattgttgcc cgagcaggtg   61740
acgctgtacc agaacctggt ctccatttac aacctgacca cctttgtcaa gcacatcgac   61800
gccgcggttt ttaagacggt acgcgattgc gtcttcgaca tcgccacgac cctcgagcac   61860
ctcagcggtg tacccgtcac gcccaatgtg gacctgctgg ccgagctcat ggcgcgctcc   61920
gtagcgcata acctgtacac caccgtcaac ccgctgatcg aggacgtgat gcgcagcagc   61980
gccggcagtc tgagaaacta tctgcgacac acgcgactct gtttcggtct ggcgcgcggc   62040
cgggcgcgcc tctcggagga cggcgtgacg gtgtacgtgg aggtacaggg tcagtacgga   62100
ctgcgcgtac ctaccacgcg tttcgtagaa cagttgcgcg aactggttcg ccgcgatcgg   62160
ctgttggccg agaatctgcg cggcttaaac gagcgcctgc tgagtgttcg cgtgcgcgta   62220
cgtcagatca gcagcgacac agaggaagta agccgacacg ccaagggtca ccgcacggtg   62280
gcccagatga gcaaggcgct caaaaagacg gcctccaaaa tcaaagtgtt ggaaacacgc   62340
gtgacattgg cgctcgagca ggcgcaacgt tccaatggcg ccgtcgttac cgcggtgcaa   62400
cgcgcgctag ccgtctttga cgtactaagt cgcgagaact tggaacgccg cggcgcacag   62460
ctctgtctga cggaagcgac gagcctactg caccgacatc gcgcgctagc gccgatgacc   62520
tggcccgcgg gcacgggcgt tgcggcggcg gccgaagcgg atcgcgcctt acgcgagttc   62580
ttggaggcgc cctgggaatc ggcgccccaa ccgccgcgac tccgcatgac gcccgacacc   62640
gatcacgaag aatcgacggc aggcgcgacg tccgtaccgg aggtcctggg tgcgcgctac   62700
gaacccgcac acctggccgc gagcgaccta ttaaactggt acatcgtccc cgtaagccag   62760
gcgcagcagg acatcttgtc ttcgatcgac ccgcccgccg gctcgacatc ggtgtccctg   62820
ccgccggcct cgccatgaaa gtcacgcagg ccagctgcca ccaggcgac atcgctcgct   62880 ttggagcgcg agcgggcaat caatgcgtct gcaacggcat catgttccta cacgccttgc   62940
acctgggtgg aacgagcgcc gtcctgcaga ccgaggcgct ggacgccatc atggaagagg   63000
gcgcgcgtct ggacgcgcgg ctagagcgcg agttgcaaaa gaagctgccc gccggcgggc   63060
ggctgccggt ctaccgactg ggcgacgaag tgccgcgccg cctggagtcg cggttcggcc   63120
ggaccgtgca cgcgctctcg cggcccttca acggcaccac cgagacgtgc gacctggacg   63180
gctacatgtg tccgggcatc ttcgactttc tgcggtacgc gcacgccaaa ccgcgtccca   63240
cctacgtact cgtcaccgtc aactcgttgg cgcgcgccgt ggtcttcacc gaggaccaca   63300
tgttggtctt tgatccgcac agctccgcgg aatgtcacaa cgccgccgtg tatcactgcg   63360
agggtctcca tcaggtgctg atggtgctca cgggcttcgg cgtgcagcta tcgcccgctt   63420
tctactatga ggccctttt ctctacatgc tggatgtggc gaccgtgcca gaggctgaga   63480
```

```
tcgccgcacg tttggtctcc acctatcgcg accgcgatat cgacctcacc ggcgtcgtcc   63540
gagaaagcgc ggacacggcg gcgacaacga ccaccgccgc accttcctta cctccgctgc   63600
ccgaccccat cgtcgacccg ggctgccctc ctggcgtggc gcccagcatt cccgtctacg   63660
atccctcgtc ctcacccaaa aaaacacccg agaaacgccg caaggacctc agcggtagca   63720
aacacggagg caaaaagaaa cccccgtcca cgacgtccaa aacactggcc accgcctcct   63780
cctcctcagc gatagcggcg gcctcttctt cgtccgcggt accaccgtcc tacagctgcg   63840
gcgaaggggc cctgccggcc ctgggccgct accaacagct ggtcgacgag gtagagcagg   63900
agttgaaggc tctgacgctg ccgccgttgc ctgccaacac cagcgcctgg acgttgcacg   63960
cggcgggtac cgaaagcggc gctaacgcgg caacggccac ggcgccgtcc ttcgacgaag   64020
ctttcctcac cgatcgtctc cagcagctca tcatccatgc cgtcaatcag cgctcgtgtc   64080
tgcgccgccc ctgcggtccg caatcggcgg cgcagcaggc ggtacgcgcc tatctgggcc   64140
tatccaagaa attggatgcc tttctgctca actggctgca ccacggcctg gatctgcggc   64200
gcatgcacga ctacctgagc cacaagacca ccaaaggcac gtactcgacg ctggatcgcg   64260
cactgctgga gaagatgcaa gtcgtcttcg atccctacgg acgtcagcac ggcccggcgc   64320
tcatcgcctg ggtggaggag atgctacgct acgtggaaag caagcccact aacgaactgt   64380
ctcaacgact gcaacgtttc gtaaccaagc gaccgatgcc cgttagcgac agcttcgtct   64440
gcctgcgacc cgtagacttt cagcgtctga cgcaggtcat cgaacagcga cgtcgggtgt   64500
tgcaacgtca acgcgaggag taccacggcg tttacgagca cttggccggc ctcatcacca   64560
gcatcgacat tcacgaccta gacgccagcg atctgaaccg acgcgaaatt ctgaaagcgc   64620
tgcagccgtt ggacgacaac gccaagcagg aactctttcg cctgggcaac gccaaaatgc   64680
tagagttgca gatggacctg gaccgtctga gcacgcagct gctaacgcgc gtgcacaatc   64740
acatcctcaa cggcttttg ccggtagagg acctgaagca gatggaacgc gtcgtcgagc   64800
aggtactgag actcttttac gacctgcgcg acctgaaact gtgtgacggc agctacgaag   64860
agggatttgt cgtcatacgc gaacaactga gctacctcat gacgggcact gtgcgcgaca   64920
acgtaccgct actgcaagag atcctgcagc tgcgacacgc gtaccagcaa gccacgcagc   64980
aaaacgaggg tcgcctcacg cagattcacg acctgcttca tgtcatcgag acgctggtgc   65040
gcgacccggg cagccgcggc tcggcgctga cactggcctt ggtacaggag cagctagctc   65100
agctggaagc gctaggcggc ctgcagctac ccgaagtgca gcagcgccta cagaacgcgc   65160
aactcgcgct aagccgcctc tacgaagagg aagaggaaac gcagcgtttc ctcgacggac   65220
tctcgtacga cgatccgccc accgaacaga ccatcaagcg acacccacaa ttacgcgaga   65280
tgttacgtcg cgacgaacag acgcgtctgc gactcatcaa cgccgtactg agcatgttcc   65340
acacattagt gatgcgactg gcgcgcgacg agtcgccgcg accgacgttt tttgacgccg   65400
tcagtttgtt gttgcagcaa ctgccacccg actcgcatga acgtgaggat ctgcgtgccg   65460
ccaacgccac gtacgcgcag atggtcaaga aactggagca gatcgagaaa gccggtaccg   65520
gcgcatccga aaaacgcttc caagcgttac gggagttggt ttactttttc cgtaatcatg   65580
aatatttctt tcaacatatg gtcggacgac tgggcgtcgg acctcaggta acggaactct   65640
acgagcgata tcaacacgag atggaagaac agcacctgga acggctggaa cgtgaatggc   65700
aagaagaggc cggcaagctc acggtaactt ctgtggagga cgtgcagcgt gtcttggccc   65760
gggcaccgag ccatcgtgtc atgcatcaaa tgcaacaaac gttaaccacc aagatgcaag   65820 acttttaga caaggagaaa cgtaaacagg aagaacagca acgcagcta ctggacggct   65880
```

```
accaaaaaaa ggtgcagcag gatttgcaac gcgtggtgga cgccgttaag ggcgagatgc    65940
tctccaccat cccgcaccaa ccactggagg ccacactcga gctgctcttg ggcctagatc    66000
aacgcgccca accgctacta gacaagttca accaggactt gctgtcggcg ctgcagcagc    66060
tgagcaaaaa actagacggg cgaatcaacg agtgtctgca cggcgtgctg acgggtgatg    66120
tagagcggcg ctgtcacccg caccgagaag cggctatgca aacccaagcc tcgctaaacc    66180
acttggacca aattttgggt ccgcaacttc tgatccatga gacgcagcag gccctgcaac    66240
acgccgtcca tcaagcgcag ttcatcgaga agtgtcaaca gggcgatcca actacagcca    66300
tcacgggcag cgagttcgag ggcgactttg cacgctaccg cagcagtcaa cagaagatgg    66360
aggaacaatt acaagagact agacaacaga tgaccgagac tagcgagcgg ctagatcgct    66420
cgctgcgcca ggatcccggg agcagctccg tcacgcgtgt acccgagaaa cccttcaagg    66480
gtcaggagct ggcgggtcgg atcacgcccc cgcccgccga cttccagcgg cccgttttca    66540
aaacgctgct agatcagcag gccgacgcgg cccggaaagc gctcagcgac gaggccgatc    66600
tgctgaatca gaaagtacag acgcagttgc gacaacgcga cgagcagctg agcacggcgc    66660
agaacctgtg gactgatctg gtcacgcgcc acaaaatgag cggcggactg gacgtgacca    66720
cccccgacgc caaggcgctg atggaaaagc cgctggagac acttcgcgag ctgttgggca    66780
aagccacgca acaactgccg tacctgtcgg cggagcgcac ggtgcgctgg atgctggctt    66840
ttctggagga agcccttgcg caaatcacca cggaccctac gcacccgcat cacggaagca    66900
ggacccacta ccggaacctg caacagcaag ccgtcgagag cgccgtgacg ctagcgcatc    66960
aaatcgaaca aaacgcggcc tgtgaaaatt ttattgcaca gcatcaagag gcgactgcca    67020
acggcgcgtc cacgccgcgg gtcgacatgg tccaggcggt ggaagcgatc tggcagcgac    67080
tggaacccgg acgcgtagcc ggcggcgccg cgcgtcatca aaaagtgcag gaactgttgc    67140
agcgcttggg tcagacgcta ggcgacctag aactgcagga aacgttggcg acggaatact    67200
ttgcgctgtt acacggcatc cagaccttca gctacgggct ggactttcgg tcgcagttgg    67260
aaaagatccg cgatctgcgg actcgttttg cggaactggc caagcgacgc ggtacacgtc    67320
tctccaacga gggagccctg cccaacccac ggaaaccgca ggcgacgact tcgctgggcg    67380
cctttacacg cggggttgaac gcactggaac gacacgtcca gctgggtcac cagtatctgc    67440
tcaacaagct caacggctca tcgctagtct ataggctgga agacattcct agcgtgcttc    67500
cgccaacaca cgagaccgac cccgcgctga taatgcgcga ccgcctgcgt cgtctatgct    67560
tcgcgcgtca ccacgacacc ttccttgaag tggtagacgt cttcggcatg cggcaaatcg    67620
tcacgcaggc cggcgaaccc attcacctgg tcaccgatta tggcaacgta gcctttaagt    67680
acttggcgct gcgagacgat ggccggcccc tggcatggcg gcgccgctgt agcggcggag    67740
gactcaagaa cgtcgtcacc acacgttata aagccatcac ggtagccgtg gccgtctgtc    67800
agacattgcg cactttctgg ccacagatct cgcagtacga cctacgaccc tacctcacgc    67860
agcatcagag ccacacgcac cccgcagaga ctcacacgtt gcataacctt aagctctttt    67920
gttatctggt gagcaccgcc tggcaccagc gcatcgacac gcagcaggag ctgacggccg    67980
ccgatcacgt aggcagcggc gagggtggtg acgtagggga acagagaccg ggccgcggta    68040
ccgtgctgcg cctgagtctg caagagtttt gtgtactcat agcagctctg taccccgagt    68100
acatctacac cgtcctcaaa tacccggtgc agatgtcact accctccctc acaactcacc    68160
tacatcagga tgtgatacac gcggtagtca ataacacaca caaaatgccc cccgaccacc    68220
```

```
ttcccgaaca ggtcaaggcc ttctgtatca cccccaccca atggcccgcc atgcagctca    68280
ataaactgtt ttgggaaaat aaactggtac agcaactgtg ccaggtaggc ccgcaaaaaa    68340
gcacaccgcc tttaggcaag ctatggctct acgccatggc cacgctggtc tttccacaag    68400
acatgctgca gtgtctgtgg ctagaactga accccagta cgccgagaca tacgcctcgg     68460
tgtccgaatt ggtacagaca ttgtttcaga ttttcacgca acaatgcgaa atggtgaccg    68520
aggggtacac gcaaccgcag ctccccaccg gagagccggt gcttcagatg atccgcgtgc    68580
gacgtcagga cacaaccacc acagacacaa acacgaccac ggagccggga cttttagatg    68640
ttttttattca aacagaaacc gccctagact acgcgctggg ctcctggctt tcggcatac    68700
ccgtgtgtct cggcgtgcat gtagccgacc tgctgaaagg ccaacgtata ctagtagcgc    68760
gccacctcga atacgtcg cgagaccgcg acttcctccg catccaacgc tcccgggatc     68820
tcaatctcag tcaactgctc caggacacgt ggaccgaaac gccgctggag cactgctggc    68880
tacaagccca aatcagacgg ctacgcgatt acctgcgttt ccccaccgc ttagagttta     68940
tttcccctagt catttacaac gcacaggacc acaccgtcgt acgcgtgctg cgaccgccct   69000
ccacgttcga acaggaccac agtcggctgg tgttggacga ggccttcccc accttcccgc    69060
tgtatgacca agatgataac tcatccgcgg acaacgtcgc tgcgtctggc gccgctccaa    69120
caccgccggt accttcaac cgcgtgccag tcaatattca gtttctgcgt gaaacccgc      69180
cacccatcgc gcgagttcag cagccgccg gccgacatcg tcatcgagcg gccgcggccg     69240
cagacgacga cggacagata gatcacgtac aagacgatac atcaaggaca gccgactctg    69300
cattagtctc taccgccttt ggcgggtccg tctttcaaga aaaccgattg ggagaaacac    69360
cactatgccg agatgaactt gtggccgtgg cgccggcgc cgccagcacc agtttcgcct     69420
cgccgcctat cacggtgctc acgcagaacg tcctcagtgc tctagaaata ctgcggctag    69480
tgcgattgga cctgcgacaa ctggcgcaat ccgtacagga cactattcaa cacatgcggt    69540
ttctctatct tttgtaaccg acactgacag tagcgggtaa taaaaacaat aggcttttta    69600
tcgtttttta tgttacaaaa caacgtatca cttttacggt gatttattct tgctattctt    69660
tttcccttg ggctgtcagc gccgggtgcg cgacacggct accatgcgca acaggtccag     69720
cttaaaggcg cacttgtcat taaacaggct ggacatgcgc gtgtacttgc tcagcatggt    69780
ggccaacacc gggtgggtgg cctctgatat ctcggtcggc agctccaaaa cgacgttgac    69840
gacgtgacgg tgttttcgt cccgcttgtt ggccaccgtg gtcccggcg cggtgttaga      69900
catggggcag gccgtggggg gaggacgaag aggaagccgc tgctaaaccg ccgcgcgcct    69960
gctgcacaat gtggccgccg acgtggcagg cggtctgttt aaccagcgcg cagccccgac    70020
acagcggggc gccgtcttcg cttttccaaac agctgtcgcg gtactcgccc gtctgacagc    70080
gcgcgcacag caggccgtgc ccgtgcgaag tgaggcgcag gagacgcggg accgtcacgc    70140
cgcgtaccac cacagtggag tcgcaggtgc gtgccgcgca gggcagaatg acgtcgaaag    70200
ccagccggtg atcgtacacg gcacaagccg cgttgaggcc cagcacggct tccagcccca    70260
cgcgtacgca gcgctgtcca aagagcgtct cggagacgag ctcgtagacg cgctgccgca    70320
ccacccgctg actgccgcag agcgagcagt gcacgagctc ggcgtgcgtg ttgaagatga    70380
cgctctttc ttgacggtcc cgataatgaga acatcgagtt gagcggaaag ttttgctggc    70440
agtgtagctt ttccttaccc aggttgaggc agtgtccgca ctgccgacag accacggcca    70500
ccagcgagcg cgcgtccaga tggcgctcgc acttgagtcg acacagacac cagagcggca    70560
ggtcgatgac gctgccgatg aggccgccgc gcagcgcggc gctgagtgca aagaggacga    70620
```

```
tcttggtggg ctctacgtga cgcgcctgct gtccggcgcc cgcgtgtcct accgccgcag   70680
ctgccgccgt cgagcctcct ccgcgcgtct cgtcgtgcag acccagtgcc cgcaacggca   70740
ccaggtatcg cggacacgtg tcgcaaaacg tctgcaccgc ttgtcgggcc agtacgtaga   70800
gcgggtttcc gcagggtacc ttcccggcgt gccggcgcaa ggctgcgatg aggcccgca   70860 gctgcggcga ccgcggctgc cgttggtgac accactggtt acggtggtat acggccaaat   70920
cagcgcgggc gtcgaagcgc ttggcgcgta gtagtgctag gcacggcgag ctggtggggt   70980
gaagcacggg cagccgaagg tccacccga aaggaaacg gtgaaggtca cctagcagcg   71040
aggaggtgac accgtccaac aacgcgtgca gccgctcggg cgggtagagc cgcagacggc   71100
gcagcaggta gtcggtgtcg tagcgttcga aacgcagaaa ggccatcgtg cggacggcca   71160
cggtgtgcag acagtccatg ctgtagacgt aagcgagaaa cacaaagtag gcttggtca   71220 taaccatacg ctgaaaaagc gccgtcaccg cctcccgctc ggcctgccga cacaccagcc   71280
attcgcgcag gaagcgttgg tagagacggt cgcccagctc gcgattcaga aagcgcttat   71340
ccgtcacgaa gagatgaagg acgcaagaac gtggcacgtg atgcaccagc tgctgctgga   71400
ggaccgccga cgtctgcgcc gcaaactgcg ccggtggctg cgacgtttct accgccgctt   71460
cctccggctg cagcgcaccg cggccgatca ccagctgcac atggaaatgg tcctcgtgaa   71520
cgcagagggc gcgaagaga cggcgcagag cctggtggaa ctcctcagtc gcggtgtgcg   71580
gagcgtgtcg gagacggcga ttggccatga ccgcgccaca gcagagccag caccagcagg   71640
agagccagca ccagcgggcc cagagtcgcg aagcgcgcgg gcagccacgg cccagactgc   71700
ggtcgcgatg gcccggagcg cgctcgccac cacgatgacg gtgcccaacg ataaccagtc   71760
cgctccaagg acggcgcgca cggcggagac ggcggatgac ggtgatgggt cgacaccct   71820 cgccgacgac tcacgtgctc ctccagaggc cgacgcgcgg accctccgac atcctggccc   71880
gccgctgccg ctgccgcctt ccttctccc gccagagcca gcaactcctc ctcctcttca   71940
tcagcgtctc cctcgcttgc gcatccgcat cgtcccatac aggcctcaca acgacacagc   72000
cgccacgacc ccgccgccat gggtggcggc ggcggccgag gcccggcagc ggcgccgcca   72060
gcggcgacca tggtgggaga gcaactcgga tgacgaggag gaggaggagg gggagatgcg   72120
gtccgagagg accgctttcc cgccgttcgc gtgagcgcgg ccgacatgcg ggcgcgccac   72180
agggacggac cgctgccgct gtgactgctt acggtgacgt ggttccggac cgccaacgac   72240
gtcgacgcgg cttcttggc gtacagctcg cgcagcagat tctcgtactc gccctcgttt   72300
tcgggtccga aggcgatgag ctcgatgttg aagaccgacg ccgaattgga tttgcgcacc   72360
acgcacttcg tcagcactcc gtaggccgag ggcttgatct cctcgatgtc cttgagcgtg   72420
acgatgagcg actcgttcac cttaagcaca ttgaactcac ctacgtggcg cgccggcgag   72480
acgagcttga cgggcgctcg cacaaaacag cagagggaga cggcacagcc agtgttttta   72540
aagataaaac aaggcacgtg gtctgtgcgg ctctcccagt agctgagcag atactcgaca   72600
caatagaccg tgtctgtctt gagcatggcg tcgcacaccg agtaattggg gttttacag   72660 atgaggccgg cgtcggtgac gcgcagctcg ctgggaccca acttgaggat acgccgcgtg   72720
gcctgcacca gatcctgatg gagaaccttg ttcatctcca tcgcaccgac gccaccgccg   72780
atttatttac ccggcgccgg ctcgtctttt ccctccagga ttccgttaat gtccatgagc   72840
ttgctgacga tcgccgttaa tagttgcgtc ttctcacgga ggatctctcc gtgactgcag   72900
gtcgcgcagt cgccgtgcac gtacttgagg aaggcggcgt acttctgacc cgcgttcacg   72960
```

```
aaatttaagc gcgcgtccag agagggcagc aacagatcgt agacgcgcgg cagcatcggc    73020
tcgaactgta atagcagatc gtcgtcaaga tcgggtagcg cgtgcccgtc ttcaccgtcc    73080
tcgtcgtcac cacctccccc ctcgagccca ccgctcgtac cagccgcggg ctccgcgtcc    73140
tcgtcgatca ccagcggtcg cgtcggcacc ggagaatcca cgtcatcctg cacgtcgttt    73200
tcctcctctc cgtcgtcatc gtccagaaac ggcacccgct gcttagccca ggacattctt    73260
tttccgcgtc ctcaatcagc ggcgccgatc gccatgaatc cgagtaccca cgtgagcagt    73320
aacggcccaa cgactccccc tcacgggccc cacaccacgt tcttccccc gaccagcccg    73380 gccccgtcca ccagctccgt cgccgccgct accttgtgca gtccgcaacg acaggccgtt    73440
tcacgttaca gcggctggag caccgagtac acccagtggc actcggactt gacaactgag    73500
ctgctatggc acgcgcaccc acgtcaagta cctatggacg aagcgctggc cgccgcggcg    73560
gccgcctcat accaggtgaa tcctcaacac cccgccaacc gttaccgtca ttacgaattc    73620
cagacgctca gtctcggcac ctcggaggta gacgaactgc tcaactgctg tgcggaagaa    73680
accacgtgcg gcggcacgca atccaccgta ctcaccaatg cgaccaacac cactaactgc    73740
ggcggagccg tcgccggcag tagcaacgca ggacccgccg gcgcttcggc cgcctgcgac    73800
ctagatgcag aactggccgg cctcgaaacc tcggcggccg actttgaaca actgcggcga    73860
ctgtgcgcgc cgctggccat cgacacacgc tgtaacctat gcgccatcat cagcatctgc    73920
ctcaaacaag actgcgacca gagctggctc ctcgagtaca gcttgctgtg cttcaaatgc    73980
agttacgcgc cccgtgcggc gctcagcacg ctcatcatca tgtccgagtt tacgcatctg    74040
ctgcagcagc acttttccga tctgcgcatc gacgacctgt tccgacacca cgttctcacg    74100
gtcttcgatt tccacctgca cttcttcata aatcgttgct ttgaaaaaca agtgggcgac    74160
gcggttgata acgagaatgt caccctgaac catctggccg tggtgcgggc catggtcatg    74220
ggcgaagaca cggtgcctta caacaagcct cggcgccacc cgcaacagaa gcaaaaaacc    74280
aacccttatc acgtcgaagt gccgcaagaa ctgatcgaca actttctaga acacagctca    74340
cctagccgcg accgcttcgt gcagctgctt ttctatatgt gggccggcac cggcgtcatg    74400
agcaccacgc cactcacgga actcacgcac actaagttcg cgcgactaga cgcgttatcc    74460
acgacctcgg aaagagaaga cgcaaggatg atgatggaag aagaggaaga tgaagaagga    74520
ggagaaaaag gaggagacga tccgggccgt cacaacggcg gtggcaccag cggggggttc    74580
agcgagagca cgctaaaaaa gaacgtgggt cccatttacc tatgtcccgt accgcctttt    74640
tttaccaaga accaaaccag taccgtgtgt ctgctgtgcg aactcatggc ctgctcctat    74700
tacgataacg tcgtcctgcg cgaactgtac cgtcgcgtcg tctcgtactg tcagaacaat    74760
gtgaagatgg tggaccgcat tcagctggta ttggccgacc tgttgcgcga atgcacgtcg    74820
ccgctcggcg cggcgcacga ggacgtggcg cgctgtggac tcgaagcgcc cacctcgccc    74880
ggaggcgact cggactatca cggcctgagc ggcgtcgacg gcgcactggc gcgacccgac    74940
ccggtatttt gccacgtcct gcgtcaagcg ggcgtcacgg gcatctacaa gcacttttc    75000 tgtgacccgc agtgcgccgg caacatccgc gtcaccaacg aggccgtgct cttcggacgc    75060
ctgcaccccc accacgtcca ggaggtgaaa ctggccatct gtcacgacaa ttactatata    75120
agtcgacttc cgcgacgtgt gtggctctgc atcacactct tcaaggcctt tcagattaca    75180
aaacgcacct acaaaggcaa agtgcacctg gcggacttta tgcgcgattt cacgcagctg    75240
ttggagagtt gcgacatcaa gctggtggac cccacgtacg tgatagacaa gtatgtctag    75300
cgtgagcggc gtgcgcacgc cgcgcgaacg acgctcagcc ttgcgctccc tgctccgcaa    75360
```

```
gcgccgccaa cgcgagctgg ccagtaaagt ggcgtcaacg gtgaacggcg ctacgtcggc   75420
caacaaccac ggcgaaccgc cgtcgccggc cgacgcgcgc ccgcgcctca cgctgcacga   75480
cctgcacgac atcttccgcg agcaccccga actggagctc aagtacctca acatgatgaa   75540
gatggccatt acgggcaaag agtccatctg cttacccttc aatttccact cgcaccggca   75600
gcacacctgc ctcgacatct cgccgtacgg caacgagcag gtctcgcgca tcgcctgcac   75660
ctcgtgcgag gacaaccgca tcctgcccac cgcctccgac gccatggtgg ccttcatcaa   75720
tcagacgtcc aacatcatga aaatagaaa cttttattac gggttctgta agagcagcga   75780
gctactcaag ctctccacca accagccgcc catcttccaa atttattacc tgctgcacgc   75840
cgctaaccac gacatcgtgc cctttatgca cgccgaggac ggccggttgc acatgcacgt   75900
catcttcgaa aaccccgacg tgcacatccc ctgcgactgc atcacgcaga tgctcacggc   75960
ggcgcgcgaa gactacagcg tcacgctcaa catcgtgcgc gaccacgtcg ttatcagcgt   76020
gctgtgtcac gccgtctcgg ccagcagcgt caagatcgac gtgactattt tgcaacgcaa   76080
gattgacgag atggacattc ccaacgacgt gagcgagtcc tttgagcgct acaaagagct   76140
cattcaggag ctgtgtcagt ccagcggcag caacctatac gaggaggcca cgtcgtccta   76200
cgcgatacgg tctcccttaa ccgcgtcgcc gttgcacgta acttccacca acggctgcgg   76260
cccctcctcc tcgtcccagt ccacgccgcc tcatctccat ccgccgtcgc aggcgacgca   76320
gccccaccac tactctcacc accagcctca gtctcagcag cattatcacc gtccccagtc   76380
accaccgccg ccgctgtttc tcaacagcat tcgtgcgcct tgacactgta cggcagaaaa   76440
gccggctcca agtgcaagcg ccgcggcagc accatgtgca aaaacttgtc cttgcgcgcg   76500
gtttcgccgc cgggaaagac gggcgacagc acgttggtta cagccttgag aacctgctca   76560
aagtacttgt cggcgtgaat gggcacgccg tgctcgcgca cgtagctcgg atcttcggct   76620
acctcgtagt tgcacacggc cgacggtggt ttccgcgccc tcttctttgg cggctctcct   76680
cctctcctgt tgctctcctc taccccgccg ccgtcagcgt cgtcgtccgt gccatcaatc   76740
gcgtccgacc gggaaaccac gccggtggtt acagaatcac cgttgtcaga ggaaccctgc   76800
ggcgccgtcc ggacaccggg cgccgtcagt acgtaaaaga cccgatcccc gaccgagggt   76860
agctcctcag aacgggccgc cagtcgctta atgacggcaa tgtgcggcag gttagattga   76920
cggtacaacg agatgtcctt agaaagcacc gacgaaagca ccaggtcctc gacacgcaca   76980
cggtgcaggt acagatcgtc gcgggcctgc accaggcggc gcaagatacg ccagaaaccg   77040
cgtggcacgc cgtatttctt gacttcatcg agtgagaggc gcgacaggcg cacggctgct   77100
tccgagacct cgcgatcctc aaagagcagc gagaggacgt cacgcgtaac gcccttgacg   77160
aactcgcaag ccgtcttgcg caccagatcc acgcccttca tgctcagacc cgaggcgccc   77220
tccactttgc cgatgtaacg tttcttgcag atcatcataa gagagacgaa gaccttttca   77280
aactccagct tgacgggctc cacaaaaaga caggccgtca cgtagtgcgc caggctgggc   77340
ccacgcgcca ccagagcctg cggcgtcaga ccacgaaagc ggacaaacac gctgtccgtg   77400
tccccgtaga tgaccgcgcc ctccaccccgc cgttcgtccg agcccctga cgatgtttcg   77460 agcccctccg gtaacgtgct gctctcctcc gaatccccct cccgcgttcc caccacataa   77520
tcttcttgat taaaaaaatt gtgcaaaaaa cacggctctg aaaagttgtc tttgatgaac   77580
cgcgccgtgc gctctagcat gtcgcgaccg atgcgcgtga tgctggcggc gatgggcaga   77640
cacggcatca tgccgttgac cacgccggta aaaccgtaga aagcgttgca cgttactttg   77700
```

```
agcgccatct gttccttgtc gagcaacata cgacgcacag ggtcttgaca ctcgcgcatg    77760
cattcgcgca cggcacgccg ctgcgaaacc cacttgttga gcagttccga aagcaccgag    77820
acgcgcaccg aagcgcgcac aaagcggtgg gtcacgccgt tctctagcgt gacgctgtat    77880
acgtcggcag ggtccacggg gtactcgcca cccggcacca acagggtgga gtagcagagg    77940
ttgtgggcca tgatgatgga agggtagagg ctggcaaaat cgaacacggc cacggggtcg    78000
ttgtagtaac ccacctcggg ctcaaacacc gtggcacctt ggtacgaaac cgccgcggta    78060
ccgccggcgc cgtgactgtc gttggaaacg ccgacgccgc cactactgcc ggagccgacg    78120
ctgaaaacgc cgacgctgct actactgtta ctaccagagc cgggtgaaac gccgtcctga    78180
ctcgacggcg cagattgcaa gggcggcgac atctgaaaca tagccgccac agaacccgcg    78240
tcgccgggca cggcggcggt agagatgata cggcgttag gtgacacggc aacgctattc     78300
gtttcgggca ccgtcgtacc tttgctgtag tggttgggca agataaaatc gcggcaggcg    78360
cactcgtcta gcagcgaggt gtagatacgg atctgctgtc cgtcaaagat gacacgccgc    78420
aacggaattt tagccagccg cgcgatggcc ccggcctcgt agtgaaaatt aatggtgttg    78480
aacagatcgc gcaccaatac ggcgtcctgc agacagtaac ggcctacctg ggcgcgcccc    78540
tcggcattag ccacgaaaca acgcgggatg tccttgtagg acaggtcatc cttgcgttgc    78600
cgcaggtaaa gctcggccat agtgttgagc ttatagttgg gcgagttagt cttggccatg    78660
catacggggt acatgtcgat aaccaccgaa cccgcaatat acaccttggt ggcggccgtg    78720
ctggccggat tattgtgaga agccgaggga aaggcggcgg cgtactgccg cttaaaaccc    78780
acggcggggc tgtgtaaaaa aaaacggccg ccctgcgccg tgggcaactt gcagaagcgc    78840
tgcgagtcca ccttatacag gtactcgagg cgcgtgagga tgtacttcaa gtcaaaagag    78900
ttgatgttgt aaccggtcac aaaggccggc gcgtaccgtt gaaagaaaag cataaagccc    78960
agcagcagct cgtattcgga agggaactcg tagacgtcta cgtctgggcc cacctgcccg    79020
caggtgccga tcgtaaagag atgaagaccc gagtgcccaa agatcacgcc ctccgaggtg    79080
cagccccgac catcgttccc gtttgggatt ccctgatcca cggcggtgtt tcctcccgtc    79140
tcgtagcaca cgcacgagat ctgaatgaca atgtcatcag acttctcggc gcagggaaaa    79200
ccaccctcgc cgctcatgca ctcgatatcg aaggacaggc accgataacg cggccacgag    79260
ctgtcgtcgg gcacggccac caggtcggag acatcgcagt cgacctcgat atcacaagtc    79320
gacgcgcgac cctgctgccg ccagtcgtaa cgattcacgg aacaccagcc gaacgtggtg    79380
atccgccgat cgatgaccaa acgcgtcagc ggatccacac ggacctcgta cacgggaaaa    79440
ccctgctcca gcagatactc gccgatcttt ctagccatgg tccagttgct gatagacaca    79500
cactgcaaat cgggcacggg tcgcgtcccg tacccgtaga tggaggtctt ggtgccggc     79560 gtgacagaca cggcgtatgg cgtccgcggt tcgggcacta gttcgcccac gctggcaatg    79620
acctcacgca gcctatcggt gtcgctgtac tcacagtaaa agtagctgcg ctgcccgaaa    79680
acgttgacgc agatactgta gccgtgttct gtggccccga agaaacgcaa cacgttcccc    79740
gaaggcacca gatgctgacg atagcgcggc gacacgtttt cgggcgagtc gaagaagagc    79800
acggcgtccg tttgatcgta ggtgtgaaaa cgaataggtc ccaccacgcg acccaccagg    79860
gtctcgcgcc aaggacacgg ccaaaccatg tcatgactca acaaatgttt aatctctcga    79920
tagaacatga gaggcaaccg tcccgtctta tgcttgatca accccgtctg accgtcgaac    79980
atgacgcctc gcggcacgat ctgcaaaaac tgtttctgtg gcggccgctt gcccgagccc    80040
tgcgcggagc cgggctgcga acgctgacgc cggccacccg caaccgcacc gccggtcacg    80100
```

```
ccgccgctca gatacgggtt gaaaaacata gcggaccgtg agaggctgac agcttacgaa   80160
gcaaaatcac aaagcaaata cacatgcagc acctagatgt ccagtttaac cccgtatatc   80220
acaagtctct gtcactttt ttgtctagtt ttttttctc ctcttggttc agacgttctc    80280
ttcttcgtcg gagtctttca agtgtcggta gccgttttg cggtgtcgca gtcggtctag   80340
caggttgggc ttctgtccct tgtcctgcgt gccagtctgt ccgtccaaag aatctgtacc   80400
gttctgctgc gctcgctgct ctgcgtccag acggaccagg gccagaagca tctggtaagc   80460
ctgctcgttg gtgtaaggcg gagccgccgt ggatgcatca gacgacggtg gtcccggtcc   80520
tttgcgacca gaattataaa cactttcctc gtaggaaggc ggagcctgta acgacgtgtc   80580
tttggtgttg cccgacgtca cggtggtccc gtcggcggac accagatagg gaaagaggtt   80640
ctgcagcggc tgcatgcaga gacgccgctg tcgagtatat atcaaataaa tgataatgac   80700
gacggctatg ccacgagga tgatggtgaa ggctccgaag gggttttga ggaaggtggc     80760 aacgccttcg accacggagg ccaccgcgcc acccacggcc caatggcta cgccaacggc    80820 ctttcccgcg gcgcccaggc cgctcatgag gtcgtccaga cccttgaggt agggcggcag   80880
cgggtcgact accttgtcct ccacgtactt tacccgctgc ttatacgaat tgaactcgcg   80940
catgatctcc tcgagatcaa aaacgttgct ggaacgcaat tctttctgcg agtaaagttc   81000
cagtaccctg aagtcggtgt tttccagcgg gtcgatgtct agggcgatca tgctgtcgac   81060
ggtggagatg ctgctgaggt caatcatgcg tttgaagagg tagtccacgt actcgtaggc   81120
cgagttgccg gcgatgaaga tcttgaggct gggaagctga cattcctcag tgcggtggtt   81180
gcccaacagg atttcgttat cctcgcccag ttgaccgtac tgcacgtacg agctgttggc   81240
gaaattaaag atgaccactg gtcgtgagta gcagcgtcct ggcgattcct tcacattcat   81300
atcacgcagc accttgacgc tggtttggtt aatggtcacg cagctggcca gacccaggac   81360
atcacccatg aaacgcgcgg caatcggttt gttgtagatg gccgagagaa tagctgacgg   81420
gttgatcttg ctaagttcct tgaagacctc tagggtgcgc cgttgatcca cacaccaggc   81480
ttctgcgatt tgcgccagcg cccggttgat gtaaccgcgc aacgtgtcat aggtgaactg   81540
cagctgggcg tagaccagat tgtgcaccga ctccatgttg gataaatgag ttgcattgtt   81600
gccatctgta cttctttgg ttctattatg agtaagattc agactggagc ggttggccaa    81660
acgttcgagt tccaccagag atttttgctt gataccttgc cagaacacca ccaaaccacc   81720
agtggtttca agacggaca cgtttccata tttttcatat gtttgattgt atgaagtatt    81780
gaaaatctgc tgtaacttat ttatggcctc atcacgtaca cagtccagcg cagagtcgga   81840
catgttcacc tcttgcttct tagataagaa agtggcggtc attttggcag aagaaaagtg   81900
atacgagtcc tcggcttcgg aacgaatggt gcgttccgag gcttcccaga agtgagttg    81960 acaagtaaca ttcttctcgt cctgtatatc ccaggagatc actgagtccg cacgttcaag   82020
aaaagccacc aacctgtggg tctctaacgc agaattcggt cttccaaagt cggagacgat   82080
agtgtagttc ggaaaaatga aaaacttgtc ggcgttttct ccaaaatagc tggcattgcg   82140
attagttccg ttgtagaaag gagaaatgtc aaccacatca cccgtggaag ttgcgaaaaa   82200
atgataggga tacttggagc gcgcagtagt gatggtcacc atacaattca gattacaggt   82260
ctcacgatag agccaggtgc tgccgcggct gtgccattga tccttgaccg tcacgtaacg   82320
ggtactgtgg gtgttggaat aatcgtcggg cattaattgc atggttttgt tttcatagct   82380
gtccctatga taagccacga aaaccgtgcc tgctataacg cggctgtagg aactgtagca   82440
```

```
ctgactgtga ctgttgatat gatgaatctc ccacatagga ggcgccacgt attccgtgtt    82500
gctgcccagc agataagtgg tgtggatgta agcgtagcta cgacgaaacg tcaaaacctt    82560
ctggtagact cgtaccttaa aggtgtgcgc gacgatgttg cgtttgtaga ccaccatgat    82620
gccctcgtcc aggtcttcat tgatgggctt catcgaggtg cagacgatat tacgttcaaa    82680
gcgaataaga tccgtaccct gtgccataga acacacgcga taggggtact tggtggtgtt    82740
gaccccaccc acatctccgt acttgagggt agtgttgtag atggtctcgt taacaccatg    82800
gctgaccgtt tgggaagaag ttacgcgttg agagactgaa ccggatcgag aatgagcagc    82860
agacgtcgta tgagaggaat ggtgactgtg agtagcagaa gttccacgag tagaagatga    82920
ggaaaccgca gcacccagac agacgataca caagttaacg cagactacca ggcaccagat    82980
cctggattcc atgttcgtcg cgggccaaat ccagcagcga tgaggcgcgt cgtggtctct    83040
tgcgtgttgc gcggaccctc cgggaaacgc ccgcggtcga ggaggagggg tacggacttg    83100
gcagccaagg tcggtccggc tccctgaagg cacccgagac ggccgcggcg gccgtcaggg    83160
tggagggctt ggccgcggga gctgttggca cgtcgccact ctcatccggt ctggacagat    83220
gcctgtagag gaggagatat agatctttgg acttataaag acttccttcg tgacgaagca    83280
gcagcggcca ctctttgtta tacgtgagaa tcacatctct gtccgggtgc agttcgtcgc    83340
gcaggcacgc gatcgagagt tgtttcccga aagtttcatt atatagtgcg acggagagca    83400
cgagctcccg cacgtgcatc cacatctcct tctgcagcac gtttagatcc tgacagtccg    83460
aaaaattgaa aaacccatg tacttcacca ccatccactc actgggatac acggtacctt    83520
ccgcgcattt gaccaaatcg tccttgacgt ggggtagtac gcccgcgttg tcgcaggcat    83580
aggccatgtc cacattgtga gagaggggat agcgatcggt gcagtgtgtg aagaggggcc    83640
cgttacacaa ctcgtagatc tgctgaccca gtagcgggag ggattccaca ggcagactct    83700
tgtggatcag gttattgacc acatacaggt gctcatcgta cgtgaactga tcccccacgt    83760
ccaccacgtc ttggtcctgg tggtattggc tgcggtatag aaacccattc atgagcttag    83820
agataaagtc cagacacaag ggccccacta ggttgacatc gatgagtttg ctagtcagac    83880
gctcctgcgt tttgatgcaa cggatcacct tgccatagcc cacctccgaa accttctgca    83940
ggtaggcgcg tttgcgcacg ttcacctcgc gggtgacgtt gtggatgcgg gaacgcgcgt    84000
ccaccaagtc gagagcctcg tgttcgtcgc agttgcgcac ccgtaagccg ttctcgctgc    84060
cgtcgccgtc ctgcccattc gcccctcccc ctaccgcttt cttgcctcct ccacgggccc    84120
ggccgccgcc accgttattc ctctgactgt gagtactgct gttgctgctg ttgctggccg    84180
tcatcaaagt cgtacccgtc cccgacatcg cctcccgtcc acgcaggtga atagcctcgc    84240
cctcggggcc gtcgccccc gtgccatcgg gcagcggacg tcgaatctcc tcgagaatat    84300
gcttgatttt ggtgtacatc tcgttgcttt cgtggagctt gttgaacacc gggttgtcct    84360
cgaaagcttg aatgctgagg gatgtgatga ggtcgatgat cctgttgggg gcggcaaaga    84420 ccgacccac gaacatgcgc tcctccccgt ccaacgcctt ttccccgagc acgaagatgt    84480
cctccacgtc ctcccgtac agatggcgac tgatgccgtt catgagcgcc cggcacagct    84540
ggtgatacac atttagctgc tggatggtga tgcccacccg cttgacgata acctccgagg    84600
tacgggacca gtaggtaaaa tccgacaagg aatatattcg ttccggtata tccgtaaaca    84660
ggttgtactc cctcagcgcc tcctccgcct cctggatgta gctgtggtag gccgatgaag    84720
aagagaatag gcttttgagg gccgaaagga ctccagccaa gtgggggatg cgcgttgtca    84780
ggtccagcag gtcctgctcc accgtctgga tattcacatc ggactggctt gacggacggt    84840
```

```
ggaccgctat atggttgcac agcaagccct gcagccgctt gttcaacgag cggccctgat   84900
tcgggatgat ggtcagctcc tcgtagcatt gggcgcatgt cgtcccttcg acgtacactt   84960
cctgacgcgc caccggcgag atgccgcata ggcgacggag aagctccagc agctgcgcgc   85020
agacctccag gccggcctcc ggcgccagga tcccgtacac gtagttcatc ttgcacagga   85080
agcgctcgat gtcgttgagt gtggccagac tgacgctgaa acggacgttg tccgtaaact   85140
ggagctccac ggtgtgatgg cgatcgcagc gatccaaacg gaggacggta cggtagaagg   85200
ccgcccggtc cggctggcgc gagtaggcca tcagcgcccg gtccagcaaa gccgtatcct   85260
cgtgcagcgc cttcagcagc atctccagat agagcgtcag cagcgaactc tgcgtacgat   85320
tctgcgccac cacctccggg tagatcttcc ggtacagata cactatagcc gccgcgtttc   85380
tcttgaacgg cgtggactcc gccagtaaca cgttcggatc gcagtacttt agacactcca   85440
gctccatggc gtattcgttg catttcgaac acactacgca tagtttctgt aacaaattca   85500
tctccatgac tcgactcgct cacgtacgag acgctgtcgt ccggtctggc gccggccaga   85560
gacatggagt cggtgcacaa ataactcgcg ggccgctcgc tatgccgact gacgttgacg   85620
ttaatatata acgacgtcgt cgacgacgcg ggttctgctc ccgacgctgt tgccgccgcc   85680
tgcggcgcaa cctcctccac caccgccgcc gccggctcct ccgcctcggg cgacggggggc  85740
tcggagatga ccggctgtgt ctgacactcc tcccctctct caggcggccc gggcgccgac   85800
gcgaatgtcg gagcttgcca gcgcggcggc ggtctctgtc tctggtgccg cggcgccaac   85860
cttcgggggct gttgctgctg ctgatgatgc gacgccgtct gtcgccgctg ttgcggcggt   85920
agctgatacg gtgtcgcctg gtgctgctgt gtcggtggct gctgttgttg ctgctgttgt   85980
tgcggtctga aaagcggcca cggggggctgc gactgttgct gctgttgttg cgatgctcgt   86040
ggctgcggcg gccgttgtcg cggcgtctgc tggcggttac aaccggctgc gtttggccgg   86100
caataacccg ctgccccgc cgcccccgct gctcccgccg acgccgccag cctcgtcttc    86160
gccggcgttc acgagaaagc agccacctcc cgtctcgccg ggcacgccga agcaaatgga   86220
gttgcccgtg acggactcgc cgagaagaag accgccaccc ccgacgccgg acgccgcgcc   86280
gacgccactg ggcgcgaaga gcgccgacag gtcgtgcacc tccccccag cggcgtccgt    86340
caatcgctgg gcgtcggcgt ccagcacgcg tcgcaagttc tccagcgaaa agtcctccac   86400
gccctgctcc tgcaacgcgg caaacttgtc catcagcgac gcggccagcg cctcgcagcc   86460
atccacgaag aagagcacat cgtcggacgc ggggatctcc tcgcgcacgc tcagaatctc   86520
gtacacggcc attacttcgg ggtcgcaatc caagttctcg gcgtccagcg ccagcatgac   86580
gcggttttt ataagatccg cgtcaaaaag cacgttctcg cggcgcgagc gtttaatgag    86640
cacgtcggcc agacgcgtag ccaagaggta gcgctggcgc atgaaacgat aatcttggcc   86700
gctcatagag ctcacgttaa ggctgcgttc cacaccgttg cccgaaaagt agccgatctg   86760
cccaaactga tagatctcct tgctgttgtt gatacccgca tattttccca cgctcacggg   86820
cacggtcacc aaggaacgat gctcaaaaac gctccgtact aacgattcac gcgccacagt   86880
ggcggccatg ggcgccggca cgcctgcggt cttcaagccc ttgacatgca acgcaaattc   86940
ggcgggcgac gagaaacgcg gactagcacc taacacgtga ggaaactgcg cgtggttctg   87000
cgtcgttaag cgcgtcgtta acccgtgcag cgagccgatg tagtctttga agccgtagta   87060
gcagaggaat ttgttatgga aacggctttc cacgtaactc agcacacagt ctggcgccac   87120
atccagcaga tcgtgctcct gatagtcagc cgtcacagcc accagaaatt tgacgaaagc   87180
```

```
attgaactcg cccatgtcac ctatgggcac attcttgggc aacgcgttgg aacagacctt    87240
ctgccaaaac tgtaagcagg ggagaccaca ttcaggaaag agtcgctcgt gatgtcgata    87300
cagcagaaat cccaagcagc ccttagccgg attacgacgc ggaacgtgat cgcggcgaaa    87360
aaacacgcta cccgcgttgc ccttgcccgc gcggtagatg ggtcggtttt tcacccgcac    87420
catgatcaac gtgggtaccg acagccgcga gagcttgatc tccatgggca ccacggcgta    87480
cgtgccctgc gcgtacagcc taaagtccag caggcggtcg tgatccgaat tcttggacga    87540
cttgatctgc ttggtgaaga gaaagccctt gcgcgacgac gtggtagaga acgcgccgtg    87600
gatggattga aagtgctgcg tcatccattt ggataccaag ttggtggtca acggattgtc    87660
cacaatgtac gaggtagcgg taataagcgc cacgttctgg atcacgtaaa agacggatct    87720
gaaataggcg taggccagca gcggctggaa ggcacggcg tagggattca gatccaggtt     87780
gaaggcctgc gtggcgcccg ccacctcgtc gcggctgctc ttgaggcgca cctccgaaac    87840
gaaacccagg gcctcgtcgt ccacaaactt gttgagcgcc gaaagacgg ccacaaagtc     87900
gcttttgccg tgcgcgctaa aggtatcctc gcccgtcacg gggtcgatga ccgcatctt    87960
gcggcagtaa tccaagatgc gattgagccg ataggtacgg tccacgctag cgcccagcat    88020
gcgaccgccg cgccccatca ttcccccgga atccccgcca cccccaccac cacgaccgcc    88080
gcccagaccg tcgctcgggc ccccgctcac gtctcgtcca ccaccccgc cagcaccgcc     88140
gcccggagcc ccgtcgtcac ctttgccgtc caaacccccg tccttggcgt cgacgttgta    88200
acgccgaccg aagctgccca aaatatccac gtcgttgaga aaacgcgact gcacggtgat    88260
cacgcagggc tccttcttgg gctgcttggg caccacgggc aagcgggtgc gcacccgcac    88320
gaaggccgtc tgataacacg tgtggcaaca agtaccccca caggcctcgc acaacccgc     88380
ggcgcagccc accaggtgat tcgtgagcgt cgacgaaccc gacaagcccg tgttatacac    88440
cgagacacga tttagatacc agacgaagcc cgaaactagc tgcggacacg tgccacacac    88500
caacgccaaa tgctgcggcc catagcgttc gtccttgagc ggcgcgcctt gaaacttgag    88560
caccttgcgc gcgtcgttgt agacgtcttc gcaggccgcc gacaacccgt tggtgaactg    88620
aatagccttg agcaacgtct cctgactggc cgtaccgccg gcgctgggat gccgcgccga    88680
cgactggaga tacaccagcc tgtgctggta gagcaccgaa ttagcgctga agaccaaggc    88740
ggccacgtgc gtcgagagat gcaacttgag ctcggtcagc gcgcggatca gatcgcggtg    88800
atcggttgcg ttggtcacta aaggccactc ggaaaagagc atagactcgg caggttggta    88860
ggccgaatca aaaaataccg aggcaaaact gaaggccaac tcgcaaacca ccgcgtcact    88920
cagcatcaga tgatccttttt ccagactgct gagtcgctgg ctcatgtacc ccaagtagcg   88980
cttatgtggc gccagcttca ccgactgctg actgtcgtgc acaaactgcc gcaacgccgc    89040
ctcgatcagc acacgcggct ccgagaagcg cagcgattga caccatgacg tgtacacgta    89100
gtagaaaagc gtctcgctta cggccggcac gtagagccct cgcgcctcca caaaagcgct    89160
gcgcgcatcc agcgagacct cgtcggcttc ggcgtcaagc tgcagcgaat taagagcgt     89220
aggcgggtac aacggcacgc gcaccgcctc gccgccgtgc agtcgcaccg tggtcgcctc    89280
ctccacgcat ggaatcagct gaccggcaaa gagaaactcc ttcaagccgt tgcccaccac    89340
cacgtgcaca gtcgtctcgg acgcctgaca gcccaccgcc gcgcacaacg ccgccagatc    89400
ggtaggcacg cgatccgcct cgggcgtgta ggcctccaac gcgtacttct ggcgggcgtc    89460
ctcgcacagc cgatgcacgt ctccgtgatc ctcggtaaaa gccacgatgc cttgcgtatg    89520
atgaaagtag agcgcaaaag gacagaagga cgtgactttc gtgagcaccc cgccgtcgta    89580
```

```
acaaagcaca ggcgtacgca cagagacgcc gaaatccgcc tccaccgtga gccccgccaa   89640
cagaggagcg atcaccacgc tcgaggaacg gtcgcataac gagagagtgg ccagaatctc   89700
ctgcgtttct gcgttcaacc tgctgaagta gagaaaagcc gcgggcccca ccggcgctag   89760
cgcggttagt tcctcgtggc tcatggtgga tgaacggaag acaatggcta cgccgccact   89820
gagtgaattt tataccaagg aaaagttcag cacgtcatgt ttgacgcacg acgtctgaga   89880
caccaccgtg gccaccactg cggtctggct gcggttgcgg accaccaaag gcgacaaccg   89940
caacgatccc agcaattcgt aagaaaagct aaccgctacg gtcgggtagc ctctcgcagc   90000
cagaccgcta gccgacgcac ccgcccgcga aaatagcgtg atgttcggga cggctttgcg   90060
tcaccgccaa ctaacgtcgg tagtcgagca cgtcgtttat cctcagcaca ccgtccgatc   90120
acaatccgtt ttcccactca gtcgcacaag cagcacataa aaaccccaca cagggcacgt   90180
gaaaacaccg tccctagaaa acggtgtttt ctgtcctacc gtcaccggta tacacaggca   90240
aatcccaagc ccgatcccg aaaacaccgt acggtgtttg tgacctccaa aatcacatca   90300
gctaacaaac cgtgaaaagt cacgtttcac gaacacggtg ttttttaaatc acaaagaacc   90360 gcctgacggt ttacaagcag aaacaccgca ccacggtggt acaagcgcga tgaatctggt   90420
ctcgcaacct caatcgccgc tatcaccacc gattttcgct gcgctccgcc gacaaaacgc   90480
cgtacaagct acacacccca aaaacccgcg cgcctacggg cgccaaacct gtgtattatc   90540
ccaacgtcac aacacgacac aaaccgcgta acgtggtttc ccgaacacgt acgcggcaca   90600
gacccccgac acgtactcga agaccttaca gtttacgagt caataaaaca ggaaaagatc   90660
cgaactttaa aattgtgtat ttttattttc ccatccccct cttttttacca aaaacacat   90720 ttttcgtctt gtaaaaagta actttcgccc attgccatga acaccgtga tgggaacgg   90780 tgttgtgtgt cgactgacgt cactacggcg atcagtatcg acgtcgtgta tacataacgg   90840
tgcccggtgt ttttattcgg ggcgttgtcg cgtcttgatg taatgtaacc tgaaaccgcc   90900
gtgcccaaga atgcggaagc cagcgtgtac tcataacggg gttttgggta caatctgacg   90960
acatctggcg gcgagcgtac accatcgaat gtggcgatcg ccggctctac gtcacaatga   91020
cgcaaaaaca cactgtaaaa cccgcgtaga cagctttcct ggtcaacgag cgccatctgg   91080
tgtcggcata agaacaggaa tcaaccccgt ggccggcgag gcggtgagca ctttcctgg   91140 tcacgtgacc atcagcgcag gaagcgaggc ccgtagaacc gcccaagagg cggtgccaga   91200
tgccaacgtc ataatcacaa ggtgatttgt tacgtcacgc gtgtgcgcac gcacgcgcgc   91260
acgcgcgcgg tagaatacag cgatccctag tgaagccaca cccattacgt gtagccatat   91320
ccgcttacgt atacagccac acccctaggt acgccacctt atctaccaat cacagaaacg   91380
gatatacaat gaccccctccc tagactccac cccttgtacg gaaatttcag ataggtgaa   91440 cccgttaggg ttccaccgtc ctcggtgtac gtacaggctt ctccgtctac cggaaatata   91500
cacctgctga cgtagacgct actcccggat acgcgtcata agctactgga ccctaggggg   91560
ggagtgtcta cagggctacg tgcacgcccc cttacctagg gtatccgccc ccttcctctg   91620
ttttgaccta gtaaacttaa cgccgccgct tctcacgtga cccctgacaa gcctacgtca   91680
cactcgtcgt aaccacaccc attccggata tacgtcatcc tgtggaattc cggacatacg   91740
gtgacgtagc gagcgtagcg agctacgtca cgtatgcgtg cgtcacctcc ggcggaaatc   91800
atctctgatg acgtagcgag cgaagcgagc tacgtcatca gtccgttcta cgtataccgg   91860
atgctaggcg acgccccgta ggggcggagc ctagcttcca cccctaggat gcatacccta   91920
```

```
tatagcataa ttcttctaac gaaacgttct acgaaaacgg actggcggaa cgggaaccac    91980
cgtaaccccc cccctcacc cccccccttc tcctccggaa ccgggggggg caaatttta      92040 ccaaatttgg gcaaccatga tttccaatgg gacggcgttt ccgtgcgcat gcgcagtcgg    92100
ggcgaatttt cggttaccag ggcgttacca cgcggattat gggatgggga ctcgagtgcg    92160
catgcgccgg ggatgccgta tggagagcct atatataaag aggggtgaac caggggcccc    92220
ggtgcgcatg cgcgggtcct ggtccgcggg agggtcgtcc tgcgcatgcg ccggtaaaat    92280
tccactgggt gtgtgtcgtg cgcatgcgcc agtattttc cactggaggc ggtcagtgcg     92340
catgcgtcgg taaatttcca ttggatgcgc gtcgtgcgca tgcgccggta tttttccact    92400
gggcggccgc acctagggag cgcgagcccc gtgccgggca tgggccgcgg cggtggaaaa    92460
ttaccgctcc gcccacctag gcggggcctc tgaaaaccta taaaacccgg cgtgcccgtc    92520 gcccccggc gcagtccgcg gcagggttcc ggccgtgctg cggtccgcac gctgcgcccg     92580
ctcccgcctg cctcccgccc tacccccac cctccccggc cgaggccgg cgccggtccg      92640 tccgcgggcc cgtcccaccg ccctggagca ccatccgggg ccgtgggccg ggcaccgggc    92700
gcggcccgct ccggacctcg gccgggggtc cctcccctcc cccgctcga ccccccatc     92760 cgacggcccg gccgggctgg gaccccgca ccggggtccc ggttcccgtc cgtggcccgg     92820
ggggacccga gcggggcttt ccacccccca ccccgctcct cccgggctc cggcccggga     92880 tccctcgctg ctcccggcga cctccgccgg cttcccggtc cacccgccgc ggaatggacg    92940
ggacccgggg tccgcgccct tcccctcccc ccacgggggg ctgggtcgcg gaccccggtt    93000
cctaggctcg ttccgcggtg ggcgaccggg gatccccac ccagctcccc ttcccggccc     93060
gccttgctgg cttttgggcc cctgcgggct tttttttcc ggctggggt cgcggcggtc      93120 ggccgacgtt aaagctgatt gatctcacgg tggtgtggac gggcgaaccc ccggctcgac    93180
ggcagtcggc cccggagggt tgggggctgg gggcccggtc aggagctccg ggagcggggt    93240
cgaccgcgac ggcttccggg tctcgcggcg gctccctctc ggcggctccg gttgggctcc    93300 cctccccct ctcgagggtc cggtcgccgg ttgtggtcgg gggtccctcg gcctagccgc     93360
cggctctcgg tccgccttac cctgggcgtt ggccggtccc gtgacgctcc cctcccccgc    93420
tgctccccaa aaactccgcc cgaaccgtcg cggtttgctg gccctgggcg tggtctcccc    93480
actcccctcc ccccatcggc cgcccagccg gggtcggcgc ctcggacccc accaggctgt    93540
ggcgtgtgtg ctggccgatg cggcggcgag gttgggtgtg gccggaagcg ctcggggtcg    93600 acggtggggcc gccatgacac ctcaattgcc gtcagtacgc ccctccacaa tcaccgtccc   93660
cacacgatgg gcccggcagt tcacccaacg ttggttcagg cccagtcggg tttttccccg    93720
gtacgaacgc acgtcccccgt gggctccacg cgttttccac cctttcctgg aggggtccgg   93780
aacaccgtga atccacgggg agggtccccgg cacgggccga ggagaccacg accgtcccac   93840
ccggcgtgtc gactcgtccg agacccggga agggaacagg ccccacctt tttcccttct    93900 ccgatttgcc gtggaaaacc cgtgaaccga tacgggtgca gacggccgaa aaaattcgag    93960
acggcaatac gacggcaggg cgtgattttc tcccccaccc gacaaaaccg tgtccctcaa    94020
aattccccac ctttctctgt tcaaatggcc ccgaaactgt aaaacaccgt ttgaccgcac    94080
cccaaccggc gccatcttgg tgaccttctc gacggttctc tcgctcgtca tgccgttctg    94140
agctccgaca tggcggacga gagaaaatgg cgtcgagagc cgaggagcgt tttcgctcca    94200
ggcgggtaaa aaaatagcac gataactttt ctgtgctttt ttgagacgtt tttgaagagc    94260 ttttttctg ctcagagcga aaaaatgata gccctgaaaa tctcgacgag tctggccgag     94320
```

```
cggcgccatc ttggaggagg ggcgagtcgc gggcaccgcc tcggtacccc ctggccgagg    94380
cgagtccgcg gtcgccgcct gttccgtgat gctacctaga gggcgccgtc gaggcgactc    94440
ttcctgtttt cgccctgagg gctaacggtc gctgacgtca aaccatctcg tgctcgctga    94500
gtcacatccg gttgttgaca agcgatggag gaccgcaccc aaagtgcgcc ctctagtcat    94560
cgcgcctgac cccttttata aactgctcga agaaaagaac accttatgtg aaaaaataca    94620
gaatgatgac aagttcattc aacacaaccg ctcaacaacg ccatatctat cagtgtccaa    94680
aaactatctt ctatcctttg aaactataaa tgctgcctat atacatattt agtatccaag    94740
actcttacca cgtagacgaa aagaagtgat acaatgatct tgacgtgtat cgtctatatc    94800
gtgctagata tattcagata agacgcgcaa accatagatt tctcatcagt atcatgaaag    94860
acctatagct ctatatacga acctagtcat tttaggacag ccgccggaga agccgacgag    94920
ggatcgggcg ggtgcagcca gaacctcacg cccgatcccg cctccggtag gcgatttgca    94980
tctgtttggt aaaaagctca taagtctgta tgtgacctat atatatatta tacgctatgt    95040
acaccgaact gtcgctgttg tataagaaga aaaaactctc catatttata tcgtctgaat    95100
ttttgcttga tagacacgtg tttggaactc tgtcccccca cgttttcact gtgtataaca    95160
aaaatatgtg tttctcaaaa gatcttgagg tgtttgaaaa cgggggaaac ctgcgtttgg    95220
gtgcgctaag ccccggactg ggacgtagcc ggcgtccggc acctatattt ttctattttt    95280
tttttacaaa atatatgatg aaccaagaat aaaactctag ctctcgtcta tttttaatat    95340
gctctactta gaacctttt aatgacagaa tgaactccat gttatacgct ctttatatag    95400
tttctctgca ctaacccttta aaaccgtatc cttccctgtt gtacaaatca tcttttgata    95460
cacaatgatg acctgatatc cctccatata tatgatcgga tattattccg ttagacttgt    95520
cctccttttt tttcctcatc tcctgtatct ggagatatat gttgaccacc accgccatga    95580
ccaccaaaaa gctagccgtc acgactagaa atgtgtagga ttcggacttt ccgtttgaga    95640
agaaagagac cgcgtctctg gacgctcttt ttgtcggtct gaatcgaccc gggatacgta    95700
agagagcggc cctacatcgg ggggcgctcg agaccgacga cgttccatct gaccagaaaa    95760
aaaaaggcac ccctcggtgg cgacctctca ccatcgtttg cccgtccgcc cgtccttcgt    95820
agccatcatc atcatctcag gctctatcgg taccatcgtt gtcatctgaa aaaaaaaact    95880
gcctcaccca cctgcgtaaa aacaccatct ttccggaggt gcggtaagac gggcaaatac    95940
ggtcgtgccg aggcaaaaaa acgcaccatc gacaccacac cctcatgagc accacctgtc    96000
ggtgttggtc gtcctccatc gttctctacg aacatctcga cgcccgggtg acggacgacg    96060
gcaagacgtc ccggagaaga cggtgttctc tcgggcggta cgctctctgg atctataata    96120
tctatagtag ctaaacgaga ctgtgagtac gacgaaccac atcatctttt ttttatgttg    96180
cttctttaga aaatgactta tgtcgacgac actcggcatc agccatctcg tgaaacacgc    96240
tcgcttttcg tctctccaag gaacactggg tccgctgaaa gggaccgtgt accgaccaaa    96300
gcaaaaaaca cacacgtagt aacatgatca accacgtctg aatgacacga aaacacaatc    96360
gtataacgct ctattcatgg aacgaacttg gaataaaaaa accatcgcag gccagaggct    96420
aagccgaaac cgtccgggga agcgggcgcg agttttccga cttagtctct ggtgctcgtt    96480
gagcctcttt ttttttttcct gattctctga agaatcaccg tcacagccct atgacgcgaa    96540
atcaattgct agaacataaa cgttctcaac aggtatgaaa tgaacaaact agatgatgct    96600
ataaccttat attgtgtgta tatagatagg tgtgaaattt gtaggataaa aagtgtcgtt    96660
```

```
gtatgatgca caacgatcgt gaaactggag actgtagctc tctaccgaat gcaaatacac   96720
aaatgacatc gattcccgtc cccacataaa gaaatgtgct ttactgtgaa agaatgaaga   96780
agattcttgt tcctcgtacg acggggccct cgctcgtcgt gcctcttccc ccctccggga   96840
gaggggacgt cggggccctc cgtcgcaccg ggccgaagcc agtgaaatgt ttactacact   96900
gtcatcagaa tatatgatgt atattatttc ctccaaactc ctcaccatag ccaccaattc   96960
gcatcactta agaaagtagt agcaaccgcg gcggcggcga ccggccggtc gtcgtctcct   97020
cgtcctcaaa tgttgtacat gtgcagaaaa atgtgtaaat acgtgttatt tatcccatgc   97080
gtcttgtaca tagatatatg tttttatata cgctatttat actttatata tccttttgca   97140
taaccataga cagtcaagga ttttaatgat ttgctcatcc gcctttgagc catcgcttag   97200
gagttagttc ctctatgttc tcggcccacc ttttcgacta cagtagcaaa cccttgtact   97260
accaccccga taaaaaccac atcatcatcg tcaccacgac ctggaaacga cacacgttcc   97320
cccccaatct tgggcatgtg tatatataaa agaatgggga gggagaggac gtggggctcg   97380
agaagaaata aacgccaagc tcgattcgaa ccaaaaaacc acatgtgtat tgtgcttttt   97440
ttttttttta cggtggggga aaaggagggg gccgtcatta acggaaaccg tgtatggggt   97500
ccggacacga acagtacaca gcttatgggg aaaaagctc acagagagaa aaaaacacca   97560
agctcaggca cgcgtacatc attatcatca tcggatatct caccacgggt catagtagta   97620
ccaaggagtg tgtaacacca ttttttcttt tctttgtaac gggataaggg acagcaatca   97680
tcacgcacaa cacccttcac tctctttta gtcatccata tcatcgctgt aacacagcat   97740
gtcctcgtaa tcgggcgtct ggcagcgcat taccaccgag tcgtcttctt gcggtaccgg   97800
tggtggtggc ggcggcggct gctgctgctg ggttgccgtc gtactgtgat taccgttggc   97860
ggactgcaca gggatgatgg gctgcttgtg gggaacctgg ggtggactgc cgccgtgaga   97920
aggcgacggc gtcatcaagt taagatcacc acggtgactc cggacaccgg cgaggggcgc   97980
cgggggactg ggagggaccg cggtcgtctt gtagacgacg gtgtccccgt gtcgatccgt   98040
ggctcgtacc agatcttgac tgctagcgtc gtcactgtct tcgtcctctt ccagctcgcc   98100
ctcagagtag tgctgctgtg gttgcgacgg tggctgggcg ggaggagcgg cggcggcgat   98160
cattggagag ggatgtcgat gactcccttc tctgtctttt ttatcgtagg ctgtcagcgt   98220
tgctgggtcc gtcctgcttt ccatatttgt gtattgctca tcggtgggat gaatttggtc   98280
tcctccccgc tgttgtccgc cggcagtggc atggttgctg gcggttgtcg ttgtcgtacc   98340
ggcaaagacg gtgagatcca atagcgactg ctcgtcgaag ggacagtacg ctatcatgaa   98400 acgataggt gccaacgcgc gttggatgcg cagttcgcac atctcgttct gacactcgtg   98460
gcactgcagg gcgcctagga tcaggtccga gacagcgccg cagcggtagg tacccatggc   98520
gttgttagta tcgaactggt caaaaaattg gggcgtaccg gtgacttgca acgcgcgacg   98580
gcgtagcgag acggccacgc gcgagaaaga gcacacgtag gccatggcgc ggtgcatggg   98640
ttgcgagaag gtctcgggcg gacgcttctg cagatcgcag acgtcgtcgc gtagccaggc   98700
gctcatttga ccgggcttct tgactaaccg tttgagcgtg ctgcaatggt cgccccagcc   98760
gtcctggtgg tccaggatgc agcccaggtc caggttgttg agtttgttga agagcagctg   98820
acgcatgccg cccaccgtct ccagataggg atcgtgcggg ttgacgggta gcccgtgcag   98880
gtggtggtac ttcatgtagc tgagcgtttc gtcgatgatg ccagcaatg tgtgtaagtt   98940 gggagcgttg tacacggcga agatcttttc caccaccagc ttgcgcagca acggttcctc   99000
cagccaatcg aactgttgac ggatgtgcaa caggtagtcg gtgtgcatga gctcgtcgtg   99060
```

```
tgacagcagg atgcgaccgc gcggctgatg atcttgcggg aaggcggtgg ggaccttgag    99120
atcggcgggg tagggtgcca gacgtagact ctcggccgtg tagcgctgaa ggtcgtagac    99180
gggcgaggta gaactcggtg aggtacccga cgaggcggcg ccgcgctgca gacgcgctct    99240
tttttctttt tcgatcaaac ggctgagttg ctgtagttcg tcctcgtcca tggcgtccag    99300
ttcgtcgtca ataagcgcca gcatctgttg ttgttgcggt ccggcggacg atccgtgatg    99360
attattggct gaggaggggt gagaagaacc gaaagtcgta ggacaactgg gaactcggcg    99420
acgaagatgc gtcgaatcgc cgccgtgatg gtgcggttcg ccgtcatcgt tgtcgtaaga    99480
cttaccgtag tggggttaa ggggcaccga ggcggacgcg ccacgcgtc gcttgaaaga     99540 ggaggacgcc ctatgtccgc cacggaagcc cgcggtgccc atgatgatgt gtccgccggt    99600
gcccccgagt gcgtggcggg aggagggtgg aaggggagga ggatagtggt ccggatcgcc    99660 tcggtatca tcgtctttgc tgtagcgggg tcgtcgtgcg gggacgcagg gtcggtgatg     99720
atgcgaggcg gcgccgacgg tatcttccgc gagatggtat tcgctggcgg ctgctccgtt    99780
ccgtgtcgac ggcgaggttg gacttcgctc gcgtcggaac ttccgtggca cgggttcgta    99840
atccagacag aagcgccgtg cgcgacgggc gcggcgttcg cgctcgctca gggaagataa    99900
cgacggagcg tcgtgacggc gcgtgagtg cagctccatg gccgtcgtcg ctaggaaggt     99960
cacgttcggg cacgctgatg tatatataga tgagaccgct gccgggggc gggtcaccgg    100020 cgccgtggaa agtgaggctc agacggcggt cgccggcggc atgggcgcgt cgggcggtct   100080
gattttgatg gaaatgtgga cgttttggc gttggagtga cacttttgg tgaaacagcg     100140 gctccagagg ctggcccaga gcgcgtagct gtgctcggtg cgcaggtcga tgaacacctg   100200
cacggtctct tgcgggttgc ggtgcgtgta gttgagacag cgaaaatccc gcgtgcgcgc   100260
gccgtcgcgc cgcttgacgg ccacgcagca ggcgccgtgg ggctgaaaga ggaggacgtg   100320
gggcgcggta aactgctcgc tgacgtgcgg ttcgtagtgt tgcgtgaggt gctcgagcag   100380
cggcggccac acgcgggtga cgacgagccg ctgcaagtcc gtgtcggaaa tcgcagcggc   100440
agtggcgccg tcgccaccgt acaggtgata ggcgagcacc tcggtgagac cgcggcgtcg   100500
ataacgcgtc acgttaagcg agcgcgtttc gatgaagttg gcttcggtcg aggggcagat   100560
tttgtcgcgc acgctgagaa tgacgcgcgg cggcggcgac aggggcaacg cgggcaggtc   100620
gtgcggcggg tggtggtgaa gcaggttacg caggtccagt tgggcgcgca caaagcctag   100680
cgggtgttcg cggtaggcgt cgggcacgat gaacagcggc aacagacggc gatgcatgaa   100740
atagccgtcg tcttggtcca ttttatacat gtagggcaga cgtacagagc gtccatggtg   100800
gtagatgcct gtgtctaggc tgctctcggg atgcgagatg gggtccagca gcgtgtgcag   100860
ttcggcgtca agacagacgg cgtgattgag cacctgcgcc acggcgcgta aaacgctggg   100920
gtgtacggcg acggtgcagg cggggaacgg cgtgatgatg cgcagcccca gtttgccctt   100980
gcagcggcag taaggggtg acgtgtcaac ggaggacgtt gttttttgaa aaacgccgtt    101040
atccgggacg ttatttttat tctctttccc gtcttcgtct tcctctgtgt cgcgctcgtc   101100
ccggtaatcg agatagtcgt cgtcatcgaa aggcgcgccg ccgcgtcta cgggcacgct    101160 gttgggtggg cacgcgcttt tgaagaaata daccgggtgc cggtcgggt gcgtagcc     101220 aaagaggctc gcccatacgg tcatccagac gcgtcgtagt ccgcgacata actcaaagac   101280
ggtgtgtcgc gccagaccgg agacgccgtc gcgcagccgt aaatcaaagt cggccacaaa   101340
attgaagacg ggcagacgtt cgttgaagac ttcgtgtcgc gtgtagtaga actgtgtctc   101400
```

```
ggggctggtg ctggccacgt cgtcgtcgtg tagccacacg gtctcggtca gggcctcatc    101460
cgagaaacgg ctgtcgggta cgtgacggag caggtcgcgc ggaaagaggc tgcgatgcca    101520
ggtttcggag gccacggcgc agaagacgtg ctggtcattg gcaggtgta cgcggtagac     101580 gggcagcggt cgctccagca gcggtgccag cgcgggctcg gtagcaggt agcgacgttg     101640 cgagtaacgc gttagcgtgc cggtggtgta ggtctgggct gtgcgtagcg aggcgcatag    101700
acgtaacaaa ccggacaggg agcgttccag cggggagaag acagactcgg aaagcgtgtt    101760
gatgcgttcg agctggcgcg ccagctgcgt ggaggtgccg aagaagcccg ccaggtgcgt    101820
gccgtcgatg cggccgccgt agccggccag ccccaggccg tgcgggctgg tcgccgagtg    101880
gggggattcg tcgaggcgca gtaggtgcgt ctccacgtag tcgtgtagaa agttgtcgag    101940
cgagaagtat ttttgcatga cgtccagcag ctcggtggaa agccggcggc ccagaaaacc    102000
cggttcgcgc gtgcactgcg cttcgggcgc cgcgtcagcg tcgtaagcca ccacgcgccg    102060
gtactcgagc aaccgcgcgc gtgccagcgc cgtgcggtag gccaggtaga cgtagtgcac    102120
gcagaccgtg tcgggcagac gcgcacgttc gcggaacgcg ttgatctgcg tgtccacctg    102180
ctctagctcg gtgtagtcgc ggcggttgcg cgccacggcg tacgccacga aagcggacac    102240
gcgctgacgg aagggcgagc ccagtagcag acgcgcgaac tcgcccatgg aggcgtgcgt    102300
ggggatgatg gtgcccaggt cgcgcgtgca gaagctgcgc acgtactcct ccacggtgga    102360
gatggtgctg tactggccct cgaataggta gtaggccatg gtcagcagca cctggccctc    102420
ggtgtgcccg aagacgctga tgaaccacga gggcgaggtg gggcagagga agacctggtt    102480
gagatgacgt agcacggccg cgtggtgaaa gtacaccagg tgcttgaatt cgcgcacctc    102540
gccgccgtgt tcgggcgaga gcacgggcgt gcggaagaga tgccggtaga gcggctgcgt    102600
ctcggcctcg tccagactgg cgataagcgc cgagagggg atgggctggc gcgcggccag    102660
gtagcgcgag agctgcagcg tttcgttgtt cacggcgaag acgggcgcca cccgccgcga    102720
gtccgagcac ttttgtgtct gtaggcagaa ataaacacgt cgcgagacct ggtgtttgac    102780
cagcaggggg aagacgcagt gatccgtcgg tgtctgcgag agtacgttgg cgactatatg    102840
agcagaatca tactctgttg cgaacagaac gagcgtcatc gtcgcgccgg cacgatgcag    102900
ctagcccagc gcctgtgcga gctgctgatg tgccgtcgca aagccgcgcc tgtggccgat    102960
tacgtgctgc tgcagcctag cgaggacgtg gagctgcgcg agctgcaggc gtttctggac    103020
gagaacttta agcagctgga gatcaccccg gccgacctgc gaaccttttc tcgcgacacg    103080
gacgtggtga accacctgct gaagctgctg ccgctctata ggcaatgcca gagcaagtgc    103140
gcgttcctca agggctatct ctcggagggc tgtttgcctc acacgcggcc ggcggccgag    103200
gtggagtgca agaaatcgca gcgcatcctg gaggccctgg acattctcat cctcaaactg    103260
gtggtgggcg agtttgccat gtccgaggcc gacagcctgg agatgttgct ggataagttc    103320
tccacggatc aggcctcgct ggtggaggtg cagcgcgtta tgggcctggt ggacatggac    103380
tgcgagaaaa gcgcgtacat gctcgaggcc ggcgtggctg cgacggttgc accaccgacg    103440
ccaccggcgg tcgttcaggg ggaaagcggc gtccgcgagg acggggaaac ggtcgccgcc    103500
gtgtcggcct ttgcctgtcc ctcggtttcg gactcgctga tccccgagga aacgggggtc    103560
acgcgtccta tgatgagttt ggctcacatt aacaccgtct cctgtcccac cgttatgagg    103620
ttcgaccagc ggctgctgga agagggcgac gaggaggatg aagtgaccgt aatgtcgccg    103680
tcacccgagc ccgtgcaaca gcagccgccg gtcgagcccg tgcagcagca gccccaggga    103740
cgtgggtctc accgtcggcg ctacaaggag tcggcgccgc aggagacgct gcctacgaat    103800
```

```
cacgaacgcg agattttgga tctcatgcga cacagcccg acgtgcctcg ggaagcggtg   103860
atgtcaccga ccatggtcac catacctcct ccccagatac cctttgtggg ttccgcgcgt   103920
gaactcaggg gcgtgaagaa aaagaaaccc acggcggcgg ccttgctgtc ctccgtgtga   103980
acagcctggc acgttttgga aaacgtacgt gatcacggac acgacgagta cggggtttct   104040
catagacgta ctttattagg tcagggatga cggggaggtt tcgggccgac gtcaaaaata   104100
acgtcactcg tgttgacagg gctttctgcg tcggagctct tttcatcttc ttctgtctcg   104160
tcgacgtcat cgtctaccgg cgagggtgtc cgttgcaaca acgcgtgctc gggcgtgtgg   104220
gtgaaaccga tgtcgggggt gggcggcacg atcatctgtc ctaggggtg actgcccacc   104280 ggcagatagg taaagcggtg ggtggtaaaa accgctttgg ctacggtggt gtgtggggag   104340
atgcagacgt tggtgtgcga agtgttgacc accgtcacgc cggccgcggt acccgggagc   104400
cagatggtgg gtcggatgat gagatccgac tgactaaact ggcgcacgcc cactatgagg   104460
gcgcagatac cggcgcgtg cacgtaggcc gcgtcaaaat agacggtttg cgtgtgaccc   104520
ggaccgatca ccagcgtctg acgggtacgt aatgaaaaga acggtgttc gttgggcggc   104580 ggcaagttca tgagctgcca aggttctggc acaaaacagg ggaaaacgcc gatatcgcct   104640
tcgatggtgc ctggaaagat ggactgaaaa gtgtcgttga ggttgacaac atccaactgc   104700
gggacttgca gcccggattc cagcagctcg ggcatgcaaa cgaattgcgc gtccaggcat   104760
ttgtaaaagg taatgccgaa aaaaccttcg gggatataga ggctgacgcc cagcgaggtg   104820
ggcactttgc gctcgcgtga tagccaaatg atgtgtttat tgtaaaaggc cagctgcgtg   104880
tggcattgtt tgacgatgaa actggaaggc atccacttgt agggaacttt gagcggcgac   104940
ggtaatggcg acgacgcttc atcttctccc ggatgctgct ctttgtcgta tttctcctcg   105000
gtcgattggg gcagcgtaaa tgtggtttga aaatcgctat cgctagcgaa acgtacgcag   105060
taacgcatgt tgacggattt ctcggctagg atgatggagc ctgatgacgg tgcggactct   105120
tccttcatta ttaacgtagg ggtctcccag aatcgctgaa acgggagcg cggcagccgc   105180 gacagtacca gttgagagtc gattcgatcg gtaaacatcg taagcatcgt ggcggtggtg   105240
tgatggagtg gaacacacta gtactaggtc ttttggtttt atcggtagcg gcaagttcca   105300
accatacgtc gactgctagc acaccgagtc cctctagctc tactcacacc tcaacgaccg   105360
tgaaggcaac gactactgcg acaactagta caactacggt gacaagtacg acttcatcaa   105420
cgactagtac caaacccggt tccaccactc acgaccccaa tgtgatgaga ccacatgctc   105480
acaatgattt ttacaaggcg cattgtacat cgcatatgta tgaactttct ctgtccagct   105540
ttgcggcctg gtggactatg cttaatgctc tcattctcat gggagttttt tgtatcgtac   105600
tacgacattg ctgtttccag aactttactg caaccaccac caaaggctat tgagggtgga   105660
caggttcaca gcccggcggt gttccggcgg ggtaaggttt ccatatgtgg acgactgtag   105720
gctgaagtta cggatttcac ttaaaaacag cagcgagtct agataatccc acatgggatc   105780
tataaacgtt ctctgaaacc tcgtcgatgg tgacgtaggt gtagttttgt tattatcgga   105840
agccgtttcg ttttccacgg gcatggtgtc gttgtaatat aaggagctca tgtcaagagt   105900
accgtaaata gtgtacggtg tttcgttgcg aatcaatacg tgcgtatttt tcataaattc   105960
tgatacggcg gtccggttac ggtttggttt acaaaaaggt tcatctcgat agcgcagagt   106020
agtatacacc cacgtcgcta gatcttttaa ctgcgtggtc agaatggatt tcataaagtt   106080
ttcgtcagga cgataaccaa ttgtagatgt gggaatccga gttgggacaa taggactata   106140
```

```
agttacatta gtactgacgt taaaaatagt tgacgtgtag gaagaatatg gtgtggtggt    106200
gctaacacga cttttcttac tgatcgattt gacaggcgct tgtttacgtt taagctttcg    106260
catagtgttc ttcagcttgg tgctgttaat atacttggga acgcggaata tattccggct    106320 catgcgtta accaggtaga agctgcgtgt acagttacgt tgcgcgtaac gtagaagcag    106380
ggcggctaaa cctaaaaaat aaattgtttg gctatccaca ttgactttac tcggaccac    106440 gtacagtttg gtgttccaac gtggtacgtt aaaaaacata ggattaaatg tggtaaaatt    106500
gccacagttt tcctccccgg tgttgttacg ccgggataca tttagcattt cagaaaggca    106560
agtcatggaa ggtatcgtac cacaggatgg gggtcgaaat gttattttt gccctgtatg     106620 attatattcc gaatacacat atttggccgg tttacggagt tgggtcgtgt gaaaatcgaa    106680
ccagaggtgg gtaatgctat gattacgaat aggtcctgct aaaatggaat tcggggaaa    106740 ctgtttcatt tctacagtta tgttatacaa cttttgctga ctaggaaatg tgaaaaactt     106800
gtaataatca cctgtttttg acgctagttc ttgcagtata cgtaatttta gttgcctctc    106860
ttcctctttt gctttctgac tctttactcg aaaacgcgct accgtgatct tacagtttat    106920
gaaagagaat agcaggaaag ttagcgacat aaggaaaaat aaattaaaaa cacctctcat    106980
ctctcccttt ctccccatga cagaggagga gaccccgcac cgtccgtctg ccttgtggtt    107040
tggcttgcct gcgtgtactc actgctgatt ctggtcgttt tgctgctcat ctaccgttgt    107100
tgcatcggct tccaagacga cctagtctcc cgcaccttgg ctgtgtaccg agcttgtatc    107160
caaggcccga tatgtaacca gacccacaac agtacctcgt aaataaagac gcacagacct    107220
cacacatata gtaccatcac accgtgtggc gtgtacttta ttacaacgag caagagtgcc    107280
cctaagtatt ggggcccgta ccgttttaga agattttgtg tgaatgtctt taactttctc    107340 tgtcccttt ctcataaact gtcaggttct acagtcagca tgtcttgagc atgcggtaga     107400
gcagatagat gccgatgatg gccgatagcg cgtagacgga catcatgagg agacgactgt    107460
cggtagcgtc cacgacgacg tcagttactt ctaggaccgt accgttttc aaaagcatga     107520 ggtagtgagt tcgcggagat gagaccacca cttcgttgta gggatccagg gcgaaaagga    107580
cgtcgtccga gtcgtgcatg tacatgatgt tgatgacgcc ttgcgtgtcg tcgtattcta    107640
gtagggcgct ttggcaaaag gcgcagtttt ctagggaaat gttgagcgcc gctgtgatgc    107700
tgtgtgtggt atgcatgttg cgcgtcagtt cgcatttagt ttgactgtcc gtctgggtga    107760
tgatgaggct ctggcctacg acggtggtgg agacagggta ggagatacct ttgatcaggt    107820
actggtttgt tacgacataa ctgacgtgtt cggagacggt cagcgcggag aaggattcgc    107880
cgagcggcag acaaaacagg tcggggaagg tttctagcgt gcttggttgc atggtagata    107940
ggatggagag ggcggcggga acggtagtgg ggacggtggc atcggggaag agacgtgtga    108000
ggcgttcgag cgagtgatcg cgtcgcccgc tactggaaca gggtgtgtac aggtcgctga    108060
ggtattcgtg gtgcggatga gctagcaact gcgtaaagtg tgatagctcg gctaatgaac    108120
agaggcccgt ttctacgatg aagatttcgc gtctctccgt cgtatgtact agcatggagt    108180
ggacgaggct gcccatgagg tagagttctt gacgcgcgaa ggctgaaaga aaagaggcca    108240
ggtgcgtttt gtgtagtttt agggcaaagt cggcgatctg tcgtagtgcc cactggggga    108300
tgagatgttg ctgattctgt ttagagagta tgtagaccag gcgtacgagg ctggtgatgt    108360
cggtgatctg attcggtgtc caaagggctc gtttggccag gtccacggcc gtgggataca    108420
gcagcaacgt ggtgcgtggt ggtgtttgtg agaggcaggt gatcataaat tcttgtatt      108480 gtaagagtgc ggcctggcgg tctagggccc gtgggacgga gacttgggcg ccggcctctt    108540
```

```
cttgtcgggc tgctgcgaac agtgctaatg cgtaggcgaa ggccatttct accgtgcggc 108600
ggtccagcat ctgacatcga ccgcttttga gtacatccac ggcgtaacgg tgaaagctgt 108660
tacgtagtag tgcgctgagg tccaggtagt tgaagtcaag tgcggcgtca agaaagtccg 108720
ggtctttgag ataagagtga cggttcagtt gatctttctt aactagcacc aggagctcgt 108780
gtttttcagt ttgtcgtagt ataaagttgt cgcgttgata gggcgcttta aagagtacgc 108840
gtggaagatg gccgaagata agcagcatgg gtgtgtcgtc gtctatggac accgtaacta 108900
cgaagaagtc ctcggtcagt gttatttaa cgtaacgtag ttcgtcgatg aggtaaaagc 108960
cttggtgcaa acaaggtgtg acggtgctga atagtagatc gtgtccatca aagaggatac 109020
aggtctggtt aaagtgtggt cggtgtagtc ctgaggtggt atgtgattct gtccagccgt 109080
gtggagtggt ttgcggtggc atccaaacgt gaggtattga caggtcaatg ggtggtggca 109140
cagtggtggg ctgttcacct aggctgtcct gtgcctttag ctgctgcgaa aaagatcggt 109200
agctggccag gtctttggat accagcgcgt aagtgttaag tctctgttgg tatcttccca 109260
gggtttcggt cagatctacc tggttcagaa actgctccgc cagaggaccc gcaaaaagac 109320
atcgaggcat atggaataca tagtattgat tatagctttg gaaaaagttg aaactgatgg 109380
cgttttccct gacgaccgtg ctgttacgga ggctgctatt gtaggtacac tgggtggtgt 109440
tttcacgcag gaagcggatg ggtctcccgt aggtgttgag cagtaggtga aacgctttgt 109500
ccagcggttc ggatatggct tctgcgccat atcgtgacga aagtaggtgg ctgaggagac 109560
agacggcgag gacgatgagg taggagggga ggcctggccg catagcgcgg ccgcgccgct 109620
gggttcagcg gcgtgatcca ggtggtggtt ggcgttacac ccgagagaag gagagaaagg 109680
atcccaggaa ggagcacccg ggtgcggcgc tacgggttac aaaagtcgcg tctccgtcta 109740
tttaatacga tgtcattggc cgctgcgaag ggagaagagg ggacacgcga gtaagtcatg 109800
ccgtccgggt gtggggacga cgctgattcg aaggggaacg ctctgcggag attgcctcac 109860
gtgcgtaagc ggatcggtaa gcgcaagcac ctggacatct accgtcgcct gctgcgggtc 109920
tttccctcat ttgtggcgct caaccgcctg ttgggaggcc ttttcccacc cgagttgcaa 109980
aagtaccgtc gccgtctttt catcgaagta cgattaagtc ggcggattcc cgactgcgtg 110040
ttggtgtttt taccgccgga ctctgggtcg cgcggcatcg tgtattgcta cgtgattgag 110100
ttcaaaacta cgtactcaga cgccgacgat cagtccgtgc ggtggcacgc cacccacagc 110160
ctgcagtacg ccgagggcct gcgccagctc aagggcgcct tggtggactt tgattttctg 110220
cgtctgccgc gcggtggcgg tcaagtctgg agcgtagtgc ccagtctggt ttttttcag 110280 caaaaggccg atcgcccatc ttttaccgg gcttttcgtt cgggccgttt cgacctgtgt 110340
accgattctg ttctggacta tctgggacgg cgtcaggatg agtctgttgc acaccttttg 110400
gcggctaccc gtcgccgtct tcttcgagcc gcacgaggaa aacgtgctgc gctgccccga 110460
gcgcgtgctt cggcggttgt tggaggacgc ggcggtggca atgcgcggcg ggggctggcg 110520
cgaggacgtg ctcatggacc gggtgcgcaa acggtatctg cgtcaggagc tgagggatct 110580
gggtcacagg gtgcagactt actgcgagga tctcgaaggg cgcgtgtccg aggcggaggc 110640
gctgttgaac cagcagtgcg agctcgacga aggaccgtcg ccgcggacgc tgctacaacc 110700
accgtgtcgt ccgcgttcgt cgtccccagg gaccggcgtg gcaggagctt ccgccgtccc 110760
acacggtctt tatagtcggc acgatgccat cacgggaccc gccacccgt ctgacgcggc 110820 gaccgcgtca gcggccgccg gtgcttcttc tacctggctg gcgcagtgcg ccgagcggcc 110880
```

```
gttgcccggg aacgtaccta gctactttgg aatcacgcag aacgatccct ttatccgctt   110940
tcacaccgat tttcgcggcg aggtggtcaa caccatgttc gagaacgcct ctacttggac   111000
tttctccttt ggtatctggt actatcggct caagcggggg ttgtacacgc aaccacggtg   111060
gaaacgagtg taccatctgg cgcagatgga caacttttcc atttcgcagg agctgctgct   111120
cggcgtggtc aacgctttgg aaaacgtgac ggtgtatccg acgtacgact gcgtactctc   111180
cgatttggaa gccgccgcct gtctgctggc cgcctacgga cacgcgcttt gggagggccg   111240
cgatccgccg gactccgtgg cgacggtgtt gggtgagctc cctcagctgt tgccgcgtct   111300
ggccgacgac gtaagtcgtg agattgccgc ttgggaaggc cctgtcgccg cgggtaacaa   111360
ctattacgcg tatcgcgact cgcccgatct acgttactac atgcccctaa gtggtgggcg   111420
ccactatcac ccgggcactt ttgatcgtca cgtgctggtg cggcttttcc acaaacgcgg   111480
cgttattcag catttgccgg gctacgggac gataacggag gagctggtgc aagagcgtct   111540
gtcgggccag gtgcgcgacg acgtgctttc cctctggagt cgacgtctgc tggtcggcaa   111600
gctgggtcgc gacgtgcccg tctttgtgca cgaacagcaa tatctgcgtt caggcctgac   111660
ctgcctggct ggcctgctgt tgttgtggaa ggtgaccaac gcggatagcg tcttcgctcc   111720
gcgcacgggc aaatttacgt tggccgacct gctgggttcg gatgccgtag ccggcggcgg   111780
gttgcctggg gggcgcgcgg gcggcgaaga ggagggctac gggggggcgg acgggcgggt   111840
acgtaacttt gagtttctcg tgcagtacta catcgggcca tggtacgcgc gcgacccgcg   111900
ggtcacgctg tcgcagctct ttcccggcct ggctctgttg gccgtgaccg agagcgtgcg   111960
cagcggttgg gatccctcac gtcgcgagga cagcgccgga ggtggcgacg gcggcggcgc   112020
cgtgctcatg cagctcagca agagcaaccc cgtggccgac tacatgttcg cgcagagctc   112080
caaacagtac ggcgatttac gtcgcttgga agtacgcgac gccctgctct ttcactacga   112140
acacgggcta gggcggctgt tgtcagtgac cctgccgcgt catcgtgtgt ccactttggg   112200
ctcgtccctc tttaacgtca acgatattta cgaactgttg tacttttag tgttgggttt   112260 tcttccgagc gtggcggtgt tgtaatttcc accacgtgtc gcttgctgca taaagggcga   112320
gcgtccccgg agagggtata ttcgttcggc gagagcgggc ggcggtggtg ggtatgtcct   112380
cttctgcgga gaagactacc tcagttaccg attccatcat gctcgctatc gtgaatttca   112440
aatacatggg cccgttcgaa ggctactcta tgtcggccga tcgcgccgct tcggacctgc   112500
tcatcggcat gtttggctcc gttagcctgg tcaacctgct gaccatcatc ggttgcctct   112560
gggtgttgcg tgttacgcgg ccgcccgtgt ccgtaatgat ttttacttgg aatctagtac   112620
ttagtcagtt ttttttccatc gtggccacca tgttgtccaa gggtatcatg ctgcgtggcg   112680
ctctaaatct cagcttctgt cgcttagtac tctttgtcga cgacgtgggc ctatattcga   112740
cggcgttgtt tttcctcttt ctgatactgg atcgtctgtc ggccatctct tatggtcgtg   112800
atctctggca tcatgagacg cgcgaaaacg ccggcgtggc gctctacgcg gtcgcctttg   112860
cctgggttct ttccatcgta gccgctgtgc ccaccgccgc tacgggttca ctggactacc   112920
gttggctagg ctgtcaaatc cctatacagt atgctgcggt ggacctcacc atcaagatgt   112980 ggttttgct gggggcgccc atgatcgccg tactggctaa cgtggtagag ttggcctaca   113040
gcgatcggcg cgaccacgtc tggtcctacg tgggtcgtgt ctgcaccttc tacgtgacgt   113100
gtctcatgct ttttgtgccc tactactgct tcagagtcct acgcggtgta ctgcagcccg   113160
ctagcgcggc cggcaccggt ttcggcatta tggattacgt ggaattggct acgcgtaccc   113220
ttctcaccat gcgtcttggc attctgccgc tcttttatcat tgcgttcttc tcccgcgagc   113280
```

```
ccaccaagga tctggatgac tcctttgatt atctggtcga gagatgtcag caaagctgcc    113340
acggtcattt cgtacgtcgg ttggtgcagg cgttgaagcg ggctatgtat agcgtggagc    113400
tggccgtgtg ttacttttct acgtccgtcc gagacgtcgc cgaggcggtg aaaaagtcct    113460
ccagccgttg ttacgctgac gcgacgtcgg cggccgttgt ggtaacgacg accacgtcgg    113520
agaaagccac gttggtagag cacgcggaag gcatggcttc cgaaatgtgt cctgggacta    113580
cgatcgacgt ttcggccgag agttcctccg tcctctgcac cgacggcgaa acaccgtcg     113640 cgacggacgc gacggtaacg gcattatgag cggcggcgtt gtacggcagc ggggagaaaa    113700
gtggcagata aattacgtca ggttcacacg tcgttagcca gcgtcggcat atgaagggcg    113760
cgggcggcca gtacggcctc tgggttgaga caggacgagg cagggtgaga agaggagga     113820 tgggggggac cggggtggtg gtgctgctgc tgttgtgggt gcggacggtg cgggtgccgg    113880
gacagcgtgc cggcgaacgt tctgtaatct tccataataa aggtaaaaat gcccgtttcg    113940
tgtcgactcc gctggatctc gaaggcgtcg ggggtaatgc gcatcttgcc ggtgccgatg    114000
agataaaagt accacatttt ttgacagatg atgcgaatca agggttcgta cgcttcggca    114060
ccccagtggc gtgtgaagaa ggccgccaga cgaaacaggc ggtgtccgta gagcgtgcct    114120
agggagaaga ggatgttgcc gttgcgcgcc aggtcttcgg ggaaaacgac cggcaggccg    114180
gtgtggcgct gcacaaagcg cgtcagcagt ccgccgctca agcgcgggtg acacaggcgc    114240
tggctgagac gggcggcgcg tgtttcatcg aacacggccg cctcaaagtc cagccccggg    114300
aaggcctggc gcagttcgcg gtacagatga ggccagtagg gttgcggcgt cttgcggcta    114360
agcacggcgt ggtccgagac acccaggttg ttcatagttt cgcgcagtag cagcgtttcg    114420
agaccgcggt gaaagaggag gacgcagatg aggcgtacga ttttgagttc ttccaaacgc    114480
agcgagctca gcggctgtcc gcgcgacatc ttctcgctaa tctgtaatat tagatgattg    114540
gcgcaagtaa aggagaattt gcctgtgcgg acccgcggga cggcgggtt ctcttcgtcg     114600 cgggccatca tcgttcgctc ggtgagcggg tagcgacggt gacgacaatg acgatggacg    114660
agcagcagcc gcaggctgtg acgccggtct acgtgggcgg cttttctcgcc cgttacgacc    114720 agtctccgga cgaggccgaa ttgctgttgc cgcgggacgt agtggagcac tggttgcacg    114780
cgcagggcca gggacagcct tcgttgtcgg tcgcgctccc gctcaacatc aaccacgacg    114840
acacggccgt tgtaggacac gttgcggcga tgcagagcgt tcgcgacggt cttttttgtc    114900
taggttgcgt cacttcgccc aggtttctgg agattgtgcg ccgcgcttcg gaaaagtccg    114960
agctggtttc gcgcgggccc gtcagtccgc tgcagccgga caaggtggtg gagtttctca    115020
gcggcagcta cgccggcctc tcgctctcca gccggcgctg cgacgacgtg gaggccgcga    115080
cgtcgctttc gggctcggaa accacgccgt tcaaacacgt ggctttgtgc agcgtgggtc    115140
ggcgtcgcgg tacgttggct gtgtacggac gcgatcccga gtgggttacc cagcggtttc    115200
cagacctcac ggcggccgac cgcgacgggc tacgtgcaca gtggcagcgc tcggcagca     115260 ctgctgtcga cgcgtcgggc gatccctttc gctcagacag ctacggcctg ttgggcaaca    115320
gcgtggacgc gctctacatc cgtgagcgac tgcccaagct gcgctacgac aagcaactag    115380
tcggcgtgac ggagcgcgag tcgtacgtca aggcgagcgt ttcgcctgag gcggcgtgcg    115440
atattaaagc ggcgtccgcc gagcgttcgg gcgacagccg cagtcaggcc gccacgccgg    115500
cggctggggc gcgtgttccc tcttcatccc cgtcgcctcc agtcgaaccg ccatctcctg    115560
tccagccgcc tgcgcttcca gcgtcgccgt ccgttctccc cgcggaatca tcgccgtcgc    115620
```

```
tttctccttc ggagccggca gaggcggcgt ccatgtcgca ccctctgagt gctgcggtta    115680
ccgccgctac ggctcctcca ggtgctaccg tggcaggtgc gtcgccggct gtgccgtctt    115740
tagcgtggcc tcacgacgga gtttatttac ccaaagacgc ttttttctcg ctacttgggg    115800
ccagtcgctc ggcagcgccc gtcatgtatc ccggcgccgt agcggcccct ccttctgctt    115860
cgccagcacc gctgcctttg ccgtcttatc ccgcgtccta cggcgcccc gtcgtgggtt     115920 acgaccagtt ggcggcacgt cactttgcgg actacgtgga tccccattat cccgggtggg    115980
gtcggcgtta cgagcccgcg ccgtctttgc atccgtctta tcccgtgccg ccgccaccat    116040
caccggccta ttaccgtcgg cgcgactctc cgggcggtat ggatgaacca ccgtccggat    116100
gggagcgtta cgacggtagt caccgtggtc agtcgcagaa gcagcaccgt cacggggca     116160 gcggcggaca caacaaacgc cgtaaggaag ccgcggcggc gtcgtcgtcc tcggacgaag    116220
acttgagttt ccccggcgag gccgagcacg gccgggcgcg aaagcgtcta aaaagtcacg    116280
tcaatagcga cggtggaagt ggcgggcacg cgggttccaa tcagcagcag caacaacgtt    116340
acgatgaact gcgggatgcc attcacgagc tgaaacgcga tctgtttgcc gcgcggcaga    116400
gttctacgtt actttcggcg gctctccccg ctgcggcctc ttcctccccg actactacta    116460
ccgtgtgtac tcccaccggc gatctgacga gcggcggagg agaaacaccg acggcacttc    116520
tatcaggagg tgccaaggta gctgagcgcg ctcaggccgg tgtggtgaac gccagttgcc    116580
gcctcgctac cgccgtcgggt tctgaggcgg caacggcagg gccttcgacg gcgggttctt    116640
cttcctgccc ggctagtgtc gtgttagccg ccgctgctgc ccaagccgcc gcagcttccc    116700
agagcccgcc caaagacatg gtggatctga atcggcggat ttttgtggct gcgctcaata    116760
agctcgagta agagagacgc tatatttagg gcttccctct cttttttttc tacaccgtga    116820
taccctaata aagcacaccg cggttattat caacgtctct gtttttatta tttagaaata    116880
aatacaggga atgggaaaaa cacgcggggg gaaaacaaag aagtctctct ctagatgcgg    116940
ggtcgactgc gtggggtgct ggaagtggaa gcggtgctga tgggcgaggg tcgtggcgcg    117000
ggcacggacc gcaacgtgct gctgatgtct gctgcggtac gcacgtcgcc gtccatgtcg    117060
ctgcgcagat aagaggtagg tcgtagtgcg gcgtgctgca cgctcaccgt taatggtacc    117120
aggtcgtcca agctcgcaaa gacgtgccac gaggggatga cgagcgtgag agccccgttg    117180
ttaccgcttc ggcgtctttg tccggtcagg atcagtgccc gggacagtcc ggcttgggtg    117240
tccgagtcct cgtcgccgct ggcctcctcg aagccggcaa acatggcctc ggacagggg    117300 gtcggtgtcg gtgtggagga gaggtcatct tcgtcgtcct cttcctcttc ttcctcctct    117360
tcctcggtgg gtggtaatcc tggcgattgc gggagaaact cggagacggc gccgcgcatg    117420
acgttgctcc gtggaaagag accgcgcgc agctgcacct ggggacgctt gatcttgtcc     117480
ggtttaccgg gtgtgagagt ccaaaaccca cggcggaaaa agtggatgcg gcctagcggc    117540
tgtcggtgtt ccaaatgaac ggcctgatcc ccggtcagcg tgacgcggag ggtgattcgc    117600
acacgatcgg gtagcgggcc ggcttctatg gagacgcccg ggatgttttc cgggaaaaaa    117660
atggtgtcgt gagtctgatt ggtctcgaaa gcattctgga tctgcacgat gtactcggga    117720
tgtatgcgcg ttagcgtaaa acttttggga atcaacagct ggaagccgtt gtccggcaag    117780
cgtcgtaggt gcgggtacgg attgtgtcgc gccaccacct cggcgcgatg cgtgtaaacc    117840
gaaaagtgca gaaacacgct ggtcggcggg tgcggtgagt cgtgatgcag aaacagcatg    117900
atccattggc ctcgctcgtc cgtctccgtt ttgtggatgt acgtgttagg gtccgaacag    117960
gccagctgct ccagggcgtc taccagcgtc agcgggatag cgccggcgcg aaaggcgaac    118020
```

```
tggctgacaa agatctggcc ggcctccaag ctgctgtcgg ttctgcggcg ccagttcggc   118080
gttacggtca gtcgcacggc ccagtagtga gccgtgcggc ggatgatggc gcgcgcctcc   118140
actcgcggcc gattttcttc gccgccgcgc cgctggctct gaaagaggtg cagtccgcta   118200
acgggcacgg ggtccagcgg cagtgcaaag gccagtaccg agaccgtgtt gttttctgag   118260
cctggcgtca ggcgtcgtgg gccaaagttg ttgaggtcca ccagcagtcg gtcctgttcg   118320
cccaccacgc agcggcccett gatgtttagg tcggtcaggt ctacggtgtc gtgcggagat   118380
ttgttctcct gaaaacagca gagaaccgag ggccggctca cctctatgtt ggtacgcagg   118440
tccaggagtc gcagacgacc ggcttccagc gagccgcctt ccacgttggt gatgagccga   118500
agcacctggc agtgcaggcg accaaagctt ccgctggcgg cttcggcctc gctgatcgcg   118560
gccgcttccg acgagggtcc ctcaccgggc gaggacgatg cctgagacat cgcgaaggcg   118620
ggatgagggg gggggtcagg ggatgcgcaa aggtgaacgg gtcttcgtgg gaggtcggga   118680
agggttccgg caactgtcgc aaatatagca gcggcgacag gtgtggcggc caaaagtcgc   118740
gtgtctgagt ggacgtgggt ttttatagag tcgtcctaag cgcgtgcgcg gcgggtggct   118800
caacctcggt gcttttggg cgtcgaggcg atgcatggcc cgggcaaggc gtcttgccgg   118860
tggcggcgac gtttgggttg cgcagcgggc tgccatacgc cttccaattc ggcgaagatg   118920
cggtagatgt cgttggcgtc ccagaagaac tcctggtact tcagattctg accctgaacc   118980
gtagccacca tgggcaccag gttgcgggcc aggatgccgg cctgccaggg cggccaggtg   119040
aacacggccg gattgtggat ttcgttgtcg gaatcctcgt cggtgtcctc ttcgggcgcg   119100
acggtggact cggccttaag gcggccgcgt gtcataacgc ccgccgtgca cgccgtcgcc   119160
gaggatgctg atttgcgttt gcggcccgcg gaagtggagg cgcccgccat ggcgccgccg   119220
ccggtaacgc ggggcgtctt gcgctcggtg gttacgagtt cctcgtcgga gtccgatccg   119280
ctggtccaga cgtcgtcgtc gccctgggcg gcaccctcgt cgtgccggtc ccaggtgtgt   119340
cggtactcaa gcttgccctg gatgcgatac tggctggtga aggtggggtg ttcgctgtac   119400
tgaggcccgc gctgcagcag caagtcgata tcgaaaaaga agagcgcagc cacgggatcg   119460
tactgacgca gttccacggt ctcgcgtatc gcttgcacct ccaggaagat ctgctgcccg   119520
ttcatcaata ggttacctga gatgctcagg cccgggatgc tcttgggaca cagcagccca   119580
aaatgctcgt gtgaggtaaa agccacatcc agcatgatgt gcgagatctt gcccggtttg   119640
attatcatat ttttgggaca caacaccgta aagccgttgc gctcgtgggg gcgcatgaag   119700
ggttgcgggt tgcgggtcat cgtcaggtcc tcttccacgt cagagcccag cgtgacgtgc   119760
ataaagagct tgccggaggg cacgtcctcg cagaaggact ccaggtacac cttgacgtac   119820
tggtcaccta tcacctgcat cttggttgcg cgcgtgttct ccatgagcga aaccagctcg   119880
tgcgcgcaca ccacgtgccg cagtgccacg tccttggtgg gaaacacgaa cgctgacgtg   119940
tagtagacgt cgggctcttt ccactggttc tgctgacgcg tccaggccag tcccgagacc   120000
gtgagacgcg cctgccacat ctgcttgccc gacgcgtgaa tcacagcgtc agctacgggc   120060
aggtgtcggt gtttgcgctc ggccgccgac gggtagtggt gcacgttgat gctggggatg   120120
ttcagcatct tgagcggcag cgcgtacaca tagatcgaca tgggctcttg gctggggcag   120180
atgctccggc ccgtggggtt gtgcacgttg accgacacgt tctccacctc gctgcccgta   120240
aagtacgtgt gctgcacctg cagctgattg tcgccgcggt ggcatggcgt cgagtcgggc   120300
gtgtactgcg acaccaggat cagcgagggc tggctcacgc gcacgtggat accgtctgc    120360
```

-continued

```
aggagtcgcg tctcgtgcgg cagcaccggc gtgtcgccgc gactaaacac ggctttcagc   120420
acgtgccccg aaatgggacc cagtacggat atcatttcgg gacaacggcg accgcgcgac   120480
tccatgctgc ctgcgcgtac gggtgtaggc gactgagcgg cgcgccctct gcggccgccg   120540
ccttacatag gcaggcgacc agacgcggaa cccgaaataa aaacgttcta cacagagaca   120600
accgcggatt attgagtgtc ttttttatt aaaaaaaga ggcaaagccc caccgtcacc     120660
acacccatc acacaccacc accgatttt ttgttttaac cccgtatcgc gcggacgcct    120720
agtgtccgtt tcccatcacc agggttctct gtttagagat cgccgcagac catggctaaa   120780
gtgacaggac tcgttttctc tgtcgtattt tccgtaagct tacagtcttg cggttccgtc   120840
tccggggacg ccagccgcat gggcagcagg tcctccaacg cgatggaagc gcccagcacc   120900
gagagctgct gttgcgacgg cgaatgggac gtggaccgcg agtgtagcgt ggatttgact   120960
tggtgcgtca ttgctgacag gcaaccgcga ttcagcgtat gctttgacga gataaaatag   121020
aggcgtccca ggagcgcgtc ccgtgggaac gtggcgccat tctcgtcgct caccagtacg   121080
gttaattcca accaggagcg cggtagccag accgtaacgg gcattttgag tccctgacgg   121140
ttgtgtggta caaaaacacc cagataaggc ccgtaaaagc ggcggtagat acgtaacgtg   121200
tgcgagttct tcagcgtcaa ttcgtaaggg acgcgcacct ccagtccctc gtccgccgcg   121260
ccagagcgtg gcggtacaaa gtaaggcagt ggcgcgtccg aaaagaaggg tcgtcgcacc   121320
gtttcgcgtc gcagccgcag gcgaaacgcc actgggtcgg ctggcgcctc ggtgcggtcg   121380
caggtcacgt tgaaacgtaa catgccgtct tggtatagcg tgagtgacga cagcgtcagg   121440
tccggcggtg attcgttcgg gtctagctcc aatcgtccaa agacggaggg tcccaatgtc   121500
ttggccgtgg tttccgagag gcgcgccgag atacggctgg tgagtccacg cggccccgag   121560
atgccgcctt ccactcgatg ccagcacagc gcgtgtcgta cgcgcaccgt cagcgtgggc   121620
gtcagatccg cgtccgttga ctccgcggca tcggcgacgg aagccgcgtt ctccgttacg   121680
ttgtttatat ccagcgtcga ctcgaacgtg agttctggca gatgcagcgc cagacagtcg   121740
tgtaacgccg tgtgatgcgc ggctttacgt cgtagcggta gccgtttcag cagcggcgtg   121800
atgatacgga gcgcgaagag attgagtgat aagcgcacga tggccatgcg cgtcagttgt   121860
tggtcgatta ccgagcgcag gatatggcag cctgggcgtg cgggaaagag agagaaggcc   121920
gggcgcacgt cagaatcctc gttggagacc acgcatagaa tgccgcgttc acgatcgtcg   121980
ttgcggtcat cctcgtcctc ttcttctttc ttctcttctt tttcctttt ttctcgagc    122040
tcgtgggaag ccgccgtttc ttcttcttgc gacgtcgcgg gggcggtttg agactcgccg   122100
ttcgcttccc ccaattgcag cggcgtagag agcagaatct ggaagggatc ccgcaattct   122160
tcgggtcgga ggtcgaggtg caactggatt agatggtaag ttccgcggtg cacccgaggc   122220
tgacggatgt cgtgtttatc cgtcaatgta aggatggtct gcggcgagcc gctgtgcttg   122280
tccagctcgt ccggcgtttt caggaggagg ctgtcgtcgt cggtactggc gacgcccatc   122340
atggtcgtgg tggtagtggt ggcgaggaaa gtgagcggcg gcgccgacag agctcggcgt   122400
tggcggcggc atttgccgct gtgtcggctg ctattgctgc caacgccacc gccgccgcct   122460
cgtctggctc gtgccggcg ggcccgattc gaaggttgg ggtcggcgcg tggcatgctt     122520
ggtgtctgcg ggcgcgagag ggccggctca gcctttaaat atgcaggtcg cggatttgtt   122580
atcgggtgaa acgtcacaca ccgtgaagac gacctgttcg cggatgaggt catccagctg   122640
tcgcagcatg acgaaaagcg ccgacagccg cgcgatctcg tcgtcgggcg acacgtgctg   122700
cggccgcgcg ggcgtgcgcg gctcgccgac gctgcgctcg cggtccagcc gcatcagcag   122760
```

```
ctcctggcac ttgacgagca gcatggagct gtcctctagc gccaacttgc gcacgtaggt   122820
catggtcagc tctgaggcta gattggccac catggacatg gagaggcagg cggtcttcat   122880
gtcgatcagc aggtgctggt cgatgaccgg atcgggatg  gtgaaggtgg cgtcgcgaaa   122940
agtaatggtc tgcagctgct gcacggcagc ctttacctcc tcgtacgaac ggtcgagcga   123000
gaagaggccc atgatgagta gtcgctggtt gatttccagc gccagtggca tgggcacgat   123060
ccagggcagc accagctccc actggcccag cgtcagcagg ttctcgcgcg ccagcggtcc   123120
gtggaagagc ggcggcagca cgcatagcgc gtcgcccttc tcccaagtca cgggtcccgt   123180
gttgaggacg gtgtagagca gtccgtgcgt cggtacgtgt aggaggatct ggttgccttc   123240
tacgcgccgc atcaacgtca gcgtcatatt gcgcagcagg ccgcgcagtc gcacgtagcc   123300
gcgggtgtga tctacgaact ggtgtaggcc cagctggtag tgcttgatga gatgtagacg   123360
ctgcggaatg ggcacgactg ccgctactag cttggtcagt ttgcctacgt cggcgatgct   123420
gagcttgtgg tcgaaagtgc agaagatgtt ggcctccatg gccgccatag cggcggtgaa   123480
atcgtggccg cgacggagga gaagcggaga cgaacaacgt ctgcaccggg cgcggcgtca   123540
gagcgagcgt ggcgcgtccg ggcccgcgtt tgcgtctagg tgactcgccg ctaacctgcg   123600
gtcgtcgccg tcctcctcac cggacggcct cacgagttaa ataacatgga ttgctgcagc   123660
gggatgattt cgcctacgac gtagttacca aagtgcgtct cggacgtggc gaaagccccg   123720
gcgccaccct tgagtttggt ctccatcagc gccagcgtgg tggtgctgag aatcggcaac   123780
gcttcctgcg tcaggcggca cgggttttcg atgagttgtt ccgtgccttc gacgcagacg   123840
tactgcgtgt ccgtgtcgcc gcggatgcag tccttggcgc gtagtaggta ctcgtcgatg   123900
gttttgaaga gcgttttgtt ggccgcgata atctcttctg tgttaaagta ctgcgcacag   123960
gggctgtaga atttggagtt gtagcccaaa cgttcgcgat gtcgggtgtt gtacagtacg   124020
tcgcttagac agccggcttg cgaggcccag ggggttgtgt ggccgcgaa  agtctgtgcg   124080 tcagcttcgc gatgatcgta gatggccttg gtggcggcct ccgtgtcgta cggatcgacg   124140
cccagcatgc aggaggcgcg tccgcgcggg ttgttggtga ttttgaagta attaacgtcc   124200
atcgttaccg gcgtgaggat gagttcgcac acggcctttt gtccgtgcac cgtggcggcg   124260
gcgttgcgct cggacatgct gccgaacgtc agcatggaga tggtctccgt atctaacagt   124320
tgcggccgtt ccacgccggc cgcgtgccgg atccagcggt ccacctcgtc gtggcggtac   124380
acgttcatag ggaagacgcg aaagaggtct tgcacgcgga cgcccatgtc ggtccgcacg   124440
cggtttacgt aggctacgca ggtatttgac gtgtaaccca gacccatgtc tacggtgtta   124500
atgttctgcg tgacgtggta cgtggtgctg atgtcgcgtt cctccttggt cacgatggga   124560
ttgttgatga taactgacgt gcatgatttg ccgctgtaga gcagcatgtc cacctcgaag   124620
gtgtcggtgc gtacggccgt gagtgcgaat cccgggtgga tgtgcgcctt ggtctgcagc   124680
accagtgaaa ctggtgagat tttgtataac atggcggcca gcgtcataac tgagtgcaac   124740
acgttgggac aggtggccga gtagcgcgaa aagggcgagc gtagccagtt gtggtactcg   124800
tgtgcgaagg ctgtgggtag cggaaaacca ccgtcgtgac ggtgatagtg cgggaactcg   124860
gtcacgtagc gtttaatgtc gtcgctcaac gccgcgcaga tggtgggtt  tgagtagaaa   124920 cggtggaaag gtacgggtag gctgtactcg atcagcgtct taggcgccgt cacgacgcag   124980
cagccgttgt aaagcacgtg ctgacgtgag ataaagtccg gcaggccctg acgttgcgcg   125040
tgatccagag gcgcgcgcac ttcgagcacc ttgacgtgct cgcccacgaa ttgcacggcc   125100
```

```
aaaaacagct cacgacaggc ctgcagcagc ggcgtatgcg cgtcggtggc gacgtcctcc   125160
accagctcgg tcagcatctc gcctacggct tgacgttgcg ccgctaccga gtcttcgggg   125220
gtgacgccgc ttgtgctctc tttcgacgtc gtacctgacg tggagaccgc ggtggcggcc   125280
ggcatcagga gaaacgccgg tcggtaaaag aggtctacta gcagcgtctt gaggttgagt   125340
cccaggccgc aggcccggtt gttggtcatg gcgggtatga ggcagagata aaagaccttt   125400
tgtaacgtcc attcgtcgtc ggtggcacgg taatcgtcca caaacagcgg ctcgtcggca   125460
tccatggcgc ccaaacgcgg tacgtcagaa acgccgtggt gtcgcgcctc gatgttggcc   125520
gggttcaacg gttgccggtc ggccactacc tgtacgcctt ccatattacg cggcaggtgc   125580
gtaacgaagg ggggccacag ccggtggtcg tgcagcgcgt tcacgtaagc cgatagcggt   125640
tcctcggcca gttgaccgtt gttaagcccc ggcagcgctg agatgcgcgt taccagacgc   125700
agcacggcga ctagattgcg gtagtgaaag agcaactgcg gtggtagggc gccatcggcc   125760
aggtgttcgg cgatcaacgt caccagcgcg tagctgtgtg caaaaaccag cagctgacgt   125820
gtgtgaaaca tgttgacgat acaacgtgct atgaaagcgc ggattagcaa aaaagcgtcg   125880
gcgttgccgt gtaccagtac gtcgaccagg tagcagagct cggggtaatt ggggctggtc   125940
acggtggttt tgaaaagtcg caacgtctct tcgtagtcgg gtggtggccg cagtcgcatg   126000
tgttccatga tctcccaggt gcgcagttcg tggaaggggc ccggtgccag tccatctggc   126060
aaattaccga tgacgatacg cggcgtacac agcgccaccg tttcgctgtt ttcctggcag   126120
tgcgtaaagt cgaagaaggg gtgcagctcg gtgtagagcg tgatgttgcc caccttgtag   126180
aagtcggtga ccacaaaatc ctgcttcatt tcgttcaccg tgcgcgggac ctcacgccgt   126240
acgcggtaaa aatgtggtat gcggcgcgcc gcaccgccca tgggctcctg ctgaaaacga   126300
cattcgagca gccgttgcat ggcgggttcc gagggcggtc cgcgttccgt gaaggcctgc   126360
agacagggcg cgggttcatg cagcaccggg tggcacagcg tcttaagcgc gtccacaaag   126420
tctatctttt gcacggcacg gtcccggttt agcaggtagg ccgtggtggg cagcgcgttg   126480
cggacggtgt cgttgagctt aactttgctt tccaccgtgg tgtaaccgcg atcctcgggc   126540
agatacagcc ctacggggaa gaaaaacgtc aggtccacgt tacgttctag cggatctttg   126600
gtatcggtgt ttttgtagac gcgccgcaag ttttccataa tcaccgtttt ttcgcccagt   126660
cgaatcacat ccatgcttag tggcgttagg ctgtgcgccc cggcctgcga aagcgagtcg   126720
ttgggcagat gcggttgacc cgaagtcaga tgggccttgt atgagttgaa atcggccagg   126780
atcgagtgat aggaaatggc ggtgacggcg ttttcgggac tgagcacaaa gttgccgtag   126840
gtggccggcg ccgagaccgt ctctttggtg atgtggcttg agagcagcga catgatgatc   126900
tgcataacgt tggccgtgct taccatcacg ccgctgatct tggcccccga gctcgtggta   126960
tacgtggtgg ggttgtctag gatgctatcg gtggccgctt cggccagacg cgtgaggaac   127020
ttgagcacat agtcgcgatc gcgcgtgcga ttcagcaaaa agagcgtggc cagcattttg   127080
gccttgaagc tctgcaagat gttgcttcgc tggatgcggt tcaatgcctg tcgcgccagc   127140
gtggcgtttt ctaccagcgt ctgcaccaca aagtacggcg gcgccttgcg tagcagtgtc   127200
tgtaaaaagc tgtgaatcaa gccgcgctcc atggcgtcgg ccgtgttttt aagcgcgcgc   127260
agcaccgtgt gcatggcttc cacgttgagg atcttgtcca agatggtgcc ctcgaatgtc   127320
tcgcgcagat acgtgaggca ggctgcgctg agctcgaagg ggatggtgat gggggatttt   127380
tcactgtatt tggtgaccat aatggtggtc tgacgactgg tgggcaaacc ggcgccgctg   127440
gccacacgcg gcacctgcac gtggaacagc attttgcccg tagtcagttt attgaggtcg   127500
```

```
tggaacttga tggcgtgcgc cgccgcggcc aagccgctgg tcaaaaaata aacccattcc   127560
aggcgattgc agaaggtgcc gaagatggct tcgaagtgaa tattgtaacg ctcggggtcg   127620
tcgccgtagt agatgcgtaa ggcctcgaac atctcctcgc cggcgctggt cttgacgtgc   127680
gtcagaaagt cagtgggaat gcctacttta ggcaggagct cgagcgccga ccagttctcc   127740
atcgcggcgg cggcgtgagc gcgaggcgtc ggagctcggg gaaagcagcg cgacccggag   127800
aatggccggc gctgcgccgc gccgcctcgg ctgcgacgct ctaatagtcg tcggcggctc   127860
cgctacgccg cgccgggttt tacacgtccc cgtgcacgtt cgcgcctgca acctcaccca   127920
agagctatcg acgggcgagg acgcccgctt ctgtcgtccg cgacccgtta acgtcgaacg   127980
ggtacgcgct gttttcgcgg ctctctaccg tgcctgtccc gtacacgcga ggaccgagtc   128040
cgagcgtgtc aagctggtac tgggtcgtct gttgctggga cccgtggccg taccctgttt   128100
ttgcgacggt gaagtggagg gccacggcga gcatctggta cccacgacgc agttttgtcg   128160
cgggccgctg ctctacgtgc accgacgttg ttgttgcgga tccgtgaccg ccgggcgcgc   128220
gctgtcctac cacgttctcg aaaaccacgt ggccacgcat gtgttacgcg gattgctctc   128280
gctgacggaa tggaatcgag agttgccggg ccttttttgc gactgtcctg gcagcggtgg   128340
cgccttggga accgaggaac gctacgccat ggcctgcttg ccgcgcgacc tcagcctgca   128400
cctggacgac tatccttacc tgatggtgga aatcggacgc gtactcagcg tcagcgaggt   128460
agacgactac gtaaccgccg tctccggcta cctgggcgag gccgcggcgc cgcgcattca   128520
ggttcactac aagctgctct ttggactcaa cgtgcgtccg caagcgccgt gcgcgttgga   128580
cgctacacgc gacttttttc tgctggagct gcaaaagctt tggctgggcg ttgaatatca   128640
ccacgaagtc acgtcggagt ttttcggtcg cgtactggct cagctgcatc gcgaccgcgc   128700
ccgcgtcatg atggcacttc gcttgcccga gcagacggtg tgccacctaa gcaccttcgt   128760
tctcagtcgc ttcaagcgac aggtactgta cttcaagtta caggtgagct acggcaagtg   128820
ccggactggc cacgctgaca gaagtggggg aggggaaac ggtggaagtc agggacacca   128880
caacctactg tgttatcgac gtcttagcgt cacgtttgcc gacacggaca cggtgtggag   128940
aaaacctttc tacgtttatt atgaactagc tcgggatctg gggtcccatg ggacagagga   129000
ccgatccgta agccgcggtt acggtgtttc ttgcgctccg aggacgtcgc ggctaccacc   129060
gtcagaaccg acgtggtttt cagccaacgg acacgcgctc tcttccaccg cgctcccgac   129120
gacgagcgcg ggtcacaagc tgtcgctgcc gcgcgacccg gccgcagatc gcgttcgacg   129180
ttacgtgtgc attatctcgc gtctcatgtt cgcccggtat ggggagagat ggcgtaaaca   129240
ccgtcgacgg cggtcggaga cgggagaaga ggaggaggaa gagacggtgg aatcggggga   129300
gactgacgcc acgccgccat ttgactttac ggggcagcag ctgcgccggg cctatcagga   129360
acaccgacgt cgtaaacatc tagccgtgca gcgttacgcg ccgtgccgtc gtaagctcat   129420
cggcgggatg gagtttgccg aggtgacggg cgttagtctg gaccgcatcg ccgtcaacgc   129480
tttcaacacc aaccgcgtta tcaatatgaa ggccgcactc tcgtccatcg ccgcgtcggg   129540
tctcggcgtg cgcgcgccgc ggcttcccaa gaacatgacc cacagttttg tgatgtacaa   129600
gcacaccttc aaggagcccg cttgcaccgt cagcactttt gtttccaacg acgccgtcta   129660
catcaactcg ctcaacgtca atattcgcgg ttcctatccc gagtttctgt actcgctggg   129720
cgtgtaccgg ctgcacgtta atatcgatca cttctttctg ccggccgtgg tgtgcaacag   129780
caactcctcg ctggacgtgc atgggctgga ggaccaggcg gtgatccgct cggagcgcag   129840
```

```
caaggtgtac tggaccacca actttccgtg catgatctcg catactaaca acgtcaacgt    129900
ggggttggttc aaagcggcta cggccattgt gccgcgcgtc tcgggcgctg acctggaagc   129960
cattctgctc aaagaactct cgtgcatcaa gaacatgcgc gacgtgtgca tcgattacgg    130020
tctgcatcgc gttttcacgc aactagagct gcgcaattcg taccagatcc ccttcctggc    130080
caagcagttg gtgctgtttc tgcgtgcttg cctgctcaag ctgcacggtc gagagaagcg    130140
gctgcagttg gaccgcctag tatttgaggc ggcacagcgg ggtctctttg actacagcaa    130200
gaacctcacg gcgcacacca agatcaagca cacttgcgcg ctcatcggca gtcgtctagc    130260
caacaacgtg cccaagatcc tggcccggaa caaaaaagtc aaattggatc acctgggccg    130320
gaacgccaac gtgctgacgg tgtgtcggca cgtggaagcc cacaagatcc ctcgcacgcg    130380
cctcaaagtg ttagtcgagg tgctgggcgc gttgcagagt atcagcggta cgccgcacac    130440
gcgtgaagtg atccaccaga cgttgtttcg attgtgctcg gcggccgcag ccacctcggg    130500
cctgtgttca tcccctcccc cattgtgtgt gtcctcatct tcctccgccc cttctgtccc    130560
aacctccgtc agcgttgacg gcagttctga acccacgtcg ccgcgagcgc ggtttgcatc    130620
acgatgatgg aagccgcggc cgctgccgcc gcggcgtttc gtccggagga gcgtccgacg    130680
ccggggttggc acgacgcagc gttgttaatg gacgacggta cggtgcgcga gcacgcgttt    130740
cgcaacggac cgctgtcgca actgattcgc cgtgtgttac cgccgccgcc cgacgccgaa    130800
gatgacgtgg ttttttgcttc agaactgtgt ttttattgca gcggtcgttt taaccgcagg    130860
tcgtccgtct tctccatcta ttggcagaag catagcgatc tggtatacgc gcttacgggc    130920
attacccatt gcgctaagtt ggtggtggaa tgccggtcagt tggggagtgg taggctacgg    130980
tggcgcgacg gtgacgtggg tggtgaggag cgccggggag acgacgacag cagggacgag    131040
ctgtacgacg tgccgggaat ttacatgatc cgcgtcaacg acggcggcag caccggcccc    131100
aggcacgtta tttggccggg taccagcgtg ctttgggcgc cggacgtggt gatcactacg    131160
gtgcagcgac gaatctcggc ggcgcgcgcc ctggtgaaca cgttccgcca gtattttttt    131220
ttgctggaac ggcgctcgca cgaggagctg gttctttgtc cgcccgagat ggaggagcgt    131280
ctagcgccgt tgttgcagag tgccacgcgt ggtgattcgg acatgtttga cggtgtggtg    131340
gccagcgctt atcaccgttt gcgaataagt aatattccgc gttcatccgc ccgtctgctg    131400
gagcactgcg tggggctggc aggtgctaag aagctgctct tgctcgacgt gccgcgtctg    131460
gagaactatt ttcttttgtca agtctgtctt tacgagctgg acgaggacga gatgggcgag    131520
gagatgctgg gtatgttggc cggaaagccc gaggacgccg ccgtctcggg cgcaagcggc    131580
ggttttctgc tacatcgcaa gacgatgaag ctggccgcct gtctatgttt gctgctcaat    131640
tcgctgcatt tgcaccagga ggcgctggag gccttggatc ctccgccgcc gcgcgtcgag    131700
gagaacgacc ttgtcaacgt ggtgctgcgc cgttactatc gcagtcacgg cggcgtgcag    131760
gcgcggacgt tggcggcggc ccgggctttg ttagccgact acgccgaaac gttttcgccc    131820
ttggggagtt ttacgcgcct gggttacgat cgtctcgttt ctgccgatgc cggcgtcagt    131880
cgccggcacc tggtggctct gctgcgtgcc tagctgaccc tgaaacggat ggcgtgtatc    131940
tcgtcacaca ggtaggtggc catgatgacg gctatgataa gatcgtccga gatacgattc    132000
tggcgcttgg ccgagtagcg tgccgtcgtg ccttcggcca gcgtgacgcg gtgcaggttc    132060
tgaatctgct ccagaagata ctcgatgggg tcgtggctca gcttgatggt gtaggagacg    132120
agctcttgcg aggctttgat gtagcccgag ttgaaacgcg agatgaactg ttctacggcc    132180
agcgccttgt cgcggcccat gaggtagaag ggctgttcga tgtggttctg gtcgggcgtg    132240
```

```
tggtagaaga gcacgcggat gagcgtgcta ctctgcacgc tctgtcggat gaggcaggcg   132300
atgcgcacgg ccgccgcctg gttagtgttg ccctccacgg cgatacgcag ttcgtccagg   132360
taagggtgca ggctcagcac cgagatgatc atgtgcgccg cgcactcggc gatggctacc   132420
tcagaactct cggagaggtc gcgcaaaaag aaatgctcta ggccgtaaat gagaaactgg   132480
tgtcggtagg cgcctacggc cgccacgccc gtgcccgagg ccttgcggtt ggtggtgaag   132540
gccgggtcca gatatacgta gagcgtcttg ccgaaataat cgtaggcgtt ggtgttgagc   132600
gtgctgtaac gcaaaatatc gaactcttcg cggctctggt ccgtgatgag cacggtgttt   132660
tgcgagatct tattggtacc gccgatgatc tcgtccatga aggcgcccgg cataaacatg   132720
ttggccgtct tgcgcacctg cgagttgagg ctgatgaagg tgggcttgtg cagtcggtag   132780
caaggacagg ccgtggcgtc gcccttctcc gtgaagctgt gcaggtgctc ttcgcacacg   132840
taagagacca cgttgagcat gtcaaagggc gcattgttga ggcgcgtcaa gaaacacgtg   132900
gcgtcactgg tagtgttggt ggacgatatg aagatgatct tggtggtatt ctgtgccagg   132960
aaccccagaa tggtgttgaa ggcctctttc ttgatgaagt gcgcctcgtc caccagcagc   133020
aagtggaagt tttgtcctcg gatgctctgt gtagagagga gacagaaaag ggactcttat   133080
gattacgcac gctcggctgg aagcctacag agtcggggtg gggccggaca ggtgagccag   133140
gtgagccgcc aggtgaggcg ggatcgccgt gtgccaaccg ggctgcgacc tgaaaaccgg   133200
aaccaatccg ccgacaccgg cgccgcgtga cgcgcgccca taaaaacgaa agtgtcgtcg   133260
tcgcgacccg ccacagccgc catgaactcg ttgctggcgg aactcaaccg actgggggtc   133320
gcgcacgcca ctacggagga tgttttttatc tttgtcgacc gcctctttca acacttttcc   133380
ttccttttcc aggccgagga gtcaggcccg cgccgcttgg aactggtcgc gtccgtgttc   133440
gagcacctga cggtggagtg cgtcaacgac atcctggacg cctgcagcca cccggacgtg   133500
aacgtcgcgg agacaagcaa cacctgtcgt ccctgcccctt ctcctgttcc ctccgccccc   133560
aaaactgtca gcgacgctca gacgtcatgt gcgacgtctc gggcgcctgt gacatgaggc   133620
acgtccagaa cgcgtttacc gaggagatcc agttacactc gctctacgcg tgcacgcgct   133680
gctttcgcac gcacctgtgt gatctgggca gcggctgcgc gtcgtctcc acgctcgagg   133740 gctccgtctg cgtcaagacg ggcctggtat acgaggctct ttatccggtg gcgcgtagcc   133800
acctgttgga acccatcgag gaggccgcac tggacgacgt caacatcatc agcgccgtgc   133860
tcagcggcgt gtacagctac ctcatgacgc acgccggccg ttacgccgac gtgatccaag   133920
aggtggtcga gcgcgaccgc ctcaaaaagc aggtggagga cagtatttac ttcacccttta   133980 ataaggtttt ccgttctatg cataacgtca accgtatttc ggtgcccgtc atcagccaac   134040
tttttattca gcttatcatc ggtatctact caaagcagac caagtacgac gcgtgtgtca   134100
tcaaggttag tcgtaagaag cgcgaggacg cgcttctgaa acagatgcgt tccgaatatg   134160
gaaacgcacc tgtattcgga tctggcgttt gaggcgcgt tcgctgacga tgagcaattg   134220
cctctacatc tggtgctcga ccaggaggtg ctgagtaacg aggaggccga gacgctgcgc   134280
tacgtctact atcgtaatgt agacagcgct ggccgatccg cgggccgcgc tccgggtgga   134340
gatgaggacg acgcaccggc ctccgacgac gccgagaacg ccgtgggcgg cgatcgcgct   134400
tttgaccgcg agcggcggac ttggcagcgt gcctgttttc gtgtactacc gcgcccactg   134460
gagttgctcg attacctacg tcaaagcggt ctcactgtga cgttagagaa agagcagcgc   134520
gtgcgcatgt tctatgccgt cttcactacg ttaggtctgc gctgccccga taatcggctc   134580
```

```
tcaggcgcgc agacgctaca cctgagactg gtctggcccg acggcagcta tcgtgactgg    134640
gaatttttag cgcgtgacct gttacgagaa gaaatggaag cgaacaagcg cgaccggcag    134700
caccaattgg ccacggccac gaatcaccgt cggcggggcg gactgcgtaa caatttagac    134760
aatgggtcgg atcgccgatt gcccgaaacg gctatggctt ctttggagac ggccgtcagt    134820
actccatttt tcgaaattcc gaacggagca ggaacctcct ccgcgaatgg cggcggcaga    134880
ttcagtaacc tggagcagcg ggtagcgcgt ttgttgcgcg cgacgagga attcatctat    134940
cacgcgggtc cattggagcc gccttccaag atacgcggtc acgagttggt gcagctgcgc    135000
ctggacgtaa atccagacct catgtacgcc accgatccgc acgaccgaga cgaggtcgcg    135060
cgtacggacg agtggaaggg cgccggcgtc tcgcgtctcc gcgaggtttg ggatgtgcag    135120
catcgcgtgc gcctccgtgt gctgtggtac gtcaattcct tttggcgcaa tcgcgagctg    135180
agctacgatg atcacgaagt cgaactatac cgggcgttgg acgcttatcg ggcgcgcatt    135240
gccgtcgagt acgtgctgat tcgcgccgtg cgcgacgaga tctatgctgt actacgacgg    135300
gacggcggcg cgttgccaca gcgtttcgcc tgccacgtgc cacggaacat gtcctggcgc    135360
gttgttgggc aactttgccg tcatgccttg gtgctctgga tggatcgggc ggacgtgcgt    135420
agctgtatta ttaaggcgct gacgcctcgt ctgagccggg gtgccgccgc tgccgctcag    135480
cgagctcgtc gccagcgcga gcgcccggcg cccaaaccgc aggagctgct tttcgggccg    135540
cggaacgaga gcggtccgcc cgccaacgg acttggtacg ctgacgtggt gcgctgcgtt    135600
cgcgcgcaag tggatttggg cgtggaagtg cgcgcggcgc gttgtcctcg caccgggctt    135660
tggatcgttc gtgatcgccg cggacgcctg cgacgttggc tctcgcagcc cgaggtgtgc    135720
gtgctctacg tcacgccaga cttggacttt tactgggtgc tgccgggcgg ctttgctgtg    135780
ttctcgcgcg tcactcttca tggcttggcg cagcgggctt tgcgagaccg attccagaac    135840
tttgaagcag ttcttgcaag aggaatgcat gtggaagctg gtcggcaaga gtcggaaaca    135900
ccgcgagtat cgggccgtcg cttgccgttc gacgatcttt agtccggagg acgacagctc    135960
gtgtatctta tgccagttgc tgttgctcta ccgcgacggc gaatggatca tctgtttttg    136020
ctgcaacggc cgttatcaag gccactatgg cgtgaatcac gtacatcggc gtcgtcgacg    136080
catctgtcat ctacctacct tgtaccaact gagcttcgga ggtccttggg gtccagccag    136140
catcgatttc ttgccgagct ttagccaggt gaccagcagt atgacgtgcg atggtattac    136200
gcccgacgtg atttacgagg tctgcatgtt ggtgccccag gatgaagcca agcgtatcct    136260
ggtcaagggt cacggtgcca tggacctgac ctgtcagaag gcagtgacgc taggcggcgc    136320
cggcgcctgg ttgctgccgc gtcccgaagg ctacacgctt ttcttttaca ttctgtgtta    136380
cgacctgttt acctcatgcg gcaatcggtg cgatatccct tccatgacgc gcctcatggc    136440
ggcggccacg gcctgcgggc aggcgggttg cagcttttgc acggatcacg agggacacgt    136500
agatcccact ggcaattacg tgggttgcac ccccgatatg ggccgttgtc tttgttacgt    136560
gccctgtggg cccatgacgc agtcgctcat ccacaacgag gaacccgcga ctttttttctg    136620
tgagagcgat gacgccaagt acctatgcgc cgtaggttct aagaccgcgg cgcaggtcac    136680
actgggagac ggcctggatt atcacatcgg tgttaaggat tctgagggcc gatggctgcc    136740
cgtcaagacc gatgtgtggg acctggtcaa ggtagaggaa cctgtgtcac gtatgatagt    136800
gtgttcctgt ccggtgctta agaacctagt gcactaacgg ggtctgacag ttcacgggga    136860
gaagaaacaa gaaacaacaa aaaaaggagg acatggactc gccacggttt gtggcaaggc    136920
gtatgttatc atcatggagc tactcacgtt ggtgttgtag caactggcaa aaagcgccgt    136980
```

```
gctcttggcg ccgcggtggt cgatgctgat cacgttgtcc ttgttctcga ccacgtagtc   137040
gcgcgcgaag gtgtggcggc agcggaactc gacctctttg agcacaaact gcgacacgtg   137100
cttttggtgc gccacgtagc cgatgctgat gccgatcatg tgcttaagca gaaacgagat   137160
aatggggatg atgaaccaag tcttgccgtg acgtcgcggc accaggaaca cggtggcttt   137220
ctgcttaaag atgtcgatgg aggtctgcga gaggaagtcg atctggaagg cgtggatgag   137280
gtactgcagc acgcgattgg ccagcacggg gatcttggtc acggctataa aaagatgac    137340 gtgtatcaat aaattctttt gaaacggttc gagtcggatg cttttgcgt cgccctcgac    137400 ggcggtactg aagccgccgt cgagccactt tttaaagtcg gtcatgaagt tgttgatctg   137460
ctgaaactgc ggatcgcggt agagctcggt caacgcgtcc agcttctggt aggaggcgcg   137520
ctgctcctcg gagcacgggc gaaacgtcag ttcatcgagc gcgctcttga ggcgctcgtg   137580
aaacagcagc tcgcgctggc tttcctcggg cgagttgtag tcgcggtggc ggccgcagaa   137640
ggccatgagc ggcaggaagg cctcgttgca cgagtgggcc agcccgagtt cggggtgcat   137700
catctggtag cgcttgcggc acagcgccgc cacattggtg aaggccgtgg agatgcagga   137760 ggtgggggtgg ctcttgcgct tctgcagctc cgcgtagcgc tcctggatct tggcggccga   137820
gtctccgcgc aacatgatgg cggcggcggt ggtgcgagcg gaggttaggc ggcagcggcg   137880
agaggagagg aaaaagatgg cggccgcgag gacgacggag gatccacccg aaaaccacgt   137940
tgttgcggac gtggcttgtg ggacgggcgc cgtcactcgt tcgtcttcgt cgtccctagt   138000
ggtgtcgtct tcctcggcgt caggctcgga cgaaccttcc tccgcctctc ctctcagttt   138060
ccccgtctgc tcccccctcaa ctgccgtcag gtctccgggg tccgccgggg tttcaacgtc   138120
cctgtgctcg gtggaacgga tggtcgagct gtcggcgcag tctccggccg ccgatttctc   138180
ggtctccgag gcttggcgct tcgaggaggc cgtaaatatg gcgctggtgg cctgcgaggc   138240
cgtgtcacct tacgatcgct ttcgcctaat tgaaacgccc gacgagaatt tcttgttggt   138300
caccaacgta attccgcgcg agtcggccga ggtgccggtg ttggatagca gtagcagcgg   138360
tggcgatagc gggccggagg acaaaaagaa aaacgtcggg aataaaaccg cgggggaaaa   138420
gaacggcggt gggtctcggg ccaaacgccg tcgtagacga cgcgctccga aaaacgacgc   138480
cgccacgccg tcttttctac gtcgacacga cgtgctggag cgtttcgcgg ccgcggctga   138540 gccttttgccg tcgctttgtg tgcgtgatta tgcgttacgc aatgctgacc gtgttaccta   138600
cgacggcgaa ttaatctacg gcagttacct gttgtatcgc aaggctcacg tggagctgtc   138660
actctccagc aacaaggtgc aacacgtgga agccgtgctg cgacaggtgt acacgccggg   138720
cttgttagat catcacaacg tgtgcgacgt ggaggccctg ctgtggctgc tgtactgcgg   138780
accgcgtagc ttttgcgcgc gtgacacctg tttcggtcgc gaaaaaaacg gttgtccttt   138840
ccccgcgttg ttgcccaaac tcttttacga acccgtgcgg gactatatga cctacatgaa   138900
tctggctgag ctgtacgtct ttgtttggta tcgcggctac gaattccctg cgccgacgcc   138960
gcaggcgacg acggcgggta gtggtggcgg cggcggggcc ggcgcttgtg cggtcgagac   139020
gagcgcgtca gcaggccggg tcgatgacgc cggcgacgag gtgcatttgc ctttaaagcc   139080
cgtctcgctg gaccgtctca gagaggtgtt gcaggcggtg cgcggccgct tctcggggcg   139140
cgaggtgccc gcctggccgg cctcgtcgcg cacctgtttg ttgtgcgcgc tctacagtca   139200
gaaccgtctc tgtttagatc tcgcgcgtga cgaggcgcgg accgtgagtt atagcccat    139260 cgttatccaa gactgcgccg cggctgtcac cgacgtcact ttgagccaca tcttgcccgg   139320
```

```
ccagagcacc gtctcgcttt tccccgtcta ccacgtcgga aagttgctgg acgccctctc   139380
gctgaacgac gcgggtctca tcacgttgaa tctatgacgt cggtcaacaa acagctctta   139440
aaggacgtga tgcgcgtcga ccttgagcga cagcagcatc agtttctgcg gcgtacctac   139500
ggaccgcagc accggcttac cacgcagcag gctttgacgg tgatgcgtgt ggccgctcgg   139560
gaacagaccc gatacagtca gcgaacgacg cagtgcgtgg ccgcacacct gttggagcaa   139620
cgggcggccg tgcagcaaga gttgcaacgc gcccgacagc tgcaatccgg taacgtggac   139680
gacgcgctgg actctttaac cgagctgaag gacacggtag acgacgtgag agccaccttg   139740
gtggactcgg tttcggcgac gtgcgatttg gacctggagg tcgacgacgc cgtctaacag   139800
gtatagcaat ccccgtcacg cctctgttca gattttatta aaaaaaaaaa acacaacata   139860
acgacagtgt cggtgtggta gctagtgcag ctctaggaac agggaagact gtcgccacta   139920
tgtcctccgc acttcggtct cgggctcgct cggcctcgct cggaacgacg actgagggct   139980
gggatccgcc gccattgcgt cgtcccagca gggcgcgccg cgccagtgg atgcgcgaag   140040
ctgcgcaggc cgccgctcaa gccgcggtgc aggccgcgca ggccgccgcc gctcaggtcg   140100
cccaggctca cgtcgatgaa gacgaggtcg tggatctgat ggccgacgag gccggcggcg   140160
gcgtcaccac tttgaccacc ctgagttccg tcagcacaac caccgtgctt ggacacgcga   140220
cttttttccgc atgcgttcga aatgacgtga tgcgtgacgg agaaaaagag gacgcggctt   140280
cggacaagga gaacctgcgt cggcccgtgg tgccgtccac gtcgtctcgc ggcagcgccg   140340
ccagcggcga cggttaccac ggcttgcgct gccgcgaaac ctcggccatg tggtcgttcg   140400
agtacgatcg cgacgcgac gtgaccagcg tacgccgcgc tctcttcacc ggcggcagcg   140460
accccctcgga cagcgtgagc ggcgtccgcg gtggacgcaa acgcccgttg cgtccgccgt   140520
tggtgtcgct ggccccgcacc ccgctgtgcc gacgtcgtgt gggcggcgtg gacgcggtgc   140580
tcgaagaaaa cgacgtggag ctgcgcgcgg aaagtcagga cagcgccgtg gcatcgggcc   140640
cgggccgcgt tccgcagccg ctcagcgta gttccgggga ggaatccgcc acggcggtgg   140700
aggccgactc cacgtcacac gacgacgtgc attgcacctg ttccaacgac cagatcatca   140760
ccacgtccat ccgcggcctt acgtgcgacc cgcgtatgtt cttgcgcctt acgcatcccg   140820
agctctgcga gctctctatc tcctacctgc tggtctacgt gcccaaagag gacgattttt   140880
gccacaagat ctgttatgcc gtggacatga gcgacgagag ctaccgcctg gccagggct   140940
ccttcggcga ggtctggccg ctcgatcgct atcgcgtggt caaggtggcg cgtaagcaca   141000
gcgagacggt gctcacggtc tggatgtcgg gcctgatccg cacgcgcgcc gctggcgagc   141060
aacagcagcc gccgtcgctg gtgggtacgg gcgtgcaccg cggtctgctc acggccacgg   141120
gctgctgtct gctgcacaac gtcacggtac atcgacgttt ccacacagac atgtttcatc   141180
acgaccagtg gaagctggcg tgcatcgaca gctaccgacg tgccttttgc acgttggccg   141240
acgctatcaa atttctcaat caccagtgtc gtgtatgcca ctttgacatt acacccatga   141300
acgtgctcat cgacgtgaac ccgcacaacc ccagcgagat cgtgcgcgcc gcgctgtgcg   141360
attacagcct cagcgagccc tatccggatt acaacgagcg ctgtgtggcc gtctttcagg   141420
agacgggcac ggcgcgccgc atccccaact gctcgcaccg tctgcgcgaa tgttaccacc   141480
ctgctttccg acccatgccg ctgcagaagc tgctcatctg cgacccgcac gcgcgtttcc   141540
ccgtagccgg tctacggcgt tattgcatgt cggagctgtc ggcgctgggc aacgtgctgg   141600
gcttttgcct catgcggctg ttggaccggc gcggtctgga cgaggtgcgc atgggcacgg   141660
aggcgttgct cttcaagcac gccggcgcgg cctgccgcgc gttggagaac ggcaagctca   141720
```

```
cgcactgctc cgacgcctgt ctgctcattc tggcggcgca aatgagctac ggcgcctgtc   141780
tcctgggcga gcatggcgcc gcgctggtgt cgcacacgct gcgctttgtg gaggccaaga   141840
tgtcctcgtg tcgcgtacgc gcctttcgcc gcttctacca cgaatgctcg cagaccatgc   141900
tgcacgaata cgtcagaaag aacgtggagc gtctgttggc cacgagcgac gggctgtatt   141960
tatataacgc ctttcggcgc accaccagca taatctgcga ggaggacctt gacggtgact   142020
gccgccaact gttccccgag taaccgggac gcggaacgtg acggttgctg aggggaaagg   142080
cgacagagaa ggtacaaacc caccggcggg gaaaataccg aggcgccgcc atcatcatgt   142140
ggggcgtctc gagtttggac tacgacgacg atgaggagct cacccggctg ctggcggttt   142200
gggacgatga gccctcagt ctctttctca tgaacacctt tttgctgcac caggagggct   142260
```

```
cgcactgctc cgacgcctgt ctgctcattc tggcggcgca aatgagctac ggcgcctgtc   141780
tcctgggcga gcatggcgcc gcgctggtgt cgcacacgct gcgctttgtg gaggccaaga   141840
tgtcctcgtg tcgcgtacgc gcctttcgcc gcttctacca cgaatgctcg cagaccatgc   141900
tgcacgaata cgtcagaaag aacgtggagc gtctgttggc cacgagcgac gggctgtatt   141960
tatataacgc ctttcggcgc accaccagca taatctgcga ggaggacctt gacggtgact   142020
gccgccaact gttccccgag taaccgggac gcggaacgtg acggttgctg aggggaaagg   142080
cgacagagaa ggtacaaacc caccggcggg gaaaataccg aggcgccgcc atcatcatgt   142140
ggggcgtctc gagtttggac tacgacgacg atgaggagct cacccggctg ctggcggttt   142200
gggacgatga gcccctcagt ctctttctca tgaacacctt tttgctgcac caggagggct   142260
tccgtaatct gcccttacg gtgctgcgtc tgtcttacgc ctaccgcatc ttcgccaaga   142320
tgctgcgggc ccacggtacg ccagtagccg aggactttat gacgcgcgtg ccgcgttgg   142380 ctcgcgacga gggtctgcgc gacattttgg gtcagcggca cgccgccgaa gcctcgcgcg   142440
ccgagatcgc cgaggccctg gagcgcgtgg ccgagcggtg cgacgaccgg cacggcggct   142500
cggacgacta cgtgtggctc agccggttgc tggatttggc gcccaactat cggcaggtcg   142560
agctcttcca gttgctggaa aaggaatcgc gcggacagtc gcgcaactcg gtgtggcatc   142620
tgttgcgtat ggacacggtt tcggccacca agttctacga ggccttcgtc agcggctgtc   142680
tgcccggcgc cgcggcggcg gacggttcgg gtggcggcgg ctcgcactac acgggctcgc   142740
gcgccggcgt ctcgccaggc atccagttcg gtatcaaaca cgagggttta gtcaaaacgc   142800
tggtggaatg ttacgtgatg cacgggcgcg agccggtgcg cgacggcctc ggtctgctca   142860
tcgaccccac gtcggggctg ctgggcgctt ccatggacct gtgcttcggc gtgctcaagc   142920
agggcagcgg tcgcaccttg ctggtggaac cgtgcgcgcg cgtctacgag atcaagtgcc   142980
gctacaaata tttgcgcaaa aaggaggacc cctttgtgca gaacgtgctg cggaggcacg   143040
acgcggcggc cgtggcctcg ctgttgcagt cacacccggt gccgggcgtg gagtttcgcg   143100
gtgaacgcga gaccccgtcg gcacgcgagt ttctgctttc gcacgacgcg gcgctcttca   143160
gggccacgct caagcgcgcg cgcccgctca agccgcctga accgctgcgc gagtacctgg   143220
ccgatctgct gtatctcaat aaggccgagt gttcggaagt gatcgtgttt gacgccaagc   143280
acctgaatga cgacaacagc gacggggacg ccacgaccac tattaacgcg agtctcggcc   143340
tagccgcggg cgacgccgct ggcggcggcg ctgatcacca cctgcggggc agcccgggcg   143400
attcgccgcc gccgatacct ttcgaggacg aaaacacgcc cgagctgctg ggccggctca   143460
acgtgtacga ggtagcgcgc ttttcactgc cggcttttgt caatccgcgt caccagtatt   143520
actttcagat gctcattcag cagtacgtgc tcagccaata ctatataaag aagcatccgg   143580 accccggagcg gatcgatttc cgcgacctgc ctaccgtcta cctggtctcg gccatcttcc   143640
gcgagcgcga ggaaagcgaa ctgggctgcg agttgctggc cggcggtcgc gtttccact   143700 gcgaccacat cccgctcctg ctcatcgtca cgcccgtggt ctttgaccct cagtttacgc   143760
gccatgccgt ctctaccgtg ctagaccgtt ggagtcgcga cctgtcccgc aagacgaacc   143820
taccgatatg ggtgccgaac tctgcaaacg aatatgttgt gagttcggta ccacgcccgg   143880
tgagcccctg aaagatgctc tgggtcgcca ggtgtctcta cgctcctacg acaacatccc   143940
tccgacttcc tcctcggacg aaggggagga cgatgacgac ggggaggatg acgataacga   144000
ggagcggcaa cagaagctgc ggctctgcgg tagtagctgc gggggaaacg acaatagtag   144060
```

```
cggcagccac cgcgaggccg cccacgacgg ctccaagaaa aatgcggtgc gctcgacgtt  144120
tcgcgaggac aaggctccga aaccgagcaa gcagtcaaaa aagaaaaaga aaccctcaaa  144180
acatcaccac catcagcaaa gctccattat gcaggagacg gacgacctag acgaagagga  144240
cacctcaatt tacctgtccc cgcccccggt ccccccgtc caggtggtgg ctaagcgact   144300
gccgaggccc gacacaccca ggactccgcg ccaaaagaag atttcacaac gtccacccac  144360
ccccgggaca aaaagcccg ccgcctcctt gcccttttaa cccataaact ttcaggtctc    144420
gcgtacgatt cgcgagtcgg gaatgggaca cccgtgggtg tttctccgtg tgtatattat  144480 ttttttttg tgtgtgtttg cgcccccgtg tgtctaatgt gctgtttgaa acacgtaaag    144540
tagctggtgg aagaacagat aaacctttaa taaaaaaaaa agtatgtgct cccgacccac  144600
ggtctgcgtg tctctttttt atgtccatgt ctccaagtct ggtgcgggtg gcggcggggt   144660
caagcgtcct cgaagtcttc atcatcgtcg tcgtcctctt cttcgcggag gcgacggctt  144720
tccaagctgt cgtggtgact gagtgcagcg acttcttcgc cggaggctgt ggccagcgcc  144780
tggtacttaa cactgccgct accgcgtccg cgaaagtaac ggacgcgcg acacgtcgta    144840 aacatggccc atatgaaaaa gagcatgccg aacgaccagc tgatgccggt gcggtattcg  144900
ttgctgagga aggtatcgta ctgcacgatg gggtagatga ggccgcagag tccaaagaag  144960
gcgcccaggt ggtagccgaa ttgcaccttg acgtattgaa aaaagacggc ctcgatcagt  145020
aaaaagtaga tgatggagat gatagcgtag accacgaaga cggctaacac catgtggcct  145080
gtacgcacga aaagttgtt tctgaagccg tagcataggg ccatggctac cacggtggtg   145140
ttgaaaccaa gcgctacctc caccaggttg acgatgagcg tgcggaactg caccgtacct  145200
ttgagcttgg ggtgcagacg cgagaagaaa aagagcgagc gtttgtagct gcggtactgc  145260
gtgaccatgc tcacgttgaa aatggtcagg cagaaaaagt gcacggcggc catgaaggcg  145320
atcatgctgg gcagccgaaa tgacatggtc agtgtgaata gttggaatgt gtccatgctg   145380
aggatgaaaa ggaaggctgt gaggctgtcg cccatgtacg agatgtcgcg tgtcgactgg   145440
tttaggctca tgcctttgtc cttgcgcatg ctgatcttga tccagcatac caggtagtag  145500
atggtcacgg ctaaaaagac gagctgcatg aacacggcgt agcacaccag ctgcaccgag  145560
tctaagaaaa gcataggcgt gtgcaggtgc attacgttgt aggccgacat gttgagcctt  145620
tcaaagtcca cgacgtgata gtagacgcag gggtagccca ggtgcggaaa attgctcagc  145680
accagatgca cgctgacgtt gacaaaagtc agcaccatga aaacgataga agcgctccat  145740
gtccgtgtat tcaccttatc cacgtgcgag ggggccatgg cgatagcggc ggcccgctcg  145800
ctcgggaggc gatgggggcg cgccgatgac gacaggctcg cgggtcgtta aatactacga  145860
tgggagccgc cgcggctcac gacgcggttt gagcgcgtcc gggcggtcgg cgaaaaaaga  145920
ccccgcgggc cttcgcgact ctcttctgtc cgaggatgac cgctcagccg ccgctgcacc  145980
accgccacca cccgtacgcc ctgttcggga ccagctgtca tctcagctgg tacgccttc    146040 tggaggcctc ggtgcccatc gtacaatgtc tgttttga tctgggtggc ggccgtgccg     146100
aaccgcggct tcacacgttc gtggtgcgcg gtgaccgtct gccgccggct gaggtgcgtg  146160
ctgtgcatcg cgccagctac gccgcgctgg cctcggccgt gactacggac gccgacgagc  146220
gccggcgcgg cctagagcag cgtagcgccg tgttggcgcg cgtgttgcta gaaggcagcg  146280
cgttaatccg cgtgttggcg cgcaccttca cgccggtgca gattcagacg gacgctagcg  146340
gcgtggagat cttggaggcc gcgccggcat tgggcgtgga aaccgcagcg ctgtcgaacg  146400
cgcttagtct tttccacgta gccaagttag tggtcatcgg ctcgtatccc gaagtgcacg  146460
```

```
agtcgcgtgt ggtcacgcat gccgcggaac gcgtctccga agagtatggc acccacgcgc   146520
acaaaaaatt gcgtcgcggt tactacgcct acgatttggc catgtcgttt cgcgtcggca   146580
ctcacaagta tgtgctggag cgcgacgacg aggccgtcct ggcacgcctc tttgaggtgc   146640
gcgaggtgtg ttttttgcgc acctgtctgc gtctggtcac gcccgtcggt ttcgtggccg   146700
tggcagtgac cgatgagcag tgttgtttat tgctgcagtc ggcctggact cacctttacg   146760
acgtgctttt tcgtggtttc gctgggcagc cgccgctacg cgactacctg gggccggacc   146820
tctttgagac gggcgctgcc cgttctttct ttttccccgg tttcccgccc gtgcccgtct   146880
acgcggtcca cggtctgcac acgttaatgc gcgagacggc gttggacgcg gcggctgagg   146940
tgctctcgtg gtgcggcctg cccgacatcg tgggctcggc cggcaagctg gaggtggaac   147000
cctgcgcgct ctcgctcggc gtgcccgagg atgagtggca ggtcttcggc accgaggccg   147060
gcggcggcgc cgtgcgtctc aatgccacgg cttttcgcga gcgaccggcc ggcagcgatc   147120
gtcgctggct gttgccgccg ctgccgcgtg acgacggcga cggtgaaaac aacgtcgtgg   147180
aagtcagcag cagcaccggc ggtgcgcacc cgccgagcga cgacgccact ttcaccgtgc   147240
acgttcgcga cgccacgcta catcgagtgc tcatcgtgga tttggtcgag cgcgtgctgg   147300
ccaagtgtgt acgcgcgcgc gacttcaatc cctacgtgcg ttatagtcat cgactccaca   147360
cttatgcggt ttgtgaaaag tttattgaaa atctgcgttt tcgctcgcga cgcgccttct   147420
ggcagatcca gagtctgctg ggctacatct ccgagcacgt tacgtcagcc tgcgcttcgg   147480
ccggcctttt gtgggttctg tcgcgcggcc accgcgagtt ttatgtctac gacggctatt   147540
cgggtcacgg acccgtctcg gccgaagtgt gcgtgcggac tgtggtcgac tgttattggc   147600
gcaaactttt tggcggcgac gatccaggtc ccacctgtcg tgttcaagag agcgcgcccg   147660
gcgtgctgtt ggtctggggc gacgagcggt tggtgggtcc cttcaacttc ttctacggca   147720
acggcggcgc cggtggtagt ccgctccacg gggtggtggg tggtttcgcg gcgggacatt   147780
gcggcggcgc ttgttgcgcg ggctgcgtcg tcactcaccg ccattctagc ggcggcggtg   147840
gtagtggcgt gggcgacgcg gaccacgcga gtggcggcgg tctagatgcc gctgccggga   147900
gtggtcataa cggcggtagt gatcgggttt ctccctccac gccgcccgcg gcgttgggtg   147960
gctgttgctg cgcggccggt ggcgactggc tctcggccgt gggtcatgtc ctgggccggc   148020
tgccggcgct gttacgggag cgcgtgagcg tgtccgagct ggaagccgtg taccgcgaga   148080
tcctctttcg cttcgtggct cgccgcaacg acgtggactt ttggttactg cgcttccagc   148140
ccggtgaaaa cgaagtaagg ccgcacgccg gggtgattga ctgcgcgccc ttccacggcg   148200
tgtgggccga gcagggccag atcatcgtac agtcacgcga tacggcgttg gcggccgata   148260
ttggctacgg cgtctatgtg gacaaggcct ttgccatgct cacggcttgc gtggaggtct   148320
gggcgcgaga gttattgtcg tcctccaccg cttccaccac cgcttgttct tcttcttccg   148380
ttctctcctc cgccttgccg tccgtcactt cgtcctcttc gggcacgcg acggtgtctc    148440
ctccgtcttg ttcttcttcg tcggcgactt ggctcgagga gcgcgacgag tgggtgcgtt   148500
cgctggcggt tgacgcgcaa cacgctgcta agcgggtggc ttccgagggc ctgcggtttt   148560
tccggctcaa cgcttaacga gtcacgtagg ggaactacgg gggtaagtga cgtggatact   148620
agtaaaaaaa agtgcgtcaa agctctcagc gtgtgacgtg gatactagta aagggacgt    148680
caaagctcac tacgtgttgc gtgttttttt ttctatgata tgcgtgtcta gttcgcttct   148740
cactcttcct ctccccgttc ccagcgcggt ggcagcttgg ggggtgaggg caaattgggg   148800
```

```
tagttggcgt tgagcacgtc tagcaggccc aggcccacgg gccaaccgtc cacggtctta  148860
cgctcggtca gcttgaggct gaacgagtgt gcctcgtctt gaccggtaag gcggaaaaag  148920
aagcgtgcta ccagctgcag gcaggtatgc tgcgtctgct ggaagagcac gaaggtagcg  148980
ggtacgtact gcacaatgtg cggttctttt tcctcaaaga gtaggtagag cgcgctgcag  149040
atcagccgcc gggcgctgtg gtgcagcagc cggccgaagc tttcgcgcac gttcaccgcg  149100
tccaggtact ggagcaggtc gtgcaggcac ttgcgcgtta agttgcaatt ttccacgcat  149160
gaaataacgg tacagagcgc gaagtgcagc aggttgtcgg ccttgacgat gccgcagcgg  149220
tgtttgagcc gcagatccga gagcctcacc tgcgtgacgg cgtcttcggt ctcgagcaaa  149280
aacacggcgg agtagcccag aaaggccgag gtgcacagca gctcgctgcg gtactcggcc  149340
atggagacca gcagcccgtg ctccgtgtgc agccacagct tgtcgccgcg caccgtaaag  149400
tcgagcactt gcggctccat gatcatcaca ttctgtctag tgaaatccgt atggacctcc  149460
agcacgccgc ggatcatcag ggcctccatt tcgaaatcgg ccgacacgct ctgggccgcg  149520
ccgctcctcg tctgccgtga tcaggcggcg cggcgcggac cttcaagcg ttcctggcc   149580
gccgctcgag gcagttcccc tttctggcac tccgcccgcc gcttcgcggc tcatttggcg  149640
tcggcgcgcc ttctcgcggc tgcaaatcag ctccacgtat cggcaaaact tgctgtcgtc  149700
gtaggcggcg ccacgatct cgccgaagga gagctgcagg taggcctcgg gtacggggtc   149760
cagcgtgccc agcgccagga tgtgacacag atagggcagg gtcacgcgct ctaccgtgta  149820
attggagtag acgatggcct cttcggcccc ctgatgcgtg accagacgcc gcaggcgaaa  149880
ggtgcggaaa tactcgtttt cccacagctg cgtgaggaag cgttccagcg actcggtgcc  149940
gggcacgaac tgcgagaaga agctgttggc caccaggcgg ttgtcctcca ccgccaacgg  150000
acggaaaggc gccgcgtcgc gcgccttgcg cacggcctcc aacacgggca ggtggtagag  150060
ttcggcgtcg cgcgcgccca ggctcatgga gtcctcgcgg cgcgaggcgt agcgcgtgag  150120
caggtcgcgc agttcgcgca cgcgattctc ccaggtctgg ttgagcgtgc gcaggtcctg  150180
gatctcgtct acctgcgact ggatctgctc ctccaggcac ttgatgacct gcttcttaaa  150240
caggtcgcgg atgtcccgct cgggcgccgc cgggccgggt ggcggcggca tcagcccgac  150300
gtggcccgcg ggtcctccca ccacggcacc gccgggcccc accacgccgg gtccacccgg  150360
accacgcgcg ggtagcagac ggttttggtc caccagcgaa ggggtcaagt cctgcaggaa  150420
ggactcgacg ctgtcctcga tgccgatgcg cgatttgctg tccgagacgt taagcaaaaa  150480
cttcataatg gacttttttgg cgtcgctgcc ccggtcgtgc tgctccatca tctccaccag  150540
cttcttgcag ttgagctcgt ggcggctggc ggtcaccact ttcacaggaa aggtattgag  150600
caactggcag atcttttggt ggcggcagag cccgtcgtag cgcagaatct cctcgtcag  150660
gtgtgccacc ggcgtggtga acagcagctt gtcgcgctca taagccagcg gttcggtcgc  150720
cacgtacaag cggatgtgct tgccgcgcag ctgcgcctcc agccgctccg agcgcacctt  150780
cttgaagacg cgtacctcgg gcgcgttggc tacgcgcaca gctcccaggc gctcggccac  150840
ctgcagcagc agcgccaggt tagcctgcag caggtcctgc gccagcgggt gtgtctcggt  150900
ggctcgctgc acgccgcgc gtacaaattg cgccgctcg gccgcctcgc tcggcttggt   150960
cttcacgtcc agcagcggta ccagtcccac cgttacgcac caatccacgt agagaccata  151020
gtcgtcgtta tcggcgtact gatataaaat gtcgcggagc gcgcccagca cgcccgtttg  151080
cacgctctgc cgcaacgagg cgctccacac caacagatac tgctccaggt cctcttcgtc  151140
cagcgcgcgg tagggaaaca gcgccgcgtg caacttccac tcttcggcca cgcgccgcac  151200
```

```
cgtgatggtg tcaaagagcg ttttgcacac tccgtagagc agctgcttgc gcagcacgca 151260
cgggtcgcgc agcacttggt gcatgctttg gccgcgacag gtccccagaa agccgtgcag 151320
caaccgcagg aagctcatcg tctggcccgt ggggaaaatg tcgatgacgg cctcgtcatc 151380
cacaccgcgg cccacgccca agtacgacga cgccttgatc ctcaacctct cgtcggccgc 151440
caagatcgaa cggatcgtcg acaaggtcaa gtccctctcg cgcgagcgct ttgcgcccga 151500
ggatttttcg ttccagtggt ttcgctccat cagtcgcgtt gaacgaacga cagataacaa 151560
cccctctgcc gcaactaccg ccgcggcaac gacgaccgtt cactcctccg cctcctcttc 151620
tgccgccgct gccgcttcgt ccgaggccgg cggcacgcgc gtgccctgcg tcgaccgttg 151680
gcccttcttt cccttccgcg cgctgctcgt caccggcacg gcgggcgccg gcaagacttc 151740
cagcatccag gtgctggcgg ccaatctaga ttgcgtgatc accggtacca cggtgatcgc 151800
cgcgcagaac ctcagcgcga tcctcaaccg cactcgctcg gcgcaggtca agaccatcta 151860
ccgcgtcttc ggcttcgtca gcaagcacgt gccgctggct gacagcgccg ttagccacga 151920
gacgctggaa cgctaccgcg tgtgcgagcc gcacgaggag accaccatcc agcgcctgca 151980
gatcaacgat ctgctcgcct actggccggt catcgccgac atcgtggaca aatgcttaaa 152040
tatgtgggag cgcaaggccg cttcggcctc cgccgcggcc gcagccgccg cctgcgagga 152100
cctctcggag ctgtgcgaga gcaatatcat cgtcatcgac gagtgcggcc ttatgctgcg 152160
ctacatgctg caggtggtgg tgttttttta ctacttttac aacgccctgg gcgacacgcg 152220
actttaccgc gaacgccgcg tgccctgcat catctgcgtc ggttcgccca cgcagaccga 152280
ggcgctggag agccgctacg accactacac gcaaaacaag agcgtacgca agggtgttga 152340
cgtgctctcg gcgctgattc agaacgaggt gctcatcaac tactgcgaca tcgccgacaa 152400
ctgggtcatg tttattcaca acaagcgttg caccgacctg gactttggcg acctgctcaa 152460
gtacatggag ttcggtatcc cgctcaagga ggaacacgtg gcctacgtgg accgcttcgt 152520
gcggccgccc agctccatcc gtaacccctc gtacgccgcc gagatgacgc ggcttttttct 152580 ctcgcacgtc gaggtgcagg cttacttcaa gcggctgcac gagcagatcc gcctgagcga 152640
gcgccaccgt ctctttgatc tgcccgtcta ctgcgtggtc aacaaccgcg cgtaccagga 152700
gctctgcgag ctggccgacc cgctgggtga ctcgccgcag cccgtcgagc tctggttccg 152760
ccagaacttg gcgcgcatca ttaactactc gcagtttgtc gaccacaacc tttccagcga 152820
gatcaccaag gaggcgctgc gccccgcggc cgacgtcgtt gccaccaaca actcctccgt 152880
ccaggctcac ggaggggggag gatctgtaat cgggagcacc ggcggcaacg acgagacggc 152940 gttttttccag gacgatgata ccaccaccgc gcccgatagc cgtgagacgc tgctcacctt 153000
gcgcattacc tacatcaagg gcagttcggt gggagtcaac tctaaggtgc gggcctgtgt 153060
tatcggatac cagggcacgg tcgaacgttt cgtggacatc ttgcaaaagg acacgtttat 153120
cgaacgcacg ccctgcgagc aggcggccta cgcctactcg ttagtttcgg gcctgctctt 153180
ctcggccatg tactacttct acgtgtcgcc ctacacgacc gaggagatgt tgcgtgagct 153240
ggcgcgcgtt gagctgcccg acgtgagttc gctttgcgcc gctgccgccg ccacggccgc 153300
cgctcccgct tggagcgggg gagagaatcc gataaataat cacgtcgacg cggattcttc 153360
tcagggcggc cagagcgtgc cggtatctca acggatggaa catggccaag aggagaccca 153420
cgacatcccc tgcctgtcca accaccatga cgactcggac gccatcacgg acgccgaact 153480
catggattac accagtctgt acgcggatcc ctttttttctc aaatacgtca agccacctag 153540
```

```
cctggcgctg ctttctttcg aggagacggt gcacatgtac actaccttcc gcgacatttt   153600
tctcaagcgc taccagctca tgcagcgtct cacgggcggt cgcttcgcca cgttgccgct   153660
cgttacctac aatcgccgta acgtggtgtt caaggccaac tgtcagatca gctcgcagac   153720
cggctccttc gtgggcatgc tttcgcatgt gtcgccggcg cagacgtaca cgctcgaggg   153780
ctacaccagc gacaacgtgc tcagtctgcc cagtgaccgc caccgcatcc accccgaggt   153840
ggtgcagcgg ggcctttcgc ggctggtgct acgcgatgcg ctcgggttcc tctttgtgct   153900
cgacgttaac gtttcgcgct tcgtcgagtc ggcgcagggc aagagtctgc acgtgtgcac   153960
caccgtggac tacggcctca cttcgcgcac ggccatgacc atcgccaaga gtcagggcct   154020
gtcgctcgag aaggtggccg tggactttgg ggaccatccc aagaacctca aaatgagcca   154080
catctacgtg gccatgtcgc gagtcacgga ccccgagcac ctcatgatga cgttaaccc    154140 gttgcgactg ccctatgaga agaacaccgc tatcaccccc tatatctgtc gcgcgctcaa   154200
agacaaacgc accacgctta ttttttgaca caacaccgtg taaggaaaac gtgactttat   154260
tgagcagggt aaaaaccacg tacaagaacc acgttgtcta tccccaaaaa aacacacacc   154320
gtcagggaac acatcgccta tagatagcgg cactttacat aaaaccaccg tacctgcatc   154380
acggtggctc gatacactgg aaattcaata aaaaccaccg tatctccgtg acagtactta   154440
tcgggtcagc gtctttctct tgagatttct gttcgtaaac ttatccgttt ccccggtccg   154500
cggtgtctcc tcgcgaggct gacagtctac gggtggtacc tgcaagagaa gaaacccggg   154560
tgggagcgac gccgtcgctg ggtatcaacc ccgcggctga ccgtcgtccg gtaaaggaac   154620
gacccgtcgt cgcaagccgg gttcgaccaa gagaaaaaac ccgggtgcgg ggggagacgg   154680
gtcgtccttt ggttgttcgc ggacggcgta catgccgcgt gggtcagtcg acggcgtcgc   154740
tccgtgcggt cggtcatcat tctgcttcac atatatgggt tgtttgtgtt tttttataa   154800 tgaatacgca ctgatcctat ccgtgactgc gcgtgtggca gagaggatgc cttataacat   154860
gtattttgaa aaattgccaa cagctataat ttctctcatg tagcagaata gagaccttt    154920 gtcgtctttt tgtttgtcat tacttgtttt ccagggaatt agagagaggg aaccgcgcct   154980
ccggcggcgg tgcccgcgga ccccggcccc ttctcgcgtg cgcggtgtga ctggttgagc   155040
gaatgagcag ctaggcttgg tggtgctccg cgtgcggggg agaagacgat taacaacaaa   155100
aaataagtgg aagtggccgg tgggtctttg tccgcgtgcg cgcccatccg tcgccggac    155160 cgagcagaaa gtgatgtggt ggtacattga ttttttcctt gacaggaaag aaaaaaaaga   155220
gttttgtttt cctatgtgag aggagaaagg tatgtgagga gatgttcgat gatcgtatgt   155280
tacagttatg ctgtaaggaa gcttttatcg tgcgtcctgt ttttcatttg atgtatatga   155340
cacaattgaa acctatcgat aggcgtatat cgaggattca tcaattctta gaatcgtcgt   155400 cttttttggct aattggactt tgcccatgtt ggttgtcatt cgtggcctga ggtcatcgtc   155460
gtccacgacg acgtgtctat agcgtgcggt gtgatcattg tgtcgagcca gagaaagcgc   155520
gcctcgcacg acgtttgcgg atcggctcgc gggtgtgtgt aattcctaag aacataatca   155580
gctggtcgtc tttctttgat gtgttgttgt cgtcgaggtc ttgcttcgtt ttctttttc    155640 ttttagtcg atggaacttt tcttcggtac gggttcttgt tatggaagct tgtgttttcg    155700
aacatgaatt cgaaaaaata aaaggccta tcttcgtttc aaaaaaagga cagatatcaa    155760
tcttcttaac ttatatcatg gtaaattcag aatcctatgg tgtcttatta tctctaaagt   155820
agtcaacatt atggtctaac ttgtatttcc ctgacgagat atatatgatc cttataacct    155880
ggctactatc atgaacaaca atatccttac ttacagtcat cttcgtgagt taatgaagta    155940
```

-continued

```
taatatcggt catctatcaa cttatctgct atgtaacgta ccctttagg tattttgcgt   156000
ttcttaacga gtgtacccgc ctgtgtgagg cgaaactctg agaagtctac cgagtcgagt   156060
tacaagtcac taaaacactt acacgagtta tctatactaa aatcactatc tatgttgttt   156120
gcttacctaa ttattatcct acatgacgaa gctacctccc aacgtaaggt aggggagag    156180
gagacagaac aataaaaagt aactaatgtt tcttagaact tacccgctaa ggacttacca   156240
aactatattc accaaaaaac aacagctacg tgtttcattt gttttaatct accgaagtaa   156300
aaaaaaaaa gatgattagc tatccagaac ctacttactt cttaatgttt taactaagga   156360
tgcctatggg attggaaaaa aaatcacagc aacttgctac taatcagttg acagcgaaga   156420
gactcataac aaagatttct gggtaatacg gttataataa tgcttatgga ctaaaggata   156480
cttggaaaaa aagaacgggc tatgactata gagattcgtc gagatatcaa acttcaaata   156540
ggcggctatc attcatggtt gtggtgacta tatcgtggag aaaaaatgtg atcgttagtt   156600
agctaggtga gacttacagc tatccatccg tctagttttt cgttgtaatg atgatagtac   156660
gtctatggtg gtgatcgatt ttggttaaca atttgttcgt ttaaaggctt aatgtactta   156720
tgctacatga tgtattattc tttgattcat cgttcctcct aagggggtgt atgtatgtat   156780
gtactagtcg tatagtgttc ctaacatcat gactattcag actatggctt catctatcgt   156840
gtctaaagtt cacttattct actattacta tatatatgca ctactatgta actaggatat   156900
ggtcctataa ggtgtcttct atcacggtgg cttgtttatc gcttggcggt tacgagcaag   156960
agttcatcac ggaccagccg tgaggcaggg cacacgcggg tcggcggcga taatgtccct   157020
cgcgaagggg acaacgaaaa caagaggccg ccggccgcgg ccacggacgc gtagcggtta   157080
cacaatgttt ggttgagcgt tttgtttcat cgtcgtggtg gttttgttgt tctctgtata   157140
tatcgtgtgg tggctttatc gtcatcatta ttatcatcat tcttgtttcc atcatcacga   157200
tgagttttct ccgttttcct ctcctccagt ggtagtcgtg tatcatcatc aatcatcgta   157260
gtgacgtcgt tgctgctgct gctcttgcct tcatggcggt atttctcttc ctcccccta   157320
accccatatt aactcgtgag tgtgatggtt agagtggctg cttgttttt ttttcttttc   157380
tctttggaac aacaaaagag gataaagatg gtcggtgaat gtattattat tattatcatc   157440
attatgatac ggtcgcggtc ttcttctccg atgacgaaac ctgcgcacat cgaagaaaag   157500
acgagcgcgc gaaccgatag ccgtccgtct gggacgaagg agaagatgat ggggagagga   157560
ggagagcccc agaagccaga gcgagagggg agacgacaga catacgtcgt caccgtcctc   157620
tggaggaggc acgcggcgc tgtttgttgt ttggatgctt gattatatcc tgttctatgg    157680
ggtagattat tatcaatagg cttggtttc aaaggtcagc ctgtgtattg tcgtgtcttt    157740
ttttttcgttc tcatgatcgc ggagaccaca cagacgtgcg cgtctcccaa tggctaggcg   157800
ttcttttag gtagtaattt tttgatcttt tttttctta acaagtctgg cttgatttct    157860
tttatctatg atcgattctt cttttctcg ggggttgcat cttccgtgaa agtaaagtga    157920
cactactcta aatggtaacc atattatctg ttgattagga gaaaaataa tttttcgca    157980
cgaaatcgat cctaagtgag gtgatttact tgctatcaca cgaaatgatt atcttttgct   158040
gctaacgtac tgaattttt aacagaattg cttctccgta actatttccg cagattcaga   158100
cagattgtca aaaaaaata cggcacagaa atagtgggtc tgtggctttt ggttcgtgta   158160
cattcgcgtt tgcgtgtcga gatttctacg gtatgtttat tcttcctgcg atgatgtagg   158220
gtccttggtg taagtaggat ttcgagtatc tctcttagag cgaacaaaat aatcaaaaaa   158280
```

```
caacagctag gaaatcgagg gttactctac gataaagtgt ctctacaaag tgaagaatgt    158340
tacgttgtgg tggaataata agactcgcgt gatcgatgag tgatcgagag cggctcgaac    158400
cttctttaag agctttgttt agtgcaactt taaattacaa ggagtagaaa gctgaaatga    158460
atctatgaag gtgctattct ttgaatatct tactttgtac gcttcacatt cgttatttgg    158520
atagagagtt gtctagagaa aatctgtgat tctctatgag tgttattttt attatccttt    158580
tggggactac gattttttctt cttgttctac ataccactac tactcgtaat cacatacatg    158640
gacgaaaaaa aaattcgtca ggcagtagat accagattct ccgacgttac ggcgtctttt    158700
tttcttttga gagagtatct gctgagattg tccgtggtgt atctagtcgc tattttttgtt    158760 gttactagta gttttgcaca cagtttattc agtatagttt ttcttcttgc catgatcaat    158820
tgagcccacc acctttttttt taagagagga ggaattttcgt cttgatctcc agccggagat    158880
aacggcggtg gtggtggtgg cgggagagac ttcaaggcaa tgaaaaaaaa aaatttcgtt    158940
ttgccatcaa gtggtgacga taacccgtca gattgataat tggttcctac agaaactatt    159000
ctaaccgcgg aagaaagaaa ttgaaaaaaa aaaattgaca aaaaacatca taacataaag    159060
gaccacctac ctgggacgcg cagttgggcg gcggactggg gcggcatgct gcggtgatgc    159120
tgtcggtgat ggtctcttcc tctctggtcc tgatcgtctt ttttctaggc gcttccgagg    159180
aggcgaagcc ggcgacgacg acgacgataa agaatacaaa gccgcagtgt cgtccagagg    159240
attacgcgac cagattgcaa gatctccgcg tcacctttca tcgagtaaaa cctacgttgg    159300
taggtcacgt aggtacggtt tattgtgacg gtctttcttt tccgcgtgtc gggtgacgta    159360
gttttcctct tgtagcaacg tgaggacgac tactccgtgt ggctcgacgg tacggtggtc    159420
aaaggctgtt ggggatgcag cgtcatggac tggttgttga ggcggtatct ggagatcgtg    159480
ttccccgcag gcgaccacgt ctatcccgga ctcaagacgg aattgcatag tatgcgctcg    159540
acgctagaat ccatctacaa agacatgcgg caatgcgtaa gtgtctctgt ggcggcgctg    159600
tccgcgcaga ggtaacaacg tgttcatagc acgctgtttt acttttgtcg ggctcccagc    159660
ctctgttagg ttgcggagat aagtccgtga ttagtcggct gtctcaggag gcggaaagga    159720
aatcggataa cggcacgcgg aaaggtctca gcgagttgga cacgttgttt agccgtctcg    159780
aagagtatct gcactcgaga aagtagcgtt gcgatttgca gtccgctccg gtgtcgttca    159840
cccagttact ttaataaacg tactgtttaa ccacgttgcg tcgtgacgtt gtttgtgggt    159900
gttgctaggc gggctggaaa gatgatgtat aaatagagtc tgcgacgggg ttcggcgctc    159960
tgccggctgc ggcggcactc gctccacggc ctccgacgag cgttgcgctc gcgctttgcg    160020
ccgccgcgtc atggatctgc ctactaccgt cgtgcgaaaa tactggactt ttacgaatcc    160080
taaccgcatc ctgcatcaga gcgtcaatca gactttcgac gtgcgccagt tcgtctttga    160140
caacgcccgt ctggtcaact gcgtggacgg cgatggcaag gtgctgcacc tcaacaaggg    160200
ctggctctgc gctaccatta tgcagcacgg cgaggcttcg gccggcgcca agacgcagca    160260
gggcttcatg tccattgaca ttacgggcga cggggaactt caggagcacc tctttgtacg    160320
cggcggtatc gtctttaaca aatccgtctc ctcggtggtg ggctccagcg acccaatga    160380 gagcgcgctg ctcactatga tttccgagaa cggtaatttg caagtgactt acgtgcggca    160440
ttacctgaaa aaccacggcg aatcctccag cggaggcggt ggttgcggcg ccgcgtctac    160500
tgcctccgcc gtctgcgtgt cctcgctggg tggcagcggc gggactcgcg acggcccttc    160560
tgcggaggaa cagcaacggc gaaggcagga acagcgtcac gaagaacggc gcaaaaaatc    160620
gtcctcgtct gccggtggtg gtggaggcgg cggcgctggt ggtggcggtg gcggcggcgg    160680
```

```
gagcggcggt cagcactcct cggactccgc caacggactg ctgcgggatc cccggttgat   160740
gaaccggcag aaggagcggc ggccgcctcc ctcctccgag aacgacggtg agtcccggcc   160800
ctcctcgcgt cacggtgctt tccgagtgga ctcgtgagcc ccccgtagcg cacgagcgag   160860
caggcgagcg gtgttggtgc gctggtggtt gtgtggatga taaccatgtg ctttttcgtg   160920
cgctatgtgt cgtcccgtct gtaggctctc ctcccctccg ggaggcgaag agacaaaaga   160980
ccaccgcaca gcacgaaggc catggcgcg gcggcaagaa cgagacggag cagcagtccg   161040
gtggtgctgg cggtggtggt ggcggcggca gcggccgcat gtcgctgccg ctggacacgt   161100
ctgaagcggt ggcctttctc aattactcgt cctcatcctc cgcggtctct tcttcctcca   161160
acaaccacca ccaccatcat caccaccata cgccgtgac ggacgtggcc gccggcaccg   161220
acggtgcgtt acttctaccc attgagcgcg gagcggtggt ttcgtcgccg tcgtcgacgt   161280
cgccgtcgtc acttctttcg ctccctcgac ccggcagcgc ccacagcgcg ggcgagacgg   161340
tgcaggagtc cgaggcggcg gcgacggcgg cggctgcggg gttaatgatg atgaggagga   161400
tgaggagggc tccggctgag gcggcggagg caccaccgca gtcggaggag gagaatgatt   161460
ccaccactcc agtctctaac tgccgtgttc ctccgaattc gcaggaatcc gcggcgcctc   161520
agcctcctcg cagtccgcgt tttgatgaca ttatacagtc attgaccaaa atgctcaatg   161580
attgtaagga gaaagattg tgcgatctcc ccctggtttc cagcagactc ttgccagaga   161640
cgtcgggcgg gactgtcgtc gtcaaccaca gcagcgtcgc gaggaccgcc gcagctgtct   161700
ccacagccgg cgttggcccc ccagcagccg catgtccgcc actcgtcacc accggtgttg   161760
taccctcagg ttccgtcgcc ggtgtcgcgc ccgttgccgc cgcagtcgaa acaccagctg   161820
ctcctccccg gcccgtgtgt gaaatcaagc cctacgtggt aaaccccgtt gtcgccaccg   161880
ccgcggctgc cagtaactct tcctcgtctt cttcggctcc gctgccgccg ccgccaccac   161940
cgccgggcgg acgtcggggt cgggcccgga ataataccg aggaggcggc ggtggtagaa   162000
acagccggcg gcaggccgca tcgtcgtcgt cctcctcctc tcggagatcg cgacggagaa   162060
acaaccgcca cgaggacgag gaggacaacg accctctgct ccggttgtcg caagtcgccg   162120
gcagcggccg ccggcgaggg ccctcgttcc tcgaggacgg actcgaaatt atcgatccca   162180
gcgaggaagc tgcgatcgcc gccgcctcga tcgcggcgtt tttcgacgat taaaaaaccg   162240
agccgagacc ggaaaaatta tgaaacagga gcgcttgga catttgggtt tccacccct   162300 ttggtgtgtg tctatatata ttggtcactg attttttta caataaagag atagacatca   162360
cagttcacca ccttgtctcc ccggtgtgtc tattatcatc aatcacccac agagtcgcca   162420
gtccatggtc tctcggtaat gcgtgtccag atacgcgttg ccagtataa aatggtcgtt   162480 gcccacaaag gcgcgggtgg tgttgcgcgg cgacgggtgg caggacttga gtaccaagtg   162540
ccgccgtcgg tcgatcaggt actcgcaggt gtgcgcgtcg gcgccccata gcatgaacac   162600
cagatgctcc cggcgctctg acagcctccg gatcacatgg ttactcagcg tctgccagcc   162660
taagtgacgg tgagatccag gctgtccgtg caccacggtg aacacggtgt tgagcagcag   162720
cacgccgcgt cgcgcccagg cgtccaggca cccgaggcc ggacgctgaa acccgtccac   162780
cgtacgcgcc agttcgcgaa acacgttgtt gagggagggt ggcggcggtc ggcccgccag   162840
cgtgccgaag gccaggccgc tggcgctgcc gtcgcagtac gggtcctggc ccacgatcac   162900
cacgcgcacc tgctcgggcg gacacagata gctccagcgg tgtacgtgct cgggtgccgg   162960
gtacaccatc tcgagttgcc gcgcgccctc caccgccgcc accgtgtcgc gcagcagcac   163020
```

```
cgtgtcgtgg tcgggcaagc tgaggaagcg gatccagtcg gcgctcagac aaaacacgcg   163080
agcctgctcg tcgggggtta acagagagcc tttattatca gcaatgttag cgagcatcca   163140
ctgcttgagg gccatagcgc gagtgagccg gcaggttgac gcgcgtctgc ttcagctcgg   163200
gcggcagtcc ggcgtagtat ttatctaggt ggcgtagcag cggcgggtcc agctggtgac   163260
gcaggcagaa ttccttcact gcgttgtaca ggccgtaaaa gagcgtgatg ccctcgggcg   163320
cggcagcggt gctcacgggc agacgcacgg cgcggttggt acgcgtggct tcgttgcgta   163380
tggccaccac cacgttaaag agagacggtg gcaccagctc gaagcctaac acgtgttccg   163440
tgaagatgct gcgcccgtat gacagtcgcg tgaggtcgta gccgcggcac aggtcgtcca   163500
cgcacgtgta cacggccggc gagccatcgc cgcactcgct gtaaccgcgc atcaccgtca   163560
tccagcgcgg cgctgtgtcc gagctcaaca gcgtcagcaa ggcccgcaat tgatccggat   163620
tgttgtacag cagggccaga gtgtccagga aagcatcgtc caacagcacg gagttggcgg   163680
cctccggcgt aacgggacgg taacgaataa gttgcgatag cgggccatcg cgtctggtaa   163740
cattcaccaa cgggcgcagc caactttcat acttgtcacc ctgaaacacc tcacccaaca   163800
ggcatcgacg cgttagttcg gggcactccg cgggaacttt ctcggcgacg gtaggagcga   163860
cgctgacggt ggctgaggaa acgatgggca gcagaaggca acaccacagc agtgccaccg   163920
gtccaggtga gaaagagaag ccgcaatccg ggcggcggca catcaagtct gcggcacgat   163980
gagagtgtga cggtaaggag ccagttggcg ccgaaagttg gcgctcaggt cttcgatccc   164040
taaaacgtta tatattgcat ccagcaggtg agccaggcta aacggattca cgtaccaggt   164100
ttggttaccc gcgacgataa cggccagacc gtgggcgcta cagttggaga ggttcctggg   164160
tacgaaggta actgagtcga tgtcgcgcca cggggggaat gagacagacg actggcgcac   164220
gctgtaatca caactgtgat tgacgtattg tagcgtgtaa tttaggttgc actcagcctc   164280
gaagtagagg gggaaccaca gttcgtcgta ctcgtcgtcg tcctccagtt ctggctcttc   164340
ttcatccacc gcaatgtcta cgctgctctg agattcctct tcgtacagga tgattgcacg   164400
gttatggcta caaaggtcct gggcgggagg acgcgtggga gcgcgggtgg tggtaatgtt   164460
ttccagatcg tcaaaagtcg gagtgtagtc tgacgccgtg acgacaccgt cgacggagat   164520
agtagaagtt gcggccggtg tcacggtggt aagtatggat acagaagggg aggggggaagt   164580 agcgttcgta ccgatggttg tggtattatt attccttgta tttcttgttt cagaaaccgt   164640
tgacgttgag atgggaatcg acgtggcgct ggacgtcaga ttgctgaccg aggaaaccgt   164700
ggtgggagtg gtgacggtgt tactcgtggt tgaagtgacg ttaggggagg tagtagtggt   164760
accggtggtg gcgacggtag tgtttgtcgt ggcggcggca gcggtggtac tggtaacggt   164820
ggtcgcgttg gtttccaccg cttcacacag taagcaaaag cacagggcca ggaaaagcaa   164880
ccagccccgc catcgccgcc gccgcttcat gaggtgggca ggcgaaagct ggtgaattcg   164940
ttgtacagcg gcaagtgggg cgccgcgatc gaagggtacg tcaacaagct gacgttgata   165000
ttaaatacgt ctggctgctt ttctacgatg gaagcgcaca gggttacggc gtcaaacagg   165060
tctttcttgg tggcgcccga gacccacatc tggtatacac ccgtctcgtg gtacgaagta   165120
gagcgcggca ccaccggacg gatgcagtcc agaacgcggt tgggatcctg gtgaaagaat   165180
ttgaacgtgg ctacggcctg tggcgtgtgc ggcatcgtct gcgtgatgag ctgctggccc   165240
gctaacacgg tgacgttgtg caacttgagc agggcactct tgagggcctg gaaagcgttg   165300
ccgcacgagg cgctgatctg cagctgcacg gccgtggagt cgtgcagccg catgagacgt   165360
gatacctctt cgaagacgta cttgtatttg ctggcaaaga gtggcgcgta ccgacagtcg   165420
```

```
gccggcaaaa tgtaggtggc gttaccgccg ttggtggcca cggcgggcgc agcggccgcg   165480
gaggccggcg taaacagcgt cagcggccgg tggtggctgg taaggtcgat catgggcggc   165540
gtggtgaccg tggcggtggc gggcatgacg gggtttgcgg cgacgggcac tccggccaca   165600
gcggcggcag cggcggccac ggcggcgctg gccgagccca cacccgccgg cagtcctccg   165660
ccacccatga cgccgccggg cagagcgtcg cccagacaga cttccacagt ggcgggcgcg   165720
ctctcggcgg tcagtacggt ttgccgatcg acctcgcgac gaaagctggt gaggaactca   165780
ctatgatcca tggccgcagg gcccgagatc ccgggattct gcgggtgctg accgagtgcg   165840
ggccgagtta tatggaagac gattagcttg gagcggagtt ttgcgtccct agctgacctg   165900
cggatcagcg acgtgccata gggatagact gtgagcggcg gccgcaacgg cggggtcggc   165960
cgccgctcgt cgtcacgggg cggcgcgagg gaggaggagg tggtgggtac gatcttgacg   166020
tggttgacgt cctgcccgtc cgggggaata cgcaaaaaac cccgccgcgg cgctaccacg   166080
atggtgcgat gggtctttct cttgttggcc ggggccaggg acttgcagat gcgtgtggag   166140
ccgtagacga tctggacgtg gtcctgggag aacatgacca tcgccgccaa cgctcagcgg   166200
ggggacgggt tgggaacaca gaggctgagg ggaaacccg tagaagtcag cgaaataaag   166260
acaacacagc agccgctcct ctcgtttctg gccctaccac tgcttgaagt agggcaccgg   166320
gtgtttcttt tcctcaacgg gctcctccag tctcttatag gaccagtccc gccggcgcgc   166380
cagcatgtag gtcacgtaca aaagaataat taccatgaac accaggaaag ccagcacgcc   166440
gtaggccagc agccggtcct cgaacagcgg gtcgctcttg ataaacacgt aggtggtggt   166500
aaaacttcgg cccgcgatct gaacgtggag acgcacgaca gtatacgtgc cgttgaggta   166560
gaagacaaac tcgcgtaacc gttgtccgtt atacgtcacg ttactaatat tccacggcgg   166620
aatgagctgg tcgccctgat gcagatgcac ggtgctgttt gggtgataga ggctgctacc   166680
gttgagcaag cagtgttcgt gttcctgaag cagcacgcgg accgcatcg tggtagcgtt   166740 caagcgagtc ccgtacacgg cgtagatggg ataggtgaaa aggtcccaag tggcgttgtg   166800
atggcggccc cagctgaaaa aagagcacgt gtactcagtg gtctcctgcg gcctgagtcc   166860
cgagataagc agctcttgag cagtagcgtt gtaggagaga tgtagttttc ctgtggataa   166920
aattcatatg ctgtttattc tgttagcagg ttggtggggg aggaagggga atagaacaga   166980
ggcggtatta cttaccttta tcaccgggcg caaaagcgct aagatacccc acctgagtga   167040 agggacccctt gcagtctgtc cgtgcataac aggtaatgga caaaatgtcg ggatttacgg   167100
tgttgttcaa cagggacact ttacaggtgg cgttgagaga cacctggtcg tagctgtagc   167160
tggcttcgca attcacagta tacaggtgcc cctctttctg cgtcgtggct gccacggagg   167220
tagcggcgga tgtgaaggta gagccggacg tggaaataga ggtttgtacc gtggtgctga   167280
cggcagaagt gacgttatta gaggtactta ttgacgtagt ggacgtgacg gtggtattaa   167340
tgggggaagt gacggcgctt gtggtgctac ttttccactcc cggtgcgtg tcgcctaaga   167400 gcgtaaccat gagcgcgatc gccagtacgg gacacatgtt gccgtgtgac gagacggagt   167460
gtggacgagc tatatgtggc aggaggccgc gtcacctctt atgacgctta aacgtccagc   167520
tccagataaa agaggcgtta ataatgaaca ctacaaaaac cacttgcgtc aatatgacga   167580
tcataaaggc tcggtgatcg ctgcgcctaa agtatgcggg attctccacc agctcactgt   167640
ctttgacaaa gtggatagat gtactagtgt taccggccgt ttcgttgacc atggattgta   167700
ctatgaaagt cccggcgcca aaagttccat tagagcccca gcaagtaacg ctgccgttta   167760
```

```
cgtaggttcc cggctggcct gtcagcatgt atgtcagttg gtgggtataa ttctgtttaa   167820
tgttttccat gtcctcgctg tagttgactt ttctagtgag aaattgcgta cgatgcggaa   167880
ggacgatcat catccctgag gccaaaaagg gcgaatcata agctgtcgtg ttacaaaaaa   167940
tagtcaggtt agtatcgttg tgctcataga tataagccat ttttacttga ggttcatacc   168000
accaccctac cctaattgta gttgccaccg tcaccgagtc ccatctcccg aaacctacca   168060
ccgccaccac taatagcgtc acccccgcac ggtacatagt taccctctcg acgtcgccgg   168120
ctgtcaatga cgtgcctgcg tcagtggcta tgatttatag cttttggaca caaccgcaac   168180
ggatctgtcg taatctacct tccacagggc cgccgcgacg atgctgaacg acaggatcag   168240
acagacggcg tataggagtc ctaggtcggc gtcgacgcgg caggtgcgga tgtctcgcag   168300
ggtgggtaga tgggcgatgc acaactcctt ctccccccgc ccgtacattc catcccgtat   168360
cagcagccgt agcgtggcat tgatggtcag cggggtaacc aaagaaatca catagggatg   168420
tgtacaggaa gtgcagtgac gggtatccgt gagatgtaag tcatcaccct catcaccctc   168480
atcatgaaag accaggactc gggtgagacg acccgatgaa tactgatct cccaccacag    168540 tctttggtcc aacaccgaga gggcgcagga gattctaagt ctccctgggt tgggggagca   168600
gatgtaagcc ccgtgtgtgc cccttgccat caaagccata cacatgaggg ggagaaggac   168660
aagtatccgg gaccacccgc accccccacat cacgagacca gagacggaga tgtataaaaa   168720
aagctacttt tattaaacag cattctcacc acacgttaat actgtcacgg gaatcacta    168780 tgtacaagag tccatgtctc tctttccagt ttttcactta ctgagacttg ttcctcaggt   168840
cctggatggc tgcctcgatg ccaggctca gggtgtccag gtcttcggga ggggtctcgg    168900
tgggctgctc aaactgcccc acggcgtagg ccttcgtggc cgtctcgtag ataggcagca   168960
tgaacccacc ctggttggtg gagaagatgc gcaccatgac ctgtttggga aacttttgca   169020
tcaggggcag gcacaggttg agagcgccca acaggtccac gggggtggca gcgtggatga   169080
tcatgttgcg gtaatcggag gaacggggggc ataattggtg ggtgtgcaat tctttgaggc   169140
tccacgcggc cttgacgcct tcgttacaag catcggctgt gcgctgcgcc actttgggtg   169200
gatgtgtcac gggcatggtg tgctccatga ggaagggagt ggagagggcc aggttgcaca   169260
tggtgcccag gcgacaccgc accgcatcca cctcactctt cacctcatga ttgcgggtgt   169320
agataatctg gatgcccttg ttgttcacct gcatggtttt gcaggctttg atggcctcat   169380
ctaacacctg gtgcatactg ggaatcgtga agggcaggtt cttgtactca agagagcgat   169440
tggtgttgcg gaacatgcgg ctcacctcgt caatcttgac gcgaccccgc cgagtctgca   169500
cgttgggtgt gcagaagggg gtgttcttat cttttcatgat attgcgcacc ttctcgttgt   169560
ccaactcgga gatgcgtttg ctcttcttct tgcggggtcc ggtgctcgcc ccgccgctgc   169620
tctgatggcc gcagctcagc agagaggagg aggccgcgcc accaaaaccg ccgcgcccat   169680
ggtggctcga ggtcacggat gctcctccgc cactgctgca tttcatctcc tcggactcac   169740
tctccgagtc cgaagccgaa ctgcaggagg aagacgaaga ggaactatct tcatcggcc    169800 ggcccaaggg atcgggaaga ggagggtggt tcatctggga gagcgggtgc gtgggagagg   169860
tcactcgcgg cgtgccgctg ccggtggaag gggaagacgc ggtagcaccg cgggtttcga   169920
cttcttcacc ctgttcttcc tcgctatcag agatcacgat acagccggcg gtatcgataa   169980
tcttgttgcg gtactggatg gtaaagtcgg gctcgggctt gatgtcttcc tgtttgatga   170040 gggggcagcat gataggcgcg ggaggcacgg gcggtttaat aatcaccttg aaaggacgcg   170100
tggttttgcg cggtttctta cgcgggctga gctcgggagt agcggatgcc ccggggagag   170160
```

```
gagtgttagt aaccgcgacg ctggtggggg tcggcttgtt aagagggggcg ctgctaacgc    170220
tgcaagagtg ggttgtcagc gtggggccgg tgctactgga atcgataccg gcatgattga    170280
cagcctgggc gaggatgtca cctgatggtg ataagaagac acgggagact tagtacggtt    170340
tcacaggcgt gacacgttta ttgagtagga ttacagagta taacatagag tataatatag    170400
agtatacaat agtgacgtgg gatccataac agtaactgat atatatatac aatagtttac    170460
tggtcagcct tgcttctagt caccataggg tgggtgctct tgcctccaga ggcggtgggt    170520
tcctcagcac catcctcctc ttcctctggg gcaacttcct ctatctcaga cactggctca    170580
gacttgacag acacagtgtc ctcccgctcc tcctgagcac cctcctcctc ttcctcatca    170640
ctctgctcac tttcttcctg atcactgttc tcagccacaa ttactgagga cagagggata    170700
gtcgcgggta caggggactc tgggggtgac accagagaat cagaggagct ggcaccagcg    170760
gtggccaaag tgtaggctac aatagcctct tcctcatctg actcctcggc gatggcccgt    170820
aggtcatcca cactaggaga gcagactctc agaggatcgg cccccagaat gtactgggca    170880
aagaccttca tgcagatctc ctcaatgcgg cgcttcatta cactgataac ctcaggcttg    170940
gttatcagag gccgcttggc cagcatcaca ctagtctcct ctaagacata gcagcacagc    171000
acccgacaga actcacttaa gagagagatg ccccgtaca tggtcatcat acaagcgtca     171060
ctagtgacct tgtactcatt acacattgtt tccacacatg tagtgaggat atccataaat    171120
atgtgatcaa tgtgcgtgag caccttgtct ctctcctcat ccaaaatctt aaatattttc    171180
tgggcataag ccataatctc atcaggggag cactgaggca agttctgcaa tgccgccatg    171240
gcctgactgc agccattggt ggtcttaggg aaggctgagt tcttggtaaa gaactctata    171300
ttcctgtagc acatatacat catctttctc ctaagttcat cctttttagc acgggcctta    171360
gcctgcagtg caccccccaa cttgttagcg gcgcccttgc tcacatcatg cagctcctta    171420
atacaagcca tccacatctc ccgcttatcc tcaggtacaa tgtagttctc atacatgctc    171480
tgcatagtta gcccaataca cttcatctcc tcgaaaggct catgaacctt atctaagata    171540
tctaaggcat tctgcaaaca tcctcccatc atattaaagg cgccagtgaa tttctcttcc    171600
gtctgggtat attttttcag catgtgctcc ttgattctat gccgcaccat gtccactcga    171660
accttaatct gtttgactgt agaggaggat aacaacacat ataagtatcc gtcctcctga    171720
ctcatttatc gctatctcga tgccccgctc acatgcaaga gttaatcttt actctatctg    171780
acatacacaa gtaaatccac gtcccatgca ggttagtata catcacatac atgtcaacag    171840
acttaccgag ttctgccagg acatctttct cggggttctc gttgcaatcc tcggtcactc    171900
gttcaaaagt tttgagggat tcttcggcca actctggaaa cagcgggtct cccagactca    171960
gctgactgtt aacctccttc ctcaacatag tctgcaggaa cgtcgtggcc ttggtcacgg    172020
gtgtctcggg cctaaacaca tgagaaatag agtcataagc acatgggtca catacaggag    172080
atatgtatat aacattaata caatttata aaaaaaggg ggggcacaaa ccccgacacg      172140
taccgtggca ccttggagga agggccctcg tcaggattat cagggtccat ctttctcttg    172200
gcagaggact ccatcgtgtc aaggacggtg actgcagaaa agacccatgg aaaggaacag    172260
tctgttagtc tgtcagctat tatgtctggt ggcgcgcgcg gcagcaacga gtactgctca    172320
gactacactg ccctccaccg ttaacagcac cgcaacggga gttacctctg actcttatca    172380
gaatacaaca actcagctgc ctgcatcttc ttctgccgct gccttaagtc ttccatctgc    172440
gtcagcggtg cgagcccaat ctccgagctc attttcagac acatacccta ccgccacggc    172500
```

```
cttgtgcggc acactggtgg tggtgggcat tgtgctgtgc ctaagtctgg cctccactgt  172560
taggagcaag gagctgccga gcgaccatga gccgctggag gcatgggacc agggctcgga  172620
tgtggaagct ccgccgctac cggagaagag cccatgtccg aacacgtac ccgagattcg   172680 cgtggagatc ccacgctatg tttaataaaa actgcgggca cggggacgg cgttgttgta    172740 tatgtgaatt tgtaaataat aaatgggacc ccatcctgta aaatacaga gtccgtgtca    172800 gtctctgaag gacagagtat tggcatatag ccaatagaga tagttgtggc aaagagccat   172860
gttatggatt agtaatggaa agtatcgtca ccaataggg agtggtcaat aatggtcaat    172920
aacccacacc tataggctaa gctataccat cacctatagc ataaggaagc ggggtgtat    172980 aggccccaag ccaaaaacag tatagcatgc ataagagcca aaggggtgtg cctatagagt   173040
ctataggcgg tacttacgtc actcttggca cggggaatcc gcgttccaat gcaccgttcc   173100
cggccgcgga ggctggatcg gtcccggtgt cttctatgga ggtcaaaaca gcgtggatgg   173160
cgtctccagg cgatctgacg gttcactaaa cgagctctgc ttatatagac ctcccaccgt   173220
acacgcctac cgcccatttg cgtcaacggg gcggggttat tacgacattt tggaaagtcc   173280
cgttgatttt ggtgccaaaa caaactccca ttgacgtcaa tggggtggag acttggaaat   173340
ccccgtgagt caaaccgcta tccacgccca ttggtgtact gccaaaaccg catcaccatg   173400
gtaatagcga tgactaatac gtagatgtac tgccaagtag gaaagtcccg taaggtcatg   173460
tactgggcat aatgccaggc gggccattta ccgtcattga cgtcaatagg gggcggactt   173520
ggcatatgat acacttgatg tactgccaag tgggcagttt accgtaaata ctccacccat   173580
tgacgtcaat ggaaagtccc tattggcgtt actatgggaa catacgtcat tattgacgtc   173640
aatgggcggg ggtcgttggg cggtcagcca ggcgggccat ttaccgtaag ttatgtaacg   173700
cggaactcca tatatgggct atgaactaat gaccccgtaa ttgattacta ttaataacta   173760
gtcaataatc aatgtcaaca tggcggtcat attggacatg agccaatata aatgtacata   173820
ttatgatata gatacaacgt atgcaatggc caatagccaa tattgattta tgctatataa   173880
ccaatgacta atatggctaa ttgccaatat tgattcaatg tatagatcga tatgcattgg   173940
ccatgtgcca gcttgatgtc gcctctatcg gcgatatagc ctcatatcgt ctgtcaccta   174000
tatcgaaact gcgatatttg cgacacacag aatcgcccaa gtcgccaaag tcgtctatcg   174060 ccatccccg taaacgatat aagcgctatc gccagatatc gcgtatgccc aaaaatcact   174120
tttggaaaaa tggcgatatc agttacacag aaactcacat cggcgacatt ttcaatatgc   174180
catattttca aatatcgatt tttccaatat cgccatctct atcggcgata aacaccacta   174240
tcgcgcgaca tgaatttagt cggcgacaga aatctcaaaa cgcgtatttc ggacaaacac   174300 acatttatt attcactgca gcatatagcc cattttagcg cggcacacat ccagccgttt    174360
gtgtttctta acgctctcca ggtactgatc caggcccacg atccgggtta tcttgtcgta   174420
ttccaggttg atccatcgat agggaacgct gccagcggcg cccagcaggt actgcgcctt   174480
gtcgttcact ttgccgcagc gtattcgccc gtcagcttcg agatataacc tacaacacgg   174540
aggggaaggg gggtacaaaa cgtgaaatta gactttttt taatgatgtt ttgtccctct    174600
ctgtcttact ctcccatagg ctgtaaggcc ctcgaggaag agacttacgg attgtagttg   174660
cagctcgtca gtttgttgtg tacgacctgg cgtgtcaatg aatgggtcat ggtggtgacg   174720
atcccgcgaa tctcagccgt tttctcggga ctgtagcaga cttcgccgtc cggacaccgc   174780
agcctgtgga ttcatgaaaa tctactctgg cattcccgag gatcgtcgat ggaacatggc   174840
tatcagaaac gtcgagagac agatccagac gcaccacaga acgcagacaa tcatgaaaat  174900
```

```
acgtacgcga cggtgaagcg attgcacatt ttgaaatcgt aacagcgttc cggcgggtgg  174960
ttgacgttta tgaattcgca acattcttct gcgcgcaccc gcggcacgcg gctgtgaccc  175020
aatagcagcc acaacgccgt caagaacggc gtcaggtttt tgggactcat gacgcgcggt  175080
tttcaaaatt ccctgcgcgc gcgacgggct caaacgatga gattgggatg ggtgcagaag  175140
gtgtaaaagt ctggttattg gcctcggtga acgtcaatcg cacctgaaaa gacacgctgt  175200
agtcccggaa gacgtgagcc cagctctcca gcttcatcac acacatctga taacgtgtgc  175260
catcgttgac gacgaagcgt agcagcttgg tctgcttggg caccatgtgc gctccaaaaa  175320
tcttggcgtc ttccacgctg atctgcacgt ttccgtcgct cggtttcgaa gccgttcggg  175380
gcatccgttg aaggatggtc tggttgcgac cgctcaggta ccagatcacc ttttcaccc   175440 aggtggagct tctctccacc aaggtctggc cttccggtt atacagcaga tacagggtct    175500
cgttgcgaca ctcgggaccc gttaataccc gctggaaccc cgagaattgc aaggggggacc  175560 gtggggcga gggatagaga aaaggacagt aaaacgtcgc cgcgtcatgc ggtttggaat    175620
acgtcagttt agaccatggc ggggacggat tctggtttgc cgttagcgtc gaccagggag   175680
acgccagaca gggcgttgcc caaaccgcgc acagaagcag gcagtgaaag tggtgacgaa   175740
gcagaagccg cagcatatta tttcccgtga cgcaggctag ttggcaaaga gccgcacgct   175800
gaactcgagg ctccgggcgt gtggcgccag cgaaccggcg gcgttgaacg tggtcctttt   175860
gttggtgccg ccgcgacggt tctgacgtct aaagtcgctg atgagcaacg acacctcggt   175920
cacgttgatt ctgcaagcac aggttccaaa cgtcatttca tccccatgc ggttacttag    175980 ccgttacccg ttcgctctta ccttcccgtt gtcatgcacc tttagcgcgt accctcacct   176040
cttgagcacg tcaaagttgt ccaagccgtg gctcgcatcg tagtggtagt tcaacgtgag   176100
gtccacgagc tgttccacat acttgtaacg ggtttggtcg ggcagcgcgc gagagcacgc   176160
gtcccagtaa tgcggtactc ggtaataatc gttttttcc gcggtttccc gctggcactg    176220
acccagcacc acggcgcaca gacaaacaga cagccacacc cgacacagcc gcatgttgca   176280
gactgagaaa gaaagcttta ttatgagaca tcatacacat agtataggcg aggtgatggg   176340
gcggggaaag agttggaacc gaaagacaaa aaaaaaagcc tagtcgtact cgggatctct   176400
gagcgagacg ggttgcatgg caactttcat tagtttggga atctgccagc tggtgctgtt   176460
cgaaggttct tccatttccg aggcggtcag ttcatcgtac accgaaacgt agtacctgat   176520
ggggtcctcc tcattgtccg agaggtgaga ttcgatggtc aaaggcgagc ctctcccata   176580
attgggattc acgaacgacg tgtccaagtt gccatccttt ctgaaataga tgacgttctc   176640
aggatcatgt ttcatgcgct cgcgggccgc ggacgcctcc tcctcctcgt cccagtcccg   176700
agtttccaac cgctgataag ggctcgagga acaaaatccg gcggggatct gagaacctcg   176760
tcgggaaccg ctgccaaacg ggctgctgcc gccactgtcg tccgtgtcgt ccaacaggtt   176820
gacggcctct tcgtcggcga aacgaaagcg gcccgggtgc ttgcaacacg aggagtaaac   176880
taccgcgatc agtaccgcta tgaagctgaa aatggaggtg cctgtcacga tgtagaagag   176940
gatagccagc actttcatga tttcgtcatt gcgcgcgtcg tgaacggaag attcgcgggc   177000
ggtggtcatg ttggtttcgg ttgtaggttc gctactcgtg gtgctctcga cggtatttct   177060
gctgctggtg ctagtaggga cgtttgtgct gctggtcata tttgtagcgt cgctgaagtc   177120
gatgtgaagc agcaacccga acgcgaccag gaccaggaat gttgcgcgaa ggagaccccg   177180
cggggccggc attcttgaga cgtggcgacg tggatttctc gttatgtccg cgaacgacgt   177240
```

```
gtgacgagga cgtggtttcc gcaagcctct accgacgccg cgacaccagg taggttatca   177300
aaacgcgagc ccatatcgcc gccatcattg taatcagcaa tgtgttgagg tactgcacga   177360
tgaatctgtc tagtgacacc agccaaccct ctgcttttgc gggcaagcgc gctttcggtg   177420
acagggtgta tcgtacgtag ccgcgggtca ggcgcgcgtt gtagcggtac acgcagaaat   177480
ctatccacag gccaacgccc ggctgtagct taggatggtg gataatagcg cggtgacgta   177540
cgccacgggg ctttagaatc tccacctgta aggccatctc ctccaggtag tgggtctgac   177600
tgcgacgcag cgtccagttc atgtaaaagt cggtctcgcc gtgtccggcc acgtagaggc   177660
tgcttactaa atcgggcgcc agagctagat caggcgtatc aaattccact gccaggcgac   177720
ctgattctaa cggttccacg atccgggaga gcgtttctag atatagagca aagcgtacca   177780
cgtctacctg cggtgtaaaa aactgttgtg ggcgttcacc gtcgttgacc acgtaagcca   177840
cgtagaggcc aacattttcc accacgggtt ctagctgcag gcggcacgta aagcttagaa   177900
acgacggctg tacggtttgg ttcccgtgaa gctgaagcgt cacttccttg ccggggctca   177960
ccgtgctgta acgccgcacc gagtcggtca tctgctccag atcggtagac cagaagggcg   178020
tgcaatgcat actgtcccag tcgcgacacg cagcccagcc tagctcggtg aagggtcgac   178080
gcacacccga aaaagtgtgc ttgaagacca ggggtcgcc tcggtagctc agtagccgaa    178140
catgcacata gtcgcggcta gcgttgacag acggcccgta gagggccagc aggacaagcg   178200
tgaacagcaa gcgcaacatg ctgcgcgggt tagaaaatgc ggcgtgccgg ccaccgcccg   178260
actcataaac gctaccagca tgacgtctca gatcacacaa gtgacgagga gcgtaccgca   178320
aatcactagg gaaaaggcca gcagagcccg atagtcttgc tcttcgcgaa cgatctcgtc   178380
cggttcctcg cagtcttcgt ggtccacaga agatgaggag caggattctt cgttaatttc   178440
tgccaggata ctagtgctgt accacaccag agcgctcagc gtgcccaggg ctaccgcacg   178500
gtaaaatagg gacatgatca ccagcgcaat ctgaagtggt ggtagttcag tttcttggcg   178560
tatttccaga gaaaggcttt gtaggccgta gggactggcc aggcaccgaa ctcaatattg   178620
gtagacacta cgtcgtaaat gcgttgttcc tcgtctaaga ttaaccgaaa aaatagccgg   178680
ttgatgtgac gacgcacggc ttgcgcgtta ggattgagac acttggtgcc cttgtccttt   178740
aaaatagcca gcacttcctg acgattgcag cttttcgctcg ccgcgattgg cttaagcaat   178800
tcagttccga ttggcagagt attcaacaga atttggttgt tacaacgaca gcgtttgtcg   178860
taatcttcca attctaaaag atggacggct aggggacata cgacaaataa catgtatgca   178920
gtcaattgca tatatcgtac cgataaaatg ttagtgtgcg gattcagaat cggatgatgc   178980
aaccgtctta gcatcatatc gaaaaagtat acatattacc gattcattat aattagggaa   179040
ttatttccaa cgcggacgtt tgttagtgac agcgttttct tctacatgcg gtccattact   179100
atcctttact tttaccaata ctctgtgcca tgagttgtct ttttaccat ccagccattt     179160 ggacaaatga tgatcgggag ctaaacatac aggtttacct cgaggaggca atagataatg   179220
ttgaggtttg tcacactcag gaggattggg agggtcacga ccaacccaaa ataagccacc   179280
tataggatga tgtaaagctt tgtgggtaca cggacaacgc aattctctac tgtgaacccc   179340
atggtaatac ataaatgcca tcaaaagact aatcagcgaa ccaaaaatta atcgcattct   179400
aattttatta actacgtcac tatcagtaat tcgtaatatc cggtattccc ggaaaatcac   179460
tcaaaactgc gtccatgaca catcaattcc cgataagtac ccccctttga aatcggatcc   179520
ccccacatac caatcaatca cacaacacac aggtttaaaa atcgatcaca cgtcaattag   179580
gtttcaaaat cgatactgtt tattatcagg aatctagact aattctacaa tgacagctct   179640
```

```
gaatttctct ctcgtctttc ttgtcaggtt ctcatcatca atcttcactt ccacccatcg  179700
aggagtcatc gtcgctccaa aacccttggg ggtcgctggt tggaaaagtc tctgacacga  179760
tccaggcacc ccgtacccag tccgactgat ctagcttacg gagcatctca acaggcatga  179820
gctgcagggc cacggctgtc acggcaggga ttattactac cgttcaggta aactgtatct  179880
ccctgagtta ccgtgatggg tctttctaca tgttgacttt gcgtaaaaaa tcgccggtaa  179940 aatgttttt  cttgttcatg taaaagtacc ggaactaaaa tgctagttag aatggttgca  180000
gttgctatta gcgcggctag taacagtagt ttagtgttac attgtatacc catgttttta  180060
ataactatga atattctgct tcacaccata agtgcttaac ccacaaaaac cacacggaga  180120
cattattggc taaaaataaa aacaaaagtt tattgatgtg catgttaggt tttagtctaa  180180
aattcatctg ggtcgtattt gggaagtttt gtataacgcg tcttctgggg acgcgacgg   180240 ctacccatgt ataaggctat aagtgccaca gataccacta tacccgccca tacagcatga  180300
attcccaggg gaatgttagt gtttttaca  gtttttatta cattgtccca cgttctgcta  180360
ttatgctggt ctgattcctc ttttgtttta catttatcag gtataggaga cgatgttgca  180420
gttcctgata acacggttaa atagtagttt tccttttac  cgtcactgta acgttgcaaa  180480
acgtattttc cagcgtgttc ggtagttacg ttgtatatag tgagagaggt cttattgcag  180540
tctaaacaca tgccgttcag tggggaagtt gaataataat gtccaatgct gcacagttgg  180600
tgtgcgcgag gtccatattt tatccattct atatcgtgcc atacatccgt tctactgcag  180660
tttttcaaag tgacgtatcc accgacatat cctgttacat taattacttc gtaatttaaa  180720
ttagagtgtt tataaacggt gtacaaactg ccattgcaag ttatgttgct ggtattcaac  180780
cagggagtag tactatgaat ggtagaaaac gttaatgttg gcgtagcgct tgacgatgat  180840
tttgaaagcg ttgaagtggt tgctgatgcg actgaagaag cggtagaggg tttgtgcgtg  180900
gttccatttg cgatagctga agtgctgtta gcatcggtga cagagttaga agaatttgtg  180960
atagtggagg cggtggaggt aaaggcaatt gcacggacag gagcacgtgt cattgcaacc  181020
ttcagatatc gtaatcatca gtaacgtcca cttaaccgta aatctccagt ccataacgtt  181080
attaaatttc ggttaacggg cattgatgtt tcttcggacg ttgttgatct ttcttgcccg  181140
tttattttct gatatggtct cataagacat ttatccggaa acgttgctta gtcctcgtgc  181200
tcaggattgt atcgaactat gaattctgat tcacttatat cgtcacttaa tggatgatat  181260
tttttattta gagctcgtcg gacgaaaaat aggagaatgc aggctacaca aattaatgct  181320
aacgtccacg tagtgcgtct gccgtgtgat gtgttagaat gattgttata gcggtataaa  181380
tgatctatag atgatgtggc tgtattgtct tcataattgg tcggtttatg agaagtgtcc  181440
cattcgtgct ttggttcttc acatacccag ggattcacgt gtgtcccgtt tgtgttgttt  181500
ctaggatgta tttgcagatt aaagttttga ttttgttcgg agggatgccc agttttataa  181560
catcgaaagc tatatttacc agaatgagta aaattaagac cgtacagaga taagataaa   181620 ttacgatcgc atgtaaaaca taaatcatag tgatgtttta gataatttgt gtgccactca  181680
catagtatac gcgaatggag gattttcaat gaatggttat gatatttcc  atttcttatg  181740 ttgggatggg tgtattttcc gtgtgtggat atattaaat  gtctaagcca ggctgttttg  181800
tagcacgatg tgatggttag gttgtgtgtt atagtaatat tgtctccttg tgccgcctcc  181860
aataatgttt cagattcttt tgatatcgta ttatttgtac tgttaggcga tgagcaagtt  181920
ggaagcggtg tagtgacgtt ttcatttgca tttatcatag tagtagtgtt ggttgataat  181980
```

```
gatatagttt gcaaagtcac agtactatcg gttacatgct gtgtcgatga attcgtgtcg  182040
ccgtttggtg aagttgttat tacagttacg ttagttgtag atgtttgggt agatatggtg  182100
gaaatagttg aggtcacgtc tgtgcctttt acagagcttg cagtgaatcc tgtggatgtg  182160
ttgacgttgc cattggagga tgtgaacata gtggtagaca tttcggtggt ttgtaacgta  182220
gatgtcagtt gtgtagtaga tattaagctt gtgggtgtaa tcgacgtgga agtattggcg  182280
atagtggtgt tgttacactt gcttttctgc agaatccaaa aaataataaa catgcatatt  182340
atttgcgtat atgatgactt gttccaccgt cgatgttgtg tgcgcatctt ttactccaaa  182400
tccccgtcca ccgtcaacaa cagaggttcc gtatctaggt ccgtccgcaa ccgttcagcg  182460
tcctgttccc cgattcgttg cgaccgcaga aagcagatga ccagtgcgcc aacaaagatc  182520
atcagtcccg aaacccaggc gcaatggagt gagaggccgg accactggcg ttttaaatcc  182580
gagataattg ctcggtctgc ctcttgggaa tccgtaacca caactctccc tggtcccgga  182640
taaaagcatc gacgcgtttc caaagctcgg cagaagctac gtgggtggat gatgaggtaa  182700
aaagcctcga catcaccggt atactgatcc tgcaggaggt agactcccgt atctttaacc  182760
gtaagattgt acagcgtgag attttggcgc gtgcacgtga agttgcgcc accctgatgc  182820
gtggtttctt tataggcgtc tgtaatgatg caaagtggcg gcatacgacg catgtatctg  182880
ctgtagatat cataacgttg ccagactacg ctgtgatggc tagtgttaag cctggtaacc  182940
agagtacgtg tacggtcctc gcaggtggcg cggtaattgg cgagctttag gggttttttg  183000
gttggttcga cggcgttcga tgaacttccc tgagttgtga acaaaaacag cgacgtgact  183060
atgacaagcg tgagggggt gctgtaggtc tgcatggtgc aaaacacgtt ctcgccttcc  183120
ttgtcagacg tcgtcgtcct cgtcctcttc gtcgtctgtg cccgtcggtt cgatcaacgg  183180
ggagttatct ttctgtctgg agggtcggta tggaatccgt tcgtagatgt tctgcttttt  183240
agccgcgtgt tgttccagct ttttgcgtgt caggctccga taggccagac attgatctac  183300
ctcggtgccc gtgttgtttt tctcctcctc gcgcgcgtaa attacgaaga agaccaccag  183360
caggactatc agcgtggcca cgaacgagcc cgcgcccag gccgagtatg cgcctagcat  183420
tgtaatgggt tctgtgaccc ggcatttgca catcgcgtgg cacctgctgc cattggtaga  183480
tgtgctattc ggattgcact tacatgttag gtgggtattt tctgttttca cgagacaatt  183540
ggtggtaacc gtgttttcgg cgcaaacggc cacgtagctt atcaaaccga gtgctaaaaa  183600
gcacaccgcg tgcattacac gcggatacat attaaaacac cgtgttccac aagcaccgca  183660
cacgtcgatc ctccccgcac ggtcttcagc ccgcccatga catgatctcc ctcacgttac  183720
ccttcaacac tctgtagtac tctgtctcgg cttccggtcc ccatgtccta atcataacaa  183780
aacaccgtgt cactgtccat ctccctgtct tttcgcgccg ccggtccccc ccaaaccatg  183840
tctctagatg ccgccagcca ccaaccggcg gcacggcggc tcttggattc ggcattggtg  183900
cgccgcgtct tggcctgcat gatcatcgtc atcatgatcg ccattagcat ctggatcctg  183960
acctacgtgc tgtttttcta ataagaaccc cggcccctga cggtaatttt cctttcttct  184020
ccgtttctcc tcagctgccg tacgtgatgc ctcacggcca tctccgacag gccctctccc  184080
cgacctcctg gacatgtgag ggcttgttgc tcctcctggg attgctggtg ctcttctttc  184140
accaccacaa ccagtcggcc gtagagaggc gtcgccgcgt ctcgttcgtc gaggtcgatc  184200
gactgccgca tgagagcgga tggtattctt ccgatgacga cggagaccgg gatggcgatg  184260
aggaaactgg agagagccac aacagaaaca gcgtgggact gtccgctgtt tttagctgag  184320
actggcgtgc gacctgtaaa ccgttactcg ggtctcaaga tggtttggaa gttgtgactc  184380
```

```
atcttcctgt gggcaatgcc caaccggacg cgagtgtccc ataaaagccg ggcgctccgg   184440
cgagaccatg ccatcctcgc cttcggacgc cccgctcctc ttctctctcc tctcctcccc   184500
gctgccgcgg ccactgccgc cgccgcccat accatcggca tgtcggccga caaatcgcag   184560
ctgtcgtcgt cgccgccgca gctgtagcag ttaacgtcgc cggccttcag gaggagatgg   184620
cgctctgcgt cgtctcttcg tcccgcctcc ctctgtggtc gtgggtggtg cgagagtaca   184680
cgatgggtgg ctctcgtctc gggggaccac agggggaggg gggtaattta ttattcgtat   184740
tactgtaatt ttgtatcgct taatttgttt agagccgcac gcttgacaac gccttgtata   184800
gccttattta tcccgatgac ttttttctcc gtacaagaaa tggacgtcac ttgagcagac   184860
acagtttcat cgaccacgac agtctcatga tctgactacc tctgacccgc caatgagaaa   184920
accgaaaagt aaaagatgac cgcgccctcg gagtcctttt ttccttttca atcatgaaag   184980
caagaggcag ccgagagaat gccagtaaga gacgaccatc gcagacacag tacgatactc   185040
atcttagaac gaaccagcga ataaccatca cacgtacagc agaatctcat gaactagtca   185100
accaacgtca taaaatcttc acacaatcgt ttttgcgaac ttttaggaac cagcaagtca   185160
acaaaagact aacaaagaaa aaccatcttg gaattaaaaa aagtagcatc gttaccttat   185220
gaaccagcag cattcagtat atacaccaga tataatatat ttattaatgt atcctctctt   185280
tctcctgatg taattttgtt tttgtaaatt caattgttga aagtctctcc ctggggaat   185340 tgcatatctt attgatgaag aagaaatccc tgccatatgt gttgtcaaac tatcattatt   185400
tctctatatg ggtatttttt ttctaagaag caaaagacta gcagcagcca aaataaacct   185460
gatgaaatct ttaactgaac tcccggtggt ctgtgtgtat atttctgttg gtggtcggtt   185520
gtctgaaccc gggtgggttg ttcggaaacg gcgggacggg gaaacgggtg gaaacagcgt   185580
cgctatatac gtgactttg atctaaacgg acgtcgctag gctgacagtt tacgaattgc   185640
taaacaaggt ggtcaggaac acaacaagcg gggctttgcc tggtaggatt tcctgtggaa   185700
acaatcaccg gatgttatcg tggctggtac ataagctggt tctggctgca agcgcttttt   185760
actgcattag gttcggcgtt agctcttgct taggaacgcc atggctataa cgggaaataa   185820
ccggtttggc agcattccat tgtgggggg ggggtactta tagcgtgttt catgacggtg   185880
tttatacatg aaggtgcggg tttcaataaa gtagaggtta aaagtggtga caatgtaacc   185940
attgaacaca aaaacgaccc gatgactacg aaatggagcc atctgaatca aggatggtta   186000
tgtaatgtaa cagggagaca tgcacctcta gtgaataatg gatcaagcgt ttgtgtaacg   186060
aattgtactc atacatcttt agatctgtgc aatatcacga agggtaacga tggcgttgtc   186120
gaccttggtc gttggttcgg agagaataaa gacgagtaca gcggtgaatt atggtatttg   186180
actactaaaa attaggttta gagagtgtta ggttacgttg acctagttag atttcctgtg   186240
tagaacaatg accggacgtg cttggactgg tacatacgca ggggctggac gtggttaccg   186300
gtcactggac tcggtttcgc tgtagctgtg gttcaacctg aacatggctc ccagagctgc   186360
taggaaccgg tccagtcaca ttttttggtg ggtgggggt actaaaaaag tgtttaatat   186420
tggggtttaa tgataaaatc caggttatgg atatgaggaa actgaatacc tcgcagggtc   186480
gaaatcttac cacagttgat gatagaagac ggttttccat cgggtgggaa acatgggatg   186540
acggtggaga gtctctatac gatgtgacta ataatggtac aacgtcatc aatacaacag   186600 cctgtgtttc aagttgttcg catacgtcgc ttgtgctttg caatatgacg cagcagactg   186660
attcgttgta cggagtgggt catcggttga atgacgaaga agatggtgaa ctgtggagag   186720
```

```
tttcggtttc ttaataatcc catacgacat gtgttcattt atatctgaat tttaggatga 186780
tgactatagt ataactctgg ggaacaaata tcatacgtta atcactttaa gttacgccgt 186840
taggaaaaga aaatcagtcc gaatgaagca tagtcagccg aatgatacag caatagcttg 186900
tttacaacgt gttcttttt acattatgaa cgtgccttgc tttttataca cacatggaga 186960
cagaggtccc tcagcccttg tcacgacaac tcccttttc taaaccgtat gtgctccaaa 187020
ccgcatctcc tcatcgtcac gtgaaatacc atgggacccc ttttcgtcac acacgtcttt 187080
ccgcttactc aacgcgtcag cccgcgctcg gcagagctac catataaaaa cgcagggtt 187140
tagcggcttc cccagatcgc tgctgccccg gcgttctcca gaagcccggg cgggcgaatc 187200
ggccggctgg tcggtcggcg ctcggacgga tggggagaac ggcggtgact tagccgcccg 187260
tggccgggag aagatggagg agccgagatg acaacggcag tcgtggaagg gtcgccaagc 187320
cccggtcctt ctcttctgtc tggtcgaatc tcgttttctt ttttcaaccg ctcttttat 187380
cacctttta tgtgagttc tcttccgcgt ctcccggccg taccatccac ccatgcagca 187440
tgcacgcgtg tatgtatgca tcgtctctcc tccgtcccga ctaccatcag cagcaccact 187500
accgccaccc ccagcgccac caccgctgcc gtcgccaccg cgttatccgt tcctcgtagg 187560
ctggtcctgg ggaacgggtc ggcggccggt cggcttctgt tttattattt tttttattt 187620
tttatcttct cctttcctta atctcggatt atcatttccc tctcctacct accacgaatc 187680
gcagatgata aacaagaggg taaaagaaa aaagctacag acatttgggt acctcagctt 187740
tccgataact cgaagaattc aaagtcgacg attcccaacg agagaaaaca gaacaaaaac 187800
aaggtcattt ttatttatcc tcatcgtcaa caacaactac cgacaacaac gaaacaccac 187860
caagaatgtc aatccgcaag ggtgttcctg ccccctcgac gcgcctgtcg cgatcctcat 187920
ggcgaggacc gcgatctccg tataggtaga tgaaattatc ccgtgtccgg tcctgattcc 187980
ccgcatgccc tgcacatcct gacgcgtcgg tcagcagcca aacaatcata ggaaatgaac 188040
cagaagaaca aaaagatcat ctctctcggt gtatagcaac accaacaaca accgcatcgc 188100
aacatcttca tccgcaagac ggaaagaaaa caacaataat gagaatgaaa tcaccacaac 188160
caagccagat ttcacgtcca tgagttttta ttatattatt atcaaaacga aaaacagaaa 188220
aactgtcata gataaatata aaaaaaaata gaaaccacaa acgactacta gtactccaat 188280
cttagatgta tatgctccta gataagattt agtattacca taatcatcga agaatgaaag 188340
acgacgatga ttccttaccg ctcctgccac ccggtctgta tgtagagaga gaagagagaa 188400
aacggtgaat ccaagatccc cgggtcggcg tcggcatgcc gctgatcgca gtggcccac 188460
ctcggcatgc cggcgccggg cgaggaattg ctcatgaaaa aagtatcttt ctgtaaaaaa 188520
agaaaacaat acatgattaa ccgaaaagaa accaacaaaa agaacccgag atcagtcgat 188580
ttcgatcact acgataaaca catggaagat ttcttgaaaa agaaaagag aaagagacca 188640
ccttcccggc ggcggacacg ctcctctccg tcgccgttct gcaccatgat tcgatcaata 188700
acaacatcat catcggagac catcttttaa tcaatcagcg ttgcagtagt cgactccctg 188760
gacacgaagg agtcatccat ttttatcctc gcacttcttc gctctcaaag ccgccttaa 188820
agttgaaatg aaaggatgga acatggaat acagttttaa ttgcacgtat caccatttta 188880
ctacaaaaag aaaaaaaaac aacttacaca tagtattacc ttaggtttac ggataagtag 188940
agtgtaggcg ttttgaaac agttcagcca atgcaatctt gtctcggcat aatcactctt 189000
tctgcatata atagtagtag tagatttatt cacatcaaca cagcgaaaaa ctccagcatc 189060
aaagtacacc tagagacagc ccttaaaata tagtttgcag cttttagatg tacttacacc 189120
```

```
aaagaagatt accgtcctta cgagaaaaca gatactcgga tataggaatc aagacagctc  189180
tgcactgaaa acacactctc ctgtcacgac accgcgccac accagaggcg tacgcgtgac  189240
ttcatcgcaa cgatccatcg tgatgtccct cgcagaacct aaaaagacca aaaaaaaatc  189300
ttggaccaca gttgtcgatt cttgaagaca atattctcgt gagaactttg agattcgcac  189360
ttgaaacctc ttaggatcca caaaacaac  aacctctgta tggaaaatgc gctattttat  189420
ctcagctttt ctcccaaacc tcggtttctt cctattctta agttttccct agtatatttg  189480
cctccttata acaaaagaag cacaagctcg gtcgcacgga ttattccttc tgctaatcta  189540
ttattttgtt ccttttttt  ttgtttgcct tcaccccctt cactccctgt agcaacacag  189600
agtagtagac acaataaatg agaagtttgc atgcatttgc cgtgtccgtg gtctgttata  189660
gcgtgtggag tgctcgggat ggatggacgt ggggacggat tcctgaggct acaaagatac  189720
gcggagacgt cgtggcgagg ggatgggttt attggatatc ggtgaagcag cgtggcggcg  189780
aaatacgcga tccctgggct ggtagatccc cctaccccgt ctaccgggga cgtttatcct  189840
tgggacatgt aaatgtttcg gccggcatcc acgcgccacg ttcaccgcgt cgtgcccagc  189900
gccatgtgcg ggtcgttcg  gcgtgaagtt ggacggcgtg gtttcgggga ttgtgaaccg  189960
tggctgaggg tgtagaaggg ataggaaaga gcgtgtcatg tgggcgagtc gtagcatgtg  190020
ggtgcgatgc ggtggatatg gtgggctggg gtggttttgg gcgtggagat gtggagatgt  190080
gggtgatccg gatgcgtggc aataggcctc gagcttgggc ttctcccgcg gatggacgtt  190140
ctaactgtac acggcggccg tggcctccga gtaaaaaaac caggtgctga cgccagacac  190200
agacgccgtc ctcggaatcg tgtgcgcgaa agcctgtgcc gcggcagcgt acgacgttcc  190260
agtcagcgag gccgtcgcgt tggcgcgcca acagtaaggt cacgataggt tggcggccca  190320
tggttccgaa gcgtccccac atgcaccagc agtcggcgtc gaagtcgctt gcgctgtcgg  190380
cccggtcgcc accgccgcgg cggatttccg cgcgggggac ggggtagccg agcgctgcgc  190440
cttcgccaat gttgtgaagt agatgcgtca gttgatggtg atgttctgtg gaaaatgag   190500 cgctttcctg agggttggcg tcggggtatg cgtgtagttg gggttgtgtt ggagcgtaga  190560
ggtgttggcg ggcctgcgcg caagcggcgt aatccgcggc gtcgagctcc atctgcgtgc  190620
ggtgttcttc gttggcgtgt ttgtccgagg tttggatagg cggttgtgtg ttgctgtggt  190680
gtaagggtag cgtgtgttgg tactgtgggt gaagcggcgt ggtgtgggtg ctgtttgtgg  190740
ctgtggctgg catgattgtg cggcaggtgt gtgttgaagt gggtggaggt taaataggcg  190800
agggcgagtc cccgtccccg cacacccgcg tcctcgccgc aaacacccgc gccaccccg   190860 tccctcggtc cggacccgca acacccgcgt cgccaacgta accccgtac  ccgcaacgcc  190920 ccggccctac cgccgtcacg cacaccccc  ggcccgcagc ccggtaccca gcgcgcccaa  190980
aaagcgccgt ggagacaccc gtacagagat ccctcagcgc gatgacgccc cgcaaacctc  191040
acgcagtccg gtcccgcgaa cagataccgt gggacgacac gcaccggtag tgcgcacaaa  191100
ggcagccgcg cttacgggcc tcaaagttcc ctcagccccg tcccgcgccg gcgtcgggtt  191160
gggtgtgccg ggggcgcggc tgggtggggtg cgtgcgtgcc gggtgtgtcg cgggcgtgtg  191220
tcgggtgtgt cggtcgggtg tgtcggtcgg gtgtgtcggt cgggtgtgtc ggtcgggtgt  191280
gccgcgggtg tgtcggtcgg gtgtgtcgcg ggcgtgtgtc gggcgcgtgg cgggtgtgtc  191340
gcgggtgtgt cggtcgggtg tgccgcgggt gtgtcagggg tgtgtcagcg gtgtgcgcgg  191400
cttcggggtg cgtgtcggcg gccggaggga acaacaagtg tgccccgggg cccgcgagcc  191460
```

```
cccccccctc ccctcggccg gacgcctctt ctgcgtgtgt cctcgacgcg ggtcgcgccg    191520
tactttgcgg ccgttgcttc ccccgcggtc cccagggtcg cgcggcgccg cgcgcttcct    191580
cttttccgcg cgcggccgtc ccccggggga cttcctcttt tccgcgtcgt ttccgcgtcg    191640
ctggcccctg ggaggcgttc ttcgtgtgtc cccggggacc cgcgctgccg tcgtcccctg    191700
gggacttcct ccgttccccg gggaatcaaa cagacacaga cacgcgtctt cttttcgccg    191760
tgcgcgccgc acgccgcttt tatgcgccgc cgccgtccca accgcaccgc aacgcgactc    191820
caagactcca aatttcaccc ccccgctaaa aacacccccc cgcccacgg ggacccaaca     191880
cacggcccgg aatggatgtc aggcgtccac ctagatgaca cgcgctcgagt gctgcgggcc   191940
tgtctcgcgt cttccttcgg gcgtctgcct ttcccagtcg agtgcgtcgt cgcctgccgg    192000
gtggttttcc acgggcttcc agactgcgcg tcgccaaggc ggcgccagca agcgccgtgc    192060
acggcgctgc ctataaaagc caggtgcgtg tcggccgtgg cacacggaca acggagacgt    192120
ccgcgtgtgt aaacggcgtg ctcgctgacg cgggttgtgt tgctatatag tggacgtcgc    192180
ctcgacgtcg gaggtgtccg gcggccatgg cccagcgcaa cggcatgtcg ccgcgccccc    192240
cgcccctcgg tcgcggccgc ggtgccggag ggccttcggg ggttgcttcc tctccttctt    192300
cttgtgtgcc gatgggagcg acgtcaacgg cgggaactgg tgcaagtact gcgggttcgg    192360
cgacgccggg ccacggcgtc caacgggtag aaccccgcgg gccgccgggc gccctccgg    192420
gtagcggcaa caatagcaac ttttggcacg ggccggagcg cctgttgctg tctcagattc    192480
cggtggagcg gcaggcgctg acggaactgg aataccaggc catgggcgcc gtgtggcgcg    192540
cggcgtttct ggccaacagc acgggccgcg ccatgcgcaa gtggtcgcag cgcgacgcgg    192600
gcacgctgct gccgctcgga cggccgtacg gattctacgc gcgggtgacg ccgcgcagcc    192660
agatgaacgg cgtgggcgcg acggacctgc gtcagctgtc gccgcgggac gcgtggatcg    192720
tgctggtggc gaccgtggtg cacgaggtag accccgcggc cgacccgacg gtgggcgaca    192780
aggccggcca tcccgagggt ctgtgcgcgc aggacggact gtacctggcg ctgggcgccg    192840
gattccgcgt gttcgtgtac gacctggcga acaacacgct gatcctggcg gcgcgcgacg    192900
cggacgagtg gtttcggcac ggcgcgggcg aggtggtgcg ggtgtaccgc tgcaaccggc    192960
tgggcgtggg caccccgcgc gcgacgctgc tgcctcagcc ggcgcttcga cagaccttgc    193020
tgcgcgccga ggaggcgacg cgcgctcgac gggagctgcg ccggcggtgg gccggcacga    193080
cggtggcgct gcagacgccg ggcaggcgac tgcagccgat ggtactgctg ggcgcgtggc    193140
aggagctggc gcagtacgag ccgttcgcgt cggcgccgca ccccgcgtcg ctgctgacgg    193200
ccgtgcgtcg gcacctgaac cagcgtctgt gctgcggctg gctggcgctg ggcgcggtgc    193260
tgcccgcgcg gtggctgggc tgcgcggcgg ggccggcgac gatgacggcg gggacgacgg    193320
cgatggcgac ggggacgacg ttgccggcgg gggcgagcgg cacggagacg gaggccgccg    193380
gcggggacgc gccgtgcgcg atagcggag ccgtgggtc tgctgtgact ttacctccgc      193440
agccgtacgg cgccgccggc gggagcgcgg tttgcgtacc aaacgcggac acgcacgcgg    193500
tggtcggaac ggatgcggcg gcgcggcag cggcggcgcc gacggtgatg gtgggtccga     193560
cggcgatggc gggtccggcg gcgtcgggga ccgtgccgcg cgccatgctg gtggtggtgc    193620
tggacgagct gggcgccgtg ttcgggtact gcccgctgga cgggacgtg tacccgctgg     193680
cggcggagct gtcgcacttt ctgcgcgcgcg gcgtgctggg cgcgctggcg ctggggcgcg    193740
agtcggcgcc cgccgccgag gccgcgcggc ggctgctgcc cgagctggac cgcgagcagt    193800
gggagcggcc gcgctgggac gcgctgcacc tgcacccgcg cgccgcgctg tgggcgcgcg    193860
```

```
agccgcacgg gcagtgggag ttcatgtttc gcgaacaacg cggtgacccc ataaatgatc 193920
ccgtcgcatt tcgtgtttcg gacgctcgaa ctctcggtct cgacctcacc accgtcatga 193980
cagagcgtca aagtcaattg cccgaaaagt atatcggttt ctatcagatt aggaaacctc 194040
cttggctcat ggaacaacct ccacccccat ctcgccaaac caaaccggac gctgcaacga 194100
tgcccccacc gctcagtgct caggcaagcg tcagctacgc gctccgatac gatgacgagt 194160
cctggcgccc gctcagcaca gttgacgacc acaaagcctg gttggatctc gacgaatcac 194220
attgggtcct cggggacagc cgacccgacg atataaaaca acgcagactg ctgaaggcca 194280
ctcaacgacg aggcgccgaa atcgacgagac ccatgcctgt cgtgcctgaa gaatgttacg 194340
accaacgctt cactaccgaa ggccaccagg tcatcccgtt gtggcaaaca gaggatggct 194400
aaccgtcgtt gcatgttcca ggccatgagc caggctaggc ccgtacacca gacgcagagc 194460
atggatgaca ggacataggc ctggattacc acggtgcgat cgaaacacag cccgatggtg 194520
gacacggata tcgtagtgag ggtggtatat accatgacca gcatcagggt cccgggtcgg 194580
cgccgacgtt ccagccagta cgcgtggcaa cgcagagcgc agggtagcag tgtgctccag 194640
aagggcagtg tatcgcgcag gtaggggggtc gtcacgcgcc acggtatgag catgaaaagg 194700
atggtagtgg ctatggtagc gctggtctgg aacacgacgg tgccgtagag acgtaccatc 194760
cagagaaagt gttgaacgct ccgcagggtg tcttcatctt tggtgattac ggtgactcga 194820
cggatcggcg gtggtgacgg cggcgacacg ggtggggggtt tctctttctt atggccgagt 194880
ggctcgcctt ggtgaaactg gatctgtacc atgacgggtg ctcgacgaac agtcgtcggg 194940
gcttcaggta cccggcaagt tttatagaga aaggggggacg atgggtggtg gctacgagcc 195000
accgccacct tcgcaatacg aggatctgaa ggcggcaaag acggtcgtcc agggcaggcg 195060
ccagaggttg ggactgagca cgatcagcgt gattttaaac atggtcacca gtcctacgta 195120
gatcagcagc gagccgcgta acgtctgagc ggccggcagt tcgtcgcgga tgtaacgcgt 195180
gccgtagaaa gtcacggtca tcataaggaa gacgatggcg ccgtagccgt agagtagaat 195240
acgctgatga tggaacacgg tctggtcgcc gataacccag agcgtgatga aaaaacgct 195300 ggtgagcacc cgtgagcata tgagctccca acgcttagcg cgaaaactgt ccccaaccat 195360
gacagcgccg gtgcaagcta tccacagcgt gaggaccagt gtgtagtcga tgaggatggc 195420
gggcaggtcg gagcaccagg tgtagaaaac cgtggtaacg gagaggaggc ctacgtagcc 195480
catggtcaat accacgtcgt cggggtgcct ttcgccctgt atcaagacca aacaccagag 195540
aagggagggg gcaaaaacca gcagcagagg ggaagattca tgttgacata tgttgtggga 195600
atcggggata cccagccaaa tcattccgca gaaagccgta ctgatggcga tgtgaaagac 195660
cactagggcg tagacccgga cgaggacagc aaaacgcgc agccacataa ggccgtggtg 195720
cagctgcagg agggaagccc attgcggcga atgtagcgac ggcagcggcg ggtccatgag 195780
gcgggtgatg cgcccgagtg aacgggtgag cgtctcggtg gagtcttctt ataaaccagc 195840
ggagctcagg cagccttgct ctggaacgtc gcggtggtgg tgttgaggat gacgctgagc 195900
gtgccgttgt caatcaggta atgatgatag gtgccgagct tggccaggta gctgaacatt 195960
tggtcccagc gtgccgacca caccacgggc gtgagcatta ggagtgtggt gtgataaatg 196020
agtgtttcgg tggcgtaaag tatcagcgag ctgcggatga tgtggctcac gggcattttg 196080
gtggcgatgt agcgcacgtc ttggaaaaga acggccagga tgcagcccac gaacacggtg 196140
tagagacaca gcagagtctt atgcaaccaa gtgtaagtag aagccaggac gctgaccatc 196200
```

```
accgtcaaaa gtgtggaggt aaaaagcgcg tcacgccaca cggagctgag acggtgctcc   196260
caagccacgc cgttgcaggc cacgaacaac gtccacgtta agatgagact ggaaacgcca   196320
atgggcgctg tggcgcacag gttgagcccg gcggtggtga acgacagaag cgccacatac   196380
agcgcaaaca ccaggccgtt gctggggtgt ctgtgatcgg taagctccag cgcgcccaga   196440
accaacaccg gtgtgcagct aagcaataac ggcgaaggat cgtcgcggca ctcgtagccc   196500
agcgaggggt aacccagcca aaccagcgcg ctaatgagca cgctgaaagc ggtttccagc   196560
gtcagcaatc cgtagacacg catgacgatc gcggtccgcc gtagccaaca caccgcatct   196620
tcggaagctg tggacgctgt ttccgaatac cgggaggaga tcgtgcttcc ctcttctaag   196680
gatcggaaag tagcgtccgt cgtttccgcg gacgcggctt ccctggtacg ctccgtttcc   196740
gacgacgcgg tttcccgctg cgtggaaact gtctccatgt cgggaccgca gcgcccggcg   196800
gcgtatccgc aaggtctcga agctacagct tgtcagagga aaagtaggtt tgcaaaaagg   196860
tgcgcagggt catgattctc agcaccatca gcagagtgaa aaccaggctg agaaacacct   196920
tgacggccgc caaaagcgcg cgttccagcg gcgtctcgta gcgtacagcc agggccgctt   196980
cgtggaaatg cgagacggct agacaggtaa tgagcacgct aaggacaag acgatcttaa   197040 agcaccagga ccaaccacgc ctcaagatga ccaccacgat tgccgtgaag gtcaacgtga   197100
tcaaagcatg gacgaccacg atctgacggc ggacggtacg ttcgggagcc aacaacgcta   197160
cgccggtgca gctgagaaag gccagtaagg tgaacaacgc ggccgagatg accaacgtac   197220
cgtccaggca gagacatatc acgatcaacg gcggcacgtg aagcagcgtg taaaagagca   197280
gaacgccgat attgctggga tgcgatgttt cgtaacagtg aatgaagatc accgacgtga   197340
cgggtatgac aaagacgagg ctgggcgagg actccgtgag acacagacgg gaatggtgaa   197400
accacgtcgc gggcgccgcg tagcagaagg cgctcaacaa cgcggtcaag ccggccagct   197460
gccaacccac ggcgccataa gtgtgcagcg ccacgcggca acagtcgacc caagccagac   197520
tgcgggtcgc cagccgggtc tcttgtatcc cgggggcac gtagatgacc gtgccatcgg   197580
tgggtacttg aaaccctttt tctcttctca tggtgcgctg cgttctctgg aaacggctgc   197640
tctgtccgaa aaccagttcc gaacgaaaat ctagggcgag agggtggaca acggcgtcga   197700
cgacgaagca tgggacaggt cgttcggcgt taacgtcatc gcgtcggacg acggtagttc   197760
taagagacgt agatcgctca gcaggtcctg acagttgcgg attcgcaaga tcagaaaaaa   197820
aagggaaatg aacgtaataa agagctgtag cgacgtatgc gccacatcgc gtggcataag   197880
aacgtgacga acgaaaagga cctgctgcga aaagtggccg gcgaagataa ggcccaccgt   197940
gctgtagaag cccaaaagca gccgcagggg ccaagtccag ggccgcgtga agacgatgag   198000
aacgttagcc agaaagacca cgacccagac gccgttgatg agggtaaatt gatcggacag   198060
ggtgcagttg tcgcgacaga tgaagactac ttccgcgcag agcaaggtga tgaccaacgt   198120
gagcacaaac gacgtcaaca cctcgcgggg ctcctggcag gcacacgtga cacctagcgc   198180
cgggatgtgc gccaggaggc cggcgagtaa tagcaccagc tgtcggaacg gacgacggca   198240
gcgcgggtgc cggtttcgct gagcgagaac cggtcgctca tagcggaaat acacgaagag   198300
cgcggaggcc acaggcacca ggaggagcac ctcgggcgcc cagacaacgt gacaaggaaa   198360
gcccggacgc gacttaagag tcgctgtagg gaagaccaga gagaagctac ccaagacggc   198420
caccgccgcg gagatttgga agaggagcaa gccggcgatt cggacgacaa cctcgaagcg   198480
atgcacccag cccagcacgg ccaccacggc cgcttcatca tagtcgtcgt tgttgccgct   198540
gtcgaacagc cgccgaaaca cgatctgtcg ctgggtcgcg gtgggaaagc gcagacccat   198600
```

```
gacagccgga ggctatatga ccgtgcgtct aaggcgcgag atccgtgggg ggactttag   198660
atgtttgggc ggcccgcggt tctaacaggc ttgattggtg gagacggccg gcgcggcggg  198720
tgggggaaac gacgagtttt tccgttacgc catggttcgc gtgaggtttc tctgtacctc  198780
ccgcaaaagg tcacagcccg aaatggaggc gcgttggtg gccccggtgg cgcgtgacga   198840
taaccaggtc atccaagcga tgagtttgtc taatgagtcc tcggtggtga agaggataag  198900
aatgagcagg tacaggtaca ccaggttctc atagagacac aaggtgagca ggtcggcctc  198960
ggaccacgcg atctcaaaca ggcgcgtggt gtcaaagacc gtgacgacca gcatgaagct  199020
gagcgccatg gcgtaatagc ccaaaaaaag tttgtgccct aacggtacgg gttgcaggta  199080
aagtgcgatc aagaacgcga taacgccgat cacaaacagc gtgatgatga cctgccatcg  199140
acggtgatta tgggcggcta gacccgtgac gcagctgcag aggctaaaaa gcacgcaagc  199200
caagaggccc gagaaggtca ccagcgtaga ggaggagcag gcgctggcca cgatcaccga  199260
aagcgtcgtg agcacgctgt aaatggtgag caggcccggg ctcggcggcg acgtgaacga  199320
tccctcgtcg cgtttgccgt gcagcagagc cagacagatg gtgggcacca ccaaactcaa  199380
aggcggcata aagccagtgc aacagagaaa gacggtgctt ttgagatgcg gaaaagccag  199440
caccaggccc agacagagca agaaggtgca ggtgccctgc acggccacgg tgctgtagac  199500
ccgcatacaa agcaaaaagc gacgtacgtc gttcgtcgag acggaggaaa tcataatgac  199560
tccgcgcgag ggtcgcgggg gtgggggcgc ccaggccgtc ccggtggcct ctgagttcgg  199620
agacatgacg gcggtggcga tcaaaaggcg cgtatgaaaa accgtttata gagtgtaata  199680
gaatcaccgt catcccaca cggcgttccc ccataaagtc acgtcacact cgagtaagcg   199740
tgaaaaagct ttattgttga ataaaaaaca cgagttgcaa accgagttgc ggtgtcctgt  199800
ctgtctactg ggtgggggag gttcatcgtc tgtctctgga gggaaggtgg ggaacgttta  199860
agcgagcagg agcgtgtcat ctccccccatc tttttataac aagctgagga gactcacgcc  199920
gtcgatgcgt ccgccgtgtt tctcggcgta ctgctgcacc cagacgtggc cgctaaagat  199980
ggcgacgctc atgtttagga gactcatgac gatggtgtac aacacgacgc tgacacagac  200040
gctgtttta gacagcgttc cacgctggta gatgagatcc agggtctcgt aaataagcac   200100
ggccgaagcg gcggtcacca ccaggacgta gagtccgctg tagatcttgc tgacccacaa  200160
cacgggcgaa aagtaaagca ataggtaaaa gacgatgacg gaccagccgt aaccaatccc  200220
gatgactttc cagcgcgtgg gattgttgcc ggccaggtag gtgagaccgc tgcagagaac  200280
gaaaaagacc atcaccaggg caaacgacag accgatgacg cgcctttctc cgcaaaagcc  200340
cgtgcacacg gtgatgccgg tgttgatcag caggcacgcc accgtgagat gagcaaaatt  200400
ggtggtgtgt gggcgaaact cggcgaaacc gcgtagcata gccagcgtgg acacgggcac  200460
gatggaggac agggctggca ctatgccgtt ggcgcactgt ccctgcacat cggggaaggc  200520
gagccaagcc agcaggcaga ccgtgagggt acaagccagc tgccacacga gcccgtgata  200580
gacctccatg agcagcttga agcgtttcaa ccattggaag agctgctgtt cggccaccag  200640
cgcgtggctg cgatggagcg gcacgatggt aaccgtcggc gactcatggt gttcggaaac  200700
cgaggcggtg tcgcccatgc tgccgcttac gaccgctgtc ggtctaaggt aggcgtcgat  200760
gaaacagtcc gtcttatcag cacccggtta ccgcggattt gattgacgtc acgagtgtgg  200820
tcaaaccgtg gcggcaccct gtatccgacc cgtcgtcatg ggctccacaa ccagagcctc  200880
agaagatggt acatgccgat gaataaagcc acattttcga catagaggcg tagcgagggc  200940
```

```
tgaaaactct ccgggaaaga actctgacag gtgatcaggg acagatcgtg aattagcatc   201000
agcgtcaccg tcaacagcgt cgtcgcgtgt aaaccgagaa agaacggggc cgcggcccgc   201060
agcagccaaa gtcccagcgc cgtagcgcag agcagagaca ggaccgacgg tagccacagc   201120
cgccggagag acgcgccagg atcgcaaccc aaaagcgagg cccccaggca gctgagatct   201180
accgccaggg cgagaagagc cgcgccgaca aaggcctgcg gcgacggctg gcacatcagc   201240
aaggtcagaa aggctagcgc gtgcggcagg cagtaagcca acaggagtgg gagtttgcgg   201300
ggacaacggt cgatcgacgg accgcgtagc agcaggaaca ggcagccgac gggcacgacg   201360
aggctgagat gagaaagcgg cggtgggtcg tcgtcccgtc cccgctcgca tagctcggcc   201420
accggtggcg gcatgagcca ccagctgagc acgctgaggg cgacggtggc ggtaagctgg   201480
aaggcgacga ggacggaggc gcgcagccat accgccagcc tctctaggta ggggactacc   201540
tcctcgacgg tccattctag cgggacgaca tgaagcatgg cgacaagcgc ggctgctgtg   201600
aaaacgggcg cggttttata ggcattagga cttccccgtc gtactggcgg ctgtcaaagt   201660
cccgttgtcc aaaggcacgc cgtccgaaag actaatccaa cggggacccg agagcatgag   201720
caacaacgtg agaaagatgg ccatgctgtc caggtagaga cagacggcgt gacggatgca   201780
ttggttaggt gggcagaaaa agatgaccat gagactgtcg taggccagaa tacccaaaaa   201840
gaagctgata gagaaggcgc acaacgtcac cactatcttc tgcagccaat cggcgtcgct   201900
tagcagagcg agcgtgagga acgaaagcag catcaccacg tagacgcagc tgatgcattt   201960
ccagcgacgt cggtcacggc cacctagaaa cgccagcccc gtaaaggaga taaacaacgc   202020
cagggtcatc acgtaggaac ctactagtac gcggctttca gagcacatct ggaagatggc   202080
cgccgtcagg ctgttggcca acagatagat gaaaagcacc gtggcgttac tagggtgttc   202140
gttgcccaac gtgtacgtga tgaacatgca acgatgggc acgagcacgg tgagaaagaa   202200
gctgtagttc tcgacgcaaa agttgcggtt ttgtgggaac cccaaccaaa aaacgcttcc   202260
caaaccgaag ctgaaagcca gctgaaagat gaagatggcg tacacgcgca gccatacggt   202320 gaacttttg aaccactcga gagcctccat gcgggagagc agcagcgcgt tagcctcctg   202380
cgcctgcatg gtggcgacgg tctcggcaca aagccgctgc ggcgcaccta cccttctctt   202440
atacacaagc gagcgagtgg ggcacggtga cgtggtcacg ccgcggacac gtcgattagg   202500
agacgaactg gggcgacgcc gctgctgtgg cagcgaccgt cgtagcgacc gtcgtctgag   202560
cagtgtgggc gctgccgggc tcggagggca tgaagtagag cacggagaca aagaggtaca   202620
tgaggtccat gtacaagcag agcgcgcccg ggatataact ctcatactcg atgtcgtgca   202680
ggatgtcctg cgtatcgcac accaccgagg tcacgatgac ggccaaaccg gctatcatca   202740
ccaggatctc acttaccgcc tcgggaaaaa gagaaaatac ggcgaacagt aatagaatca   202800
gcgtggatgc gcccgtcaat agggaacgct gtaattccac gtcgcgggca aacagatacg   202860
tagcgagcgt aaggaaacaa aatagcgtta ctgtggccac catggcataa atgactgaac   202920
gatgactaaa gtggaagcct gacgccgtga cagccacgct ggtaagcaac gtgtacgtca   202980
gtaagatcca tacgttttg ggaaagttgg gctcggccca acgcaacaga cctaggcaca   203040
cgatggagat cattaagcaa gacagcgtca gacgcacgct ggaaaagagc tgctccagcc   203100
ggtgcggcaa caccagccag caaaaggcgc agacgctcat aaggatgagg cattgcaccc   203160
agataaggat gtagatgcgc agcaggaaga ccgaccgggc tatctggacc tgaccgcgga   203220
gcgacatggc ggcaacgccg gcggttatcg ccgagattcg tctaaataca caaagcgaac   203280
tagaaaacgc acacacgtga tttgcaaaaa gaaagcagct gccggcttat tatttatta    203340
```

```
aaaatttatc tgtgcagaat cataagttta tgatgaataa aaacggggaa agggaatctg   203400
cttttaggga cccgggtctg gtccgtcgtc tcccatctgg tcggttcgg ggatggggac   203460 ctgtttcagc gtgtgtccgc gggcgtgcat ggcttttgct cgccggccgc gctgtaacca   203520
ggcctctttc tctgtggtcg gcgagtcttc cgacgggtag ggagtctggg agtccatcgc   203580
ttcaggccca ccgctcgctc cctcgaccgt cgtgtcgtcc tcgttttcgc tattacacgg   203640
ggtttctgga gtatcgccta tacggttggc gattctccgg gggcggccgc tctcgtcctc   203700
gtcgctgcta tcgccgcccg gtaattcgac gccgcattcg ttgtacggag cgcggcacat   203760
gggcggcgga aagaacttgg gcatgcgaaa gcagcgttgt ccatccacgg tctgcgtggt   203820
ttcatcgtta tcctcccata atccccctg tagcgccggc agcgtttcga cgctgtgaga   203880
ggggaaggcc cagttctggt tgtcttgcag cgcgcccgtg ggcagtaggt ccgtgcggcc   203940
ccaggcgctg ctgttgttgg gtaccttgtc agtgccgcga gtaggtcgca gaaaccagtc   204000
cagagcgctc tctaactgcg agcgtgtgat ggtgcccagt gcgccgtgcc agcgcagcac   204060
gtctcttttc agcgtgtggt gacagacggg cagctcctcc aaccgacact cgccgcgcaa   204120
tccgcggtcg aagcggcaga gaccacgcag tttaagcaga ccgcacttga gaaacatgtg   204180
aaaattatcg gcaatgcgat acaggtctga gtcctcgatc ttgtgtaggt agaccacgcc   204240
aaacttgtcg agcagcacca ggccgctggg cacaaaaggc ccgtaggcca ggtaatagcc   204300
cacgaggccg acgacgtacc actcgcagca taagcgttga cgaataaagt tcagaagatc   204360
gcgaaagtcc gcggccggca tgtggtcaaa aggccggcag gcgcgcaggc cctcgatgga   204420
gcccagcatg agcaacggct ccacctcggt gcgacccggc gtgcggatga ccaggttgag   204480
accgctcatt tcgcgggccg tcttggccac ggccgcagcg tcagtggggt cggtgcagag   204540
gaattttgtg catgatagc gcggttcggt ggtggcgaac ggcgtttgtg ggtgccgata   204600
cacatattcg caccagagta ggccgttctt ggaaaaggct ttgatatcac tggccacctc   204660
gtagagcccg tcggtctccc agtcgtagac gtagacggtg ccgtaatgac ttagcatgag   204720
cacacagggc agttcctgcg cctgcttggt gtttcgtgtt agatcgctgt cgggtggacg   204780
tacggctaat acaccgacgg cttccagggt gtcatcgcag cagagatagt cggcggccag   204840
agaacgtgcg taaatctgcg ggatggcgac ctgttcgcgc atcactagga accagttggc   204900
ggggttgcgc agtgctacgg tggttccttg gtggcgctgc acgtaggttc tcagcgccgg   204960
aggatcgtac tggcgcagat agaggccttg cagcatcgat aacgtctttt gaaagacggt   205020
gtttctaaac tgaaaaacgc cgtagtcgca gcggatagca tcttcgcagc gctcgtcgcg   205080
ctgtcggaga taggtgcccc aggcttcggc ggcggctttg gtgagtaggg acatgccggc   205140
ggagccgtct cgacgcgag tcggataaag cgcgctgcgc gaaagcttaa tataggagca   205200
gcgtcagacg aatcgcggct ggtggccctg ggggtgggac gcgccgccta cacaaagtgc   205260
tcccgaaaat cgaaactctt gacccactcc ggagacaaat ccgtattcag attgatgcgt   205320
cgcgcttcca cttcggcttc cgaaacctcg gcctccgtcc ggtaggcgtt aacgatacgc   205380
tgacccaggt gccaacgctc tttctctgcc aaacgccgtt gctcaaacca ttcgtctacg   205440
tccttgaggt caaagacagt gtcctcctca aggtcaaagc ctaggtcttc ccactcgtcg   205500
tcatcgctct cgtggccggc ggccatacgc gcggcaaccg cgtcctcccc tcctcttctt   205560
tcaacgttgg gtaccacgtt attttcttcg ggttccatag gttctgcgcc actgtcgtca   205620
tcatcctctc cctgctcctc atcgtccgcc aaggcgtcgt ggattatctc caggttctga   205680
```

```
ttgtcgggta cgacgtggtt atcttcgtcg tcgtcgcgtg gcatgggcgg cggccgacgg   205740
cggacgaccg gcatggcgcg gccgtcgttt ccttcgtctt cctcttcacc gtctcccaag   205800
gaacgcggtc gacgacgttc cgcgaagtcg ccgcggacta cgcgcgcctg ccaaatggta   205860
aacgcgtccc aaccgtccca gttattgagc atttcggcgc gaaaacggtc gcctcgacag   205920
agccagcgaa actgccgcgc gtagtcgcgg tctacgccgc tgtcgaacat ggtaaagtgc   205980
agacgcgccg cctcgcccat gtgtacgcag cctccgttgc gttccagcct ggccgcgcgc   206040
cgtagaccgt gttcgtagcg gcgacgcacg tacaccttca tgaggccggc gcgaaaaagt   206100
tcctctaggc tgtcggccag acggtagatt tcaccggcta gacgctgcag aggcggcgag   206160
cggtccagat gcgatttgac aatcaccacg taaaaacgac agaaacggtc gaagatgatg   206220
aggaaggacg tgtcaaaaaa accaccggcg cggtaggagc ccacggcgcc cagcaggtac   206280
cagcggcaac gcagttgcag cgtgacgtac atttcgcact cggccaagcg ggcggctggc   206340
gctacctcga agggccaaca gtccgtcaag cagccgaaac tggtcaggag tttcaacgtt   206400
ttggcatggc gtccaggtgt atgaaagttc acgtcgcgtc cgtgatgttc gccaacgcag   206460
gcggccaacg cgtcggcgtc atgaccgtga cgcagcagca tcgctaccac gtcgtgcggt   206520
acccgcgtag caaacggcgt ctgtggctga cggtatacgg cttcggtgta catcataccg   206580
taacgcgcca gctcgtccag atgacgcgcg cacagcagca gaatctcttg cgagggttcg   206640
tagatgtaga ggcgcgtacc gccacccatg cagagcacca gctccgtctc ttcgtagtga   206700
tcttccacca tgatcacgca cttgcctagc acgataaggc gttcggggca acaaatcacg   206760
tcgtccagca gctggtcgcg tagctccggc atggtgctgc cgggccgtac ctgcaggaac   206820
cagttgtgcg gaatgccgag cgacagcacc tggtcgacgt ggttacggac ccagtcgcga   206880
agcacgtcgg cgctgtactg gcactcaaag atgccctgaa agtcgcccat gacccgcaga   206940
aaagtttcgt agcgcgtgtg gcaatagagg aattcatcgt ttcgcgtaaa cgtgggagct   207000
ccgtcttccc aacgtgtacg ccacatgtca aagaggccg ccagctagac accccagaaa   207060
agaagcagag aaagagactt ctttgtgcga cacgttttat tccgcgttct ccgctcgacg   207120
ttcaaatctg gatgtactcg cgcacacccg tcaggctctt taagggaaaa gggtccgagt   207180
acgtcactaa ccgcgactga tgcaccaggg cggtaatcac ccgctccgcg ccctcgcgcg   207240
tcgacgaacg cgtcgtcacc aggcagtgca gccgcgggcc cgtatcgtcc tgatgaccag   207300
cggcctcgcg ctcggctgct tccacaccga caatgtcggg atccaacacg tagctctgcg   207360
agttggtatc gtagcggtgt agcaccaacg tgttggggtc cagacgctcc cacgcgccct   207420
cgtgcgggtc aaaacgctcc gttaaacaga gccagtcata ctgctgctgc agaatacgcc   207480
gctcgcgctc gcgtcgctca tcgggcaacg cggcgtcttc gttgaagaga atgtcccgct   207540
tgtggtctac ggcacgctcg tggtgatgcg ggcacagatg acggtgttcc atacgcgtct   207600
gacgttgacg ctcgcgctcg aaacgccggt gtcgaaagac cattttcagc aaccccatgc   207660
ggaaaaactc cgtgatggtg ttggcaacgc gccgcacgta gtggttgggg tcgtccatct   207720
ggatggcgta cacggcaccg aaccagtcca acagtaccag cacttcggcc acaaaactgc   207780
gtcccggtcg cggacgtccc gtcacgccta gcacatacca cggcgtggcc agattagcac   207840
ggacagccca ccaccaacga cggctctcca cctcggtgag cgcacaaaag ggccaaatgc   207900
ggtgtaactg ctgcaccgtt ttcatcagcc gcataatcac cgtgccgtaa cccggtgtat   207960
gcaacttcac gtcgcaaccc aggattcgtt cggccgtggc gtacgagccc tcaggtgtgg   208020
tgtcattgag aaacaaaaca tgcatggtac gcgcgcccctt agggtatcgt cgcggaacag   208080
```

```
gtaccgtcat tctccgcaga gtggtgtgaa tcacgtcgcg atacgcaatc tccgaacgtg    208140
acacaccgta acgtgccagt tcgtccaggt tgtgcgatac caacaccatg tactttcac    208200 gagtgtcgta ggcgtagacg cgagaaaagc gacccataaa aaccacgtac ggggtagcca    208260
ccatgccatc atggtgatcg cgacgtggct cgggcaacaa aataacagcg tatcccaacg    208320
gcgtcagcgg ctcgcggcaa cagatgagct tgacgccgc ctgtttggcg gcggtaatga    208380
tcccgtcctc cgtacgtaac atcacatgcc agcccttggg gggacccaag gacagacagc    208440
gtccctcgtt acgatgaacg taacgcgtga tttccattgg ctccaggcaa aagaacagtt    208500
ccttaaaatc tcgcaacact tgtcggtata acgccatggg atcctcggcc gccacaggca    208560
gcgcggggag ctccggcggc acaactgcag cgccgtcggg gccagaaccc gcagccggat    208620
ccatcattgc gcgacactct cagccggaca accggcgtca ctgacagaag ccgagccaaa    208680
tacagagaaa gcaacgccac accgtcaccc cgctcccaag cgccgcggaa agtgctccga    208740
tttttcaccg tcgttcacga cgttgatttg cctcggtctg agaaccgacc tagcgttcgg    208800
accggtgcgc agaaacagcc ggcggtccga gccactgagc ggttcacagc cccggccgcc    208860
gatagttatc ggagagacgt tcgagctgca ggtacatcgg cgctccccgc ttcgccaccc    208920
cgcgcccgcc ccagtttata ctctccgacg ccccttccaa cgcgcctgtg gagggccaat    208980
cggaccgcgg gagctctcca agtggatgac aggcacagcc gggtgcccga ccgtgaagag    209040
ccctcatcca cctgaacaga ccgctaaccg aaggaccccg agtcgcgtcc gtcagtcccg    209100
acgtccgtcg ccatctggct ccctgctgtt ggctacctct cggatttcaa aaaagagcac    209160
gtgccgatga cggtgcacag gaaagagcca aagtgtcaca gcgtcttttt ttatttgtat    209220
tcctttcctg ttttgtactc gtaaactgtt gacgttgttt ttacatccaa aagggcaagt    209280
aagaaacagg atgaggcatg gtaggtttgg gcgtggggcg gccctccagc acggcggccc    209340
gggccgcccg gcgggtgagc acccggccgtt gcgccgtgtc tatcttgtgt ttcttctgtg    209400 tcttttttcct atcttgttcc gcgacggcct cttcatcac gttcagcatg cgttcctcga    209460 cgcccctccag ggatcctggg gaggaggag tcctagtgag gcttccaatg ttgttttgtg    209520
gattttcggt ttcctcttct tggtcgtcat cgtcggacgt gtcgtcttcc tcttgatcct    209580
cttcttcgtc cgagtagtag acgcatagtc cttggttcat caggctggga ttcatcaggt    209640
tctgacgggg aatccgctgt tgtagacgtt taaccgcccg ttccaggcga gagctcatgc    209700
cgcaccagac gctgtaacgc cgcacgggcc cgtagcgggc tgtttgttcg cgtacatgat    209760
cgttgagctc ttgccaatat tgtttggcac actccagatc ggaggtttgt ggatagtcgg    209820
gtcggatccg tggatcccaa ctgacatcgg cggtgccgga gacttcgtcc agactgttac    209880
gcatagagca ccagtcgggt cggacgataa acctgtcctt gcggattaac catttataac    209940
gtagttcgtg atggcgtgta gaggcccgta cacgctccac ggtcccaaag cggtcccaga    210000
agggaaagtt ttcgtggggg cagcgacccg gcacttccag acgttcggcg tcgtccacgg    210060
cgtagtgaaa acgccggccg gcctggtaaa ttttgagcag acccactgtt aacaacatat    210120
ccacgctgtc agccaaccgc cagatctcgc ggcgagacac gtcaaaatag aaaaattcgc    210180
aggctcggtc gaccaggatc acgaaatcgg cgtgaaagac gccggagggt agcgattcgc    210240
ccaccacacc cattatcatg gtttcacagc ataagcggtc cacaaagaac ttcaacaggt    210300
cgttgaattg ctccgtctcc atacagatga agggccagac gcctttgagg ttctcggcct    210360
ggccgcagag cagtagcgga cgtgtcatct cgcccggagt gcgcagaggc acgcattcgc    210420
```

```
cgcgataacg acaggtcaca cgctgtagtt cgctgatgct gttgtcgtgc aggcgaaggt 210480
cgcagataat atgatccggt tgcgtggtta gcagcggcgt gcgcatttgc tcgccgtaga 210540
tggcctcgca gtgcaacagc ccgtgtcgcg caaaatcgtc cagactgtgc gccaggtagt 210600
aaagcacccc gcgatcgcgg tctagacacc acacggtttc gtaacgtcct aacaggagca 210660
ccagacgggc ctggctaggt ggctcaattt cctctacata cacgaaaaag tcgtcatcgt 210720
ccgagtcctc gtcctcagaa gaggaccgcg gcccgtgtac tctgggcaac acggtggtag 210780
agaactgcag gacgcccaga gactcgagcg actcttcgca gcagatgagc tgaccccagg 210840
gcgtttcggg cccgtcggtg acagccgcgc tgccaaagat gtcctcaaac tctacaaaat 210900
ctagacgcca tccgggtggc gctgaaatgg gaaggctaat gttcatatca gcataactac 210960
gaactaagtg gcggatgtcc tgccgcaagt cttggcagag aatgagcttt cgtaaaccct 211020
tgagggtcct ccgaacaacg gccccagacg cgtagcgata ggactggcgc atggtgccgc 211080
ggcgtggagc ggcacttggc agcctatttt atggagtttc ttcagtgacg tggcttgttc 211140
acgtcgttcg tgggctgcgg ttggcagctc cggtctgtaa accacccgaa aagactgaca 211200
tcgacgtcaa agactcacgt aatttggaac atgtgcgacc gcaaagtgcg tcagaatagc 211260
acgtggcttt aggacataaa aagtaccgtg aggtctagac gtggtttttg tgattgacac 211320
ttacaccagg taagccaagg gacggtgaaa ctgtatgtga ggaacctggg tgcttagaca 211380
actaacgtgt aatgcttttt acaggaccgt tcaacaggtg atactacctg caaggtaatg 211440
actacatcta ctacaactac cactaatatc atgctacagg tgagcaacgt aacgaatcac 211500
accctgaata gcaccgaaat ttatcagttg ttcgagtaca ctcggttcgg ggtatggttg 211560
atgtgcatcg tgggcacgtt tctgaacgtg ctggtgatta ccaccatcct gtactaccgt 211620
cgtaagaaaa aatctccgag cgatacctac atctgcaacc tggctgtagc cgatctgttg 211680
attgtcgtcg gcctgccgtt ttttctagaa tatgccaagc atcaccccaa actcagccga 211740
gaggtgattt gttcgggact caacgcttgt ttctacatct gtcttttgc cggcgtttgt 211800
tttctcatca acctgtcgat ggatcgctac tgcgtcattg tctggggtgt agaattgaac 211860
cgcgttcgaa ataacaagcg ggctaccgt tgggtggtga ttttttggat actggccgcg 211920
ctcatgggga tgccacacta cctgatgtac agtcatacca ataacgagtg tgttggtgaa 211980
tttgctaacg agacttcagg ttggttcccc gtctttttga acaccaaagt caacatttgc 212040
ggctacctgg cgcccatcgt gctgatggcg tacacgtaca accgtatggt gcggtttatc 212100
attaactacg tgggtaaatg gcacatgcag acgctccacg ttcttttagt tgtggttgta 212160
tcttttgcca gcttttggtt cccttcaac ctggcactat ttttagaatc catccgtctt 212220
ttagcgggaa cgcaaaacga gactctccaa accgttatta cttctgtct atacgtcggt 212280
cagttttgg cctacgttcg cgcttgtctg aatcctggaa tctacatcct agtaggcact 212340
caaatgagga aggacatgtg gacaacccta agggtattcg cctgttgctg cgtgaagcag 212400
gagatacctt accaggacat tgatattgag ctacaaaagg acatacaaag aagggccaaa 212460
cacaccaaac gtacccatta tgacagaaaa aatgcaccta tggagtccgg ggaggaggaa 212520
tttctgttgt aattcgatcc tctctcacgc gtccgccgca catctatttt tgctaattgc 212580
acgtttcttc gtggtcacgt cggctcgaag aggttggtgt gaaaacgtca tctcgccgac 212640
gtggtgaacc gctcatatag accaaaccgg acgctgcctc agtctctcgg tgcgtggacc 212700
agacggcgtc catgcaccga gggcagaact ggtgctatca tgcaccgac gacgacgacc 212760
gcggaactca cgacggagtt tgactacgat gaagacgcga ctccttgtgt tttcaccgac 212820
```

```
gtgcttaatc agtcaaagcc agtcacgttg tttctgtacg gcgttgtctt tctcttcggt  212880
tccatcggca acttcttggt gatcttcacc atcacctggc gacgtcggat tcaatgctcc  212940
ggcgatgttt actttatcaa cctcgcggcc gccgatttgc ttttcgtttg tacactacct  213000
ctgtggatgc aatacctcct agatcacaac tccctagcca gcgtgccgtg tacgttactc  213060
actgcctgtt tctacgtggc tatgtttgcc agtttgtgtt ttatcacgga gattgcactc  213120
gatcgctact acgctattgt ttacatgaga tatcggcctg taaaacaggc ctgccttttc  213180
agtatttttt ggtggatctt tgccgtgatc atcgccattc cacactttat ggtggtgacc  213240
aaaaaagaca atcaatgtat gaccgactac gactacttag aggtcagtta cccgatcatc  213300
ctcaacgtag aactcatgct tggtgctttc gtgatcccgc tcagtgttat cagctactgc  213360
tactaccgca tttccagaat cgttgcggtg tctcagtcgc gccacaaagg tcgcattgta  213420
cgggtactta tagcggtcgt gcttgtcttt atcatctttt ggctgccgta ccacctaacg  213480
ctgtttgtgg acacgttaaa actcctcaaa tggatctcca gcagctgcga gttcgaaaga  213540
tcgctcaaac gtgcgctcat cttgaccgag tcgctcgcct tttgtcactg ttgtctcaat  213600
ccgctgctgt acgtcttcgt gggcaccaag tttcggcaag aactgcactg tctgctggcc  213660
gagtttcgcc agcgactctt ttccgcgat gtatcctggt accacagcat gagcttttcg  213720
cgtcggagct cgccgagtcg aagagagaca tcttccgaca cgctgtccga cgaggtgtgt  213780
cgcgtctcac aaattatacc gtaataaaaa agcgctacct cggcctttc atacaaaccc  213840 cgtgtccgcc cctctttttcc ccgtgcccga tatacacgat attaaaccca cgaccatttc  213900
cgtgcgatta gcgaaccgga aaagtttatg gggaaaaaga cgtaggaaag gatcatgtag  213960
aaaaacatgc ggtgtttccg atggtggctc tacagtgggt ggtggtggct cacgtttgga  214020
tgtgctcgga ccgtgacggt gggtttcgtc gcgcccacgg tccgggcaca atcaaccgtg  214080
gtccgctctg agccggctcc gccgtcggaa cccgacgag acaacaatga cacgtcttac  214140
ttcagcagca cctcttttcca ttcttccgtg tcccctgcca cctcagtgga ccgtcaattt  214200
cgacggacca cgtacgaccg ttgggacggt cgacgttggc tgcgcacccg ctacgggaac  214260
gccagcgcct gcgtgacggg cacccaatgg agcaccaact ttttttctc tcagtgtgag  214320 cactaccctc gtttcgtgaa actcaacggg gtgcagcgct ggacacctgt tcggagacct  214380
atgggcgagg ttgcctacta cggggttgt tgtatggtgg gcggggtaa tcgtgcgtac  214440 gtgatactcg tgagcggtta cgggaccgcc agctacggca acgctttacg cgtggatttt  214500
ggccgcggca actgtacggc gccgaaacgc acctaccctc ggcgcttgga actgcacgat  214560
ggccgcacag accctagccg ttgcgatccc taccaagtgt atttctacgg tctacagtgt  214620
cctgagcaac tggttatcac cgcccacggc ggcgtgggta tgcgccgctg tcctaccggc  214680
tctcgtccca ccccgtcccg gccccaccgg catgacttgg agaacgagct acatggtctg  214740
tgtgtggatc ttctggtgtg cgtccttta ttagctctgc tgctgttgga gctcgttccc  214800
atggaagccg tgcgtcaccc gctgcttttc tggcgacgcg tggcgttatc gccgtccact  214860
tccaaggtgg atcgcgccgt caagctgtgt cttcggcgca tgctgggtct gccgccgcca  214920
ccgtcagtcg caccacctgg ggaaaagaag gagctaccgg ctcaggcggc cttgtcgccg  214980
ccactgacca cctggtcact accgccgttt ccgtccacgc ggatacctga cagtccgccg  215040
ccaccgtacc agcttcgtca cgccacgtca ctagtgacgg tacccacgct gctgttatat  215100
acgtcatccg acatcggtga cacagcttca gaaacaacgt gtgtggcgca cgctacttat  215160
```

-continued

```
ggggaaccccc cggagcccgc tcgatcgacg gctacggttc aggaatgtgc cgttcttacc 215220
gccccaaatt gcggcatcgt caacaacgac ggcgcggtct ctgaaggcca agaccatgga 215280
gatacggttc accatagcct ggatgtggtt tcccagtgtg ctgctgatac tggggttgtt 215340
gacgcctccg agtaacggct gcactgtcga tgtcggacga acatgtcca ttcgagaaca 215400 gtgccgtctt cgagacggtg cgacgttctc caagggagac atcgaaggta acttcagtgg 215460
gcccgtcgtc gtggagttgg actacgaaga cgtcgatatt actggcgaac ggcagcgact 215520
tcggtttcat ctcagcggac tcgggtgtcc tacaaaggaa aatataagaa aagacaatga 215580
aagcgacgtc agcggtggaa ttcgctgggc tctatatata caaaccggcg acaccaagta 215640
cggtattcgt aatcagcatt tgagtatacg gttgatgtat cctggggaaa aaaatacaca 215700
acagctgttg ggttctgatt tcagttgcga acgtcaccgg agaccgtcca cgccgttggg 215760
aaataacgcc aaagtgcctt tcacgacccg cacgtcttct acatacggcg tcctcagcgc 215820
ctttgtggtg tggatcggat ccggcctcaa tatcatctgg tggaccggca tcgtgcttct 215880
ggcggcggac gctctcgggc ttggcgagcg ttggctgagg ttggcgctgt cccaccggga 215940
caaacatcac gcatcgcgaa cgcggcgct ccagtgtcaa cgcgacatgt tacttcggca 216000
acgtcgacgg gctcggcggc tgcacgccgt ttctgaaggc aaactgcagg aagagaagaa 216060
acgacagtct gctctggtct ggaacgttga ggcgcgaccc tttccgtcca cacatcagct 216120
gattgtgctg cccctcctg tagcgtcagc tcctcctgca gttccctcgc agcccccga 216180 gtattcgtct gtgtttccgc ctgtataaaa ataaagagac gggaggctga tcgcggcctt 216240
cagcgtctca tttgtcttta ctctcgagtg cggtcggtgt ctcgtcggtg agacgaggcc 216300
gccgcccgac aagttcgatc tcatgtcgct cttggagcgc gaagagagtt ggcgtcgcgt 216360
agtcgactac tcgcacaact tgtggtgtac gtgcggtaac tggcagagcc acgttgagat 216420
tcaggacgag gagcccaact gcgagcagcc ggagcccgca cactggctgg aatacgtggc 216480
ggtccagtgg caggcccggg ttcgcgattc tcacgatcgc tggtgtctct gcaacgcctg 216540
gcgtgatcac gccttgcgcg gccgttgggg tacggcgtat tcctcgggtt cctcggcctc 216600
ttcctccggt ttcgtcgcgg agagcaagtt cacctggtgg aaacgactgc gccacagtac 216660
tcggcgctgg ttgtttcgcc gccggcgagc tcgatacact ccgtctaact gtggggaaag 216720
tagcactagc agcggccaga gtagcggtga cgagagtaac tgcagtctac gcacccacgg 216780
cgtgtacaca cggggtgaac aacactaatc gataagtcgc gtgtaggcga ctggctacat 216840
caaccggata tctgcgggga tttaaaaaga cgaccgttg tcatccggct tagagcaaac 216900
cgtcctttta tcatcttccg tcgccatggc tatgtacaca tccgaatccg aacgcgactg 216960
gcgtcgtgta atccacgact cgcacggcct gtggtgcgac tgcggcgact ggcgagagca 217020
cctctattgt gtgtacgaca gccattttca gcgacgaccc acgacccgag ccgaacggag 217080
ggccgccaat tggcggcgac agatgcgcgc gttacaccgt ctgtggtgtt tttgtcagga 217140
ctggaagtgt cacgcgttat acgccgagtg ggacggcaaa gaatccgacg acgagtcgtc 217200
ggcgtcttcc tcgggcgaag cgccagagca acaggtcccc gcttggaaga ccgtgcgagc 217260
cttctcgcgg gcctaccatc accgcattaa ccggggtctg cggggcacgc ccccaccgcg 217320
caacttgccg ggatacgagc acgcctccga gggctggcgg ttttgcagtc gacgggaacg 217380
gcgagaggac gatcttcgca cgcgggctga gccggaccgc gtggtgttcc agttaggggg 217440
agtgccgcct cgccgtcacc gggaaactta cgtgtaagaa cacggcatga caataaacaa 217500
catagcgtaa atccccgtgt gatgtgtgtg attgacgttc aggaaacatg tccccatcat 217560
```

-continued

```
cagcgtcaca actgacgtgg gttgggtact gacgtgcagg atattacgcg agtcagagaa 217620
tcgcataaga acggggtggt gagcgggttc ccacaggagt ttctggcaca gaggcaccat 217680
gagccttaag ttcccccgaga gggtggggtta cgagaaattg ggacaccgcc cgtataccaa 217740
acgcgtgcgg gtgcatgacc cgttgggatt gacgcggttt atcatgaggc aactcatgat 217800 gtaccccgctg gtgttgccgt tcactttttcc gttttacgtg ccgcggtcct agcacgtcag 217860
tggtgacgct gataattgca acatggccca tgacgaaccc gcttgggacg aacgtcaata 217920
ccacgtcaaa ccaccgtgac ttggctgaac gttgaaacat aaagccaaag cgccgtcggc 217980
acttggcttc agagcagcgc ctcggggcga tgcgacggcg atgaacttag agcaactcat 218040
caacgtcctt ggtctgctcg tctggattgc cgctcgtgct gtcagccgcg ttggtccgca 218100
tggctccgga ctcgtttatc gtgagcttca tgatttctac gggtatttgc agctggacct 218160
tctgggacca gtggtggcgg ggaatcgctc agtccggacc tggagagagc aggcggaccg 218220
agccagaggg accttcgctc ggcgttcagg ccttaatact agccacatct tacctgtcgg 218280
cagcatgtat cggggctccg acaccttatc cgccggcctg tatcgttcca agaagaggt 218340 gttcctcctc ttgaaccgct gtcacgggcc actgtcaacg ccgaaaaacg cttgtctggc 218400
tgaggttggt gtcgttaatg aactttttt gtctcgcttc aatgtcggtg attttcacgg 218460
agcgtcatgg gaaaacggta ccgctcccga tggagagccc ggggtatgct gaaattcttc 218520
ttaaaattac gtaaacgacg tcgtccagtc gttgtgccgc gattcgtacg gttcatcgtc 218580
tacgtcgttt tgttcaccgt cgctgtgcaa cgtgtgaaac aagagcgcga tgcgcacctt 218640
cggcggtatg aagaacggtt acggaaaaat cacgcacggc gtcggcagtc ttttccgtga 218700
cttggggcga tgggtccgag ctgcggtatg ggtcacggcg gcgtgtgtct tagtgacgaa 218760
gatgccgatg tgtgactaaa aacgtcccag ccccagagcg atgtgtttca ataaaaaaat 218820
atgtagtatc atattatgcg tgtcctggtt tttcatttct ggatgtattt gttacataaa 218880
aggcggtggg atatggggat gaaacatatg tagatacgca gtttgattat ccgaacaaag 218940
ctcgtgtgat gcgaaaaacg gtactgcagg atgaaagtcc cgttgggggg ggggaagca 219000 gagaatagtc gcttttgccg ctgggcatac gctatgcttg tatttgtgac tatactatgt 219060
gcagtcgtgt gtcgatgttc ctattgggaa gggtgtgaat gtacgaggta taagaatgg 219120 tgggacgtag agaggcatcg ctagacacag gttgatcgtt gtgctagccc cacgtgagca 219180
gcgtcatggg taaagcggtg attaagcgtg aaaacaccgt aagggggggg gggcaggaag 219240
cttggtggca gtgccgtta gataccttac gtgtctgtat tggtacattt gcgacttgtc 219300
gggtacgacg gtatagttta actatgatta tattatgtat gcgcaggata caatgcccta 219360
aaacattgta acacgaaact cgcgagtatt aaagcaattg gtgtctctgt gctagtctaa 219420
caacacctgt gtaatgcgta caacgagaaa aaagacgcga aagcaacgtg tatgggggg 219480 gggggaata atattgctaa tcatgcgtct tgcagtacag atagccgctg tatcttacgc 219540
gtattgtcgc aacagttcca catcggtgta attggatgtc tggtacttat cactggcgtc 219600
gttataacat tgtaaaacaa gttttcgaaa cataacgaca gctgcaaaag aaaaccagtt 219660
tattgagcat tgtaatggta gtgtgtggct atattagaaa acgtgacgcg tcgcatgtcg 219720
cggcacaatc tggcagcggg gtcggggtag ggtacggtgg gaggcatgta cacagatgga 219780
acaaaagcag aagtaacgtg agaaggagca tacagtccag tatccagcgg ttcctgagta 219840
gcaccaccca tcaactgaat gccctcatga gtaaaagtct gcgggcgaca gcccttgggg 219900
```

```
accgttggca tgggacgatc aatctccaaa ccacagcgta acaccgtttt cttccaacgt   219960
cgttgataga cgtcgttttt acggttactc ccaagaaccc agaaagtctc gtccaagtcg   220020
taccaggaat cttctccggg gagacgcgac ggtttccaat cctcgtcgtc tcgtctcaaa   220080
gcacgtccca aactggcttg aggagtcaac ggtggttctg tgggtcgggt gtagcgcgag   220140
tgttttccct tcatgagcga ttcatcctcc ttgcctttag gcttttttggt cttttttgtgt  220200 atcatctggc cgccggcctc cataaccacc gtggccaagt ccagtcccag agcttgagcg   220260
tcggcgcggc gtcgggcgtc ttgcaggtag tcttccacat ttgcacagat ggccgggtgt   220320
ttggtggcta gggtgaggac ctcagcctcg ccgcgacccg gacgtagcaa aaaagccaac   220380
tgcccgtgcg gctcgcgcgc ccacagcgcg gcgcgcgggt gcaggtgcag cgcgtcccag   220440
cgcggccgct cccactgctc gcggtccagc tcggcagca gccgccgcgc ggcctcggcg   220500
gcgggcgcca actcgcgccc cagcgccagc gcgcccagca cgcccgcgcg cagaaagtgc   220560
gacagctccg ccgccagcgg gtacacgtgc ccgtccagcg ggcagtaccc gaacacggcg   220620
cccagctcgt ccagcaccac caccagcatg gcgcgcggca cggtccccga cgccgccgga   220680
cccgccatcg ccgtcggacc caccatcacc gtcggcgccg ccgctgccgc cgccgccgca   220740
tccgttccga ccaccgcgtg cgtgtccgcg tttggtacgc aaaccgcgct cccgccggcg   220800
gcgccgtacg gctgcggagg taaagtcaca gcagacccca cggctcccgc tatcgcgcac   220860
ggcgcgtccc cgccggcggc ctccgtctcc gtgccgctcg ccccgccgg caacgtcgtc   220920 cccgtcgcca tcgccgtcgt ccccgccgtc atcgtcgccg gccccgccgc gcagcccagc   220980
caccgcgcgg gcagcaccgc gcccagcgcc agccagccgc agcacagacg ctggttcagg   221040
tgccgacgca cggccgtcag cagcgacgcg gggtgcggcg ccgacgcgaa cggctcgtac   221100
tgcgccagct cctgccacgc gcccagcagt accatcggct gcagtcgcct gcccggcgtc   221160
tgcagcgcca ccgtcgtgcc ggcccaccgc cggcgcagct cccgtccgag cgccgtcgcc   221220
tcctcggcgc gcagcaaggt ctgtcgaagc gccggctgag gcagcagcgt cgcgcgcggg   221280
gtgcccacgc ccagccggtt gcagcggtac acccgcacca cctcgcccgc gccgtgccga   221340
aaccactcgt ccgcgtcgcg cgccgccagg atcagcgtgt tgttcgccag gtcgtacacg   221400
aacacgcgga atccggcgcc cagcgccagg tacagtccgt cctgcgcgca cagaccctcg   221460
ggatggccgg ccttgtcgcc caccgtcggg tcggccgcgg ggtctacctc gtgcaccacg   221520
gtcgccacca gcacgatcca cgcgtcccgc ggcgacagct gacgcaggtc cgtcgcgccc   221580
acgccgttca tctggctgcg cggcgtcacc cgcgcgtaga atccgtacgg ccgtccgagc   221640
ggcagcagcg tgcccgcgtc gcgctgcgac cacttgcgca tggcgcggcc cgtgctgttg   221700
gccagaaacg ccgcgcgcca cacggcgccc atggcctggt attccagttc cgtcagcgcc   221760
tgccgctcca ccggaatctg agacagcaac aggcgctccg gcccgtgcca aaagttgcta   221820
ttgttgccgc tacccggagg ggcgcccggc ggcccgcggg gttctacccg ttggacgccg   221880
tggcccggcg tcgccgaacc cgcagtactt gcaccagttc ccgccgttga cgtcgctccc   221940
atcggcacac aagaagaagg agaggaagca accccgaag gccctccggc accgcggccg   222000
cgaccgaggg gcgggggggcg cggcgacatg ccgttgcgct gggccat            222047
```